(12) United States Patent
An et al.

(10) Patent No.: US 10,428,388 B2
(45) Date of Patent: Oct. 1, 2019

(54) METHOD FOR DETECTING THE METHYLATION OF COLORECTAL-CANCER-SPECIFIC METHYLATION MARKER GENES FOR COLORECTAL CANCER DIAGNOSIS

(71) Applicant: GENOMICTREE, INC., Daejeon (KR)

(72) Inventors: Sung Whan An, Daejeon (KR); Young Ho Moon, Daejeon (KR); Tae Jeong Oh, Daejeon (KR); Hyun Cheol Chung, Seoul (KR)

(73) Assignee: GENOMICTREE, INC., Daejeon (KR)

( * ) Notice: Subject to any disclaimer, the term of this patent is extended or adjusted under 35 U.S.C. 154(b) by 10 days.

(21) Appl. No.: 15/659,582

(22) Filed: Jul. 25, 2017

(65) Prior Publication Data

US 2017/0335405 A1 Nov. 23, 2017

Related U.S. Application Data

(63) Continuation-in-part of application No. 13/508,534, filed as application No. PCT/KR2010/007030 on Oct. 14, 2010, now Pat. No. 9,745,622.

(30) Foreign Application Priority Data

Nov. 5, 2009 (KR) .................. 10-2009-0106445

(51) Int. Cl.
*C12Q 1/6886* (2018.01)

(52) U.S. Cl.
CPC ..... *C12Q 1/6886* (2013.01); *C12Q 2600/154* (2013.01)

(58) Field of Classification Search
CPC ............ C12Q 1/6886; C12Q 2600/154; C12Q 2600/158
See application file for complete search history.

(56) References Cited

U.S. PATENT DOCUMENTS 9,315,870 B2  4/2016 An et al.
9,745,622 B2 * 8/2017 An .................... C12Q 1/686
(Continued)

FOREIGN PATENT DOCUMENTS

CN  1845991 A   10/2006
DE  20121960 U1  1/2004
(Continued)

OTHER PUBLICATIONS

Ahlquist, D., et al., "Colorectal Cancer Screening by Detection of Altered Human DNA in Stool: Feasibility of a Multitarget Assay Panel", "Gastroenterology", Nov. 2000, pp. 1219-1227, vol. 119, No. 5.

(Continued)

*Primary Examiner* — Diana B Johannsen
(74) *Attorney, Agent, or Firm* — Hultquist, PLLC; Steven J. Hultquist

(57) ABSTRACT

The present disclosure relates to a method for detecting CpG methylation of SDC2 (Syndecan 2) gene, a kit for detecting CpG methylation of SDC2 (Syndecan 2) gene, and a method for detecting CpG methylation of SDC2 (Syndecan 2) gene for a colorectal cancer diagnosis.

12 Claims, 2 Drawing Sheets

Specification includes a Sequence Listing.

(56) References Cited

U.S. PATENT DOCUMENTS

| | | | |
|---|---|---|---|
| 2004/0234960 A1* | 11/2004 | Olek | C12Q 1/6827 435/6.11 |
| 2008/0292546 A1 | 11/2008 | Clarke et al. | |
| 2009/0208514 A1 | 8/2009 | Nakamura et al. | |
| 2010/0131432 A1 | 5/2010 | Kennedy et al. | |
| 2010/0303795 A1 | 12/2010 | Sorensen et al. | |
| 2012/0101023 A1 | 4/2012 | Zwarthoff et al. | |
| 2012/0264640 A1 | 10/2012 | An et al. | |

FOREIGN PATENT DOCUMENTS

| | | |
|---|---|---|
| EP | 1862555 A1 | 12/2007 |
| WO | 2007149269 A2 | 12/2007 |
| WO | 2008045133 A2 | 4/2008 |
| WO | 2008100913 A2 | 8/2008 |
| WO | 2008102002 A2 | 8/2008 |
| WO | 2009052567 A1 | 4/2009 |

OTHER PUBLICATIONS

Chen, X., et al., "Detecting tumor-related alterations in plasma or serum DNA of patients diagnosed with breast cancer", "Clin Cancer Res.", Sep. 1999, pp. 2297-2303, vol. 5, No. 9.

Cheng, Y., et al., "CpG Island Metylator Phenotype Associates with Low-Degree Chromosomal Abnormalities in Colorectal Cancer", "Clinical Cancer Research", Oct. 1, 2008, pp. 6005-6013, vol. 14, No. 19.

Colella, S., et al., "Sensitive and Quantitative Universal Pyrosequencing Methylation Analysis of CpG Sites", "BioTechniques", Jul. 2003, pp. 1-5, vol. 35, No. 1.

Cross, S., et al., "CpG islands and genes", "Current Opinion in Genetics and Development", Jun. 1995, pp. 309-314, vol. 5, No. 3.

Ebert, M., "Aristaless-like Homeobox-4 Gene Methylation Is a Potential Marker for Colorectal Adenocarcinomas", "Gastroenterology", Nov. 2006, pp. 1418-1430, vol. 131, No. 5.

Esteller, M., et al., "Detection of Aberrant Promoter Hypermethylation of Tumor Suppressor Genes in Serum DNA from Non-Small Cell Lung Cancer Patients", "Cancer Research", Jan. 1, 1999, pp. 67-70, vol. 59.

Foltz, G., et al., "DNA Methyltransferase-Mediated Transcriptional Silencing in Malignant Glioma: a Combined Whole-Genome Microarray and Promoter Array Analysis", "Oncogene", May 25, 2009, pp. 2667-2677, vol. 28, No. 29.

Gitan, R., et al., "Methylation-Specific Oligonucleotide Microarray: A New Potential for High-Throughput Methylation Analysis", "Genome Research", Dec. 2001, pp. 158-164, vol. 12.

Goessl, C., et al., "Fluorescent Methylation-specific Polymerase Chain Reaction for DNA-based Detection of Prostate Cancer in Bodily Fluids", "Cancer Research", Nov. 1, 2000, pp. 5941-5945, vol. 60.

Han, I., et al., "New Insights into Syndecan-2 Expression and Tumourigenic Activity in Colon Carcinoma Cells", "Journal of Molecular Histology", Mar. 1, 2004, pp. 319-326, vol. 35, No. 3, Publisher: Kluwer Academic Publishers.

Herman, James G., et al., "Methylation-specific PCR: a novel PCR assay for methylation status of CpG islands", "Proceedings of the National Academy of Sciences", Sep. 1996, pp. 9821-9826, vol. 93.

Hoehn, B., et al., "Abstract 4517: Syndecan-2 methylation is an early detection biomarker for colorectal cancer with high sensitivity and specificity in small serum sample volumes", "Cancer Research", Apr. 15, 2012, p. 4517, vol. 72 (8 Supplement).

"Illumina DNA Methylation Analysis Data Sheet", "Data Sheet: Epigenetics", Apr. 6, 2012, pp. 1-7; (http://www.illumina.com/Documents/products/datasheets/datasheet_dna_methylation_analysis.pdf).

Kopreski, M., et al., "Detection of Tumor Messenger RNA in the Serum of Patients with Malignant Melanoma", "Clinical Cancer Research", Aug. 1999, pp. 1961-1965, vol. 5.

Kristensen, L.S., et al., "PCR-Based Methods for Detecting Single-Locus DNA Methylation Biomarkers in Cancer Diagnostics, Prognostics, and Response to Treatment", "Clinical Chemistry", 2009, pp. 1471-1483, vol. 55, No. 8.

Lin, S.-Y., et al., "Promoter CpG Methylation of Caveolin-1 in Sporadic Colorectal Cancer", "Anticancer Research", 2004, pp. 1645-1650, vol. 24.

Malik, K., et al., "Epigenetic gene deregulation in cancer", "British Journal of Cancer", Dec. 2000, pp. 1583-1588, vol. 83, No. 12.

Masanori, N., et al., "DNA Methylation Abnormality in Colon Cancer", "Molecular Gastrointestinal Medicine", 2008, pp. 364-369, vol. 5, No. 4.

Matsusaka, K., et al., "Classification of Epstein-Barr Virus-Positive Gastric Cancers by Definition of DNA Methylation Epigenotypes", "Cancer Research", Dec. 1, 2011, pp. 7187-7197, vol. 71, No. 23.

Miyamoto, K., et al., "Identification of 20 Genes Aberrantly Methylated in Human Breast Cancers", "International Journal of Cancer", Apr. 7, 2005, pp. 407-414, vol. 116.

Miyashiro, I., et al., "Molecular Strategy for Detecting Metastatic Cancers with Use of Multiple Tumor-specific MAGE-A Genes", "Clinical Chemistry", Mar. 2001, pp. 505-512, vol. 47, No. 3.

Oh, T., et al., "Genome-Wide Identification and Validation of a Novel Methylation Biomarker, SDC2, for Blood-Based Detection of Colorectal Cancer", "The Journal of Molecular Diagnostics", Jul. 2013, pp. 498-507, vol. 15, No. 4.

Palmisano, W., et al., "Predicting Lung Cancer by Detecting Aberrant Promoter Methylation in Sputum", "Cancer Research", Nov. 1, 2000, pp. 5954-5958, vol. 60.

Park, H., et al., "Syndecan-2 Mediates Adhesion and Proliferation of Colon Carcinoma Cells", "The Journal of Biological Chemistry", Aug. 16, 2002, pp. 29730-29736, vol. 277, No. 33.

Robertson, K., et al., "DNA Methylation: past, present and future directions", "Carcinogenesis", Mar. 2000, pp. 461-467, vol. 21, No. 3.

Sanchez-Cespedes, M., et al., "Gene Promoter Hypermethylation in Tumors and Serum of Head and Neck Cancer Patients", "Cancer Research", Feb. 15, 2000, pp. 892-895, vol. 60.

Shen, L., et al., "Methods of DNA Methylation Analysis", "Current Opinion in Clinical Nutrition and Metabolic Care", 2007, pp. 576-581, vol. 10.

Singal, R., et al., "DNA Methylation", "Blood", Jun. 15, 1999, pp. 4059-4070, vol. 93, No. 12.

Sozzi, G., et al., "Detection of Microsatellite Alterations in Plasma DNA of Non-Small Cell Lung Cancer Patients: A Prospect for Early Diagnosis", "Clinical Cancer Research", Oct. 1999, pp. 2689-2692, vol. 5.

Sueoka, E., et al., "Heterogeneous Nuclear Ribonucleoprotein B1 as a New Marker of Early Detection for Human Lung Cancers", "Cancer Research", Apr. 1, 1999, pp. 1404-1407, vol. 59.

Yuji, H., et al., "Over-Methylation of Tumor Suppressor Genes in Colon Cancer", "Yamaguchi Medical Article", 2006, pp. 193-194, vol. 55, No. 6.

Zouridis, H., et al., "Methylation Subtypes and Large-Scale Epigenetic Alterations in Gastric Cancer", "Science Translational Medicine", Oct. 17, 2012, pp. 1-12, vol. 4, No. 156.

Das, P., et al., "DNA Methylation and Cancer", "Journal of Clinical Oncology", Nov. 15, 2004, pp. 4632-4642, vol. 22, No. 22, Publisher: American Society of Clinical Oncology.

* cited by examiner

SEQUENCE LISTING

```
<160> NUMBER OF SEQ ID NOS: 843

<210> SEQ ID NO 1
<211> LENGTH: 820
<212> TYPE: DNA
<213> ORGANISM: Artificial Sequence
<220> FEATURE:
<223> OTHER INFORMATION: SDC2

<400> SEQUENCE: 1
ggagagagga aaagtgggga gagaaaggaa gaaaaggact gagaaaacgc aggagccctg      60
gcttgccggt gagcagagcc ggcgcagcca cagcgcggag ccgcggcgcc cactggtcct     120
cggagctgcc aatcggcgtg taatcctgta ggaatttctc ccgggtttat ctgggagtca     180
cactgccgcc tcctctcccc agtcgcccag gggagcccgg agaagcaggc tcaggaggga     240
gggagccaga ggaaaagaag aggaggagaa ggaggaggac ccggggaggg aggcgcggcg     300
cgggaggagg aggggcgcag ccgcggagcc agtggccccg cttggacgcg ctgctctcca     360
gatacccccg gagctccagc cgcgcggatc gcgcgctccc gccgctctgc ccctaaactt     420
ctgccgtagc tcccttttcaa gccagcgaat ttattcctta aaaccagaaa ctgaacctcg     480
gcacgggaaa ggagtccgcg gaggagcaaa accacagcag agcaagaaga gcttcagaga     540
gcagccttcc cggagcacca actccgtgtc gggagtgcag aaaccaacaa gtgagagggc     600
gccgcgttcc cggggcgcag ctgcgggcgg cgggagcagg cgcaggagga ggaagcgagc     660
gcccccgagc cccgagcccg agtccccgag cctgagccgc aatcgctgcg gtactctgct     720
ccggattcgt gtgcgcgggc tgcgccgagc gctgggcagg aggcttcgtt ttgccctggt     780
tgcaagcagc ggctgggagc agccggtccc tggggaatat                            820

<210> SEQ ID NO 2
<211> LENGTH: 820
<212> TYPE: DNA
<213> ORGANISM: Artificial Sequence
<220> FEATURE:
<223> OTHER INFORMATION: Bisulfite treated SDC2

<400> SEQUENCE: 2
ggagagagga aaagtgggga gagaaaggaa gaaaaggatt gagaaaacgt aggagttttg      60
gtttgtcggt gagtagagtc ggcgtagtta tagcgcggag tcgcggcgtt tattggtttt     120
cggagttgtt aatcggcgtg taattttgta ggattttttt tcgggtttat ttgggagtta     180
tattgtcgtt ttttttttt agtcgtttag gggagttcgg agaagtaggt ttaggaggga     240
gggagttaga ggaaaagaag aggaggagaa ggaggaggat tcggggaggg aggcgcggcg     300
cgggaggagg aggggcgtag tcgcggagtt agtggtttcg tttggacgcg ttgttttta     360 gatattttcg gagttttagt cgcgcggatc gcgcgttttc gtcgttttgt ttttaaattt     420
ttgtcgtagt ttttttttaa gttagcgaat ttattttta aaattagaaa ttgaatttcg     480
gtacgggaaa ggagttcgcg gaggagtaaa attatagtag agtaagaaga gttttagaga     540
gtagtttttt cggagtatta atttcgtgtc gggagtgtag aaattaataa gtgagagggc     600
gtcgcgtttt cggggcgtag ttgcgggcgg cgggagtagg cgtaggagga ggaagcgagc     660
```

```
gttttcgagt tcgagttcg agtttcgag tttgagtcgt aatcgttgcg gtattttgtt    720
tcggattcgt gtgcgcgggt tgcgtcgagc gttgggtagg aggtttcgtt ttgttttggt    780
tgtaagtagc ggttgggagt agtcggtttt tggggaatat                         820
```

<210> SEQ ID NO 3
<211> LENGTH: 14
<212> TYPE: DNA
<213> ORGANISM: Artificial Sequence
<220> FEATURE:
<223> OTHER INFORMATION: Synthetic Construct

<400> SEQUENCE: 3

```
ggagagagga aaag                                                     14
```

<210> SEQ ID NO 4
<211> LENGTH: 14
<212> TYPE: DNA
<213> ORGANISM: Artificial Sequence
<220> FEATURE:
<223> OTHER INFORMATION: Synthetic Construct

<400> SEQUENCE: 4

```
cacgccgatt aaca                                                     14
```

<210> SEQ ID NO 5
<211> LENGTH: 28
<212> TYPE: DNA
<213> ORGANISM: Artificial Sequence
<220> FEATURE:
<223> OTHER INFORMATION: Synthetic Construct

<400> SEQUENCE: 5

```
agtcgcggcg tttattggtt ttcggagt                                      28
```

<210> SEQ ID NO 6
<211> LENGTH: 14
<212> TYPE: DNA
<213> ORGANISM: Artificial Sequence
<220> FEATURE:
<223> OTHER INFORMATION: Synthetic Construct

<400> SEQUENCE: 6

```
gagagaggaa aagt                                                     14
```

<210> SEQ ID NO 7
<211> LENGTH: 14
<212> TYPE: DNA
<213> ORGANISM: Artificial Sequence
<220> FEATURE:
<223> OTHER INFORMATION: Synthetic Construct

<400> SEQUENCE: 7

```
agagaggaaa agtg                                                     14
```

<210> SEQ ID NO 8
<211> LENGTH: 14
<212> TYPE: DNA
<213> ORGANISM: Artificial Sequence
<220> FEATURE:
<223> OTHER INFORMATION: Synthetic Construct

<400> SEQUENCE: 8

```
gagaggaaaa gtgg                                                     14
```

```
<210> SEQ ID NO 9
<211> LENGTH: 14
<212> TYPE: DNA
<213> ORGANISM: Artificial Sequence
<220> FEATURE:
<223> OTHER INFORMATION: Synthetic Construct

<400> SEQUENCE: 9
agaggaaaag tggg                                                      14

<210> SEQ ID NO 10
<211> LENGTH: 14
<212> TYPE: DNA
<213> ORGANISM: Artificial Sequence
<220> FEATURE:
<223> OTHER INFORMATION: Synthetic Construct

<400> SEQUENCE: 10
gaggaaaagt gggg                                                      14

<210> SEQ ID NO 11
<211> LENGTH: 14
<212> TYPE: DNA
<213> ORGANISM: Artificial Sequence
<220> FEATURE:
<223> OTHER INFORMATION: Synthetic Construct

<400> SEQUENCE: 11
aggaaaagtg ggga                                                      14

<210> SEQ ID NO 12
<211> LENGTH: 14
<212> TYPE: DNA
<213> ORGANISM: Artificial Sequence
<220> FEATURE:
<223> OTHER INFORMATION: Synthetic Construct

<400> SEQUENCE: 12
ggaaaagtgg ggag                                                      14

<210> SEQ ID NO 13
<211> LENGTH: 14
<212> TYPE: DNA
<213> ORGANISM: Artificial Sequence
<220> FEATURE:
<223> OTHER INFORMATION: Synthetic Construct

<400> SEQUENCE: 13
gaaaagtggg gaga                                                      14

<210> SEQ ID NO 14
<211> LENGTH: 14
<212> TYPE: DNA
<213> ORGANISM: Artificial Sequence
<220> FEATURE:
<223> OTHER INFORMATION: Synthetic Construct

<400> SEQUENCE: 14
aaaagtgggg agag                                                      14

<210> SEQ ID NO 15
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 15
aaagtgggga gaga                                                         14

<210> SEQ ID NO 16
<211> LENGTH: 14
<212> TYPE: DNA
<213> ORGANISM: Artificial Sequence
<220> FEATURE:
<223> OTHER INFORMATION: Synthetic Construct

<400> SEQUENCE: 16
aagtggggag agaa                                                         14

<210> SEQ ID NO 17
<211> LENGTH: 14
<212> TYPE: DNA
<213> ORGANISM: Artificial Sequence
<220> FEATURE:
<223> OTHER INFORMATION: Synthetic Construct

<400> SEQUENCE: 17
agtggggaga gaaa                                                         14

<210> SEQ ID NO 18
<211> LENGTH: 14
<212> TYPE: DNA
<213> ORGANISM: Artificial Sequence
<220> FEATURE:
<223> OTHER INFORMATION: Synthetic Construct

<400> SEQUENCE: 18
gtggggagag aaag                                                         14

<210> SEQ ID NO 19
<211> LENGTH: 14
<212> TYPE: DNA
<213> ORGANISM: Artificial Sequence
<220> FEATURE:
<223> OTHER INFORMATION: Synthetic Construct

<400> SEQUENCE: 19
tggggagaga aagg                                                         14

<210> SEQ ID NO 20
<211> LENGTH: 14
<212> TYPE: DNA
<213> ORGANISM: Artificial Sequence
<220> FEATURE:
<223> OTHER INFORMATION: Synthetic Construct

<400> SEQUENCE: 20
ggggagagaa agga                                                         14

<210> SEQ ID NO 21
<211> LENGTH: 14
<212> TYPE: DNA
<213> ORGANISM: Artificial Sequence
<220> FEATURE:
<223> OTHER INFORMATION: Synthetic Construct

<400> SEQUENCE: 21
gggagagaaa ggaa                                                         14

<210> SEQ ID NO 22

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 22
ggagagaaag gaag                                                      14

<210> SEQ ID NO 23
<211> LENGTH: 14
<212> TYPE: DNA
<213> ORGANISM: Artificial Sequence
<220> FEATURE:
<223> OTHER INFORMATION: Synthetic Construct

<400> SEQUENCE: 23
gagagaaagg aaga                                                      14

<210> SEQ ID NO 24
<211> LENGTH: 14
<212> TYPE: DNA
<213> ORGANISM: Artificial Sequence
<220> FEATURE:
<223> OTHER INFORMATION: Synthetic Construct

<400> SEQUENCE: 24
agagaaagga agaa                                                      14

<210> SEQ ID NO 25
<211> LENGTH: 14
<212> TYPE: DNA
<213> ORGANISM: Artificial Sequence
<220> FEATURE:
<223> OTHER INFORMATION: Synthetic Construct

<400> SEQUENCE: 25
gagaaaggaa gaaa                                                      14

<210> SEQ ID NO 26
<211> LENGTH: 14
<212> TYPE: DNA
<213> ORGANISM: Artificial Sequence
<220> FEATURE:
<223> OTHER INFORMATION: Synthetic Construct

<400> SEQUENCE: 26
agaaaggaag aaaa                                                      14

<210> SEQ ID NO 27
<211> LENGTH: 14
<212> TYPE: DNA
<213> ORGANISM: Artificial Sequence
<220> FEATURE:
<223> OTHER INFORMATION: Synthetic Construct

<400> SEQUENCE: 27
gaaaggaaga aaag                                                      14

<210> SEQ ID NO 28
<211> LENGTH: 14
<212> TYPE: DNA
<213> ORGANISM: Artificial Sequence
<220> FEATURE:
<223> OTHER INFORMATION: Synthetic Construct

<400> SEQUENCE: 28
```
aaaggaagaa aagg 14

<210> SEQ ID NO 29
<211> LENGTH: 14
<212> TYPE: DNA
<213> ORGANISM: Artificial Sequence
<220> FEATURE:
<223> OTHER INFORMATION: Synthetic Construct

<400> SEQUENCE: 29
aaggaagaaa agga 14

<210> SEQ ID NO 30
<211> LENGTH: 14
<212> TYPE: DNA
<213> ORGANISM: Artificial Sequence
<220> FEATURE:
<223> OTHER INFORMATION: Synthetic Construct

<400> SEQUENCE: 30
aggaagaaaa ggat 14

<210> SEQ ID NO 31
<211> LENGTH: 14
<212> TYPE: DNA
<213> ORGANISM: Artificial Sequence
<220> FEATURE:
<223> OTHER INFORMATION: Synthetic Construct

<400> SEQUENCE: 31
ggaagaaaag gatt 14

<210> SEQ ID NO 32
<211> LENGTH: 14
<212> TYPE: DNA
<213> ORGANISM: Artificial Sequence
<220> FEATURE:
<223> OTHER INFORMATION: Synthetic Construct

<400> SEQUENCE: 32
gaagaaaagg attg 14

<210> SEQ ID NO 33
<211> LENGTH: 14
<212> TYPE: DNA
<213> ORGANISM: Artificial Sequence
<220> FEATURE:
<223> OTHER INFORMATION: Synthetic Construct

<400> SEQUENCE: 33
aagaaaagga ttga 14

<210> SEQ ID NO 34
<211> LENGTH: 14
<212> TYPE: DNA
<213> ORGANISM: Artificial Sequence
<220> FEATURE:
<223> OTHER INFORMATION: Synthetic Construct

<400> SEQUENCE: 34
agaaaaggat tgag 14

<210> SEQ ID NO 35
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 35
gaaaaggatt gaga                                                    14

<210> SEQ ID NO 36
<211> LENGTH: 14
<212> TYPE: DNA
<213> ORGANISM: Artificial Sequence
<220> FEATURE:
<223> OTHER INFORMATION: Synthetic Construct

<400> SEQUENCE: 36
aaaaggattg agaa                                                    14

<210> SEQ ID NO 37
<211> LENGTH: 14
<212> TYPE: DNA
<213> ORGANISM: Artificial Sequence
<220> FEATURE:
<223> OTHER INFORMATION: Synthetic Construct

<400> SEQUENCE: 37
aaaggattga gaaa                                                    14

<210> SEQ ID NO 38
<211> LENGTH: 14
<212> TYPE: DNA
<213> ORGANISM: Artificial Sequence
<220> FEATURE:
<223> OTHER INFORMATION: Synthetic Construct

<400> SEQUENCE: 38
aaggattgag aaaa                                                    14

<210> SEQ ID NO 39
<211> LENGTH: 14
<212> TYPE: DNA
<213> ORGANISM: Artificial Sequence
<220> FEATURE:
<223> OTHER INFORMATION: Synthetic Construct

<400> SEQUENCE: 39
aggattgaga aaac                                                    14

<210> SEQ ID NO 40
<211> LENGTH: 14
<212> TYPE: DNA
<213> ORGANISM: Artificial Sequence
<220> FEATURE:
<223> OTHER INFORMATION: Synthetic Construct

<400> SEQUENCE: 40
ggattgagaa aacg                                                    14

<210> SEQ ID NO 41
<211> LENGTH: 14
<212> TYPE: DNA
<213> ORGANISM: Artificial Sequence
<220> FEATURE:
<223> OTHER INFORMATION: Synthetic Construct

<400> SEQUENCE: 41
gattgagaaa acgt                                                    14
```

<210> SEQ ID NO 42
<211> LENGTH: 14
<212> TYPE: DNA
<213> ORGANISM: Artificial Sequence
<220> FEATURE:
<223> OTHER INFORMATION: Synthetic Construct

<400> SEQUENCE: 42
attgagaaaa cgta                                                        14

<210> SEQ ID NO 43
<211> LENGTH: 14
<212> TYPE: DNA
<213> ORGANISM: Artificial Sequence
<220> FEATURE:
<223> OTHER INFORMATION: Synthetic Construct

<400> SEQUENCE: 43
ttgagaaaac gtag                                                        14

<210> SEQ ID NO 44
<211> LENGTH: 14
<212> TYPE: DNA
<213> ORGANISM: Artificial Sequence
<220> FEATURE:
<223> OTHER INFORMATION: Synthetic Construct

<400> SEQUENCE: 44
tgagaaaacg tagg                                                        14

<210> SEQ ID NO 45
<211> LENGTH: 14
<212> TYPE: DNA
<213> ORGANISM: Artificial Sequence
<220> FEATURE:
<223> OTHER INFORMATION: Synthetic Construct

<400> SEQUENCE: 45
gagaaaacgt agga                                                        14

<210> SEQ ID NO 46
<211> LENGTH: 14
<212> TYPE: DNA
<213> ORGANISM: Artificial Sequence
<220> FEATURE:
<223> OTHER INFORMATION: Synthetic Construct

<400> SEQUENCE: 46
agaaaacgta ggag                                                        14

<210> SEQ ID NO 47
<211> LENGTH: 14
<212> TYPE: DNA
<213> ORGANISM: Artificial Sequence
<220> FEATURE:
<223> OTHER INFORMATION: Synthetic Construct

<400> SEQUENCE: 47
gaaaacgtag gagt                                                        14

<210> SEQ ID NO 48
<211> LENGTH: 14
<212> TYPE: DNA
<213> ORGANISM: Artificial Sequence
<220> FEATURE:

<223> OTHER INFORMATION: Synthetic Construct

<400> SEQUENCE: 48
aaaacgtagg agtt                                                                          14

<210> SEQ ID NO 49
<211> LENGTH: 14
<212> TYPE: DNA
<213> ORGANISM: Artificial Sequence
<220> FEATURE:
<223> OTHER INFORMATION: Synthetic Construct

<400> SEQUENCE: 49
aaacgtagga gttt                                                                          14

<210> SEQ ID NO 50
<211> LENGTH: 14
<212> TYPE: DNA
<213> ORGANISM: Artificial Sequence
<220> FEATURE:
<223> OTHER INFORMATION: Synthetic Construct

<400> SEQUENCE: 50
aacgtaggag tttt                                                                          14

<210> SEQ ID NO 51
<211> LENGTH: 14
<212> TYPE: DNA
<213> ORGANISM: Artificial Sequence
<220> FEATURE:
<223> OTHER INFORMATION: Synthetic Construct

<400> SEQUENCE: 51
acgtaggagt tttg                                                                          14

<210> SEQ ID NO 52
<211> LENGTH: 14
<212> TYPE: DNA
<213> ORGANISM: Artificial Sequence
<220> FEATURE:
<223> OTHER INFORMATION: Synthetic Construct

<400> SEQUENCE: 52
cgtaggagtt ttgg                                                                          14

<210> SEQ ID NO 53
<211> LENGTH: 14
<212> TYPE: DNA
<213> ORGANISM: Artificial Sequence
<220> FEATURE:
<223> OTHER INFORMATION: Synthetic Construct

<400> SEQUENCE: 53
gtaggagttt tggt                                                                          14

<210> SEQ ID NO 54
<211> LENGTH: 14
<212> TYPE: DNA
<213> ORGANISM: Artificial Sequence
<220> FEATURE:
<223> OTHER INFORMATION: Synthetic Construct

<400> SEQUENCE: 54
taggagtttt ggtt                                                                          14

-continued

<210> SEQ ID NO 55
<211> LENGTH: 14
<212> TYPE: DNA
<213> ORGANISM: Artificial Sequence
<220> FEATURE:
<223> OTHER INFORMATION: Synthetic Construct

<400> SEQUENCE: 55
aggagttttg gttt                                                     14

<210> SEQ ID NO 56
<211> LENGTH: 14
<212> TYPE: DNA
<213> ORGANISM: Artificial Sequence
<220> FEATURE:
<223> OTHER INFORMATION: Synthetic Construct

<400> SEQUENCE: 56
ggagttttgg tttg                                                     14

<210> SEQ ID NO 57
<211> LENGTH: 14
<212> TYPE: DNA
<213> ORGANISM: Artificial Sequence
<220> FEATURE:
<223> OTHER INFORMATION: Synthetic Construct

<400> SEQUENCE: 57
gagttttggt tgt                                                      14

<210> SEQ ID NO 58
<211> LENGTH: 14
<212> TYPE: DNA
<213> ORGANISM: Artificial Sequence
<220> FEATURE:
<223> OTHER INFORMATION: Synthetic Construct

<400> SEQUENCE: 58
agttttggtt tgtc                                                     14

<210> SEQ ID NO 59
<211> LENGTH: 14
<212> TYPE: DNA
<213> ORGANISM: Artificial Sequence
<220> FEATURE:
<223> OTHER INFORMATION: Synthetic Construct

<400> SEQUENCE: 59
gttttggttt gtcg                                                     14

<210> SEQ ID NO 60
<211> LENGTH: 14
<212> TYPE: DNA
<213> ORGANISM: Artificial Sequence
<220> FEATURE:
<223> OTHER INFORMATION: Synthetic Construct

<400> SEQUENCE: 60
ttttggtttg tcgg                                                     14

<210> SEQ ID NO 61
<211> LENGTH: 14
<212> TYPE: DNA
<213> ORGANISM: Artificial Sequence
<220> FEATURE:
<223> OTHER INFORMATION: Synthetic Construct

```
<400> SEQUENCE: 61
tttggtttgt cggt                                                        14

<210> SEQ ID NO 62
<211> LENGTH: 14
<212> TYPE: DNA
<213> ORGANISM: Artificial Sequence
<220> FEATURE:
<223> OTHER INFORMATION: Synthetic Construct

<400> SEQUENCE: 62
ttggtttgtc ggtg                                                        14

<210> SEQ ID NO 63
<211> LENGTH: 14
<212> TYPE: DNA
<213> ORGANISM: Artificial Sequence
<220> FEATURE:
<223> OTHER INFORMATION: Synthetic Construct

<400> SEQUENCE: 63
tggtttgtcg gtga                                                        14

<210> SEQ ID NO 64
<211> LENGTH: 14
<212> TYPE: DNA
<213> ORGANISM: Artificial Sequence
<220> FEATURE:
<223> OTHER INFORMATION: Synthetic Construct

<400> SEQUENCE: 64
ggtttgtcgg tgag                                                        14

<210> SEQ ID NO 65
<211> LENGTH: 14
<212> TYPE: DNA
<213> ORGANISM: Artificial Sequence
<220> FEATURE:
<223> OTHER INFORMATION: Synthetic Construct

<400> SEQUENCE: 65
gtttgtcggt gagt                                                        14

<210> SEQ ID NO 66
<211> LENGTH: 14
<212> TYPE: DNA
<213> ORGANISM: Artificial Sequence
<220> FEATURE:
<223> OTHER INFORMATION: Synthetic Construct

<400> SEQUENCE: 66
tttgtcggtg agta                                                        14

<210> SEQ ID NO 67
<211> LENGTH: 14
<212> TYPE: DNA
<213> ORGANISM: Artificial Sequence
<220> FEATURE:
<223> OTHER INFORMATION: Synthetic Construct

<400> SEQUENCE: 67
aataaacccg aaaa                                                        14

<210> SEQ ID NO 68
<211> LENGTH: 24
```

<212> TYPE: DNA
<213> ORGANISM: Artificial Sequence
<220> FEATURE:
<223> OTHER INFORMATION: Synthetic Construct

<400> SEQUENCE: 68
cggcgtgtaa ttttgtagga attt                                            24

<210> SEQ ID NO 69
<211> LENGTH: 14
<212> TYPE: DNA
<213> ORGANISM: Artificial Sequence
<220> FEATURE:
<223> OTHER INFORMATION: Synthetic Construct

<400> SEQUENCE: 69
ttgtcggtga gtag                                                       14

<210> SEQ ID NO 70
<211> LENGTH: 14
<212> TYPE: DNA
<213> ORGANISM: Artificial Sequence
<220> FEATURE:
<223> OTHER INFORMATION: Synthetic Construct

<400> SEQUENCE: 70
tgtcggtgag taga                                                       14

<210> SEQ ID NO 71
<211> LENGTH: 14
<212> TYPE: DNA
<213> ORGANISM: Artificial Sequence
<220> FEATURE:
<223> OTHER INFORMATION: Synthetic Construct

<400> SEQUENCE: 71
gtcggtgagt agag                                                       14

<210> SEQ ID NO 72
<211> LENGTH: 14
<212> TYPE: DNA
<213> ORGANISM: Artificial Sequence
<220> FEATURE:
<223> OTHER INFORMATION: Synthetic Construct

<400> SEQUENCE: 72
tcggtgagta gagt                                                       14

<210> SEQ ID NO 73
<211> LENGTH: 14
<212> TYPE: DNA
<213> ORGANISM: Artificial Sequence
<220> FEATURE:
<223> OTHER INFORMATION: Synthetic Construct

<400> SEQUENCE: 73
cggtgagtag agtc                                                       14

<210> SEQ ID NO 74
<211> LENGTH: 14
<212> TYPE: DNA
<213> ORGANISM: Artificial Sequence
<220> FEATURE:
<223> OTHER INFORMATION: Synthetic Construct

<400> SEQUENCE: 74
ggtgagtaga gtcg                                    14

<210> SEQ ID NO 75
<211> LENGTH: 14
<212> TYPE: DNA
<213> ORGANISM: Artificial Sequence
<220> FEATURE:
<223> OTHER INFORMATION: Synthetic Construct

<400> SEQUENCE: 75
gtgagtagag tcgg                                    14

<210> SEQ ID NO 76
<211> LENGTH: 14
<212> TYPE: DNA
<213> ORGANISM: Artificial Sequence
<220> FEATURE:
<223> OTHER INFORMATION: Synthetic Construct

<400> SEQUENCE: 76
tgagtagagt cggc                                    14

<210> SEQ ID NO 77
<211> LENGTH: 14
<212> TYPE: DNA
<213> ORGANISM: Artificial Sequence
<220> FEATURE:
<223> OTHER INFORMATION: Synthetic Construct

<400> SEQUENCE: 77
gagtagagtc ggcg                                    14

<210> SEQ ID NO 78
<211> LENGTH: 14
<212> TYPE: DNA
<213> ORGANISM: Artificial Sequence
<220> FEATURE:
<223> OTHER INFORMATION: Synthetic Construct

<400> SEQUENCE: 78
agtagagtcg gcgt                                    14

<210> SEQ ID NO 79
<211> LENGTH: 14
<212> TYPE: DNA
<213> ORGANISM: Artificial Sequence
<220> FEATURE:
<223> OTHER INFORMATION: Synthetic Construct

<400> SEQUENCE: 79
gtagagtcgg cgta                                    14

<210> SEQ ID NO 80
<211> LENGTH: 14
<212> TYPE: DNA
<213> ORGANISM: Artificial Sequence
<220> FEATURE:
<223> OTHER INFORMATION: Synthetic Construct

<400> SEQUENCE: 80
tagagtcggc gtag                                    14

<210> SEQ ID NO 81
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 81
agagtcggcg tagt                                                         14

<210> SEQ ID NO 82
<211> LENGTH: 14
<212> TYPE: DNA
<213> ORGANISM: Artificial Sequence
<220> FEATURE:
<223> OTHER INFORMATION: Synthetic Construct

<400> SEQUENCE: 82
gagtcggcgt agtt                                                         14

<210> SEQ ID NO 83
<211> LENGTH: 14
<212> TYPE: DNA
<213> ORGANISM: Artificial Sequence
<220> FEATURE:
<223> OTHER INFORMATION: Synthetic Construct

<400> SEQUENCE: 83
agtcggcgta gtta                                                         14

<210> SEQ ID NO 84
<211> LENGTH: 14
<212> TYPE: DNA
<213> ORGANISM: Artificial Sequence
<220> FEATURE:
<223> OTHER INFORMATION: Synthetic Construct

<400> SEQUENCE: 84
gtcggcgtag ttat                                                         14

<210> SEQ ID NO 85
<211> LENGTH: 14
<212> TYPE: DNA
<213> ORGANISM: Artificial Sequence
<220> FEATURE:
<223> OTHER INFORMATION: Synthetic Construct

<400> SEQUENCE: 85
tcggcgtagt tata                                                         14

<210> SEQ ID NO 86
<211> LENGTH: 14
<212> TYPE: DNA
<213> ORGANISM: Artificial Sequence
<220> FEATURE:
<223> OTHER INFORMATION: Synthetic Construct

<400> SEQUENCE: 86
cggcgtagtt atag                                                         14

<210> SEQ ID NO 87
<211> LENGTH: 14
<212> TYPE: DNA
<213> ORGANISM: Artificial Sequence
<220> FEATURE:
<223> OTHER INFORMATION: Synthetic Construct

<400> SEQUENCE: 87
ggcgtagtta tagc                                                         14
```

<210> SEQ ID NO 88
<211> LENGTH: 14
<212> TYPE: DNA
<213> ORGANISM: Artificial Sequence
<220> FEATURE:
<223> OTHER INFORMATION: Synthetic Construct

<400> SEQUENCE: 88
gcgtagttat agcg                                                         14

<210> SEQ ID NO 89
<211> LENGTH: 14
<212> TYPE: DNA
<213> ORGANISM: Artificial Sequence
<220> FEATURE:
<223> OTHER INFORMATION: Synthetic Construct

<400> SEQUENCE: 89
cgtagttata gcgc                                                         14

<210> SEQ ID NO 90
<211> LENGTH: 14
<212> TYPE: DNA
<213> ORGANISM: Artificial Sequence
<220> FEATURE:
<223> OTHER INFORMATION: Synthetic Construct

<400> SEQUENCE: 90
gtagttatag cgcg                                                         14

<210> SEQ ID NO 91
<211> LENGTH: 14
<212> TYPE: DNA
<213> ORGANISM: Artificial Sequence
<220> FEATURE:
<223> OTHER INFORMATION: Synthetic Construct

<400> SEQUENCE: 91
tagttatagc gcgg                                                         14

<210> SEQ ID NO 92
<211> LENGTH: 14
<212> TYPE: DNA
<213> ORGANISM: Artificial Sequence
<220> FEATURE:
<223> OTHER INFORMATION: Synthetic Construct

<400> SEQUENCE: 92
agttatagcg cgga                                                         14

<210> SEQ ID NO 93
<211> LENGTH: 14
<212> TYPE: DNA
<213> ORGANISM: Artificial Sequence
<220> FEATURE:
<223> OTHER INFORMATION: Synthetic Construct

<400> SEQUENCE: 93
gttatagcgc ggag                                                         14

<210> SEQ ID NO 94
<211> LENGTH: 14
<212> TYPE: DNA
<213> ORGANISM: Artificial Sequence
<220> FEATURE:
<223> OTHER INFORMATION: Synthetic Construct

```
<400> SEQUENCE: 94
ttatagcgcg gagt                                                    14

<210> SEQ ID NO 95
<211> LENGTH: 14
<212> TYPE: DNA
<213> ORGANISM: Artificial Sequence
<220> FEATURE:
<223> OTHER INFORMATION: Synthetic Construct

<400> SEQUENCE: 95
tatagcgcgg agtc                                                    14

<210> SEQ ID NO 96
<211> LENGTH: 14
<212> TYPE: DNA
<213> ORGANISM: Artificial Sequence
<220> FEATURE:
<223> OTHER INFORMATION: Synthetic Construct

<400> SEQUENCE: 96
atagcgcgga gtcg                                                    14

<210> SEQ ID NO 97
<211> LENGTH: 14
<212> TYPE: DNA
<213> ORGANISM: Artificial Sequence
<220> FEATURE:
<223> OTHER INFORMATION: Synthetic Construct

<400> SEQUENCE: 97
tagcgcggag tcgc                                                    14

<210> SEQ ID NO 98
<211> LENGTH: 14
<212> TYPE: DNA
<213> ORGANISM: Artificial Sequence
<220> FEATURE:
<223> OTHER INFORMATION: Synthetic Construct

<400> SEQUENCE: 98
agcgcggagt cgcg                                                    14

<210> SEQ ID NO 99
<211> LENGTH: 14
<212> TYPE: DNA
<213> ORGANISM: Artificial Sequence
<220> FEATURE:
<223> OTHER INFORMATION: Synthetic Construct

<400> SEQUENCE: 99
gcgcggagtc gcgg                                                    14

<210> SEQ ID NO 100
<211> LENGTH: 14
<212> TYPE: DNA
<213> ORGANISM: Artificial Sequence
<220> FEATURE:
<223> OTHER INFORMATION: Synthetic Construct

<400> SEQUENCE: 100
ctccgaactc ccct                                                    14

<210> SEQ ID NO 101
```

```
<211> LENGTH: 22
<212> TYPE: DNA
<213> ORGANISM: Artificial Sequence
<220> FEATURE:
<223> OTHER INFORMATION: Synthetic Construct

<400> SEQUENCE: 101
cgtttttttt ttttagtcgt tt                                              22

<210> SEQ ID NO 102
<211> LENGTH: 14
<212> TYPE: DNA
<213> ORGANISM: Artificial Sequence
<220> FEATURE:
<223> OTHER INFORMATION: Synthetic Construct

<400> SEQUENCE: 102
cgcggagtcg cggc                                                       14

<210> SEQ ID NO 103
<211> LENGTH: 14
<212> TYPE: DNA
<213> ORGANISM: Artificial Sequence
<220> FEATURE:
<223> OTHER INFORMATION: Synthetic Construct

<400> SEQUENCE: 103
gcggagtcgc ggcg                                                       14

<210> SEQ ID NO 104
<211> LENGTH: 14
<212> TYPE: DNA
<213> ORGANISM: Artificial Sequence
<220> FEATURE:
<223> OTHER INFORMATION: Synthetic Construct

<400> SEQUENCE: 104
cggagtcgcg gcgt                                                       14

<210> SEQ ID NO 105
<211> LENGTH: 14
<212> TYPE: DNA
<213> ORGANISM: Artificial Sequence
<220> FEATURE:
<223> OTHER INFORMATION: Synthetic Construct

<400> SEQUENCE: 105
ggagtcgcgg cgtt                                                       14

<210> SEQ ID NO 106
<211> LENGTH: 14
<212> TYPE: DNA
<213> ORGANISM: Artificial Sequence
<220> FEATURE:
<223> OTHER INFORMATION: Synthetic Construct

<400> SEQUENCE: 106
gagtcgcggc gttt                                                       14

<210> SEQ ID NO 107
<211> LENGTH: 14
<212> TYPE: DNA
<213> ORGANISM: Artificial Sequence
<220> FEATURE:
<223> OTHER INFORMATION: Synthetic Construct

<400> SEQUENCE: 107
```
agtcgcggcg ttta                                            14

<210> SEQ ID NO 108
<211> LENGTH: 14
<212> TYPE: DNA
<213> ORGANISM: Artificial Sequence
<220> FEATURE:
<223> OTHER INFORMATION: Synthetic Construct

<400> SEQUENCE: 108
gtcgcggcgt ttat                                            14

<210> SEQ ID NO 109
<211> LENGTH: 14
<212> TYPE: DNA
<213> ORGANISM: Artificial Sequence
<220> FEATURE:
<223> OTHER INFORMATION: Synthetic Construct

<400> SEQUENCE: 109
tcgcggcgtt tatt                                            14

<210> SEQ ID NO 110
<211> LENGTH: 14
<212> TYPE: DNA
<213> ORGANISM: Artificial Sequence
<220> FEATURE:
<223> OTHER INFORMATION: Synthetic Construct

<400> SEQUENCE: 110
cgcggcgttt attg                                            14

<210> SEQ ID NO 111
<211> LENGTH: 14
<212> TYPE: DNA
<213> ORGANISM: Artificial Sequence
<220> FEATURE:
<223> OTHER INFORMATION: Synthetic Construct

<400> SEQUENCE: 111
gcggcgttta ttgg                                            14

<210> SEQ ID NO 112
<211> LENGTH: 14
<212> TYPE: DNA
<213> ORGANISM: Artificial Sequence
<220> FEATURE:
<223> OTHER INFORMATION: Synthetic Construct

<400> SEQUENCE: 112
cggcgtttat tggt                                            14

<210> SEQ ID NO 113
<211> LENGTH: 14
<212> TYPE: DNA
<213> ORGANISM: Artificial Sequence
<220> FEATURE:
<223> OTHER INFORMATION: Synthetic Construct

<400> SEQUENCE: 113
ggcgtttatt ggtt                                            14

<210> SEQ ID NO 114
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 114
gcgtttattg gttt                                                        14

<210> SEQ ID NO 115
<211> LENGTH: 14
<212> TYPE: DNA
<213> ORGANISM: Artificial Sequence
<220> FEATURE:
<223> OTHER INFORMATION: Synthetic Construct

<400> SEQUENCE: 115
cgtttattgg tttt                                                        14

<210> SEQ ID NO 116
<211> LENGTH: 14
<212> TYPE: DNA
<213> ORGANISM: Artificial Sequence
<220> FEATURE:
<223> OTHER INFORMATION: Synthetic Construct

<400> SEQUENCE: 116
gtttattggt tttc                                                        14

<210> SEQ ID NO 117
<211> LENGTH: 14
<212> TYPE: DNA
<213> ORGANISM: Artificial Sequence
<220> FEATURE:
<223> OTHER INFORMATION: Synthetic Construct

<400> SEQUENCE: 117
tttattggtt ttcg                                                        14

<210> SEQ ID NO 118
<211> LENGTH: 14
<212> TYPE: DNA
<213> ORGANISM: Artificial Sequence
<220> FEATURE:
<223> OTHER INFORMATION: Synthetic Construct

<400> SEQUENCE: 118
ttattggttt tcgg                                                        14

<210> SEQ ID NO 119
<211> LENGTH: 14
<212> TYPE: DNA
<213> ORGANISM: Artificial Sequence
<220> FEATURE:
<223> OTHER INFORMATION: Synthetic Construct

<400> SEQUENCE: 119
tattggtttt cgga                                                        14

<210> SEQ ID NO 120
<211> LENGTH: 14
<212> TYPE: DNA
<213> ORGANISM: Artificial Sequence
<220> FEATURE:
<223> OTHER INFORMATION: Synthetic Construct

<400> SEQUENCE: 120
attggttttc ggag                                                        14
```

<210> SEQ ID NO 121
<211> LENGTH: 14
<212> TYPE: DNA
<213> ORGANISM: Artificial Sequence
<220> FEATURE:
<223> OTHER INFORMATION: Synthetic Construct

<400> SEQUENCE: 121
ttggttttcg gagt                                                            14

<210> SEQ ID NO 122
<211> LENGTH: 14
<212> TYPE: DNA
<213> ORGANISM: Artificial Sequence
<220> FEATURE:
<223> OTHER INFORMATION: Synthetic Construct

<400> SEQUENCE: 122
tggttttcgg agtt                                                            14

<210> SEQ ID NO 123
<211> LENGTH: 14
<212> TYPE: DNA
<213> ORGANISM: Artificial Sequence
<220> FEATURE:
<223> OTHER INFORMATION: Synthetic Construct

<400> SEQUENCE: 123
ggttttcgga gttg                                                            14

<210> SEQ ID NO 124
<211> LENGTH: 14
<212> TYPE: DNA
<213> ORGANISM: Artificial Sequence
<220> FEATURE:
<223> OTHER INFORMATION: Synthetic Construct

<400> SEQUENCE: 124
gttttcggag ttgt                                                            14

<210> SEQ ID NO 125
<211> LENGTH: 14
<212> TYPE: DNA
<213> ORGANISM: Artificial Sequence
<220> FEATURE:
<223> OTHER INFORMATION: Synthetic Construct

<400> SEQUENCE: 125
ttttcggagt tgtt                                                            14

<210> SEQ ID NO 126
<211> LENGTH: 14
<212> TYPE: DNA
<213> ORGANISM: Artificial Sequence
<220> FEATURE:
<223> OTHER INFORMATION: Synthetic Construct

<400> SEQUENCE: 126
tttcggagtt gtta                                                            14

<210> SEQ ID NO 127
<211> LENGTH: 14
<212> TYPE: DNA
<213> ORGANISM: Artificial Sequence
<220> FEATURE:

<223> OTHER INFORMATION: Synthetic Construct

<400> SEQUENCE: 127
ttcggagttg ttaa                                                         14

<210> SEQ ID NO 128
<211> LENGTH: 14
<212> TYPE: DNA
<213> ORGANISM: Artificial Sequence
<220> FEATURE:
<223> OTHER INFORMATION: Synthetic Construct

<400> SEQUENCE: 128
tcggagttgt taat                                                         14

<210> SEQ ID NO 129
<211> LENGTH: 14
<212> TYPE: DNA
<213> ORGANISM: Artificial Sequence
<220> FEATURE:
<223> OTHER INFORMATION: Synthetic Construct

<400> SEQUENCE: 129
cggagttgtt aatc                                                         14

<210> SEQ ID NO 130
<211> LENGTH: 14
<212> TYPE: DNA
<213> ORGANISM: Artificial Sequence
<220> FEATURE:
<223> OTHER INFORMATION: Synthetic Construct

<400> SEQUENCE: 130
ggagttgtta atcg                                                         14

<210> SEQ ID NO 131
<211> LENGTH: 14
<212> TYPE: DNA
<213> ORGANISM: Artificial Sequence
<220> FEATURE:
<223> OTHER INFORMATION: Synthetic Construct

<400> SEQUENCE: 131
gagttgttaa tcgg                                                         14

<210> SEQ ID NO 132
<211> LENGTH: 14
<212> TYPE: DNA
<213> ORGANISM: Artificial Sequence
<220> FEATURE:
<223> OTHER INFORMATION: Synthetic Construct

<400> SEQUENCE: 132
agttgttaat cggc                                                         14

<210> SEQ ID NO 133
<211> LENGTH: 14
<212> TYPE: DNA
<213> ORGANISM: Artificial Sequence
<220> FEATURE:
<223> OTHER INFORMATION: Synthetic Construct

<400> SEQUENCE: 133
gttgttaatc ggcg                                                         14

```
<210> SEQ ID NO 134
<211> LENGTH: 14
<212> TYPE: DNA
<213> ORGANISM: Artificial Sequence
<220> FEATURE:
<223> OTHER INFORMATION: Synthetic Construct

<400> SEQUENCE: 134
ttgttaatcg gcgt                                                         14

<210> SEQ ID NO 135
<211> LENGTH: 14
<212> TYPE: DNA
<213> ORGANISM: Artificial Sequence
<220> FEATURE:
<223> OTHER INFORMATION: Synthetic Construct

<400> SEQUENCE: 135
tgttaatcgg cgtg                                                         14

<210> SEQ ID NO 136
<211> LENGTH: 14
<212> TYPE: DNA
<213> ORGANISM: Artificial Sequence
<220> FEATURE:
<223> OTHER INFORMATION: Synthetic Construct

<400> SEQUENCE: 136
gttaatcggc gtgt                                                         14

<210> SEQ ID NO 137
<211> LENGTH: 14
<212> TYPE: DNA
<213> ORGANISM: Artificial Sequence
<220> FEATURE:
<223> OTHER INFORMATION: Synthetic Construct

<400> SEQUENCE: 137
ttaatcggcg tgta                                                         14

<210> SEQ ID NO 138
<211> LENGTH: 14
<212> TYPE: DNA
<213> ORGANISM: Artificial Sequence
<220> FEATURE:
<223> OTHER INFORMATION: Synthetic Construct

<400> SEQUENCE: 138
taatcggcgt gtaa                                                         14

<210> SEQ ID NO 139
<211> LENGTH: 14
<212> TYPE: DNA
<213> ORGANISM: Artificial Sequence
<220> FEATURE:
<223> OTHER INFORMATION: Synthetic Construct

<400> SEQUENCE: 139
aatcggcgtg taat                                                         14

<210> SEQ ID NO 140
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 140
atcggcgtgt aatt                                                           14

<210> SEQ ID NO 141
<211> LENGTH: 14
<212> TYPE: DNA
<213> ORGANISM: Artificial Sequence
<220> FEATURE:
<223> OTHER INFORMATION: Synthetic Construct

<400> SEQUENCE: 141
tcggcgtgta attt                                                           14

<210> SEQ ID NO 142
<211> LENGTH: 14
<212> TYPE: DNA
<213> ORGANISM: Artificial Sequence
<220> FEATURE:
<223> OTHER INFORMATION: Synthetic Construct

<400> SEQUENCE: 142
cggcgtgtaa tttt                                                           14

<210> SEQ ID NO 143
<211> LENGTH: 14
<212> TYPE: DNA
<213> ORGANISM: Artificial Sequence
<220> FEATURE:
<223> OTHER INFORMATION: Synthetic Construct

<400> SEQUENCE: 143
ggcgtgtaat tttg                                                           14

<210> SEQ ID NO 144
<211> LENGTH: 14
<212> TYPE: DNA
<213> ORGANISM: Artificial Sequence
<220> FEATURE:
<223> OTHER INFORMATION: Synthetic Construct

<400> SEQUENCE: 144
gcgtgtaatt ttgt                                                           14

<210> SEQ ID NO 145
<211> LENGTH: 14
<212> TYPE: DNA
<213> ORGANISM: Artificial Sequence
<220> FEATURE:
<223> OTHER INFORMATION: Synthetic Construct

<400> SEQUENCE: 145
cgtgtaattt tgta                                                           14

<210> SEQ ID NO 146
<211> LENGTH: 14
<212> TYPE: DNA
<213> ORGANISM: Artificial Sequence
<220> FEATURE:
<223> OTHER INFORMATION: Synthetic Construct

<400> SEQUENCE: 146
gtgtaatttt gtag                                                           14

<210> SEQ ID NO 147
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 147
tgtaattttg tagg                                                       14

<210> SEQ ID NO 148
<211> LENGTH: 14
<212> TYPE: DNA
<213> ORGANISM: Artificial Sequence
<220> FEATURE:
<223> OTHER INFORMATION: Synthetic Construct

<400> SEQUENCE: 148
gtaattttgt agga                                                       14

<210> SEQ ID NO 149
<211> LENGTH: 14
<212> TYPE: DNA
<213> ORGANISM: Artificial Sequence
<220> FEATURE:
<223> OTHER INFORMATION: Synthetic Construct

<400> SEQUENCE: 149
taattttgta ggaa                                                       14

<210> SEQ ID NO 150
<211> LENGTH: 14
<212> TYPE: DNA
<213> ORGANISM: Artificial Sequence
<220> FEATURE:
<223> OTHER INFORMATION: Synthetic Construct

<400> SEQUENCE: 150
aattttgtag gaat                                                       14

<210> SEQ ID NO 151
<211> LENGTH: 14
<212> TYPE: DNA
<213> ORGANISM: Artificial Sequence
<220> FEATURE:
<223> OTHER INFORMATION: Synthetic Construct

<400> SEQUENCE: 151
attttgtagg aatt                                                       14

<210> SEQ ID NO 152
<211> LENGTH: 14
<212> TYPE: DNA
<213> ORGANISM: Artificial Sequence
<220> FEATURE:
<223> OTHER INFORMATION: Synthetic Construct

<400> SEQUENCE: 152
ttttgtagga attt                                                       14

<210> SEQ ID NO 153
<211> LENGTH: 14
<212> TYPE: DNA
<213> ORGANISM: Artificial Sequence
<220> FEATURE:
<223> OTHER INFORMATION: Synthetic Construct

<400> SEQUENCE: 153
```
cgaatcctcc tcct                                                       14

<210> SEQ ID NO 154
<211> LENGTH: 24
<212> TYPE: DNA
<213> ORGANISM: Artificial Sequence
<220> FEATURE:
<223> OTHER INFORMATION: Synthetic Construct

<400> SEQUENCE: 154
ttagaggaaa agaagaggag gaga                                            24

<210> SEQ ID NO 155
<211> LENGTH: 14
<212> TYPE: DNA
<213> ORGANISM: Artificial Sequence
<220> FEATURE:
<223> OTHER INFORMATION: Synthetic Construct

<400> SEQUENCE: 155
tttgtaggaa tttt                                                       14

<210> SEQ ID NO 156
<211> LENGTH: 14
<212> TYPE: DNA
<213> ORGANISM: Artificial Sequence
<220> FEATURE:
<223> OTHER INFORMATION: Synthetic Construct

<400> SEQUENCE: 156
ttgtaggaat tttt                                                       14

<210> SEQ ID NO 157
<211> LENGTH: 14
<212> TYPE: DNA
<213> ORGANISM: Artificial Sequence
<220> FEATURE:
<223> OTHER INFORMATION: Synthetic Construct

<400> SEQUENCE: 157
tgtaggaatt tttt                                                       14

<210> SEQ ID NO 158
<211> LENGTH: 14
<212> TYPE: DNA
<213> ORGANISM: Artificial Sequence
<220> FEATURE:
<223> OTHER INFORMATION: Synthetic Construct

<400> SEQUENCE: 158
gtaggaattt tttt                                                       14

<210> SEQ ID NO 159
<211> LENGTH: 14
<212> TYPE: DNA
<213> ORGANISM: Artificial Sequence
<220> FEATURE:
<223> OTHER INFORMATION: Synthetic Construct

<400> SEQUENCE: 159
taggaatttt tttc                                                       14

<210> SEQ ID NO 160
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 160
aggaattttt ttcg                                                          14

<210> SEQ ID NO 161
<211> LENGTH: 14
<212> TYPE: DNA
<213> ORGANISM: Artificial Sequence
<220> FEATURE:
<223> OTHER INFORMATION: Synthetic Construct

<400> SEQUENCE: 161
ggaatttttt tcgg                                                          14

<210> SEQ ID NO 162
<211> LENGTH: 14
<212> TYPE: DNA
<213> ORGANISM: Artificial Sequence
<220> FEATURE:
<223> OTHER INFORMATION: Synthetic Construct

<400> SEQUENCE: 162
gaattttttt cggg                                                          14

<210> SEQ ID NO 163
<211> LENGTH: 14
<212> TYPE: DNA
<213> ORGANISM: Artificial Sequence
<220> FEATURE:
<223> OTHER INFORMATION: Synthetic Construct

<400> SEQUENCE: 163 aattttttc gggt                                                           14

<210> SEQ ID NO 164
<211> LENGTH: 14
<212> TYPE: DNA
<213> ORGANISM: Artificial Sequence
<220> FEATURE:
<223> OTHER INFORMATION: Synthetic Construct

<400> SEQUENCE: 164 attttttcg ggtt                                                           14

<210> SEQ ID NO 165
<211> LENGTH: 14
<212> TYPE: DNA
<213> ORGANISM: Artificial Sequence
<220> FEATURE:
<223> OTHER INFORMATION: Synthetic Construct

<400> SEQUENCE: 165 ttttttcgg gttt                                                           14

<210> SEQ ID NO 166
<211> LENGTH: 14
<212> TYPE: DNA
<213> ORGANISM: Artificial Sequence
<220> FEATURE:
<223> OTHER INFORMATION: Synthetic Construct

<400> SEQUENCE: 166 tttttcggg ttta                                                           14
```

```
<210> SEQ ID NO 167
<211> LENGTH: 14
<212> TYPE: DNA
<213> ORGANISM: Artificial Sequence
<220> FEATURE:
<223> OTHER INFORMATION: Synthetic Construct

<400> SEQUENCE: 167
tttttcgggt ttat                                                    14

<210> SEQ ID NO 168
<211> LENGTH: 14
<212> TYPE: DNA
<213> ORGANISM: Artificial Sequence
<220> FEATURE:
<223> OTHER INFORMATION: Synthetic Construct

<400> SEQUENCE: 168
ttttcgggtt tatt                                                    14

<210> SEQ ID NO 169
<211> LENGTH: 14
<212> TYPE: DNA
<213> ORGANISM: Artificial Sequence
<220> FEATURE:
<223> OTHER INFORMATION: Synthetic Construct

<400> SEQUENCE: 169
tttcgggttt attt                                                    14

<210> SEQ ID NO 170
<211> LENGTH: 14
<212> TYPE: DNA
<213> ORGANISM: Artificial Sequence
<220> FEATURE:
<223> OTHER INFORMATION: Synthetic Construct

<400> SEQUENCE: 170
ttcgggttta tttg                                                    14

<210> SEQ ID NO 171
<211> LENGTH: 14
<212> TYPE: DNA
<213> ORGANISM: Artificial Sequence
<220> FEATURE:
<223> OTHER INFORMATION: Synthetic Construct

<400> SEQUENCE: 171
tcgggtttat ttgg                                                    14

<210> SEQ ID NO 172
<211> LENGTH: 14
<212> TYPE: DNA
<213> ORGANISM: Artificial Sequence
<220> FEATURE:
<223> OTHER INFORMATION: Synthetic Construct

<400> SEQUENCE: 172
cgggtttatt tggg                                                    14

<210> SEQ ID NO 173
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 173
gggtttattt ggga                                                  14

<210> SEQ ID NO 174
<211> LENGTH: 14
<212> TYPE: DNA
<213> ORGANISM: Artificial Sequence
<220> FEATURE:
<223> OTHER INFORMATION: Synthetic Construct

<400> SEQUENCE: 174
ggtttatttg ggag                                                  14

<210> SEQ ID NO 175
<211> LENGTH: 14
<212> TYPE: DNA
<213> ORGANISM: Artificial Sequence
<220> FEATURE:
<223> OTHER INFORMATION: Synthetic Construct

<400> SEQUENCE: 175
gtttatttgg gagt                                                  14

<210> SEQ ID NO 176
<211> LENGTH: 14
<212> TYPE: DNA
<213> ORGANISM: Artificial Sequence
<220> FEATURE:
<223> OTHER INFORMATION: Synthetic Construct

<400> SEQUENCE: 176
tttatttggg agtt                                                  14

<210> SEQ ID NO 177
<211> LENGTH: 14
<212> TYPE: DNA
<213> ORGANISM: Artificial Sequence
<220> FEATURE:
<223> OTHER INFORMATION: Synthetic Construct

<400> SEQUENCE: 177
ttatttggga gtta                                                  14

<210> SEQ ID NO 178
<211> LENGTH: 14
<212> TYPE: DNA
<213> ORGANISM: Artificial Sequence
<220> FEATURE:
<223> OTHER INFORMATION: Synthetic Construct

<400> SEQUENCE: 178
tatttgggag ttat                                                  14

<210> SEQ ID NO 179
<211> LENGTH: 14
<212> TYPE: DNA
<213> ORGANISM: Artificial Sequence
<220> FEATURE:
<223> OTHER INFORMATION: Synthetic Construct

<400> SEQUENCE: 179
atttgggagt tata                                                  14

<210> SEQ ID NO 180
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 180
tttgggagtt atat                                                    14

<210> SEQ ID NO 181
<211> LENGTH: 14
<212> TYPE: DNA
<213> ORGANISM: Artificial Sequence
<220> FEATURE:
<223> OTHER INFORMATION: Synthetic Construct

<400> SEQUENCE: 181
ttgggagtta tatt                                                    14

<210> SEQ ID NO 182
<211> LENGTH: 14
<212> TYPE: DNA
<213> ORGANISM: Artificial Sequence
<220> FEATURE:
<223> OTHER INFORMATION: Synthetic Construct

<400> SEQUENCE: 182
tgggagttat attg                                                    14

<210> SEQ ID NO 183
<211> LENGTH: 14
<212> TYPE: DNA
<213> ORGANISM: Artificial Sequence
<220> FEATURE:
<223> OTHER INFORMATION: Synthetic Construct

<400> SEQUENCE: 183
gggagttata ttgt                                                    14

<210> SEQ ID NO 184
<211> LENGTH: 14
<212> TYPE: DNA
<213> ORGANISM: Artificial Sequence
<220> FEATURE:
<223> OTHER INFORMATION: Synthetic Construct

<400> SEQUENCE: 184
ggagttatat tgtc                                                    14

<210> SEQ ID NO 185
<211> LENGTH: 14
<212> TYPE: DNA
<213> ORGANISM: Artificial Sequence
<220> FEATURE:
<223> OTHER INFORMATION: Synthetic Construct

<400> SEQUENCE: 185
gagttatatt gtcg                                                    14

<210> SEQ ID NO 186
<211> LENGTH: 14
<212> TYPE: DNA
<213> ORGANISM: Artificial Sequence
<220> FEATURE:
<223> OTHER INFORMATION: Synthetic Construct

<400> SEQUENCE: 186
```
agttatattg tcgt    14

<210> SEQ ID NO 187
<211> LENGTH: 14
<212> TYPE: DNA
<213> ORGANISM: Artificial Sequence
<220> FEATURE:
<223> OTHER INFORMATION: Synthetic Construct

<400> SEQUENCE: 187
gttatattgt cgtt    14

<210> SEQ ID NO 188
<211> LENGTH: 14
<212> TYPE: DNA
<213> ORGANISM: Artificial Sequence
<220> FEATURE:
<223> OTHER INFORMATION: Synthetic Construct

<400> SEQUENCE: 188
ttatattgtc gttt    14

<210> SEQ ID NO 189
<211> LENGTH: 14
<212> TYPE: DNA
<213> ORGANISM: Artificial Sequence
<220> FEATURE:
<223> OTHER INFORMATION: Synthetic Construct

<400> SEQUENCE: 189
tatattgtcg tttt    14

<210> SEQ ID NO 190
<211> LENGTH: 14
<212> TYPE: DNA
<213> ORGANISM: Artificial Sequence
<220> FEATURE:
<223> OTHER INFORMATION: Synthetic Construct

<400> SEQUENCE: 190
atattgtcgt tttt    14

<210> SEQ ID NO 191
<211> LENGTH: 14
<212> TYPE: DNA
<213> ORGANISM: Artificial Sequence
<220> FEATURE:
<223> OTHER INFORMATION: Synthetic Construct

<400> SEQUENCE: 191
tattgtcgtt tttt    14

<210> SEQ ID NO 192
<211> LENGTH: 14
<212> TYPE: DNA
<213> ORGANISM: Artificial Sequence
<220> FEATURE:
<223> OTHER INFORMATION: Synthetic Construct

<400> SEQUENCE: 192
attgtcgttt tttt    14

<210> SEQ ID NO 193
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 193
ttgtcgtttt tttt                                                        14

<210> SEQ ID NO 194
<211> LENGTH: 14
<212> TYPE: DNA
<213> ORGANISM: Artificial Sequence
<220> FEATURE:
<223> OTHER INFORMATION: Synthetic Construct

<400> SEQUENCE: 194
tgtcgttttt tttt                                                        14

<210> SEQ ID NO 195
<211> LENGTH: 14
<212> TYPE: DNA
<213> ORGANISM: Artificial Sequence
<220> FEATURE:
<223> OTHER INFORMATION: Synthetic Construct

<400> SEQUENCE: 195
gtcgtttttt tttt                                                        14

<210> SEQ ID NO 196
<211> LENGTH: 14
<212> TYPE: DNA
<213> ORGANISM: Artificial Sequence
<220> FEATURE:
<223> OTHER INFORMATION: Synthetic Construct

<400> SEQUENCE: 196
tcgttttttt tttt                                                        14

<210> SEQ ID NO 197
<211> LENGTH: 14
<212> TYPE: DNA
<213> ORGANISM: Artificial Sequence
<220> FEATURE:
<223> OTHER INFORMATION: Synthetic Construct

<400> SEQUENCE: 197
cgtttttttt tttt                                                        14

<210> SEQ ID NO 198
<211> LENGTH: 14
<212> TYPE: DNA
<213> ORGANISM: Artificial Sequence
<220> FEATURE:
<223> OTHER INFORMATION: Synthetic Construct

<400> SEQUENCE: 198
gttttttttt ttta                                                        14

<210> SEQ ID NO 199
<211> LENGTH: 14
<212> TYPE: DNA
<213> ORGANISM: Artificial Sequence
<220> FEATURE:
<223> OTHER INFORMATION: Synthetic Construct

<400> SEQUENCE: 199
tttttttttt ttag                                                        14
```

<210> SEQ ID NO 200
<211> LENGTH: 14
<212> TYPE: DNA
<213> ORGANISM: Artificial Sequence
<220> FEATURE:
<223> OTHER INFORMATION: Synthetic Construct

<400> SEQUENCE: 200
tttttttttt tagt                                                         14

<210> SEQ ID NO 201
<211> LENGTH: 14
<212> TYPE: DNA
<213> ORGANISM: Artificial Sequence
<220> FEATURE:
<223> OTHER INFORMATION: Synthetic Construct

<400> SEQUENCE: 201 ttttttttt agtc                                                          14

<210> SEQ ID NO 202
<211> LENGTH: 14
<212> TYPE: DNA
<213> ORGANISM: Artificial Sequence
<220> FEATURE:
<223> OTHER INFORMATION: Synthetic Construct

<400> SEQUENCE: 202 tttttttta gtcg                                                          14

<210> SEQ ID NO 203
<211> LENGTH: 14
<212> TYPE: DNA
<213> ORGANISM: Artificial Sequence
<220> FEATURE:
<223> OTHER INFORMATION: Synthetic Construct

<400> SEQUENCE: 203
ttttttttag tcgt                                                         14

<210> SEQ ID NO 204
<211> LENGTH: 14
<212> TYPE: DNA
<213> ORGANISM: Artificial Sequence
<220> FEATURE:
<223> OTHER INFORMATION: Synthetic Construct

<400> SEQUENCE: 204
tttttttagt cgtt                                                         14

<210> SEQ ID NO 205
<211> LENGTH: 14
<212> TYPE: DNA
<213> ORGANISM: Artificial Sequence
<220> FEATURE:
<223> OTHER INFORMATION: Synthetic Construct

<400> SEQUENCE: 205
ttttttagtc gttt                                                         14

<210> SEQ ID NO 206
<211> LENGTH: 14
<212> TYPE: DNA
<213> ORGANISM: Artificial Sequence
<220> FEATURE:

```
<223> OTHER INFORMATION: Synthetic Construct

<400> SEQUENCE: 206
tttttagtcg ttta                                                        14

<210> SEQ ID NO 207
<211> LENGTH: 14
<212> TYPE: DNA
<213> ORGANISM: Artificial Sequence
<220> FEATURE:
<223> OTHER INFORMATION: Synthetic Construct

<400> SEQUENCE: 207
ttttagtcgt ttag                                                        14

<210> SEQ ID NO 208
<211> LENGTH: 14
<212> TYPE: DNA
<213> ORGANISM: Artificial Sequence
<220> FEATURE:
<223> OTHER INFORMATION: Synthetic Construct

<400> SEQUENCE: 208
tttagtcgtt tagg                                                        14

<210> SEQ ID NO 209
<211> LENGTH: 14
<212> TYPE: DNA
<213> ORGANISM: Artificial Sequence
<220> FEATURE:
<223> OTHER INFORMATION: Synthetic Construct

<400> SEQUENCE: 209
ttagtcgttt aggg                                                        14

<210> SEQ ID NO 210
<211> LENGTH: 14
<212> TYPE: DNA
<213> ORGANISM: Artificial Sequence
<220> FEATURE:
<223> OTHER INFORMATION: Synthetic Construct

<400> SEQUENCE: 210
tagtcgttta gggg                                                        14

<210> SEQ ID NO 211
<211> LENGTH: 14
<212> TYPE: DNA
<213> ORGANISM: Artificial Sequence
<220> FEATURE:
<223> OTHER INFORMATION: Synthetic Construct

<400> SEQUENCE: 211
agtcgtttag ggga                                                        14

<210> SEQ ID NO 212
<211> LENGTH: 14
<212> TYPE: DNA
<213> ORGANISM: Artificial Sequence
<220> FEATURE:
<223> OTHER INFORMATION: Synthetic Construct

<400> SEQUENCE: 212
gtcgtttagg ggag                                                        14
```

```
<210> SEQ ID NO 213
<211> LENGTH: 14
<212> TYPE: DNA
<213> ORGANISM: Artificial Sequence
<220> FEATURE:
<223> OTHER INFORMATION: Synthetic Construct

<400> SEQUENCE: 213
tcgtttaggg gagt                                                         14

<210> SEQ ID NO 214
<211> LENGTH: 14
<212> TYPE: DNA
<213> ORGANISM: Artificial Sequence
<220> FEATURE:
<223> OTHER INFORMATION: Synthetic Construct

<400> SEQUENCE: 214
cgtttagggg agtt                                                         14

<210> SEQ ID NO 215
<211> LENGTH: 14
<212> TYPE: DNA
<213> ORGANISM: Artificial Sequence
<220> FEATURE:
<223> OTHER INFORMATION: Synthetic Construct

<400> SEQUENCE: 215
gtttagggga gttc                                                         14

<210> SEQ ID NO 216
<211> LENGTH: 14
<212> TYPE: DNA
<213> ORGANISM: Artificial Sequence
<220> FEATURE:
<223> OTHER INFORMATION: Synthetic Construct

<400> SEQUENCE: 216
caaacgaaac cact                                                         14

<210> SEQ ID NO 217
<211> LENGTH: 20
<212> TYPE: DNA
<213> ORGANISM: Artificial Sequence
<220> FEATURE:
<223> OTHER INFORMATION: Synthetic Construct

<400> SEQUENCE: 217
aggggcgtag tcgcggagtt                                                   20

<210> SEQ ID NO 218
<211> LENGTH: 14
<212> TYPE: DNA
<213> ORGANISM: Artificial Sequence
<220> FEATURE:
<223> OTHER INFORMATION: Synthetic Construct

<400> SEQUENCE: 218
tttaggggag ttcg                                                         14

<210> SEQ ID NO 219
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 219
ttaggggagt tcgg                                                    14

<210> SEQ ID NO 220
<211> LENGTH: 14
<212> TYPE: DNA
<213> ORGANISM: Artificial Sequence
<220> FEATURE:
<223> OTHER INFORMATION: Synthetic Construct

<400> SEQUENCE: 220 tagggagtt cgga                                                     14

<210> SEQ ID NO 221
<211> LENGTH: 14
<212> TYPE: DNA
<213> ORGANISM: Artificial Sequence
<220> FEATURE:
<223> OTHER INFORMATION: Synthetic Construct

<400> SEQUENCE: 221
aggggagttc ggag                                                    14

<210> SEQ ID NO 222
<211> LENGTH: 14
<212> TYPE: DNA
<213> ORGANISM: Artificial Sequence
<220> FEATURE:
<223> OTHER INFORMATION: Synthetic Construct

<400> SEQUENCE: 222
ggggagttcg gaga                                                    14

<210> SEQ ID NO 223
<211> LENGTH: 14
<212> TYPE: DNA
<213> ORGANISM: Artificial Sequence
<220> FEATURE:
<223> OTHER INFORMATION: Synthetic Construct

<400> SEQUENCE: 223
gggagttcgg agaa                                                    14

<210> SEQ ID NO 224
<211> LENGTH: 14
<212> TYPE: DNA
<213> ORGANISM: Artificial Sequence
<220> FEATURE:
<223> OTHER INFORMATION: Synthetic Construct

<400> SEQUENCE: 224
ggagttcgga gaag                                                    14

<210> SEQ ID NO 225
<211> LENGTH: 14
<212> TYPE: DNA
<213> ORGANISM: Artificial Sequence
<220> FEATURE:
<223> OTHER INFORMATION: Synthetic Construct

<400> SEQUENCE: 225
gagttcggag aagt                                                    14

<210> SEQ ID NO 226
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 226
agttcggaga agta                                                     14

<210> SEQ ID NO 227
<211> LENGTH: 14
<212> TYPE: DNA
<213> ORGANISM: Artificial Sequence
<220> FEATURE:
<223> OTHER INFORMATION: Synthetic Construct

<400> SEQUENCE: 227
gttcggagaa gtag                                                     14

<210> SEQ ID NO 228
<211> LENGTH: 14
<212> TYPE: DNA
<213> ORGANISM: Artificial Sequence
<220> FEATURE:
<223> OTHER INFORMATION: Synthetic Construct

<400> SEQUENCE: 228
ttcggagaag tagg                                                     14

<210> SEQ ID NO 229
<211> LENGTH: 14
<212> TYPE: DNA
<213> ORGANISM: Artificial Sequence
<220> FEATURE:
<223> OTHER INFORMATION: Synthetic Construct

<400> SEQUENCE: 229
tcggagaagt aggt                                                     14

<210> SEQ ID NO 230
<211> LENGTH: 14
<212> TYPE: DNA
<213> ORGANISM: Artificial Sequence
<220> FEATURE:
<223> OTHER INFORMATION: Synthetic Construct

<400> SEQUENCE: 230
cggagaagta ggtt                                                     14

<210> SEQ ID NO 231
<211> LENGTH: 14
<212> TYPE: DNA
<213> ORGANISM: Artificial Sequence
<220> FEATURE:
<223> OTHER INFORMATION: Synthetic Construct

<400> SEQUENCE: 231
ggagaagtag gttt                                                     14

<210> SEQ ID NO 232
<211> LENGTH: 14
<212> TYPE: DNA
<213> ORGANISM: Artificial Sequence
<220> FEATURE:
<223> OTHER INFORMATION: Synthetic Construct

<400> SEQUENCE: 232
```
gagaagtagg ttta 14

<210> SEQ ID NO 233
<211> LENGTH: 14
<212> TYPE: DNA
<213> ORGANISM: Artificial Sequence
<220> FEATURE:
<223> OTHER INFORMATION: Synthetic Construct

<400> SEQUENCE: 233
agaagtaggt ttag 14

<210> SEQ ID NO 234
<211> LENGTH: 14
<212> TYPE: DNA
<213> ORGANISM: Artificial Sequence
<220> FEATURE:
<223> OTHER INFORMATION: Synthetic Construct

<400> SEQUENCE: 234
gaagtaggtt tagg 14

<210> SEQ ID NO 235
<211> LENGTH: 14
<212> TYPE: DNA
<213> ORGANISM: Artificial Sequence
<220> FEATURE:
<223> OTHER INFORMATION: Synthetic Construct

<400> SEQUENCE: 235
aagtaggttt agga 14

<210> SEQ ID NO 236
<211> LENGTH: 14
<212> TYPE: DNA
<213> ORGANISM: Artificial Sequence
<220> FEATURE:
<223> OTHER INFORMATION: Synthetic Construct

<400> SEQUENCE: 236
agtaggttta ggag 14

<210> SEQ ID NO 237
<211> LENGTH: 14
<212> TYPE: DNA
<213> ORGANISM: Artificial Sequence
<220> FEATURE:
<223> OTHER INFORMATION: Synthetic Construct

<400> SEQUENCE: 237
gtaggtttag gagg 14

<210> SEQ ID NO 238
<211> LENGTH: 14
<212> TYPE: DNA
<213> ORGANISM: Artificial Sequence
<220> FEATURE:
<223> OTHER INFORMATION: Synthetic Construct

<400> SEQUENCE: 238
taggtttagg aggg 14

<210> SEQ ID NO 239
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 239
aggtttagga ggga                                              14

<210> SEQ ID NO 240
<211> LENGTH: 14
<212> TYPE: DNA
<213> ORGANISM: Artificial Sequence
<220> FEATURE:
<223> OTHER INFORMATION: Synthetic Construct

<400> SEQUENCE: 240
ggtttaggag ggag                                              14

<210> SEQ ID NO 241
<211> LENGTH: 14
<212> TYPE: DNA
<213> ORGANISM: Artificial Sequence
<220> FEATURE:
<223> OTHER INFORMATION: Synthetic Construct

<400> SEQUENCE: 241
gtttaggagg gagg                                              14

<210> SEQ ID NO 242
<211> LENGTH: 14
<212> TYPE: DNA
<213> ORGANISM: Artificial Sequence
<220> FEATURE:
<223> OTHER INFORMATION: Synthetic Construct

<400> SEQUENCE: 242
tttaggaggg aggg                                              14

<210> SEQ ID NO 243
<211> LENGTH: 14
<212> TYPE: DNA
<213> ORGANISM: Artificial Sequence
<220> FEATURE:
<223> OTHER INFORMATION: Synthetic Construct

<400> SEQUENCE: 243
ttaggaggga ggga                                              14

<210> SEQ ID NO 244
<211> LENGTH: 14
<212> TYPE: DNA
<213> ORGANISM: Artificial Sequence
<220> FEATURE:
<223> OTHER INFORMATION: Synthetic Construct

<400> SEQUENCE: 244
taggagggag ggag                                              14

<210> SEQ ID NO 245
<211> LENGTH: 14
<212> TYPE: DNA
<213> ORGANISM: Artificial Sequence
<220> FEATURE:
<223> OTHER INFORMATION: Synthetic Construct

<400> SEQUENCE: 245
aggagggagg gagt                                              14
```

```
<210> SEQ ID NO 246
<211> LENGTH: 14
<212> TYPE: DNA
<213> ORGANISM: Artificial Sequence
<220> FEATURE:
<223> OTHER INFORMATION: Synthetic Construct

<400> SEQUENCE: 246
ggagggaggg agtt                                                       14

<210> SEQ ID NO 247
<211> LENGTH: 14
<212> TYPE: DNA
<213> ORGANISM: Artificial Sequence
<220> FEATURE:
<223> OTHER INFORMATION: Synthetic Construct

<400> SEQUENCE: 247
gagggaggga gtta                                                       14

<210> SEQ ID NO 248
<211> LENGTH: 14
<212> TYPE: DNA
<213> ORGANISM: Artificial Sequence
<220> FEATURE:
<223> OTHER INFORMATION: Synthetic Construct

<400> SEQUENCE: 248
agggagggag ttag                                                       14

<210> SEQ ID NO 249
<211> LENGTH: 14
<212> TYPE: DNA
<213> ORGANISM: Artificial Sequence
<220> FEATURE:
<223> OTHER INFORMATION: Synthetic Construct

<400> SEQUENCE: 249
gggagggagt taga                                                       14

<210> SEQ ID NO 250
<211> LENGTH: 14
<212> TYPE: DNA
<213> ORGANISM: Artificial Sequence
<220> FEATURE:
<223> OTHER INFORMATION: Synthetic Construct

<400> SEQUENCE: 250
ggagggagtt agag                                                       14

<210> SEQ ID NO 251
<211> LENGTH: 14
<212> TYPE: DNA
<213> ORGANISM: Artificial Sequence
<220> FEATURE:
<223> OTHER INFORMATION: Synthetic Construct

<400> SEQUENCE: 251
gagggagtta gagg                                                       14

<210> SEQ ID NO 252
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 252
agggagttag agga                                                         14

<210> SEQ ID NO 253
<211> LENGTH: 14
<212> TYPE: DNA
<213> ORGANISM: Artificial Sequence
<220> FEATURE:
<223> OTHER INFORMATION: Synthetic Construct

<400> SEQUENCE: 253
gggagttaga ggaa                                                         14

<210> SEQ ID NO 254
<211> LENGTH: 14
<212> TYPE: DNA
<213> ORGANISM: Artificial Sequence
<220> FEATURE:
<223> OTHER INFORMATION: Synthetic Construct

<400> SEQUENCE: 254
ggagttagag gaaa                                                         14

<210> SEQ ID NO 255
<211> LENGTH: 14
<212> TYPE: DNA
<213> ORGANISM: Artificial Sequence
<220> FEATURE:
<223> OTHER INFORMATION: Synthetic Construct

<400> SEQUENCE: 255
gagttagagg aaaa                                                         14

<210> SEQ ID NO 256
<211> LENGTH: 14
<212> TYPE: DNA
<213> ORGANISM: Artificial Sequence
<220> FEATURE:
<223> OTHER INFORMATION: Synthetic Construct

<400> SEQUENCE: 256
agttagagga aaag                                                         14

<210> SEQ ID NO 257
<211> LENGTH: 14
<212> TYPE: DNA
<213> ORGANISM: Artificial Sequence
<220> FEATURE:
<223> OTHER INFORMATION: Synthetic Construct

<400> SEQUENCE: 257
gttagaggaa aaga                                                         14

<210> SEQ ID NO 258
<211> LENGTH: 14
<212> TYPE: DNA
<213> ORGANISM: Artificial Sequence
<220> FEATURE:
<223> OTHER INFORMATION: Synthetic Construct

<400> SEQUENCE: 258
ttagaggaaa agaa                                                         14

<210> SEQ ID NO 259

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 259
tagaggaaaa gaag                                                       14

<210> SEQ ID NO 260
<211> LENGTH: 14
<212> TYPE: DNA
<213> ORGANISM: Artificial Sequence
<220> FEATURE:
<223> OTHER INFORMATION: Synthetic Construct

<400> SEQUENCE: 260
agaggaaaag aaga                                                       14

<210> SEQ ID NO 261
<211> LENGTH: 14
<212> TYPE: DNA
<213> ORGANISM: Artificial Sequence
<220> FEATURE:
<223> OTHER INFORMATION: Synthetic Construct

<400> SEQUENCE: 261
gaggaaaaga agag                                                       14

<210> SEQ ID NO 262
<211> LENGTH: 14
<212> TYPE: DNA
<213> ORGANISM: Artificial Sequence
<220> FEATURE:
<223> OTHER INFORMATION: Synthetic Construct

<400> SEQUENCE: 262
aggaaaagaa gagg                                                       14

<210> SEQ ID NO 263
<211> LENGTH: 14
<212> TYPE: DNA
<213> ORGANISM: Artificial Sequence
<220> FEATURE:
<223> OTHER INFORMATION: Synthetic Construct

<400> SEQUENCE: 263
ggaaaagaag agga                                                       14

<210> SEQ ID NO 264
<211> LENGTH: 14
<212> TYPE: DNA
<213> ORGANISM: Artificial Sequence
<220> FEATURE:
<223> OTHER INFORMATION: Synthetic Construct

<400> SEQUENCE: 264
gaaaagaaga ggag                                                       14

<210> SEQ ID NO 265
<211> LENGTH: 14
<212> TYPE: DNA
<213> ORGANISM: Artificial Sequence
<220> FEATURE:
<223> OTHER INFORMATION: Synthetic Construct

<400> SEQUENCE: 265
```
aaaagaagag gagg 14

<210> SEQ ID NO 266
<211> LENGTH: 14
<212> TYPE: DNA
<213> ORGANISM: Artificial Sequence
<220> FEATURE:
<223> OTHER INFORMATION: Synthetic Construct

<400> SEQUENCE: 266
aaagaagagg agga 14

<210> SEQ ID NO 267
<211> LENGTH: 14
<212> TYPE: DNA
<213> ORGANISM: Artificial Sequence
<220> FEATURE:
<223> OTHER INFORMATION: Synthetic Construct

<400> SEQUENCE: 267
aagaagagga ggag 14

<210> SEQ ID NO 268
<211> LENGTH: 14
<212> TYPE: DNA
<213> ORGANISM: Artificial Sequence
<220> FEATURE:
<223> OTHER INFORMATION: Synthetic Construct

<400> SEQUENCE: 268
agaagaggag gaga 14

<210> SEQ ID NO 269
<211> LENGTH: 14
<212> TYPE: DNA
<213> ORGANISM: Artificial Sequence
<220> FEATURE:
<223> OTHER INFORMATION: Synthetic Construct

<400> SEQUENCE: 269
gaagaggagg agaa 14

<210> SEQ ID NO 270
<211> LENGTH: 14
<212> TYPE: DNA
<213> ORGANISM: Artificial Sequence
<220> FEATURE:
<223> OTHER INFORMATION: Synthetic Construct

<400> SEQUENCE: 270
aagaggagga gaag 14

<210> SEQ ID NO 271
<211> LENGTH: 14
<212> TYPE: DNA
<213> ORGANISM: Artificial Sequence
<220> FEATURE:
<223> OTHER INFORMATION: Synthetic Construct

<400> SEQUENCE: 271
agaggaggag aagg 14

<210> SEQ ID NO 272
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 272
gaggaggaga agga                                                        14

<210> SEQ ID NO 273
<211> LENGTH: 14
<212> TYPE: DNA
<213> ORGANISM: Artificial Sequence
<220> FEATURE:
<223> OTHER INFORMATION: Synthetic Construct

<400> SEQUENCE: 273
aggaggagaa ggag                                                        14

<210> SEQ ID NO 274
<211> LENGTH: 14
<212> TYPE: DNA
<213> ORGANISM: Artificial Sequence
<220> FEATURE:
<223> OTHER INFORMATION: Synthetic Construct

<400> SEQUENCE: 274
ggaggagaag gagg                                                        14

<210> SEQ ID NO 275
<211> LENGTH: 14
<212> TYPE: DNA
<213> ORGANISM: Artificial Sequence
<220> FEATURE:
<223> OTHER INFORMATION: Synthetic Construct

<400> SEQUENCE: 275
gaggagaagg agga                                                        14

<210> SEQ ID NO 276
<211> LENGTH: 14
<212> TYPE: DNA
<213> ORGANISM: Artificial Sequence
<220> FEATURE:
<223> OTHER INFORMATION: Synthetic Construct

<400> SEQUENCE: 276
aggagaagga ggag                                                        14

<210> SEQ ID NO 277
<211> LENGTH: 14
<212> TYPE: DNA
<213> ORGANISM: Artificial Sequence
<220> FEATURE:
<223> OTHER INFORMATION: Synthetic Construct

<400> SEQUENCE: 277
ggagaaggag gagg                                                        14

<210> SEQ ID NO 278
<211> LENGTH: 14
<212> TYPE: DNA
<213> ORGANISM: Artificial Sequence
<220> FEATURE:
<223> OTHER INFORMATION: Synthetic Construct

<400> SEQUENCE: 278
gagaaggagg agga                                                        14
```

```
<210> SEQ ID NO 279
<211> LENGTH: 14
<212> TYPE: DNA
<213> ORGANISM: Artificial Sequence
<220> FEATURE:
<223> OTHER INFORMATION: Synthetic Construct

<400> SEQUENCE: 279
acgacgaaaa cgcg                                                         14

<210> SEQ ID NO 280
<211> LENGTH: 23
<212> TYPE: DNA
<213> ORGANISM: Artificial Sequence
<220> FEATURE:
<223> OTHER INFORMATION: Synthetic Construct

<400> SEQUENCE: 280
cggagtttta gtcgcgcgga tcg                                               23

<210> SEQ ID NO 281
<211> LENGTH: 14
<212> TYPE: DNA
<213> ORGANISM: Artificial Sequence
<220> FEATURE:
<223> OTHER INFORMATION: Synthetic Construct

<400> SEQUENCE: 281
agaaggagga ggat                                                         14

<210> SEQ ID NO 282
<211> LENGTH: 14
<212> TYPE: DNA
<213> ORGANISM: Artificial Sequence
<220> FEATURE:
<223> OTHER INFORMATION: Synthetic Construct

<400> SEQUENCE: 282
gaaggaggag gatt                                                         14

<210> SEQ ID NO 283
<211> LENGTH: 14
<212> TYPE: DNA
<213> ORGANISM: Artificial Sequence
<220> FEATURE:
<223> OTHER INFORMATION: Synthetic Construct

<400> SEQUENCE: 283
aaggaggagg attc                                                         14

<210> SEQ ID NO 284
<211> LENGTH: 14
<212> TYPE: DNA
<213> ORGANISM: Artificial Sequence
<220> FEATURE:
<223> OTHER INFORMATION: Synthetic Construct

<400> SEQUENCE: 284
aggaggagga ttcg                                                         14

<210> SEQ ID NO 285
<211> LENGTH: 14
<212> TYPE: DNA
<213> ORGANISM: Artificial Sequence
<220> FEATURE:
```

<223> OTHER INFORMATION: Synthetic Construct

<400> SEQUENCE: 285
ggaggaggat tcgg                                                          14

<210> SEQ ID NO 286
<211> LENGTH: 14
<212> TYPE: DNA
<213> ORGANISM: Artificial Sequence
<220> FEATURE:
<223> OTHER INFORMATION: Synthetic Construct

<400> SEQUENCE: 286
gaggaggatt cggg                                                          14

<210> SEQ ID NO 287
<211> LENGTH: 14
<212> TYPE: DNA
<213> ORGANISM: Artificial Sequence
<220> FEATURE:
<223> OTHER INFORMATION: Synthetic Construct

<400> SEQUENCE: 287
aggaggattc gggg                                                          14

<210> SEQ ID NO 288
<211> LENGTH: 14
<212> TYPE: DNA
<213> ORGANISM: Artificial Sequence
<220> FEATURE:
<223> OTHER INFORMATION: Synthetic Construct

<400> SEQUENCE: 288
ggaggattcg ggga                                                          14

<210> SEQ ID NO 289
<211> LENGTH: 14
<212> TYPE: DNA
<213> ORGANISM: Artificial Sequence
<220> FEATURE:
<223> OTHER INFORMATION: Synthetic Construct

<400> SEQUENCE: 289
gaggattcgg ggag                                                          14

<210> SEQ ID NO 290
<211> LENGTH: 14
<212> TYPE: DNA
<213> ORGANISM: Artificial Sequence
<220> FEATURE:
<223> OTHER INFORMATION: Synthetic Construct

<400> SEQUENCE: 290
aggattcggg gagg                                                          14

<210> SEQ ID NO 291
<211> LENGTH: 14
<212> TYPE: DNA
<213> ORGANISM: Artificial Sequence
<220> FEATURE:
<223> OTHER INFORMATION: Synthetic Construct

<400> SEQUENCE: 291
ggattcgggg aggg                                                          14

```
<210> SEQ ID NO 292
<211> LENGTH: 14
<212> TYPE: DNA
<213> ORGANISM: Artificial Sequence
<220> FEATURE:
<223> OTHER INFORMATION: Synthetic Construct

<400> SEQUENCE: 292
gattcgggga ggga                                                       14

<210> SEQ ID NO 293
<211> LENGTH: 14
<212> TYPE: DNA
<213> ORGANISM: Artificial Sequence
<220> FEATURE:
<223> OTHER INFORMATION: Synthetic Construct

<400> SEQUENCE: 293
attcggggag ggag                                                       14

<210> SEQ ID NO 294
<211> LENGTH: 14
<212> TYPE: DNA
<213> ORGANISM: Artificial Sequence
<220> FEATURE:
<223> OTHER INFORMATION: Synthetic Construct

<400> SEQUENCE: 294
ttcggggagg gagg                                                       14

<210> SEQ ID NO 295
<211> LENGTH: 14
<212> TYPE: DNA
<213> ORGANISM: Artificial Sequence
<220> FEATURE:
<223> OTHER INFORMATION: Synthetic Construct

<400> SEQUENCE: 295
tcggggaggg aggc                                                       14

<210> SEQ ID NO 296
<211> LENGTH: 14
<212> TYPE: DNA
<213> ORGANISM: Artificial Sequence
<220> FEATURE:
<223> OTHER INFORMATION: Synthetic Construct

<400> SEQUENCE: 296
cggggaggga ggcg                                                       14

<210> SEQ ID NO 297
<211> LENGTH: 14
<212> TYPE: DNA
<213> ORGANISM: Artificial Sequence
<220> FEATURE:
<223> OTHER INFORMATION: Synthetic Construct

<400> SEQUENCE: 297
ggggagggag gcgc                                                       14

<210> SEQ ID NO 298
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 298
gggagggagg cgcg                                            14

<210> SEQ ID NO 299
<211> LENGTH: 14
<212> TYPE: DNA
<213> ORGANISM: Artificial Sequence
<220> FEATURE:
<223> OTHER INFORMATION: Synthetic Construct

<400> SEQUENCE: 299
ggagggaggc gcgg                                            14

<210> SEQ ID NO 300
<211> LENGTH: 14
<212> TYPE: DNA
<213> ORGANISM: Artificial Sequence
<220> FEATURE:
<223> OTHER INFORMATION: Synthetic Construct

<400> SEQUENCE: 300
gagggaggcg cggc                                            14

<210> SEQ ID NO 301
<211> LENGTH: 14
<212> TYPE: DNA
<213> ORGANISM: Artificial Sequence
<220> FEATURE:
<223> OTHER INFORMATION: Synthetic Construct

<400> SEQUENCE: 301
agggaggcgc ggcg                                            14

<210> SEQ ID NO 302
<211> LENGTH: 14
<212> TYPE: DNA
<213> ORGANISM: Artificial Sequence
<220> FEATURE:
<223> OTHER INFORMATION: Synthetic Construct

<400> SEQUENCE: 302
gggaggcgcg gcgc                                            14

<210> SEQ ID NO 303
<211> LENGTH: 14
<212> TYPE: DNA
<213> ORGANISM: Artificial Sequence
<220> FEATURE:
<223> OTHER INFORMATION: Synthetic Construct

<400> SEQUENCE: 303
ggaggcgcgg cgcg                                            14

<210> SEQ ID NO 304
<211> LENGTH: 14
<212> TYPE: DNA
<213> ORGANISM: Artificial Sequence
<220> FEATURE:
<223> OTHER INFORMATION: Synthetic Construct

<400> SEQUENCE: 304
gaggcgcggc gcgg                                            14

<210> SEQ ID NO 305
<211> LENGTH: 14

```
<212> TYPE: DNA
<213> ORGANISM: Artificial Sequence
<220> FEATURE:
<223> OTHER INFORMATION: Synthetic Construct

<400> SEQUENCE: 305
aggcgcggcg cggg                                                      14

<210> SEQ ID NO 306
<211> LENGTH: 14
<212> TYPE: DNA
<213> ORGANISM: Artificial Sequence
<220> FEATURE:
<223> OTHER INFORMATION: Synthetic Construct

<400> SEQUENCE: 306
ggcgcggcgc ggga                                                      14

<210> SEQ ID NO 307
<211> LENGTH: 14
<212> TYPE: DNA
<213> ORGANISM: Artificial Sequence
<220> FEATURE:
<223> OTHER INFORMATION: Synthetic Construct

<400> SEQUENCE: 307
gcgcggcgcg ggag                                                      14

<210> SEQ ID NO 308
<211> LENGTH: 14
<212> TYPE: DNA
<213> ORGANISM: Artificial Sequence
<220> FEATURE:
<223> OTHER INFORMATION: Synthetic Construct

<400> SEQUENCE: 308
cgcggcgcgg gagg                                                      14

<210> SEQ ID NO 309
<211> LENGTH: 14
<212> TYPE: DNA
<213> ORGANISM: Artificial Sequence
<220> FEATURE:
<223> OTHER INFORMATION: Synthetic Construct

<400> SEQUENCE: 309
gcggcgcggg agga                                                      14

<210> SEQ ID NO 310
<211> LENGTH: 14
<212> TYPE: DNA
<213> ORGANISM: Artificial Sequence
<220> FEATURE:
<223> OTHER INFORMATION: Synthetic Construct

<400> SEQUENCE: 310
cggcgcggga ggag                                                      14

<210> SEQ ID NO 311
<211> LENGTH: 14
<212> TYPE: DNA
<213> ORGANISM: Artificial Sequence
<220> FEATURE:
<223> OTHER INFORMATION: Synthetic Construct

<400> SEQUENCE: 311
```
ggcgcgggag gagg                                                  14

<210> SEQ ID NO 312
<211> LENGTH: 14
<212> TYPE: DNA
<213> ORGANISM: Artificial Sequence
<220> FEATURE:
<223> OTHER INFORMATION: Synthetic Construct

<400> SEQUENCE: 312
gcgcgggagg agga                                                  14

<210> SEQ ID NO 313
<211> LENGTH: 14
<212> TYPE: DNA
<213> ORGANISM: Artificial Sequence
<220> FEATURE:
<223> OTHER INFORMATION: Synthetic Construct

<400> SEQUENCE: 313
cgcgggagga ggag                                                  14

<210> SEQ ID NO 314
<211> LENGTH: 14
<212> TYPE: DNA
<213> ORGANISM: Artificial Sequence
<220> FEATURE:
<223> OTHER INFORMATION: Synthetic Construct

<400> SEQUENCE: 314
gcgggaggag gagg                                                  14

<210> SEQ ID NO 315
<211> LENGTH: 14
<212> TYPE: DNA
<213> ORGANISM: Artificial Sequence
<220> FEATURE:
<223> OTHER INFORMATION: Synthetic Construct

<400> SEQUENCE: 315
cgggaggagg aggg                                                  14

<210> SEQ ID NO 316
<211> LENGTH: 14
<212> TYPE: DNA
<213> ORGANISM: Artificial Sequence
<220> FEATURE:
<223> OTHER INFORMATION: Synthetic Construct

<400> SEQUENCE: 316
gggaggagga gggg                                                  14

<210> SEQ ID NO 317
<211> LENGTH: 14
<212> TYPE: DNA
<213> ORGANISM: Artificial Sequence
<220> FEATURE:
<223> OTHER INFORMATION: Synthetic Construct

<400> SEQUENCE: 317
ggaggaggag gggc                                                  14

<210> SEQ ID NO 318
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 318
gaggaggagg ggcg                                                        14

<210> SEQ ID NO 319
<211> LENGTH: 14
<212> TYPE: DNA
<213> ORGANISM: Artificial Sequence
<220> FEATURE:
<223> OTHER INFORMATION: Synthetic Construct

<400> SEQUENCE: 319
aggaggaggg gcgt                                                        14

<210> SEQ ID NO 320
<211> LENGTH: 14
<212> TYPE: DNA
<213> ORGANISM: Artificial Sequence
<220> FEATURE:
<223> OTHER INFORMATION: Synthetic Construct

<400> SEQUENCE: 320
ggaggagggg cgta                                                        14

<210> SEQ ID NO 321
<211> LENGTH: 14
<212> TYPE: DNA
<213> ORGANISM: Artificial Sequence
<220> FEATURE:
<223> OTHER INFORMATION: Synthetic Construct

<400> SEQUENCE: 321
gaggaggggc gtag                                                        14

<210> SEQ ID NO 322
<211> LENGTH: 14
<212> TYPE: DNA
<213> ORGANISM: Artificial Sequence
<220> FEATURE:
<223> OTHER INFORMATION: Synthetic Construct

<400> SEQUENCE: 322
aggaggggcg tagt                                                        14

<210> SEQ ID NO 323
<211> LENGTH: 14
<212> TYPE: DNA
<213> ORGANISM: Artificial Sequence
<220> FEATURE:
<223> OTHER INFORMATION: Synthetic Construct

<400> SEQUENCE: 323
ggaggggcgt agtc                                                        14

<210> SEQ ID NO 324
<211> LENGTH: 14
<212> TYPE: DNA
<213> ORGANISM: Artificial Sequence
<220> FEATURE:
<223> OTHER INFORMATION: Synthetic Construct

<400> SEQUENCE: 324
gaggggcgta gtcg                                                        14
```

```
<210> SEQ ID NO 325
<211> LENGTH: 14
<212> TYPE: DNA
<213> ORGANISM: Artificial Sequence
<220> FEATURE:
<223> OTHER INFORMATION: Synthetic Construct

<400> SEQUENCE: 325 agggggcgtag tcgc                                                        14

<210> SEQ ID NO 326
<211> LENGTH: 14
<212> TYPE: DNA
<213> ORGANISM: Artificial Sequence
<220> FEATURE:
<223> OTHER INFORMATION: Synthetic Construct

<400> SEQUENCE: 326
ggggcgtagt cgcg                                                         14

<210> SEQ ID NO 327
<211> LENGTH: 14
<212> TYPE: DNA
<213> ORGANISM: Artificial Sequence
<220> FEATURE:
<223> OTHER INFORMATION: Synthetic Construct

<400> SEQUENCE: 327
gggcgtagtc gcgg                                                         14

<210> SEQ ID NO 328
<211> LENGTH: 14
<212> TYPE: DNA
<213> ORGANISM: Artificial Sequence
<220> FEATURE:
<223> OTHER INFORMATION: Synthetic Construct

<400> SEQUENCE: 328
ggcgtagtcg cgga                                                         14

<210> SEQ ID NO 329
<211> LENGTH: 14
<212> TYPE: DNA
<213> ORGANISM: Artificial Sequence
<220> FEATURE:
<223> OTHER INFORMATION: Synthetic Construct

<400> SEQUENCE: 329
gcgtagtcgc ggag                                                         14

<210> SEQ ID NO 330
<211> LENGTH: 14
<212> TYPE: DNA
<213> ORGANISM: Artificial Sequence
<220> FEATURE:
<223> OTHER INFORMATION: Synthetic Construct

<400> SEQUENCE: 330
cgtagtcgcg gagt                                                         14

<210> SEQ ID NO 331
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 331
gtagtcgcgg agtt                                                    14

<210> SEQ ID NO 332
<211> LENGTH: 14
<212> TYPE: DNA
<213> ORGANISM: Artificial Sequence
<220> FEATURE:
<223> OTHER INFORMATION: Synthetic Construct

<400> SEQUENCE: 332
tagtcgcgga gtta                                                    14

<210> SEQ ID NO 333
<211> LENGTH: 14
<212> TYPE: DNA
<213> ORGANISM: Artificial Sequence
<220> FEATURE:
<223> OTHER INFORMATION: Synthetic Construct

<400> SEQUENCE: 333
agtcgcggag ttag                                                    14

<210> SEQ ID NO 334
<211> LENGTH: 14
<212> TYPE: DNA
<213> ORGANISM: Artificial Sequence
<220> FEATURE:
<223> OTHER INFORMATION: Synthetic Construct

<400> SEQUENCE: 334
gtcgcggagt tagt                                                    14

<210> SEQ ID NO 335
<211> LENGTH: 14
<212> TYPE: DNA
<213> ORGANISM: Artificial Sequence
<220> FEATURE:
<223> OTHER INFORMATION: Synthetic Construct

<400> SEQUENCE: 335
tcgcggagtt agtg                                                    14

<210> SEQ ID NO 336
<211> LENGTH: 14
<212> TYPE: DNA
<213> ORGANISM: Artificial Sequence
<220> FEATURE:
<223> OTHER INFORMATION: Synthetic Construct

<400> SEQUENCE: 336
cgcggagtta gtgg                                                    14

<210> SEQ ID NO 337
<211> LENGTH: 14
<212> TYPE: DNA
<213> ORGANISM: Artificial Sequence
<220> FEATURE:
<223> OTHER INFORMATION: Synthetic Construct

<400> SEQUENCE: 337
gcggagttag tggt                                                    14

<210> SEQ ID NO 338
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 338
cggagttagt ggtt                                                        14

<210> SEQ ID NO 339
<211> LENGTH: 14
<212> TYPE: DNA
<213> ORGANISM: Artificial Sequence
<220> FEATURE:
<223> OTHER INFORMATION: Synthetic Construct

<400> SEQUENCE: 339
ggagttagtg gttt                                                        14

<210> SEQ ID NO 340
<211> LENGTH: 14
<212> TYPE: DNA
<213> ORGANISM: Artificial Sequence
<220> FEATURE:
<223> OTHER INFORMATION: Synthetic Construct

<400> SEQUENCE: 340
gagttagtgg tttc                                                        14

<210> SEQ ID NO 341
<211> LENGTH: 14
<212> TYPE: DNA
<213> ORGANISM: Artificial Sequence
<220> FEATURE:
<223> OTHER INFORMATION: Synthetic Construct

<400> SEQUENCE: 341
agttagtggt ttcg                                                        14

<210> SEQ ID NO 342
<211> LENGTH: 14
<212> TYPE: DNA
<213> ORGANISM: Artificial Sequence
<220> FEATURE:
<223> OTHER INFORMATION: Synthetic Construct

<400> SEQUENCE: 342
aaataaattc gcta                                                        14

<210> SEQ ID NO 343
<211> LENGTH: 23
<212> TYPE: DNA
<213> ORGANISM: Artificial Sequence
<220> FEATURE:
<223> OTHER INFORMATION: Synthetic Construct

<400> SEQUENCE: 343
tttgtcgtag ttttttttta agt                                              23

<210> SEQ ID NO 344
<211> LENGTH: 14
<212> TYPE: DNA
<213> ORGANISM: Artificial Sequence
<220> FEATURE:
<223> OTHER INFORMATION: Synthetic Construct

<400> SEQUENCE: 344
```
gttagtggtt tcgt                                    14

<210> SEQ ID NO 345
<211> LENGTH: 14
<212> TYPE: DNA
<213> ORGANISM: Artificial Sequence
<220> FEATURE:
<223> OTHER INFORMATION: Synthetic Construct

<400> SEQUENCE: 345
ttagtggttt cgtt                                    14

<210> SEQ ID NO 346
<211> LENGTH: 14
<212> TYPE: DNA
<213> ORGANISM: Artificial Sequence
<220> FEATURE:
<223> OTHER INFORMATION: Synthetic Construct

<400> SEQUENCE: 346
tagtggtttc gttt                                    14

<210> SEQ ID NO 347
<211> LENGTH: 14
<212> TYPE: DNA
<213> ORGANISM: Artificial Sequence
<220> FEATURE:
<223> OTHER INFORMATION: Synthetic Construct

<400> SEQUENCE: 347
agtggtttcg tttg                                    14

<210> SEQ ID NO 348
<211> LENGTH: 14
<212> TYPE: DNA
<213> ORGANISM: Artificial Sequence
<220> FEATURE:
<223> OTHER INFORMATION: Synthetic Construct

<400> SEQUENCE: 348
gtggtttcgt ttgg                                    14

<210> SEQ ID NO 349
<211> LENGTH: 14
<212> TYPE: DNA
<213> ORGANISM: Artificial Sequence
<220> FEATURE:
<223> OTHER INFORMATION: Synthetic Construct

<400> SEQUENCE: 349
tggtttcgtt tgga                                    14

<210> SEQ ID NO 350
<211> LENGTH: 14
<212> TYPE: DNA
<213> ORGANISM: Artificial Sequence
<220> FEATURE:
<223> OTHER INFORMATION: Synthetic Construct

<400> SEQUENCE: 350
ggtttcgttt ggac                                    14

<210> SEQ ID NO 351
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 351
gtttcgtttg gacg                                                        14

<210> SEQ ID NO 352
<211> LENGTH: 14
<212> TYPE: DNA
<213> ORGANISM: Artificial Sequence
<220> FEATURE:
<223> OTHER INFORMATION: Synthetic Construct

<400> SEQUENCE: 352
tttcgtttgg acgc                                                        14

<210> SEQ ID NO 353
<211> LENGTH: 14
<212> TYPE: DNA
<213> ORGANISM: Artificial Sequence
<220> FEATURE:
<223> OTHER INFORMATION: Synthetic Construct

<400> SEQUENCE: 353
ttcgtttgga cgcg                                                        14

<210> SEQ ID NO 354
<211> LENGTH: 14
<212> TYPE: DNA
<213> ORGANISM: Artificial Sequence
<220> FEATURE:
<223> OTHER INFORMATION: Synthetic Construct

<400> SEQUENCE: 354
tcgtttggac gcgt                                                        14

<210> SEQ ID NO 355
<211> LENGTH: 14
<212> TYPE: DNA
<213> ORGANISM: Artificial Sequence
<220> FEATURE:
<223> OTHER INFORMATION: Synthetic Construct

<400> SEQUENCE: 355
cgtttggacg cgtt                                                        14

<210> SEQ ID NO 356
<211> LENGTH: 14
<212> TYPE: DNA
<213> ORGANISM: Artificial Sequence
<220> FEATURE:
<223> OTHER INFORMATION: Synthetic Construct

<400> SEQUENCE: 356
gtttggacgc gttg                                                        14

<210> SEQ ID NO 357
<211> LENGTH: 14
<212> TYPE: DNA
<213> ORGANISM: Artificial Sequence
<220> FEATURE:
<223> OTHER INFORMATION: Synthetic Construct

<400> SEQUENCE: 357
tttggacgcg ttgt                                                        14
```

```
<210> SEQ ID NO 358
<211> LENGTH: 14
<212> TYPE: DNA
<213> ORGANISM: Artificial Sequence
<220> FEATURE:
<223> OTHER INFORMATION: Synthetic Construct

<400> SEQUENCE: 358
ttggacgcgt tgtt                                                    14

<210> SEQ ID NO 359
<211> LENGTH: 14
<212> TYPE: DNA
<213> ORGANISM: Artificial Sequence
<220> FEATURE:
<223> OTHER INFORMATION: Synthetic Construct

<400> SEQUENCE: 359
tggacgcgtt gttt                                                    14

<210> SEQ ID NO 360
<211> LENGTH: 14
<212> TYPE: DNA
<213> ORGANISM: Artificial Sequence
<220> FEATURE:
<223> OTHER INFORMATION: Synthetic Construct

<400> SEQUENCE: 360
ggacgcgttg tttt                                                    14

<210> SEQ ID NO 361
<211> LENGTH: 14
<212> TYPE: DNA
<213> ORGANISM: Artificial Sequence
<220> FEATURE:
<223> OTHER INFORMATION: Synthetic Construct

<400> SEQUENCE: 361
gacgcgttgt tttt                                                    14

<210> SEQ ID NO 362
<211> LENGTH: 14
<212> TYPE: DNA
<213> ORGANISM: Artificial Sequence
<220> FEATURE:
<223> OTHER INFORMATION: Synthetic Construct

<400> SEQUENCE: 362
acgcgttgtt tttt                                                    14

<210> SEQ ID NO 363
<211> LENGTH: 14
<212> TYPE: DNA
<213> ORGANISM: Artificial Sequence
<220> FEATURE:
<223> OTHER INFORMATION: Synthetic Construct

<400> SEQUENCE: 363
cgcgttgttt ttta                                                    14

<210> SEQ ID NO 364
<211> LENGTH: 14
<212> TYPE: DNA
<213> ORGANISM: Artificial Sequence
<220> FEATURE:
```

<223> OTHER INFORMATION: Synthetic Construct

<400> SEQUENCE: 364
gcgttgtttt ttag                                                      14

<210> SEQ ID NO 365
<211> LENGTH: 14
<212> TYPE: DNA
<213> ORGANISM: Artificial Sequence
<220> FEATURE:
<223> OTHER INFORMATION: Synthetic Construct

<400> SEQUENCE: 365
cgttgttttt taga                                                      14

<210> SEQ ID NO 366
<211> LENGTH: 14
<212> TYPE: DNA
<213> ORGANISM: Artificial Sequence
<220> FEATURE:
<223> OTHER INFORMATION: Synthetic Construct

<400> SEQUENCE: 366
gttgtttttt agat                                                      14

<210> SEQ ID NO 367
<211> LENGTH: 14
<212> TYPE: DNA
<213> ORGANISM: Artificial Sequence
<220> FEATURE:
<223> OTHER INFORMATION: Synthetic Construct

<400> SEQUENCE: 367
ttgtttttta gata                                                      14

<210> SEQ ID NO 368
<211> LENGTH: 14
<212> TYPE: DNA
<213> ORGANISM: Artificial Sequence
<220> FEATURE:
<223> OTHER INFORMATION: Synthetic Construct

<400> SEQUENCE: 368
tgttttttag atat                                                      14

<210> SEQ ID NO 369
<211> LENGTH: 14
<212> TYPE: DNA
<213> ORGANISM: Artificial Sequence
<220> FEATURE:
<223> OTHER INFORMATION: Synthetic Construct

<400> SEQUENCE: 369
gttttttaga tatt                                                      14

<210> SEQ ID NO 370
<211> LENGTH: 14
<212> TYPE: DNA
<213> ORGANISM: Artificial Sequence
<220> FEATURE:
<223> OTHER INFORMATION: Synthetic Construct

<400> SEQUENCE: 370
ttttttagat attt                                                      14

<210> SEQ ID NO 371
<211> LENGTH: 14
<212> TYPE: DNA
<213> ORGANISM: Artificial Sequence
<220> FEATURE:
<223> OTHER INFORMATION: Synthetic Construct

<400> SEQUENCE: 371
tttttagata tttt                                                              14

<210> SEQ ID NO 372
<211> LENGTH: 14
<212> TYPE: DNA
<213> ORGANISM: Artificial Sequence
<220> FEATURE:
<223> OTHER INFORMATION: Synthetic Construct

<400> SEQUENCE: 372
ttttagatat tttc                                                              14

<210> SEQ ID NO 373
<211> LENGTH: 14
<212> TYPE: DNA
<213> ORGANISM: Artificial Sequence
<220> FEATURE:
<223> OTHER INFORMATION: Synthetic Construct

<400> SEQUENCE: 373
tttagatatt ttcg                                                              14

<210> SEQ ID NO 374
<211> LENGTH: 14
<212> TYPE: DNA
<213> ORGANISM: Artificial Sequence
<220> FEATURE:
<223> OTHER INFORMATION: Synthetic Construct

<400> SEQUENCE: 374
ttagatattt tcgg                                                              14

<210> SEQ ID NO 375
<211> LENGTH: 14
<212> TYPE: DNA
<213> ORGANISM: Artificial Sequence
<220> FEATURE:
<223> OTHER INFORMATION: Synthetic Construct

<400> SEQUENCE: 375
tagatatttt cgga                                                              14

<210> SEQ ID NO 376
<211> LENGTH: 14
<212> TYPE: DNA
<213> ORGANISM: Artificial Sequence
<220> FEATURE:
<223> OTHER INFORMATION: Synthetic Construct

<400> SEQUENCE: 376
agatattttc ggag                                                              14

<210> SEQ ID NO 377
<211> LENGTH: 14
<212> TYPE: DNA
<213> ORGANISM: Artificial Sequence
<220> FEATURE:
<223> OTHER INFORMATION: Synthetic Construct

<400> SEQUENCE: 377
gatattttcg gagt                                                        14

<210> SEQ ID NO 378
<211> LENGTH: 14
<212> TYPE: DNA
<213> ORGANISM: Artificial Sequence
<220> FEATURE:
<223> OTHER INFORMATION: Synthetic Construct

<400> SEQUENCE: 378
atattttcgg agtt                                                        14

<210> SEQ ID NO 379
<211> LENGTH: 14
<212> TYPE: DNA
<213> ORGANISM: Artificial Sequence
<220> FEATURE:
<223> OTHER INFORMATION: Synthetic Construct

<400> SEQUENCE: 379
tattttcgga gttt                                                        14

<210> SEQ ID NO 380
<211> LENGTH: 14
<212> TYPE: DNA
<213> ORGANISM: Artificial Sequence
<220> FEATURE:
<223> OTHER INFORMATION: Synthetic Construct

<400> SEQUENCE: 380
attttcggag tttt                                                        14

<210> SEQ ID NO 381
<211> LENGTH: 14
<212> TYPE: DNA
<213> ORGANISM: Artificial Sequence
<220> FEATURE:
<223> OTHER INFORMATION: Synthetic Construct

<400> SEQUENCE: 381
ttttcggagt ttta                                                        14

<210> SEQ ID NO 382
<211> LENGTH: 14
<212> TYPE: DNA
<213> ORGANISM: Artificial Sequence
<220> FEATURE:
<223> OTHER INFORMATION: Synthetic Construct

<400> SEQUENCE: 382
tttcggagtt ttag                                                        14

<210> SEQ ID NO 383
<211> LENGTH: 14
<212> TYPE: DNA
<213> ORGANISM: Artificial Sequence
<220> FEATURE:
<223> OTHER INFORMATION: Synthetic Construct

<400> SEQUENCE: 383
ttcggagttt tagt                                                        14

<210> SEQ ID NO 384
<211> LENGTH: 14

-continued

<212> TYPE: DNA
<213> ORGANISM: Artificial Sequence
<220> FEATURE:
<223> OTHER INFORMATION: Synthetic Construct

<400> SEQUENCE: 384
tcggagtttt agtc                                                         14

<210> SEQ ID NO 385
<211> LENGTH: 14
<212> TYPE: DNA
<213> ORGANISM: Artificial Sequence
<220> FEATURE:
<223> OTHER INFORMATION: Synthetic Construct

<400> SEQUENCE: 385
cggagtttta gtcg                                                         14

<210> SEQ ID NO 386
<211> LENGTH: 14
<212> TYPE: DNA
<213> ORGANISM: Artificial Sequence
<220> FEATURE:
<223> OTHER INFORMATION: Synthetic Construct

<400> SEQUENCE: 386
ggagttttag tcgc                                                         14

<210> SEQ ID NO 387
<211> LENGTH: 14
<212> TYPE: DNA
<213> ORGANISM: Artificial Sequence
<220> FEATURE:
<223> OTHER INFORMATION: Synthetic Construct

<400> SEQUENCE: 387
gagttttagt cgcg                                                         14

<210> SEQ ID NO 388
<211> LENGTH: 14
<212> TYPE: DNA
<213> ORGANISM: Artificial Sequence
<220> FEATURE:
<223> OTHER INFORMATION: Synthetic Construct

<400> SEQUENCE: 388
agttttagtc gcgc                                                         14

<210> SEQ ID NO 389
<211> LENGTH: 14
<212> TYPE: DNA
<213> ORGANISM: Artificial Sequence
<220> FEATURE:
<223> OTHER INFORMATION: Synthetic Construct

<400> SEQUENCE: 389
gttttagtcg cgcg                                                         14

<210> SEQ ID NO 390
<211> LENGTH: 14
<212> TYPE: DNA
<213> ORGANISM: Artificial Sequence
<220> FEATURE:
<223> OTHER INFORMATION: Synthetic Construct

<400> SEQUENCE: 390

| | |
|---|---|
| ttttagtcgc gcgg | 14 |

<210> SEQ ID NO 391
<211> LENGTH: 14
<212> TYPE: DNA
<213> ORGANISM: Artificial Sequence
<220> FEATURE:
<223> OTHER INFORMATION: Synthetic Construct

<400> SEQUENCE: 391

| | |
|---|---|
| tttagtcgcg cgga | 14 |

<210> SEQ ID NO 392
<211> LENGTH: 14
<212> TYPE: DNA
<213> ORGANISM: Artificial Sequence
<220> FEATURE:
<223> OTHER INFORMATION: Synthetic Construct

<400> SEQUENCE: 392

| | |
|---|---|
| ttagtcgcgc ggat | 14 |

<210> SEQ ID NO 393
<211> LENGTH: 14
<212> TYPE: DNA
<213> ORGANISM: Artificial Sequence
<220> FEATURE:
<223> OTHER INFORMATION: Synthetic Construct

<400> SEQUENCE: 393

| | |
|---|---|
| tagtcgcgcg gatc | 14 |

<210> SEQ ID NO 394
<211> LENGTH: 14
<212> TYPE: DNA
<213> ORGANISM: Artificial Sequence
<220> FEATURE:
<223> OTHER INFORMATION: Synthetic Construct

<400> SEQUENCE: 394

| | |
|---|---|
| agtcgcgcgg atcg | 14 |

<210> SEQ ID NO 395
<211> LENGTH: 14
<212> TYPE: DNA
<213> ORGANISM: Artificial Sequence
<220> FEATURE:
<223> OTHER INFORMATION: Synthetic Construct

<400> SEQUENCE: 395

| | |
|---|---|
| actcctccgc gaac | 14 |

<210> SEQ ID NO 396
<211> LENGTH: 25
<212> TYPE: DNA
<213> ORGANISM: Artificial Sequence
<220> FEATURE:
<223> OTHER INFORMATION: Synthetic Construct

<400> SEQUENCE: 396

| | |
|---|---|
| aattgaattt cggtacggga aagga | 25 |

<210> SEQ ID NO 397
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 397
gtcgcgcgga tcgc                                                    14

<210> SEQ ID NO 398
<211> LENGTH: 14
<212> TYPE: DNA
<213> ORGANISM: Artificial Sequence
<220> FEATURE:
<223> OTHER INFORMATION: Synthetic Construct

<400> SEQUENCE: 398
tcgcgcggat cgcg                                                    14

<210> SEQ ID NO 399
<211> LENGTH: 14
<212> TYPE: DNA
<213> ORGANISM: Artificial Sequence
<220> FEATURE:
<223> OTHER INFORMATION: Synthetic Construct

<400> SEQUENCE: 399
cgcgcggatc gcgc                                                    14

<210> SEQ ID NO 400
<211> LENGTH: 14
<212> TYPE: DNA
<213> ORGANISM: Artificial Sequence
<220> FEATURE:
<223> OTHER INFORMATION: Synthetic Construct

<400> SEQUENCE: 400
gcgcggatcg cgcg                                                    14

<210> SEQ ID NO 401
<211> LENGTH: 14
<212> TYPE: DNA
<213> ORGANISM: Artificial Sequence
<220> FEATURE:
<223> OTHER INFORMATION: Synthetic Construct

<400> SEQUENCE: 401
cgcggatcgc gcgt                                                    14

<210> SEQ ID NO 402
<211> LENGTH: 14
<212> TYPE: DNA
<213> ORGANISM: Artificial Sequence
<220> FEATURE:
<223> OTHER INFORMATION: Synthetic Construct

<400> SEQUENCE: 402
gcggatcgcg cgtt                                                    14

<210> SEQ ID NO 403
<211> LENGTH: 14
<212> TYPE: DNA
<213> ORGANISM: Artificial Sequence
<220> FEATURE:
<223> OTHER INFORMATION: Synthetic Construct

<400> SEQUENCE: 403
cggatcgcgc gttt                                                    14
```

<210> SEQ ID NO 404
<211> LENGTH: 14
<212> TYPE: DNA
<213> ORGANISM: Artificial Sequence
<220> FEATURE:
<223> OTHER INFORMATION: Synthetic Construct

<400> SEQUENCE: 404
ggatcgcgcg tttt                                                         14

<210> SEQ ID NO 405
<211> LENGTH: 14
<212> TYPE: DNA
<213> ORGANISM: Artificial Sequence
<220> FEATURE:
<223> OTHER INFORMATION: Synthetic Construct

<400> SEQUENCE: 405
gatcgcgcgt tttc                                                         14

<210> SEQ ID NO 406
<211> LENGTH: 14
<212> TYPE: DNA
<213> ORGANISM: Artificial Sequence
<220> FEATURE:
<223> OTHER INFORMATION: Synthetic Construct

<400> SEQUENCE: 406
atcgcgcgtt ttcg                                                         14

<210> SEQ ID NO 407
<211> LENGTH: 14
<212> TYPE: DNA
<213> ORGANISM: Artificial Sequence
<220> FEATURE:
<223> OTHER INFORMATION: Synthetic Construct

<400> SEQUENCE: 407
tcgcgcgttt tcgt                                                         14

<210> SEQ ID NO 408
<211> LENGTH: 14
<212> TYPE: DNA
<213> ORGANISM: Artificial Sequence
<220> FEATURE:
<223> OTHER INFORMATION: Synthetic Construct

<400> SEQUENCE: 408
cgcgcgtttt cgtc                                                         14

<210> SEQ ID NO 409
<211> LENGTH: 14
<212> TYPE: DNA
<213> ORGANISM: Artificial Sequence
<220> FEATURE:
<223> OTHER INFORMATION: Synthetic Construct

<400> SEQUENCE: 409
gcgcgttttc gtcg                                                         14

<210> SEQ ID NO 410
<211> LENGTH: 14
<212> TYPE: DNA
<213> ORGANISM: Artificial Sequence
<220> FEATURE:
<223> OTHER INFORMATION: Synthetic Construct

<400> SEQUENCE: 410
cgcgttttcg tcgt                                                     14

<210> SEQ ID NO 411
<211> LENGTH: 14
<212> TYPE: DNA
<213> ORGANISM: Artificial Sequence
<220> FEATURE:
<223> OTHER INFORMATION: Synthetic Construct

<400> SEQUENCE: 411
gcgttttcgt cgtt                                                     14

<210> SEQ ID NO 412
<211> LENGTH: 14
<212> TYPE: DNA
<213> ORGANISM: Artificial Sequence
<220> FEATURE:
<223> OTHER INFORMATION: Synthetic Construct

<400> SEQUENCE: 412
cgttttcgtc gttt                                                     14

<210> SEQ ID NO 413
<211> LENGTH: 14
<212> TYPE: DNA
<213> ORGANISM: Artificial Sequence
<220> FEATURE:
<223> OTHER INFORMATION: Synthetic Construct

<400> SEQUENCE: 413
gttttcgtcg tttt                                                     14

<210> SEQ ID NO 414
<211> LENGTH: 14
<212> TYPE: DNA
<213> ORGANISM: Artificial Sequence
<220> FEATURE:
<223> OTHER INFORMATION: Synthetic Construct

<400> SEQUENCE: 414
ttttcgtcgt tttg                                                     14

<210> SEQ ID NO 415
<211> LENGTH: 14
<212> TYPE: DNA
<213> ORGANISM: Artificial Sequence
<220> FEATURE:
<223> OTHER INFORMATION: Synthetic Construct

<400> SEQUENCE: 415
tttcgtcgtt ttgt                                                     14

<210> SEQ ID NO 416
<211> LENGTH: 14
<212> TYPE: DNA
<213> ORGANISM: Artificial Sequence
<220> FEATURE:
<223> OTHER INFORMATION: Synthetic Construct

<400> SEQUENCE: 416
ttcgtcgttt tgtt                                                     14

<210> SEQ ID NO 417

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 417
tcgtcgtttt gttt                                                        14

<210> SEQ ID NO 418
<211> LENGTH: 14
<212> TYPE: DNA
<213> ORGANISM: Artificial Sequence
<220> FEATURE:
<223> OTHER INFORMATION: Synthetic Construct

<400> SEQUENCE: 418
cgtcgttttg tttt                                                        14

<210> SEQ ID NO 419
<211> LENGTH: 14
<212> TYPE: DNA
<213> ORGANISM: Artificial Sequence
<220> FEATURE:
<223> OTHER INFORMATION: Synthetic Construct

<400> SEQUENCE: 419
gtcgttttgt tttt                                                        14

<210> SEQ ID NO 420
<211> LENGTH: 14
<212> TYPE: DNA
<213> ORGANISM: Artificial Sequence
<220> FEATURE:
<223> OTHER INFORMATION: Synthetic Construct

<400> SEQUENCE: 420
tcgttttgtt ttta                                                        14

<210> SEQ ID NO 421
<211> LENGTH: 14
<212> TYPE: DNA
<213> ORGANISM: Artificial Sequence
<220> FEATURE:
<223> OTHER INFORMATION: Synthetic Construct

<400> SEQUENCE: 421
cgttttgttt ttaa                                                        14

<210> SEQ ID NO 422
<211> LENGTH: 14
<212> TYPE: DNA
<213> ORGANISM: Artificial Sequence
<220> FEATURE:
<223> OTHER INFORMATION: Synthetic Construct

<400> SEQUENCE: 422
gttttgtttt taaa                                                        14

<210> SEQ ID NO 423
<211> LENGTH: 14
<212> TYPE: DNA
<213> ORGANISM: Artificial Sequence
<220> FEATURE:
<223> OTHER INFORMATION: Synthetic Construct

<400> SEQUENCE: 423
```
ttttgttttt aaat                                    14

<210> SEQ ID NO 424
<211> LENGTH: 14
<212> TYPE: DNA
<213> ORGANISM: Artificial Sequence
<220> FEATURE:
<223> OTHER INFORMATION: Synthetic Construct

<400> SEQUENCE: 424
tttgttttta aatt                                    14

<210> SEQ ID NO 425
<211> LENGTH: 14
<212> TYPE: DNA
<213> ORGANISM: Artificial Sequence
<220> FEATURE:
<223> OTHER INFORMATION: Synthetic Construct

<400> SEQUENCE: 425
ttgtttttaa attt                                    14

<210> SEQ ID NO 426
<211> LENGTH: 14
<212> TYPE: DNA
<213> ORGANISM: Artificial Sequence
<220> FEATURE:
<223> OTHER INFORMATION: Synthetic Construct

<400> SEQUENCE: 426 tgttttaaa tttt                                     14

<210> SEQ ID NO 427
<211> LENGTH: 14
<212> TYPE: DNA
<213> ORGANISM: Artificial Sequence
<220> FEATURE:
<223> OTHER INFORMATION: Synthetic Construct

<400> SEQUENCE: 427
gtttttaaat tttt                                    14

<210> SEQ ID NO 428
<211> LENGTH: 14
<212> TYPE: DNA
<213> ORGANISM: Artificial Sequence
<220> FEATURE:
<223> OTHER INFORMATION: Synthetic Construct

<400> SEQUENCE: 428
tttttaaatt tttg                                    14

<210> SEQ ID NO 429
<211> LENGTH: 14
<212> TYPE: DNA
<213> ORGANISM: Artificial Sequence
<220> FEATURE:
<223> OTHER INFORMATION: Synthetic Construct

<400> SEQUENCE: 429
ttttaaattt ttgt                                    14

<210> SEQ ID NO 430
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 430 tttaaattttt tgtc                                                      14

<210> SEQ ID NO 431
<211> LENGTH: 14
<212> TYPE: DNA
<213> ORGANISM: Artificial Sequence
<220> FEATURE:
<223> OTHER INFORMATION: Synthetic Construct

<400> SEQUENCE: 431
ttaaattttt gtcg                                                       14

<210> SEQ ID NO 432
<211> LENGTH: 14
<212> TYPE: DNA
<213> ORGANISM: Artificial Sequence
<220> FEATURE:
<223> OTHER INFORMATION: Synthetic Construct

<400> SEQUENCE: 432
taaatttttg tcgt                                                       14

<210> SEQ ID NO 433
<211> LENGTH: 14
<212> TYPE: DNA
<213> ORGANISM: Artificial Sequence
<220> FEATURE:
<223> OTHER INFORMATION: Synthetic Construct

<400> SEQUENCE: 433 aaattttttgt cgta                                                      14

<210> SEQ ID NO 434
<211> LENGTH: 14
<212> TYPE: DNA
<213> ORGANISM: Artificial Sequence
<220> FEATURE:
<223> OTHER INFORMATION: Synthetic Construct

<400> SEQUENCE: 434 aattttgtc gtag                                                        14

<210> SEQ ID NO 435
<211> LENGTH: 14
<212> TYPE: DNA
<213> ORGANISM: Artificial Sequence
<220> FEATURE:
<223> OTHER INFORMATION: Synthetic Construct

<400> SEQUENCE: 435 attttgtcg tagt                                                        14

<210> SEQ ID NO 436
<211> LENGTH: 14
<212> TYPE: DNA
<213> ORGANISM: Artificial Sequence
<220> FEATURE:
<223> OTHER INFORMATION: Synthetic Construct

<400> SEQUENCE: 436
tttttgtcgt agtt                                                       14
```

<210> SEQ ID NO 437
<211> LENGTH: 14
<212> TYPE: DNA
<213> ORGANISM: Artificial Sequence
<220> FEATURE:
<223> OTHER INFORMATION: Synthetic Construct

<400> SEQUENCE: 437
ttttgtcgta gttt                                                        14

<210> SEQ ID NO 438
<211> LENGTH: 14
<212> TYPE: DNA
<213> ORGANISM: Artificial Sequence
<220> FEATURE:
<223> OTHER INFORMATION: Synthetic Construct

<400> SEQUENCE: 438
tttgtcgtag tttt                                                        14

<210> SEQ ID NO 439
<211> LENGTH: 14
<212> TYPE: DNA
<213> ORGANISM: Artificial Sequence
<220> FEATURE:
<223> OTHER INFORMATION: Synthetic Construct

<400> SEQUENCE: 439
ttgtcgtagt tttt                                                        14

<210> SEQ ID NO 440
<211> LENGTH: 14
<212> TYPE: DNA
<213> ORGANISM: Artificial Sequence
<220> FEATURE:
<223> OTHER INFORMATION: Synthetic Construct

<400> SEQUENCE: 440
tgtcgtagtt tttt                                                        14

<210> SEQ ID NO 441
<211> LENGTH: 14
<212> TYPE: DNA
<213> ORGANISM: Artificial Sequence
<220> FEATURE:
<223> OTHER INFORMATION: Synthetic Construct

<400> SEQUENCE: 441
gtcgtagttt tttt                                                        14

<210> SEQ ID NO 442
<211> LENGTH: 14
<212> TYPE: DNA
<213> ORGANISM: Artificial Sequence
<220> FEATURE:
<223> OTHER INFORMATION: Synthetic Construct

<400> SEQUENCE: 442
tcgtagtttt tttt                                                        14

<210> SEQ ID NO 443
<211> LENGTH: 14
<212> TYPE: DNA
<213> ORGANISM: Artificial Sequence
<220> FEATURE:

<223> OTHER INFORMATION: Synthetic Construct

<400> SEQUENCE: 443
cgtagttttt tttt                                                         14

<210> SEQ ID NO 444
<211> LENGTH: 14
<212> TYPE: DNA
<213> ORGANISM: Artificial Sequence
<220> FEATURE:
<223> OTHER INFORMATION: Synthetic Construct

<400> SEQUENCE: 444 gtagttttttt ttta                                                         14

<210> SEQ ID NO 445
<211> LENGTH: 14
<212> TYPE: DNA
<213> ORGANISM: Artificial Sequence
<220> FEATURE:
<223> OTHER INFORMATION: Synthetic Construct

<400> SEQUENCE: 445 tagtttttttt ttaa                                                         14

<210> SEQ ID NO 446
<211> LENGTH: 14
<212> TYPE: DNA
<213> ORGANISM: Artificial Sequence
<220> FEATURE:
<223> OTHER INFORMATION: Synthetic Construct

<400> SEQUENCE: 446
agtttttttt taag                                                          14

<210> SEQ ID NO 447
<211> LENGTH: 14
<212> TYPE: DNA
<213> ORGANISM: Artificial Sequence
<220> FEATURE:
<223> OTHER INFORMATION: Synthetic Construct

<400> SEQUENCE: 447 gtttttttttt aagt                                                         14

<210> SEQ ID NO 448
<211> LENGTH: 14
<212> TYPE: DNA
<213> ORGANISM: Artificial Sequence
<220> FEATURE:
<223> OTHER INFORMATION: Synthetic Construct

<400> SEQUENCE: 448
cacgaaatta atac                                                          14

<210> SEQ ID NO 449
<211> LENGTH: 24
<212> TYPE: DNA
<213> ORGANISM: Artificial Sequence
<220> FEATURE:
<223> OTHER INFORMATION: Synthetic Construct

<400> SEQUENCE: 449
gttttagaga gtagttttttt cgga                                              24

```
<210> SEQ ID NO 450
<211> LENGTH: 14
<212> TYPE: DNA
<213> ORGANISM: Artificial Sequence
<220> FEATURE:
<223> OTHER INFORMATION: Synthetic Construct

<400> SEQUENCE: 450 tttttttttta agtt                                                      14

<210> SEQ ID NO 451
<211> LENGTH: 14
<212> TYPE: DNA
<213> ORGANISM: Artificial Sequence
<220> FEATURE:
<223> OTHER INFORMATION: Synthetic Construct

<400> SEQUENCE: 451
ttttttttaa gtta                                                       14

<210> SEQ ID NO 452
<211> LENGTH: 14
<212> TYPE: DNA
<213> ORGANISM: Artificial Sequence
<220> FEATURE:
<223> OTHER INFORMATION: Synthetic Construct

<400> SEQUENCE: 452
tttttttaag ttag                                                       14

<210> SEQ ID NO 453
<211> LENGTH: 14
<212> TYPE: DNA
<213> ORGANISM: Artificial Sequence
<220> FEATURE:
<223> OTHER INFORMATION: Synthetic Construct

<400> SEQUENCE: 453
ttttttaagt tagc                                                       14

<210> SEQ ID NO 454
<211> LENGTH: 14
<212> TYPE: DNA
<213> ORGANISM: Artificial Sequence
<220> FEATURE:
<223> OTHER INFORMATION: Synthetic Construct

<400> SEQUENCE: 454
tttttaagtt agcg                                                       14

<210> SEQ ID NO 455
<211> LENGTH: 14
<212> TYPE: DNA
<213> ORGANISM: Artificial Sequence
<220> FEATURE:
<223> OTHER INFORMATION: Synthetic Construct

<400> SEQUENCE: 455
ttttaagtta gcga                                                       14

<210> SEQ ID NO 456
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 456
tttaagttag cgaa                                                        14

<210> SEQ ID NO 457
<211> LENGTH: 14
<212> TYPE: DNA
<213> ORGANISM: Artificial Sequence
<220> FEATURE:
<223> OTHER INFORMATION: Synthetic Construct

<400> SEQUENCE: 457
ttaagttagc gaat                                                        14

<210> SEQ ID NO 458
<211> LENGTH: 14
<212> TYPE: DNA
<213> ORGANISM: Artificial Sequence
<220> FEATURE:
<223> OTHER INFORMATION: Synthetic Construct

<400> SEQUENCE: 458
taagttagcg aatt                                                        14

<210> SEQ ID NO 459
<211> LENGTH: 14
<212> TYPE: DNA
<213> ORGANISM: Artificial Sequence
<220> FEATURE:
<223> OTHER INFORMATION: Synthetic Construct

<400> SEQUENCE: 459
aagttagcga attt                                                        14

<210> SEQ ID NO 460
<211> LENGTH: 14
<212> TYPE: DNA
<213> ORGANISM: Artificial Sequence
<220> FEATURE:
<223> OTHER INFORMATION: Synthetic Construct

<400> SEQUENCE: 460
agttagcgaa ttta                                                        14

<210> SEQ ID NO 461
<211> LENGTH: 14
<212> TYPE: DNA
<213> ORGANISM: Artificial Sequence
<220> FEATURE:
<223> OTHER INFORMATION: Synthetic Construct

<400> SEQUENCE: 461
gttagcgaat ttat                                                        14

<210> SEQ ID NO 462
<211> LENGTH: 14
<212> TYPE: DNA
<213> ORGANISM: Artificial Sequence
<220> FEATURE:
<223> OTHER INFORMATION: Synthetic Construct

<400> SEQUENCE: 462
ttagcgaatt tatt                                                        14

<210> SEQ ID NO 463
<211> LENGTH: 14
```

-continued

<212> TYPE: DNA
<213> ORGANISM: Artificial Sequence
<220> FEATURE:
<223> OTHER INFORMATION: Synthetic Construct

<400> SEQUENCE: 463
tagcgaattt attt                                                       14

<210> SEQ ID NO 464
<211> LENGTH: 14
<212> TYPE: DNA
<213> ORGANISM: Artificial Sequence
<220> FEATURE:
<223> OTHER INFORMATION: Synthetic Construct

<400> SEQUENCE: 464
agcgaattta tttt                                                       14

<210> SEQ ID NO 465
<211> LENGTH: 14
<212> TYPE: DNA
<213> ORGANISM: Artificial Sequence
<220> FEATURE:
<223> OTHER INFORMATION: Synthetic Construct

<400> SEQUENCE: 465
gcgaatttat tttt                                                       14

<210> SEQ ID NO 466
<211> LENGTH: 14
<212> TYPE: DNA
<213> ORGANISM: Artificial Sequence
<220> FEATURE:
<223> OTHER INFORMATION: Synthetic Construct

<400> SEQUENCE: 466
cgaatttatt tttt                                                       14

<210> SEQ ID NO 467
<211> LENGTH: 14
<212> TYPE: DNA
<213> ORGANISM: Artificial Sequence
<220> FEATURE:
<223> OTHER INFORMATION: Synthetic Construct

<400> SEQUENCE: 467
gaatttattt ttta                                                       14

<210> SEQ ID NO 468
<211> LENGTH: 14
<212> TYPE: DNA
<213> ORGANISM: Artificial Sequence
<220> FEATURE:
<223> OTHER INFORMATION: Synthetic Construct

<400> SEQUENCE: 468
aatttatttt ttaa                                                       14

<210> SEQ ID NO 469
<211> LENGTH: 14
<212> TYPE: DNA
<213> ORGANISM: Artificial Sequence
<220> FEATURE:
<223> OTHER INFORMATION: Synthetic Construct

<400> SEQUENCE: 469
atttattttt taaa                                       14

<210> SEQ ID NO 470
<211> LENGTH: 14
<212> TYPE: DNA
<213> ORGANISM: Artificial Sequence
<220> FEATURE:
<223> OTHER INFORMATION: Synthetic Construct

<400> SEQUENCE: 470 tttattttt aaaa                                        14

<210> SEQ ID NO 471
<211> LENGTH: 14
<212> TYPE: DNA
<213> ORGANISM: Artificial Sequence
<220> FEATURE:
<223> OTHER INFORMATION: Synthetic Construct

<400> SEQUENCE: 471 ttattttta aaat                                        14

<210> SEQ ID NO 472
<211> LENGTH: 14
<212> TYPE: DNA
<213> ORGANISM: Artificial Sequence
<220> FEATURE:
<223> OTHER INFORMATION: Synthetic Construct

<400> SEQUENCE: 472 tatttttaa aatt                                        14

<210> SEQ ID NO 473
<211> LENGTH: 14
<212> TYPE: DNA
<213> ORGANISM: Artificial Sequence
<220> FEATURE:
<223> OTHER INFORMATION: Synthetic Construct

<400> SEQUENCE: 473
attttttaaa atta                                       14

<210> SEQ ID NO 474
<211> LENGTH: 14
<212> TYPE: DNA
<213> ORGANISM: Artificial Sequence
<220> FEATURE:
<223> OTHER INFORMATION: Synthetic Construct

<400> SEQUENCE: 474 tttttaaaa ttag                                        14

<210> SEQ ID NO 475
<211> LENGTH: 14
<212> TYPE: DNA
<213> ORGANISM: Artificial Sequence
<220> FEATURE:
<223> OTHER INFORMATION: Synthetic Construct

<400> SEQUENCE: 475
tttttaaaat taga                                       14

<210> SEQ ID NO 476
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 476
ttttaaaatt agaa                                                    14

<210> SEQ ID NO 477
<211> LENGTH: 14
<212> TYPE: DNA
<213> ORGANISM: Artificial Sequence
<220> FEATURE:
<223> OTHER INFORMATION: Synthetic Construct

<400> SEQUENCE: 477
tttaaaatta gaaa                                                    14

<210> SEQ ID NO 478
<211> LENGTH: 14
<212> TYPE: DNA
<213> ORGANISM: Artificial Sequence
<220> FEATURE:
<223> OTHER INFORMATION: Synthetic Construct

<400> SEQUENCE: 478
ttaaaattag aaat                                                    14

<210> SEQ ID NO 479
<211> LENGTH: 14
<212> TYPE: DNA
<213> ORGANISM: Artificial Sequence
<220> FEATURE:
<223> OTHER INFORMATION: Synthetic Construct

<400> SEQUENCE: 479
taaaattaga aatt                                                    14

<210> SEQ ID NO 480
<211> LENGTH: 14
<212> TYPE: DNA
<213> ORGANISM: Artificial Sequence
<220> FEATURE:
<223> OTHER INFORMATION: Synthetic Construct

<400> SEQUENCE: 480
aaaattagaa attg                                                    14

<210> SEQ ID NO 481
<211> LENGTH: 14
<212> TYPE: DNA
<213> ORGANISM: Artificial Sequence
<220> FEATURE:
<223> OTHER INFORMATION: Synthetic Construct

<400> SEQUENCE: 481
aaattagaaa ttga                                                    14

<210> SEQ ID NO 482
<211> LENGTH: 14
<212> TYPE: DNA
<213> ORGANISM: Artificial Sequence
<220> FEATURE:
<223> OTHER INFORMATION: Synthetic Construct

<400> SEQUENCE: 482
aattagaaat tgaa                                                    14
```

```
<210> SEQ ID NO 483
<211> LENGTH: 14
<212> TYPE: DNA
<213> ORGANISM: Artificial Sequence
<220> FEATURE:
<223> OTHER INFORMATION: Synthetic Construct

<400> SEQUENCE: 483
attagaaatt gaat                                                         14

<210> SEQ ID NO 484
<211> LENGTH: 14
<212> TYPE: DNA
<213> ORGANISM: Artificial Sequence
<220> FEATURE:
<223> OTHER INFORMATION: Synthetic Construct

<400> SEQUENCE: 484
ttagaaattg aatt                                                         14

<210> SEQ ID NO 485
<211> LENGTH: 14
<212> TYPE: DNA
<213> ORGANISM: Artificial Sequence
<220> FEATURE:
<223> OTHER INFORMATION: Synthetic Construct

<400> SEQUENCE: 485
tagaaattga attt                                                         14

<210> SEQ ID NO 486
<211> LENGTH: 14
<212> TYPE: DNA
<213> ORGANISM: Artificial Sequence
<220> FEATURE:
<223> OTHER INFORMATION: Synthetic Construct

<400> SEQUENCE: 486
agaaattgaa tttc                                                         14

<210> SEQ ID NO 487
<211> LENGTH: 14
<212> TYPE: DNA
<213> ORGANISM: Artificial Sequence
<220> FEATURE:
<223> OTHER INFORMATION: Synthetic Construct

<400> SEQUENCE: 487
gaaattgaat ttcg                                                         14

<210> SEQ ID NO 488
<211> LENGTH: 14
<212> TYPE: DNA
<213> ORGANISM: Artificial Sequence
<220> FEATURE:
<223> OTHER INFORMATION: Synthetic Construct

<400> SEQUENCE: 488
aaattgaatt tcgg                                                         14

<210> SEQ ID NO 489
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 489
aattgaattt cggt                                                     14

<210> SEQ ID NO 490
<211> LENGTH: 14
<212> TYPE: DNA
<213> ORGANISM: Artificial Sequence
<220> FEATURE:
<223> OTHER INFORMATION: Synthetic Construct

<400> SEQUENCE: 490
attgaatttc ggta                                                     14

<210> SEQ ID NO 491
<211> LENGTH: 14
<212> TYPE: DNA
<213> ORGANISM: Artificial Sequence
<220> FEATURE:
<223> OTHER INFORMATION: Synthetic Construct

<400> SEQUENCE: 491
ttgaatttcg gtac                                                     14

<210> SEQ ID NO 492
<211> LENGTH: 14
<212> TYPE: DNA
<213> ORGANISM: Artificial Sequence
<220> FEATURE:
<223> OTHER INFORMATION: Synthetic Construct

<400> SEQUENCE: 492
tgaatttcgg tacg                                                     14

<210> SEQ ID NO 493
<211> LENGTH: 14
<212> TYPE: DNA
<213> ORGANISM: Artificial Sequence
<220> FEATURE:
<223> OTHER INFORMATION: Synthetic Construct

<400> SEQUENCE: 493
gaatttcggt acgg                                                     14

<210> SEQ ID NO 494
<211> LENGTH: 14
<212> TYPE: DNA
<213> ORGANISM: Artificial Sequence
<220> FEATURE:
<223> OTHER INFORMATION: Synthetic Construct

<400> SEQUENCE: 494
aatttcggta cggg                                                     14

<210> SEQ ID NO 495
<211> LENGTH: 14
<212> TYPE: DNA
<213> ORGANISM: Artificial Sequence
<220> FEATURE:
<223> OTHER INFORMATION: Synthetic Construct

<400> SEQUENCE: 495
atttcggtac ggga                                                     14

<210> SEQ ID NO 496
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 496
tttcggtacg ggaa                                                        14

<210> SEQ ID NO 497
<211> LENGTH: 14
<212> TYPE: DNA
<213> ORGANISM: Artificial Sequence
<220> FEATURE:
<223> OTHER INFORMATION: Synthetic Construct

<400> SEQUENCE: 497
ttcggtacgg gaaa                                                        14

<210> SEQ ID NO 498
<211> LENGTH: 14
<212> TYPE: DNA
<213> ORGANISM: Artificial Sequence
<220> FEATURE:
<223> OTHER INFORMATION: Synthetic Construct

<400> SEQUENCE: 498
tcggtacggg aaag                                                        14

<210> SEQ ID NO 499
<211> LENGTH: 14
<212> TYPE: DNA
<213> ORGANISM: Artificial Sequence
<220> FEATURE:
<223> OTHER INFORMATION: Synthetic Construct

<400> SEQUENCE: 499
cggtacggga aagg                                                        14

<210> SEQ ID NO 500
<211> LENGTH: 14
<212> TYPE: DNA
<213> ORGANISM: Artificial Sequence
<220> FEATURE:
<223> OTHER INFORMATION: Synthetic Construct

<400> SEQUENCE: 500
ggtacgggaa agga                                                        14

<210> SEQ ID NO 501
<211> LENGTH: 14
<212> TYPE: DNA
<213> ORGANISM: Artificial Sequence
<220> FEATURE:
<223> OTHER INFORMATION: Synthetic Construct

<400> SEQUENCE: 501
gtacgggaaa ggag                                                        14

<210> SEQ ID NO 502
<211> LENGTH: 14
<212> TYPE: DNA
<213> ORGANISM: Artificial Sequence
<220> FEATURE:
<223> OTHER INFORMATION: Synthetic Construct

<400> SEQUENCE: 502
```
tacgggaaag gagt                                        14

<210> SEQ ID NO 503
<211> LENGTH: 14
<212> TYPE: DNA
<213> ORGANISM: Artificial Sequence
<220> FEATURE:
<223> OTHER INFORMATION: Synthetic Construct

<400> SEQUENCE: 503
acgggaaagg agtt                                        14

<210> SEQ ID NO 504
<211> LENGTH: 14
<212> TYPE: DNA
<213> ORGANISM: Artificial Sequence
<220> FEATURE:
<223> OTHER INFORMATION: Synthetic Construct

<400> SEQUENCE: 504
cgggaaagga gttc                                        14

<210> SEQ ID NO 505
<211> LENGTH: 14
<212> TYPE: DNA
<213> ORGANISM: Artificial Sequence
<220> FEATURE:
<223> OTHER INFORMATION: Synthetic Construct

<400> SEQUENCE: 505
gggaaaggag ttcg                                        14

<210> SEQ ID NO 506
<211> LENGTH: 14
<212> TYPE: DNA
<213> ORGANISM: Artificial Sequence
<220> FEATURE:
<223> OTHER INFORMATION: Synthetic Construct

<400> SEQUENCE: 506
ggaaaggagt tcgc                                        14

<210> SEQ ID NO 507
<211> LENGTH: 14
<212> TYPE: DNA
<213> ORGANISM: Artificial Sequence
<220> FEATURE:
<223> OTHER INFORMATION: Synthetic Construct

<400> SEQUENCE: 507
gaaaggagtt cgcg                                        14

<210> SEQ ID NO 508
<211> LENGTH: 14
<212> TYPE: DNA
<213> ORGANISM: Artificial Sequence
<220> FEATURE:
<223> OTHER INFORMATION: Synthetic Construct

<400> SEQUENCE: 508
aaaggagttc gcgg                                        14

<210> SEQ ID NO 509
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 509
aaggagttcg cgga                                                    14

<210> SEQ ID NO 510
<211> LENGTH: 14
<212> TYPE: DNA
<213> ORGANISM: Artificial Sequence
<220> FEATURE:
<223> OTHER INFORMATION: Synthetic Construct

<400> SEQUENCE: 510
aggagttcgc ggag                                                    14

<210> SEQ ID NO 511
<211> LENGTH: 14
<212> TYPE: DNA
<213> ORGANISM: Artificial Sequence
<220> FEATURE:
<223> OTHER INFORMATION: Synthetic Construct

<400> SEQUENCE: 511
cgcccgcaac tacg                                                    14

<210> SEQ ID NO 512
<211> LENGTH: 25
<212> TYPE: DNA
<213> ORGANISM: Artificial Sequence
<220> FEATURE:
<223> OTHER INFORMATION: Synthetic Construct

<400> SEQUENCE: 512
gtgagagggc gtcgcgtttt cgggg                                        25

<210> SEQ ID NO 513
<211> LENGTH: 14
<212> TYPE: DNA
<213> ORGANISM: Artificial Sequence
<220> FEATURE:
<223> OTHER INFORMATION: Synthetic Construct

<400> SEQUENCE: 513
ggagttcgcg gagg                                                    14

<210> SEQ ID NO 514
<211> LENGTH: 14
<212> TYPE: DNA
<213> ORGANISM: Artificial Sequence
<220> FEATURE:
<223> OTHER INFORMATION: Synthetic Construct

<400> SEQUENCE: 514
gagttcgcgg agga                                                    14

<210> SEQ ID NO 515
<211> LENGTH: 14
<212> TYPE: DNA
<213> ORGANISM: Artificial Sequence
<220> FEATURE:
<223> OTHER INFORMATION: Synthetic Construct

<400> SEQUENCE: 515
agttcgcgga ggag                                                    14
```

<210> SEQ ID NO 516
<211> LENGTH: 14
<212> TYPE: DNA
<213> ORGANISM: Artificial Sequence
<220> FEATURE:
<223> OTHER INFORMATION: Synthetic Construct

<400> SEQUENCE: 516
gttcgcggag gagt                                                         14

<210> SEQ ID NO 517
<211> LENGTH: 14
<212> TYPE: DNA
<213> ORGANISM: Artificial Sequence
<220> FEATURE:
<223> OTHER INFORMATION: Synthetic Construct

<400> SEQUENCE: 517
ttcgcggagg agta                                                         14

<210> SEQ ID NO 518
<211> LENGTH: 14
<212> TYPE: DNA
<213> ORGANISM: Artificial Sequence
<220> FEATURE:
<223> OTHER INFORMATION: Synthetic Construct

<400> SEQUENCE: 518
tcgcggagga gtaa                                                         14

<210> SEQ ID NO 519
<211> LENGTH: 14
<212> TYPE: DNA
<213> ORGANISM: Artificial Sequence
<220> FEATURE:
<223> OTHER INFORMATION: Synthetic Construct

<400> SEQUENCE: 519
cgcggaggag taaa                                                         14

<210> SEQ ID NO 520
<211> LENGTH: 14
<212> TYPE: DNA
<213> ORGANISM: Artificial Sequence
<220> FEATURE:
<223> OTHER INFORMATION: Synthetic Construct

<400> SEQUENCE: 520
gcggaggagt aaaa                                                         14

<210> SEQ ID NO 521
<211> LENGTH: 14
<212> TYPE: DNA
<213> ORGANISM: Artificial Sequence
<220> FEATURE:
<223> OTHER INFORMATION: Synthetic Construct

<400> SEQUENCE: 521
cggaggagta aaat                                                         14

<210> SEQ ID NO 522
<211> LENGTH: 14
<212> TYPE: DNA
<213> ORGANISM: Artificial Sequence
<220> FEATURE:

<223> OTHER INFORMATION: Synthetic Construct

<400> SEQUENCE: 522
ggaggagtaa aatt                                                      14

<210> SEQ ID NO 523
<211> LENGTH: 14
<212> TYPE: DNA
<213> ORGANISM: Artificial Sequence
<220> FEATURE:
<223> OTHER INFORMATION: Synthetic Construct

<400> SEQUENCE: 523
gaggagtaaa atta                                                      14

<210> SEQ ID NO 524
<211> LENGTH: 14
<212> TYPE: DNA
<213> ORGANISM: Artificial Sequence
<220> FEATURE:
<223> OTHER INFORMATION: Synthetic Construct

<400> SEQUENCE: 524
aggagtaaaa ttat                                                      14

<210> SEQ ID NO 525
<211> LENGTH: 14
<212> TYPE: DNA
<213> ORGANISM: Artificial Sequence
<220> FEATURE:
<223> OTHER INFORMATION: Synthetic Construct

<400> SEQUENCE: 525
ggagtaaaat tata                                                      14

<210> SEQ ID NO 526
<211> LENGTH: 14
<212> TYPE: DNA
<213> ORGANISM: Artificial Sequence
<220> FEATURE:
<223> OTHER INFORMATION: Synthetic Construct

<400> SEQUENCE: 526
gagtaaaatt atag                                                      14

<210> SEQ ID NO 527
<211> LENGTH: 14
<212> TYPE: DNA
<213> ORGANISM: Artificial Sequence
<220> FEATURE:
<223> OTHER INFORMATION: Synthetic Construct

<400> SEQUENCE: 527
agtaaaatta tagt                                                      14

<210> SEQ ID NO 528
<211> LENGTH: 14
<212> TYPE: DNA
<213> ORGANISM: Artificial Sequence
<220> FEATURE:
<223> OTHER INFORMATION: Synthetic Construct

<400> SEQUENCE: 528
gtaaaattat agta                                                      14

```
<210> SEQ ID NO 529
<211> LENGTH: 14
<212> TYPE: DNA
<213> ORGANISM: Artificial Sequence
<220> FEATURE:
<223> OTHER INFORMATION: Synthetic Construct

<400> SEQUENCE: 529
taaaattata gtag                                                        14

<210> SEQ ID NO 530
<211> LENGTH: 14
<212> TYPE: DNA
<213> ORGANISM: Artificial Sequence
<220> FEATURE:
<223> OTHER INFORMATION: Synthetic Construct

<400> SEQUENCE: 530
aaaattatag taga                                                        14

<210> SEQ ID NO 531
<211> LENGTH: 14
<212> TYPE: DNA
<213> ORGANISM: Artificial Sequence
<220> FEATURE:
<223> OTHER INFORMATION: Synthetic Construct

<400> SEQUENCE: 531
aaattatagt agag                                                        14

<210> SEQ ID NO 532
<211> LENGTH: 14
<212> TYPE: DNA
<213> ORGANISM: Artificial Sequence
<220> FEATURE:
<223> OTHER INFORMATION: Synthetic Construct

<400> SEQUENCE: 532
aattatagta gagt                                                        14

<210> SEQ ID NO 533
<211> LENGTH: 14
<212> TYPE: DNA
<213> ORGANISM: Artificial Sequence
<220> FEATURE:
<223> OTHER INFORMATION: Synthetic Construct

<400> SEQUENCE: 533
attatagtag agta                                                        14

<210> SEQ ID NO 534
<211> LENGTH: 14
<212> TYPE: DNA
<213> ORGANISM: Artificial Sequence
<220> FEATURE:
<223> OTHER INFORMATION: Synthetic Construct

<400> SEQUENCE: 534
ttatagtaga gtaa                                                        14

<210> SEQ ID NO 535
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 535
tatagtagag taag                                                    14

<210> SEQ ID NO 536
<211> LENGTH: 14
<212> TYPE: DNA
<213> ORGANISM: Artificial Sequence
<220> FEATURE:
<223> OTHER INFORMATION: Synthetic Construct

<400> SEQUENCE: 536
atagtagagt aaga                                                    14

<210> SEQ ID NO 537
<211> LENGTH: 14
<212> TYPE: DNA
<213> ORGANISM: Artificial Sequence
<220> FEATURE:
<223> OTHER INFORMATION: Synthetic Construct

<400> SEQUENCE: 537
tagtagagta agaa                                                    14

<210> SEQ ID NO 538
<211> LENGTH: 14
<212> TYPE: DNA
<213> ORGANISM: Artificial Sequence
<220> FEATURE:
<223> OTHER INFORMATION: Synthetic Construct

<400> SEQUENCE: 538
agtagagtaa gaag                                                    14

<210> SEQ ID NO 539
<211> LENGTH: 14
<212> TYPE: DNA
<213> ORGANISM: Artificial Sequence
<220> FEATURE:
<223> OTHER INFORMATION: Synthetic Construct

<400> SEQUENCE: 539
gtagagtaag aaga                                                    14

<210> SEQ ID NO 540
<211> LENGTH: 14
<212> TYPE: DNA
<213> ORGANISM: Artificial Sequence
<220> FEATURE:
<223> OTHER INFORMATION: Synthetic Construct

<400> SEQUENCE: 540
tagagtaaga agag                                                    14

<210> SEQ ID NO 541
<211> LENGTH: 14
<212> TYPE: DNA
<213> ORGANISM: Artificial Sequence
<220> FEATURE:
<223> OTHER INFORMATION: Synthetic Construct

<400> SEQUENCE: 541
agagtaagaa gagt                                                    14

<210> SEQ ID NO 542
<211> LENGTH: 14

```
<212> TYPE: DNA
<213> ORGANISM: Artificial Sequence
<220> FEATURE:
<223> OTHER INFORMATION: Synthetic Construct

<400> SEQUENCE: 542
gagtaagaag agtt                                                    14

<210> SEQ ID NO 543
<211> LENGTH: 14
<212> TYPE: DNA
<213> ORGANISM: Artificial Sequence
<220> FEATURE:
<223> OTHER INFORMATION: Synthetic Construct

<400> SEQUENCE: 543
agtaagaaga gttt                                                    14

<210> SEQ ID NO 544
<211> LENGTH: 14
<212> TYPE: DNA
<213> ORGANISM: Artificial Sequence
<220> FEATURE:
<223> OTHER INFORMATION: Synthetic Construct

<400> SEQUENCE: 544
gtaagaagag tttt                                                    14

<210> SEQ ID NO 545
<211> LENGTH: 14
<212> TYPE: DNA
<213> ORGANISM: Artificial Sequence
<220> FEATURE:
<223> OTHER INFORMATION: Synthetic Construct

<400> SEQUENCE: 545
taagaagagt ttta                                                    14

<210> SEQ ID NO 546
<211> LENGTH: 14
<212> TYPE: DNA
<213> ORGANISM: Artificial Sequence
<220> FEATURE:
<223> OTHER INFORMATION: Synthetic Construct

<400> SEQUENCE: 546
aagaagagtt ttag                                                    14

<210> SEQ ID NO 547
<211> LENGTH: 14
<212> TYPE: DNA
<213> ORGANISM: Artificial Sequence
<220> FEATURE:
<223> OTHER INFORMATION: Synthetic Construct

<400> SEQUENCE: 547
agaagagttt taga                                                    14

<210> SEQ ID NO 548
<211> LENGTH: 14
<212> TYPE: DNA
<213> ORGANISM: Artificial Sequence
<220> FEATURE:
<223> OTHER INFORMATION: Synthetic Construct

<400> SEQUENCE: 548
```

-continued gaagagtttt agag                                                14

<210> SEQ ID NO 549
<211> LENGTH: 14
<212> TYPE: DNA
<213> ORGANISM: Artificial Sequence
<220> FEATURE:
<223> OTHER INFORMATION: Synthetic Construct

<400> SEQUENCE: 549 aagagttttta gaga                                                14

<210> SEQ ID NO 550
<211> LENGTH: 14
<212> TYPE: DNA
<213> ORGANISM: Artificial Sequence
<220> FEATURE:
<223> OTHER INFORMATION: Synthetic Construct

<400> SEQUENCE: 550
agagttttag agag                                                 14

<210> SEQ ID NO 551
<211> LENGTH: 14
<212> TYPE: DNA
<213> ORGANISM: Artificial Sequence
<220> FEATURE:
<223> OTHER INFORMATION: Synthetic Construct

<400> SEQUENCE: 551
gagttttaga gagt                                                 14

<210> SEQ ID NO 552
<211> LENGTH: 14
<212> TYPE: DNA
<213> ORGANISM: Artificial Sequence
<220> FEATURE:
<223> OTHER INFORMATION: Synthetic Construct

<400> SEQUENCE: 552
agttttagag agta                                                 14

<210> SEQ ID NO 553
<211> LENGTH: 14
<212> TYPE: DNA
<213> ORGANISM: Artificial Sequence
<220> FEATURE:
<223> OTHER INFORMATION: Synthetic Construct

<400> SEQUENCE: 553
gttttagaga gtag                                                 14

<210> SEQ ID NO 554
<211> LENGTH: 14
<212> TYPE: DNA
<213> ORGANISM: Artificial Sequence
<220> FEATURE:
<223> OTHER INFORMATION: Synthetic Construct

<400> SEQUENCE: 554
ttttagagag tagt                                                 14

<210> SEQ ID NO 555
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 555
tttagagagt agtt                                                        14

<210> SEQ ID NO 556
<211> LENGTH: 14
<212> TYPE: DNA
<213> ORGANISM: Artificial Sequence
<220> FEATURE:
<223> OTHER INFORMATION: Synthetic Construct

<400> SEQUENCE: 556
ttagagagta gttt                                                        14

<210> SEQ ID NO 557
<211> LENGTH: 14
<212> TYPE: DNA
<213> ORGANISM: Artificial Sequence
<220> FEATURE:
<223> OTHER INFORMATION: Synthetic Construct

<400> SEQUENCE: 557
tagagagtag tttt                                                        14

<210> SEQ ID NO 558
<211> LENGTH: 14
<212> TYPE: DNA
<213> ORGANISM: Artificial Sequence
<220> FEATURE:
<223> OTHER INFORMATION: Synthetic Construct

<400> SEQUENCE: 558
agagagtagt tttt                                                        14

<210> SEQ ID NO 559
<211> LENGTH: 14
<212> TYPE: DNA
<213> ORGANISM: Artificial Sequence
<220> FEATURE:
<223> OTHER INFORMATION: Synthetic Construct

<400> SEQUENCE: 559
gagagtagtt tttt                                                        14

<210> SEQ ID NO 560
<211> LENGTH: 14
<212> TYPE: DNA
<213> ORGANISM: Artificial Sequence
<220> FEATURE:
<223> OTHER INFORMATION: Synthetic Construct

<400> SEQUENCE: 560
agagtagttt tttc                                                        14

<210> SEQ ID NO 561
<211> LENGTH: 14
<212> TYPE: DNA
<213> ORGANISM: Artificial Sequence
<220> FEATURE:
<223> OTHER INFORMATION: Synthetic Construct

<400> SEQUENCE: 561
gagtagtttt ttcg                                                        14
```

```
<210> SEQ ID NO 562
<211> LENGTH: 14
<212> TYPE: DNA
<213> ORGANISM: Artificial Sequence
<220> FEATURE:
<223> OTHER INFORMATION: Synthetic Construct

<400> SEQUENCE: 562
agtagttttt tcgg                                                       14

<210> SEQ ID NO 563
<211> LENGTH: 14
<212> TYPE: DNA
<213> ORGANISM: Artificial Sequence
<220> FEATURE:
<223> OTHER INFORMATION: Synthetic Construct

<400> SEQUENCE: 563 gtagttttttt cgga                                                      14

<210> SEQ ID NO 564
<211> LENGTH: 14
<212> TYPE: DNA
<213> ORGANISM: Artificial Sequence
<220> FEATURE:
<223> OTHER INFORMATION: Synthetic Construct

<400> SEQUENCE: 564
tagttttttc ggag                                                       14

<210> SEQ ID NO 565
<211> LENGTH: 14
<212> TYPE: DNA
<213> ORGANISM: Artificial Sequence
<220> FEATURE:
<223> OTHER INFORMATION: Synthetic Construct

<400> SEQUENCE: 565
agttttttcg gagt                                                       14

<210> SEQ ID NO 566
<211> LENGTH: 14
<212> TYPE: DNA
<213> ORGANISM: Artificial Sequence
<220> FEATURE:
<223> OTHER INFORMATION: Synthetic Construct

<400> SEQUENCE: 566
gttttttcgg agta                                                       14

<210> SEQ ID NO 567
<211> LENGTH: 14
<212> TYPE: DNA
<213> ORGANISM: Artificial Sequence
<220> FEATURE:
<223> OTHER INFORMATION: Synthetic Construct

<400> SEQUENCE: 567
ttttttcgga gtat                                                       14

<210> SEQ ID NO 568
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 568
tttttcggag tatt                                                14

<210> SEQ ID NO 569
<211> LENGTH: 14
<212> TYPE: DNA
<213> ORGANISM: Artificial Sequence
<220> FEATURE:
<223> OTHER INFORMATION: Synthetic Construct

<400> SEQUENCE: 569
ttttcggagt atta                                                14

<210> SEQ ID NO 570
<211> LENGTH: 14
<212> TYPE: DNA
<213> ORGANISM: Artificial Sequence
<220> FEATURE:
<223> OTHER INFORMATION: Synthetic Construct

<400> SEQUENCE: 570
tttcggagta ttaa                                                14

<210> SEQ ID NO 571
<211> LENGTH: 14
<212> TYPE: DNA
<213> ORGANISM: Artificial Sequence
<220> FEATURE:
<223> OTHER INFORMATION: Synthetic Construct

<400> SEQUENCE: 571
ttcggagtat taat                                                14

<210> SEQ ID NO 572
<211> LENGTH: 14
<212> TYPE: DNA
<213> ORGANISM: Artificial Sequence
<220> FEATURE:
<223> OTHER INFORMATION: Synthetic Construct

<400> SEQUENCE: 572
tcggagtatt aatt                                                14

<210> SEQ ID NO 573
<211> LENGTH: 14
<212> TYPE: DNA
<213> ORGANISM: Artificial Sequence
<220> FEATURE:
<223> OTHER INFORMATION: Synthetic Construct

<400> SEQUENCE: 573
cggagtatta attt                                                14

<210> SEQ ID NO 574
<211> LENGTH: 14
<212> TYPE: DNA
<213> ORGANISM: Artificial Sequence
<220> FEATURE:
<223> OTHER INFORMATION: Synthetic Construct

<400> SEQUENCE: 574
ctcgaaaact cgaa                                                14

<210> SEQ ID NO 575
```

```
<211> LENGTH: 24
<212> TYPE: DNA
<213> ORGANISM: Artificial Sequence
<220> FEATURE:
<223> OTHER INFORMATION: Synthetic Construct

<400> SEQUENCE: 575
aagcgagcgt tttcgagttt cgag                                              24

<210> SEQ ID NO 576
<211> LENGTH: 14
<212> TYPE: DNA
<213> ORGANISM: Artificial Sequence
<220> FEATURE:
<223> OTHER INFORMATION: Synthetic Construct

<400> SEQUENCE: 576
ggagtattaa tttc                                                         14

<210> SEQ ID NO 577
<211> LENGTH: 14
<212> TYPE: DNA
<213> ORGANISM: Artificial Sequence
<220> FEATURE:
<223> OTHER INFORMATION: Synthetic Construct

<400> SEQUENCE: 577
gagtattaat ttcg                                                         14

<210> SEQ ID NO 578
<211> LENGTH: 14
<212> TYPE: DNA
<213> ORGANISM: Artificial Sequence
<220> FEATURE:
<223> OTHER INFORMATION: Synthetic Construct

<400> SEQUENCE: 578
agtattaatt tcgt                                                         14

<210> SEQ ID NO 579
<211> LENGTH: 14
<212> TYPE: DNA
<213> ORGANISM: Artificial Sequence
<220> FEATURE:
<223> OTHER INFORMATION: Synthetic Construct

<400> SEQUENCE: 579
gtattaattt cgtg                                                         14

<210> SEQ ID NO 580
<211> LENGTH: 14
<212> TYPE: DNA
<213> ORGANISM: Artificial Sequence
<220> FEATURE:
<223> OTHER INFORMATION: Synthetic Construct

<400> SEQUENCE: 580
tattaatttc gtgt                                                         14

<210> SEQ ID NO 581
<211> LENGTH: 14
<212> TYPE: DNA
<213> ORGANISM: Artificial Sequence
<220> FEATURE:
<223> OTHER INFORMATION: Synthetic Construct

<400> SEQUENCE: 581
```
attaatttcg tgtc						14

<210> SEQ ID NO 582
<211> LENGTH: 14
<212> TYPE: DNA
<213> ORGANISM: Artificial Sequence
<220> FEATURE:
<223> OTHER INFORMATION: Synthetic Construct

<400> SEQUENCE: 582
ttaatttcgt gtcg						14

<210> SEQ ID NO 583
<211> LENGTH: 14
<212> TYPE: DNA
<213> ORGANISM: Artificial Sequence
<220> FEATURE:
<223> OTHER INFORMATION: Synthetic Construct

<400> SEQUENCE: 583
taatttcgtg tcgg						14

<210> SEQ ID NO 584
<211> LENGTH: 14
<212> TYPE: DNA
<213> ORGANISM: Artificial Sequence
<220> FEATURE:
<223> OTHER INFORMATION: Synthetic Construct

<400> SEQUENCE: 584
aatttcgtgt cggg						14

<210> SEQ ID NO 585
<211> LENGTH: 14
<212> TYPE: DNA
<213> ORGANISM: Artificial Sequence
<220> FEATURE:
<223> OTHER INFORMATION: Synthetic Construct

<400> SEQUENCE: 585
atttcgtgtc ggga						14

<210> SEQ ID NO 586
<211> LENGTH: 14
<212> TYPE: DNA
<213> ORGANISM: Artificial Sequence
<220> FEATURE:
<223> OTHER INFORMATION: Synthetic Construct

<400> SEQUENCE: 586
tttcgtgtcg ggag						14

<210> SEQ ID NO 587
<211> LENGTH: 14
<212> TYPE: DNA
<213> ORGANISM: Artificial Sequence
<220> FEATURE:
<223> OTHER INFORMATION: Synthetic Construct

<400> SEQUENCE: 587
ttcgtgtcgg gagt						14

<210> SEQ ID NO 588
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 588
tcgtgtcggg agtg                                                    14

<210> SEQ ID NO 589
<211> LENGTH: 14
<212> TYPE: DNA
<213> ORGANISM: Artificial Sequence
<220> FEATURE:
<223> OTHER INFORMATION: Synthetic Construct

<400> SEQUENCE: 589
cgtgtcggga gtgt                                                    14

<210> SEQ ID NO 590
<211> LENGTH: 14
<212> TYPE: DNA
<213> ORGANISM: Artificial Sequence
<220> FEATURE:
<223> OTHER INFORMATION: Synthetic Construct

<400> SEQUENCE: 590
gtgtcgggag tgta                                                    14

<210> SEQ ID NO 591
<211> LENGTH: 14
<212> TYPE: DNA
<213> ORGANISM: Artificial Sequence
<220> FEATURE:
<223> OTHER INFORMATION: Synthetic Construct

<400> SEQUENCE: 591
tgtcgggagt gtag                                                    14

<210> SEQ ID NO 592
<211> LENGTH: 14
<212> TYPE: DNA
<213> ORGANISM: Artificial Sequence
<220> FEATURE:
<223> OTHER INFORMATION: Synthetic Construct

<400> SEQUENCE: 592
gtcgggagtg taga                                                    14

<210> SEQ ID NO 593
<211> LENGTH: 14
<212> TYPE: DNA
<213> ORGANISM: Artificial Sequence
<220> FEATURE:
<223> OTHER INFORMATION: Synthetic Construct

<400> SEQUENCE: 593
tcgggagtgt agaa                                                    14

<210> SEQ ID NO 594
<211> LENGTH: 14
<212> TYPE: DNA
<213> ORGANISM: Artificial Sequence
<220> FEATURE:
<223> OTHER INFORMATION: Synthetic Construct

<400> SEQUENCE: 594
cgggagtgta gaaa                                                    14
```

<210> SEQ ID NO 595
<211> LENGTH: 14
<212> TYPE: DNA
<213> ORGANISM: Artificial Sequence
<220> FEATURE:
<223> OTHER INFORMATION: Synthetic Construct

<400> SEQUENCE: 595
gggagtgtag aaat                                                        14

<210> SEQ ID NO 596
<211> LENGTH: 14
<212> TYPE: DNA
<213> ORGANISM: Artificial Sequence
<220> FEATURE:
<223> OTHER INFORMATION: Synthetic Construct

<400> SEQUENCE: 596
ggagtgtaga aatt                                                        14

<210> SEQ ID NO 597
<211> LENGTH: 14
<212> TYPE: DNA
<213> ORGANISM: Artificial Sequence
<220> FEATURE:
<223> OTHER INFORMATION: Synthetic Construct

<400> SEQUENCE: 597
gagtgtagaa atta                                                        14

<210> SEQ ID NO 598
<211> LENGTH: 14
<212> TYPE: DNA
<213> ORGANISM: Artificial Sequence
<220> FEATURE:
<223> OTHER INFORMATION: Synthetic Construct

<400> SEQUENCE: 598
agtgtagaaa ttaa                                                        14

<210> SEQ ID NO 599
<211> LENGTH: 14
<212> TYPE: DNA
<213> ORGANISM: Artificial Sequence
<220> FEATURE:
<223> OTHER INFORMATION: Synthetic Construct

<400> SEQUENCE: 599
gtgtagaaat taat                                                        14

<210> SEQ ID NO 600
<211> LENGTH: 14
<212> TYPE: DNA
<213> ORGANISM: Artificial Sequence
<220> FEATURE:
<223> OTHER INFORMATION: Synthetic Construct

<400> SEQUENCE: 600
tgtagaaatt aata                                                        14

<210> SEQ ID NO 601
<211> LENGTH: 14
<212> TYPE: DNA
<213> ORGANISM: Artificial Sequence
<220> FEATURE:

<223> OTHER INFORMATION: Synthetic Construct

<400> SEQUENCE: 601
gtagaaatta ataa                                                        14

<210> SEQ ID NO 602
<211> LENGTH: 14
<212> TYPE: DNA
<213> ORGANISM: Artificial Sequence
<220> FEATURE:
<223> OTHER INFORMATION: Synthetic Construct

<400> SEQUENCE: 602
tagaaattaa taag                                                        14

<210> SEQ ID NO 603
<211> LENGTH: 14
<212> TYPE: DNA
<213> ORGANISM: Artificial Sequence
<220> FEATURE:
<223> OTHER INFORMATION: Synthetic Construct

<400> SEQUENCE: 603
agaaattaat aagt                                                        14

<210> SEQ ID NO 604
<211> LENGTH: 14
<212> TYPE: DNA
<213> ORGANISM: Artificial Sequence
<220> FEATURE:
<223> OTHER INFORMATION: Synthetic Construct

<400> SEQUENCE: 604
gaaattaata agtg                                                        14

<210> SEQ ID NO 605
<211> LENGTH: 14
<212> TYPE: DNA
<213> ORGANISM: Artificial Sequence
<220> FEATURE:
<223> OTHER INFORMATION: Synthetic Construct

<400> SEQUENCE: 605
aaattaataa gtga                                                        14

<210> SEQ ID NO 606
<211> LENGTH: 14
<212> TYPE: DNA
<213> ORGANISM: Artificial Sequence
<220> FEATURE:
<223> OTHER INFORMATION: Synthetic Construct

<400> SEQUENCE: 606
aattaataag tgag                                                        14

<210> SEQ ID NO 607
<211> LENGTH: 14
<212> TYPE: DNA
<213> ORGANISM: Artificial Sequence
<220> FEATURE:
<223> OTHER INFORMATION: Synthetic Construct

<400> SEQUENCE: 607
attaataagt gaga                                                        14

```
<210> SEQ ID NO 608
<211> LENGTH: 14
<212> TYPE: DNA
<213> ORGANISM: Artificial Sequence
<220> FEATURE:
<223> OTHER INFORMATION: Synthetic Construct

<400> SEQUENCE: 608
ttaataagtg agag                                                           14

<210> SEQ ID NO 609
<211> LENGTH: 14
<212> TYPE: DNA
<213> ORGANISM: Artificial Sequence
<220> FEATURE:
<223> OTHER INFORMATION: Synthetic Construct

<400> SEQUENCE: 609
taataagtga gagg                                                           14

<210> SEQ ID NO 610
<211> LENGTH: 14
<212> TYPE: DNA
<213> ORGANISM: Artificial Sequence
<220> FEATURE:
<223> OTHER INFORMATION: Synthetic Construct

<400> SEQUENCE: 610
aataagtgag aggg                                                           14

<210> SEQ ID NO 611
<211> LENGTH: 14
<212> TYPE: DNA
<213> ORGANISM: Artificial Sequence
<220> FEATURE:
<223> OTHER INFORMATION: Synthetic Construct

<400> SEQUENCE: 611
ataagtgaga gggc                                                           14

<210> SEQ ID NO 612
<211> LENGTH: 14
<212> TYPE: DNA
<213> ORGANISM: Artificial Sequence
<220> FEATURE:
<223> OTHER INFORMATION: Synthetic Construct

<400> SEQUENCE: 612
taagtgagag ggcg                                                           14

<210> SEQ ID NO 613
<211> LENGTH: 14
<212> TYPE: DNA
<213> ORGANISM: Artificial Sequence
<220> FEATURE:
<223> OTHER INFORMATION: Synthetic Construct

<400> SEQUENCE: 613
aagtgagagg gcgt                                                           14

<210> SEQ ID NO 614
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 614
agtgagaggg cgtc                                                       14

<210> SEQ ID NO 615
<211> LENGTH: 14
<212> TYPE: DNA
<213> ORGANISM: Artificial Sequence
<220> FEATURE:
<223> OTHER INFORMATION: Synthetic Construct

<400> SEQUENCE: 615
gtgagagggc gtcg                                                       14

<210> SEQ ID NO 616
<211> LENGTH: 14
<212> TYPE: DNA
<213> ORGANISM: Artificial Sequence
<220> FEATURE:
<223> OTHER INFORMATION: Synthetic Construct

<400> SEQUENCE: 616
tgagagggcg tcgc                                                       14

<210> SEQ ID NO 617
<211> LENGTH: 14
<212> TYPE: DNA
<213> ORGANISM: Artificial Sequence
<220> FEATURE:
<223> OTHER INFORMATION: Synthetic Construct

<400> SEQUENCE: 617
gagagggcgt cgcg                                                       14

<210> SEQ ID NO 618
<211> LENGTH: 14
<212> TYPE: DNA
<213> ORGANISM: Artificial Sequence
<220> FEATURE:
<223> OTHER INFORMATION: Synthetic Construct

<400> SEQUENCE: 618
agagggcgtc gcgt                                                       14

<210> SEQ ID NO 619
<211> LENGTH: 14
<212> TYPE: DNA
<213> ORGANISM: Artificial Sequence
<220> FEATURE:
<223> OTHER INFORMATION: Synthetic Construct

<400> SEQUENCE: 619
gagggcgtcg cgtt                                                       14

<210> SEQ ID NO 620
<211> LENGTH: 14
<212> TYPE: DNA
<213> ORGANISM: Artificial Sequence
<220> FEATURE:
<223> OTHER INFORMATION: Synthetic Construct

<400> SEQUENCE: 620
agggcgtcgc gttt                                                       14

<210> SEQ ID NO 621
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 621
gggcgtcgcg tttt                                                   14

<210> SEQ ID NO 622
<211> LENGTH: 14
<212> TYPE: DNA
<213> ORGANISM: Artificial Sequence
<220> FEATURE:
<223> OTHER INFORMATION: Synthetic Construct

<400> SEQUENCE: 622
ggcgtcgcgt tttc                                                   14

<210> SEQ ID NO 623
<211> LENGTH: 14
<212> TYPE: DNA
<213> ORGANISM: Artificial Sequence
<220> FEATURE:
<223> OTHER INFORMATION: Synthetic Construct

<400> SEQUENCE: 623
gcgtcgcgtt ttcg                                                   14

<210> SEQ ID NO 624
<211> LENGTH: 14
<212> TYPE: DNA
<213> ORGANISM: Artificial Sequence
<220> FEATURE:
<223> OTHER INFORMATION: Synthetic Construct

<400> SEQUENCE: 624
cgtcgcgttt tcgg                                                   14

<210> SEQ ID NO 625
<211> LENGTH: 14
<212> TYPE: DNA
<213> ORGANISM: Artificial Sequence
<220> FEATURE:
<223> OTHER INFORMATION: Synthetic Construct

<400> SEQUENCE: 625
gtcgcgtttt cggg                                                   14

<210> SEQ ID NO 626
<211> LENGTH: 14
<212> TYPE: DNA
<213> ORGANISM: Artificial Sequence
<220> FEATURE:
<223> OTHER INFORMATION: Synthetic Construct

<400> SEQUENCE: 626
tcgcgttttc gggg                                                   14

<210> SEQ ID NO 627
<211> LENGTH: 14
<212> TYPE: DNA
<213> ORGANISM: Artificial Sequence
<220> FEATURE:
<223> OTHER INFORMATION: Synthetic Construct

<400> SEQUENCE: 627
```
cgcgttttcg gggc 14

<210> SEQ ID NO 628
<211> LENGTH: 14
<212> TYPE: DNA
<213> ORGANISM: Artificial Sequence
<220> FEATURE:
<223> OTHER INFORMATION: Synthetic Construct

<400> SEQUENCE: 628
gcgttttcgg ggcg 14

<210> SEQ ID NO 629
<211> LENGTH: 14
<212> TYPE: DNA
<213> ORGANISM: Artificial Sequence
<220> FEATURE:
<223> OTHER INFORMATION: Synthetic Construct

<400> SEQUENCE: 629
cgttttcggg gcgt 14

<210> SEQ ID NO 630
<211> LENGTH: 14
<212> TYPE: DNA
<213> ORGANISM: Artificial Sequence
<220> FEATURE:
<223> OTHER INFORMATION: Synthetic Construct

<400> SEQUENCE: 630
gttttcgggg cgta 14

<210> SEQ ID NO 631
<211> LENGTH: 14
<212> TYPE: DNA
<213> ORGANISM: Artificial Sequence
<220> FEATURE:
<223> OTHER INFORMATION: Synthetic Construct

<400> SEQUENCE: 631
ttttcggggc gtag 14

<210> SEQ ID NO 632
<211> LENGTH: 14
<212> TYPE: DNA
<213> ORGANISM: Artificial Sequence
<220> FEATURE:
<223> OTHER INFORMATION: Synthetic Construct

<400> SEQUENCE: 632
tttcggggcg tagt 14

<210> SEQ ID NO 633
<211> LENGTH: 14
<212> TYPE: DNA
<213> ORGANISM: Artificial Sequence
<220> FEATURE:
<223> OTHER INFORMATION: Synthetic Construct

<400> SEQUENCE: 633
ttcggggcgt agtt 14

<210> SEQ ID NO 634
<211> LENGTH: 14
<212> TYPE: DNA
<213> ORGANISM: Artificial Sequence
<220> FEATURE:
<223> OTHER INFORMATION: Synthetic Construct

<400> SEQUENCE: 634
tcggggcgta gttg                                                        14

<210> SEQ ID NO 635
<211> LENGTH: 14
<212> TYPE: DNA
<213> ORGANISM: Artificial Sequence
<220> FEATURE:
<223> OTHER INFORMATION: Synthetic Construct

<400> SEQUENCE: 635
cggggcgtag ttgc                                                        14

<210> SEQ ID NO 636
<211> LENGTH: 14
<212> TYPE: DNA
<213> ORGANISM: Artificial Sequence
<220> FEATURE:
<223> OTHER INFORMATION: Synthetic Construct

<400> SEQUENCE: 636
ggggcgtagt tgcg                                                        14

<210> SEQ ID NO 637
<211> LENGTH: 14
<212> TYPE: DNA
<213> ORGANISM: Artificial Sequence
<220> FEATURE:
<223> OTHER INFORMATION: Synthetic Construct

<400> SEQUENCE: 637
cgctcgacgc aacc                                                        14

<210> SEQ ID NO 638
<211> LENGTH: 26
<212> TYPE: DNA
<213> ORGANISM: Artificial Sequence
<220> FEATURE:
<223> OTHER INFORMATION: Synthetic Construct

<400> SEQUENCE: 638
tattttgttt cggattcgtg tgcgcg                                           26

<210> SEQ ID NO 639
<211> LENGTH: 14
<212> TYPE: DNA
<213> ORGANISM: Artificial Sequence
<220> FEATURE:
<223> OTHER INFORMATION: Synthetic Construct

<400> SEQUENCE: 639
gggcgtagtt gcgg                                                        14

<210> SEQ ID NO 640
<211> LENGTH: 14
<212> TYPE: DNA
<213> ORGANISM: Artificial Sequence
<220> FEATURE:
<223> OTHER INFORMATION: Synthetic Construct

<400> SEQUENCE: 640
ggcgtagttg cggg                                                        14

<210> SEQ ID NO 641
<211> LENGTH: 14
<212> TYPE: DNA
<213> ORGANISM: Artificial Sequence
<220> FEATURE:
<223> OTHER INFORMATION: Synthetic Construct

<400> SEQUENCE: 641
gcgtagttgc gggc                                                      14

<210> SEQ ID NO 642
<211> LENGTH: 14
<212> TYPE: DNA
<213> ORGANISM: Artificial Sequence
<220> FEATURE:
<223> OTHER INFORMATION: Synthetic Construct

<400> SEQUENCE: 642
cgtagttgcg ggcg                                                      14

<210> SEQ ID NO 643
<211> LENGTH: 14
<212> TYPE: DNA
<213> ORGANISM: Artificial Sequence
<220> FEATURE:
<223> OTHER INFORMATION: Synthetic Construct

<400> SEQUENCE: 643
gtagttgcgg gcgg                                                      14

<210> SEQ ID NO 644
<211> LENGTH: 14
<212> TYPE: DNA
<213> ORGANISM: Artificial Sequence
<220> FEATURE:
<223> OTHER INFORMATION: Synthetic Construct

<400> SEQUENCE: 644
tagttgcggg cggc                                                      14

<210> SEQ ID NO 645
<211> LENGTH: 14
<212> TYPE: DNA
<213> ORGANISM: Artificial Sequence
<220> FEATURE:
<223> OTHER INFORMATION: Synthetic Construct

<400> SEQUENCE: 645
agttgcgggc ggcg                                                      14

<210> SEQ ID NO 646
<211> LENGTH: 14
<212> TYPE: DNA
<213> ORGANISM: Artificial Sequence
<220> FEATURE:
<223> OTHER INFORMATION: Synthetic Construct

<400> SEQUENCE: 646
gttgcgggcg gcgg                                                      14

<210> SEQ ID NO 647
<211> LENGTH: 14
<212> TYPE: DNA
<213> ORGANISM: Artificial Sequence
<220> FEATURE:
<223> OTHER INFORMATION: Synthetic Construct

```
<400> SEQUENCE: 647
ttgcgggcgg cggg                                                        14

<210> SEQ ID NO 648
<211> LENGTH: 14
<212> TYPE: DNA
<213> ORGANISM: Artificial Sequence
<220> FEATURE:
<223> OTHER INFORMATION: Synthetic Construct

<400> SEQUENCE: 648
tgcgggcggc ggga                                                        14

<210> SEQ ID NO 649
<211> LENGTH: 14
<212> TYPE: DNA
<213> ORGANISM: Artificial Sequence
<220> FEATURE:
<223> OTHER INFORMATION: Synthetic Construct

<400> SEQUENCE: 649
gcgggcggcg ggag                                                        14

<210> SEQ ID NO 650
<211> LENGTH: 14
<212> TYPE: DNA
<213> ORGANISM: Artificial Sequence
<220> FEATURE:
<223> OTHER INFORMATION: Synthetic Construct

<400> SEQUENCE: 650
cgggcggcgg gagt                                                        14

<210> SEQ ID NO 651
<211> LENGTH: 14
<212> TYPE: DNA
<213> ORGANISM: Artificial Sequence
<220> FEATURE:
<223> OTHER INFORMATION: Synthetic Construct

<400> SEQUENCE: 651
gggcggcggg agta                                                        14

<210> SEQ ID NO 652
<211> LENGTH: 14
<212> TYPE: DNA
<213> ORGANISM: Artificial Sequence
<220> FEATURE:
<223> OTHER INFORMATION: Synthetic Construct

<400> SEQUENCE: 652
ggcggcggga gtag                                                        14

<210> SEQ ID NO 653
<211> LENGTH: 14
<212> TYPE: DNA
<213> ORGANISM: Artificial Sequence
<220> FEATURE:
<223> OTHER INFORMATION: Synthetic Construct

<400> SEQUENCE: 653
gcggcgggag tagg                                                        14

<210> SEQ ID NO 654
```

-continued

<211> LENGTH: 14
<212> TYPE: DNA
<213> ORGANISM: Artificial Sequence
<220> FEATURE:
<223> OTHER INFORMATION: Synthetic Construct

<400> SEQUENCE: 654
cggcgggagt aggc                                                                 14

<210> SEQ ID NO 655
<211> LENGTH: 14
<212> TYPE: DNA
<213> ORGANISM: Artificial Sequence
<220> FEATURE:
<223> OTHER INFORMATION: Synthetic Construct

<400> SEQUENCE: 655
ggcgggagta ggcg                                                                 14

<210> SEQ ID NO 656
<211> LENGTH: 14
<212> TYPE: DNA
<213> ORGANISM: Artificial Sequence
<220> FEATURE:
<223> OTHER INFORMATION: Synthetic Construct

<400> SEQUENCE: 656
gcgggagtag gcgt                                                                 14

<210> SEQ ID NO 657
<211> LENGTH: 14
<212> TYPE: DNA
<213> ORGANISM: Artificial Sequence
<220> FEATURE:
<223> OTHER INFORMATION: Synthetic Construct

<400> SEQUENCE: 657
cgggagtagg cgta                                                                 14

<210> SEQ ID NO 658
<211> LENGTH: 14
<212> TYPE: DNA
<213> ORGANISM: Artificial Sequence
<220> FEATURE:
<223> OTHER INFORMATION: Synthetic Construct

<400> SEQUENCE: 658
gggagtaggc gtag                                                                 14

<210> SEQ ID NO 659
<211> LENGTH: 14
<212> TYPE: DNA
<213> ORGANISM: Artificial Sequence
<220> FEATURE:
<223> OTHER INFORMATION: Synthetic Construct

<400> SEQUENCE: 659
ggagtaggcg tagg                                                                 14

<210> SEQ ID NO 660
<211> LENGTH: 14
<212> TYPE: DNA
<213> ORGANISM: Artificial Sequence
<220> FEATURE:
<223> OTHER INFORMATION: Synthetic Construct

<400> SEQUENCE: 660
gagtaggcgt agga                                                14

<210> SEQ ID NO 661
<211> LENGTH: 14
<212> TYPE: DNA
<213> ORGANISM: Artificial Sequence
<220> FEATURE:
<223> OTHER INFORMATION: Synthetic Construct

<400> SEQUENCE: 661
agtaggcgta ggag                                                14

<210> SEQ ID NO 662
<211> LENGTH: 14
<212> TYPE: DNA
<213> ORGANISM: Artificial Sequence
<220> FEATURE:
<223> OTHER INFORMATION: Synthetic Construct

<400> SEQUENCE: 662
gtaggcgtag gagg                                                14

<210> SEQ ID NO 663
<211> LENGTH: 14
<212> TYPE: DNA
<213> ORGANISM: Artificial Sequence
<220> FEATURE:
<223> OTHER INFORMATION: Synthetic Construct

<400> SEQUENCE: 663
taggcgtagg agga                                                14

<210> SEQ ID NO 664
<211> LENGTH: 14
<212> TYPE: DNA
<213> ORGANISM: Artificial Sequence
<220> FEATURE:
<223> OTHER INFORMATION: Synthetic Construct

<400> SEQUENCE: 664
aggcgtagga ggag                                                14

<210> SEQ ID NO 665
<211> LENGTH: 14
<212> TYPE: DNA
<213> ORGANISM: Artificial Sequence
<220> FEATURE:
<223> OTHER INFORMATION: Synthetic Construct

<400> SEQUENCE: 665
ggcgtaggag gagg                                                14

<210> SEQ ID NO 666
<211> LENGTH: 14
<212> TYPE: DNA
<213> ORGANISM: Artificial Sequence
<220> FEATURE:
<223> OTHER INFORMATION: Synthetic Construct

<400> SEQUENCE: 666
gcgtaggagg agga                                                14

<210> SEQ ID NO 667
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 667
cgtaggagga ggaa                                                    14

<210> SEQ ID NO 668
<211> LENGTH: 14
<212> TYPE: DNA
<213> ORGANISM: Artificial Sequence
<220> FEATURE:
<223> OTHER INFORMATION: Synthetic Construct

<400> SEQUENCE: 668
gtaggaggag gaag                                                    14

<210> SEQ ID NO 669
<211> LENGTH: 14
<212> TYPE: DNA
<213> ORGANISM: Artificial Sequence
<220> FEATURE:
<223> OTHER INFORMATION: Synthetic Construct

<400> SEQUENCE: 669
taggaggagg aagc                                                    14

<210> SEQ ID NO 670
<211> LENGTH: 14
<212> TYPE: DNA
<213> ORGANISM: Artificial Sequence
<220> FEATURE:
<223> OTHER INFORMATION: Synthetic Construct

<400> SEQUENCE: 670
aggaggagga agcg                                                    14

<210> SEQ ID NO 671
<211> LENGTH: 14
<212> TYPE: DNA
<213> ORGANISM: Artificial Sequence
<220> FEATURE:
<223> OTHER INFORMATION: Synthetic Construct

<400> SEQUENCE: 671
ggaggaggaa gcga                                                    14

<210> SEQ ID NO 672
<211> LENGTH: 14
<212> TYPE: DNA
<213> ORGANISM: Artificial Sequence
<220> FEATURE:
<223> OTHER INFORMATION: Synthetic Construct

<400> SEQUENCE: 672
gaggaggaag cgag                                                    14

<210> SEQ ID NO 673
<211> LENGTH: 14
<212> TYPE: DNA
<213> ORGANISM: Artificial Sequence
<220> FEATURE:
<223> OTHER INFORMATION: Synthetic Construct

<400> SEQUENCE: 673
aggaggaagc gagc                                                    14
```

```
<210> SEQ ID NO 674
<211> LENGTH: 14
<212> TYPE: DNA
<213> ORGANISM: Artificial Sequence
<220> FEATURE:
<223> OTHER INFORMATION: Synthetic Construct

<400> SEQUENCE: 674
ggaggaagcg agcg                                                       14

<210> SEQ ID NO 675
<211> LENGTH: 14
<212> TYPE: DNA
<213> ORGANISM: Artificial Sequence
<220> FEATURE:
<223> OTHER INFORMATION: Synthetic Construct

<400> SEQUENCE: 675
gaggaagcga gcgt                                                       14

<210> SEQ ID NO 676
<211> LENGTH: 14
<212> TYPE: DNA
<213> ORGANISM: Artificial Sequence
<220> FEATURE:
<223> OTHER INFORMATION: Synthetic Construct

<400> SEQUENCE: 676
aggaagcgag cgtt                                                       14

<210> SEQ ID NO 677
<211> LENGTH: 14
<212> TYPE: DNA
<213> ORGANISM: Artificial Sequence
<220> FEATURE:
<223> OTHER INFORMATION: Synthetic Construct

<400> SEQUENCE: 677
ggaagcgagc gttt                                                       14

<210> SEQ ID NO 678
<211> LENGTH: 14
<212> TYPE: DNA
<213> ORGANISM: Artificial Sequence
<220> FEATURE:
<223> OTHER INFORMATION: Synthetic Construct

<400> SEQUENCE: 678
gaagcgagcg tttt                                                       14

<210> SEQ ID NO 679
<211> LENGTH: 14
<212> TYPE: DNA
<213> ORGANISM: Artificial Sequence
<220> FEATURE:
<223> OTHER INFORMATION: Synthetic Construct

<400> SEQUENCE: 679
aagcgagcgt tttc                                                       14

<210> SEQ ID NO 680
<211> LENGTH: 14
<212> TYPE: DNA
<213> ORGANISM: Artificial Sequence
<220> FEATURE:
```

<223> OTHER INFORMATION: Synthetic Construct

<400> SEQUENCE: 680
agcgagcgtt ttcg                                                              14

<210> SEQ ID NO 681
<211> LENGTH: 14
<212> TYPE: DNA
<213> ORGANISM: Artificial Sequence
<220> FEATURE:
<223> OTHER INFORMATION: Synthetic Construct

<400> SEQUENCE: 681
gcgagcgttt tcga                                                              14

<210> SEQ ID NO 682
<211> LENGTH: 14
<212> TYPE: DNA
<213> ORGANISM: Artificial Sequence
<220> FEATURE:
<223> OTHER INFORMATION: Synthetic Construct

<400> SEQUENCE: 682
cgagcgtttt cgag                                                              14

<210> SEQ ID NO 683
<211> LENGTH: 14
<212> TYPE: DNA
<213> ORGANISM: Artificial Sequence
<220> FEATURE:
<223> OTHER INFORMATION: Synthetic Construct

<400> SEQUENCE: 683
gagcgttttc gagt                                                              14

<210> SEQ ID NO 684
<211> LENGTH: 14
<212> TYPE: DNA
<213> ORGANISM: Artificial Sequence
<220> FEATURE:
<223> OTHER INFORMATION: Synthetic Construct

<400> SEQUENCE: 684
agcgttttcg agtt                                                              14

<210> SEQ ID NO 685
<211> LENGTH: 14
<212> TYPE: DNA
<213> ORGANISM: Artificial Sequence
<220> FEATURE:
<223> OTHER INFORMATION: Synthetic Construct

<400> SEQUENCE: 685
gcgttttcga gttt                                                              14

<210> SEQ ID NO 686
<211> LENGTH: 14
<212> TYPE: DNA
<213> ORGANISM: Artificial Sequence
<220> FEATURE:
<223> OTHER INFORMATION: Synthetic Construct

<400> SEQUENCE: 686
cgttttcgag tttc                                                              14

```
<210> SEQ ID NO 687
<211> LENGTH: 14
<212> TYPE: DNA
<213> ORGANISM: Artificial Sequence
<220> FEATURE:
<223> OTHER INFORMATION: Synthetic Construct

<400> SEQUENCE: 687
gttttcgagt ttcg                                                      14

<210> SEQ ID NO 688
<211> LENGTH: 14
<212> TYPE: DNA
<213> ORGANISM: Artificial Sequence
<220> FEATURE:
<223> OTHER INFORMATION: Synthetic Construct

<400> SEQUENCE: 688
ttttcgagtt tcga                                                      14

<210> SEQ ID NO 689
<211> LENGTH: 14
<212> TYPE: DNA
<213> ORGANISM: Artificial Sequence
<220> FEATURE:
<223> OTHER INFORMATION: Synthetic Construct

<400> SEQUENCE: 689
tttcgagttt cgag                                                      14

<210> SEQ ID NO 690
<211> LENGTH: 14
<212> TYPE: DNA
<213> ORGANISM: Artificial Sequence
<220> FEATURE:
<223> OTHER INFORMATION: Synthetic Construct

<400> SEQUENCE: 690
ttcgagtttc gagt                                                      14

<210> SEQ ID NO 691
<211> LENGTH: 14
<212> TYPE: DNA
<213> ORGANISM: Artificial Sequence
<220> FEATURE:
<223> OTHER INFORMATION: Synthetic Construct

<400> SEQUENCE: 691
tcgagtttcg agtt                                                      14

<210> SEQ ID NO 692
<211> LENGTH: 14
<212> TYPE: DNA
<213> ORGANISM: Artificial Sequence
<220> FEATURE:
<223> OTHER INFORMATION: Synthetic Construct

<400> SEQUENCE: 692
cgagtttcga gttc                                                      14

<210> SEQ ID NO 693
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 693
gagtttcgag ttcg                                                                14

<210> SEQ ID NO 694
<211> LENGTH: 14
<212> TYPE: DNA
<213> ORGANISM: Artificial Sequence
<220> FEATURE:
<223> OTHER INFORMATION: Synthetic Construct

<400> SEQUENCE: 694
agtttcgagt tcga                                                                14

<210> SEQ ID NO 695
<211> LENGTH: 14
<212> TYPE: DNA
<213> ORGANISM: Artificial Sequence
<220> FEATURE:
<223> OTHER INFORMATION: Synthetic Construct

<400> SEQUENCE: 695
gtttcgagtt cgag                                                                14

<210> SEQ ID NO 696
<211> LENGTH: 14
<212> TYPE: DNA
<213> ORGANISM: Artificial Sequence
<220> FEATURE:
<223> OTHER INFORMATION: Synthetic Construct

<400> SEQUENCE: 696
tttcgagttc gagt                                                                14

<210> SEQ ID NO 697
<211> LENGTH: 14
<212> TYPE: DNA
<213> ORGANISM: Artificial Sequence
<220> FEATURE:
<223> OTHER INFORMATION: Synthetic Construct

<400> SEQUENCE: 697
ttcgagttcg agtt                                                                14

<210> SEQ ID NO 698
<211> LENGTH: 14
<212> TYPE: DNA
<213> ORGANISM: Artificial Sequence
<220> FEATURE:
<223> OTHER INFORMATION: Synthetic Construct

<400> SEQUENCE: 698
tcgagttcga gttt                                                                14

<210> SEQ ID NO 699
<211> LENGTH: 14
<212> TYPE: DNA
<213> ORGANISM: Artificial Sequence
<220> FEATURE:
<223> OTHER INFORMATION: Synthetic Construct

<400> SEQUENCE: 699
cgagttcgag tttt                                                                14

<210> SEQ ID NO 700
<211> LENGTH: 14

```
<212> TYPE: DNA
<213> ORGANISM: Artificial Sequence
<220> FEATURE:
<223> OTHER INFORMATION: Synthetic Construct

<400> SEQUENCE: 700
caaaaaccga ctac                                                         14

<210> SEQ ID NO 701
<211> LENGTH: 24
<212> TYPE: DNA
<213> ORGANISM: Artificial Sequence
<220> FEATURE:
<223> OTHER INFORMATION: Synthetic Construct

<400> SEQUENCE: 701
tttggttgta agtagcggtt ggga                                              24

<210> SEQ ID NO 702
<211> LENGTH: 14
<212> TYPE: DNA
<213> ORGANISM: Artificial Sequence
<220> FEATURE:
<223> OTHER INFORMATION: Synthetic Construct

<400> SEQUENCE: 702
gagttcgagt tttc                                                         14

<210> SEQ ID NO 703
<211> LENGTH: 14
<212> TYPE: DNA
<213> ORGANISM: Artificial Sequence
<220> FEATURE:
<223> OTHER INFORMATION: Synthetic Construct

<400> SEQUENCE: 703
agttcgagtt ttcg                                                         14

<210> SEQ ID NO 704
<211> LENGTH: 14
<212> TYPE: DNA
<213> ORGANISM: Artificial Sequence
<220> FEATURE:
<223> OTHER INFORMATION: Synthetic Construct

<400> SEQUENCE: 704
gttcgagttt tcga                                                         14

<210> SEQ ID NO 705
<211> LENGTH: 14
<212> TYPE: DNA
<213> ORGANISM: Artificial Sequence
<220> FEATURE:
<223> OTHER INFORMATION: Synthetic Construct

<400> SEQUENCE: 705
ttcgagtttt cgag                                                         14

<210> SEQ ID NO 706
<211> LENGTH: 14
<212> TYPE: DNA
<213> ORGANISM: Artificial Sequence
<220> FEATURE:
<223> OTHER INFORMATION: Synthetic Construct

<400> SEQUENCE: 706
```

|  |  |
|---|---|
| tcgagttttc gagt | 14 |

<210> SEQ ID NO 707
<211> LENGTH: 14
<212> TYPE: DNA
<213> ORGANISM: Artificial Sequence
<220> FEATURE:
<223> OTHER INFORMATION: Synthetic Construct

<400> SEQUENCE: 707

|  |  |
|---|---|
| cgagttttcg agtt | 14 |

<210> SEQ ID NO 708
<211> LENGTH: 14
<212> TYPE: DNA
<213> ORGANISM: Artificial Sequence
<220> FEATURE:
<223> OTHER INFORMATION: Synthetic Construct

<400> SEQUENCE: 708

|  |  |
|---|---|
| gagttttcga gttt | 14 |

<210> SEQ ID NO 709
<211> LENGTH: 14
<212> TYPE: DNA
<213> ORGANISM: Artificial Sequence
<220> FEATURE:
<223> OTHER INFORMATION: Synthetic Construct

<400> SEQUENCE: 709

|  |  |
|---|---|
| agttttcgag tttg | 14 |

<210> SEQ ID NO 710
<211> LENGTH: 14
<212> TYPE: DNA
<213> ORGANISM: Artificial Sequence
<220> FEATURE:
<223> OTHER INFORMATION: Synthetic Construct

<400> SEQUENCE: 710

|  |  |
|---|---|
| gttttcgagt ttga | 14 |

<210> SEQ ID NO 711
<211> LENGTH: 14
<212> TYPE: DNA
<213> ORGANISM: Artificial Sequence
<220> FEATURE:
<223> OTHER INFORMATION: Synthetic Construct

<400> SEQUENCE: 711

|  |  |
|---|---|
| ttttcgagtt tgag | 14 |

<210> SEQ ID NO 712
<211> LENGTH: 14
<212> TYPE: DNA
<213> ORGANISM: Artificial Sequence
<220> FEATURE:
<223> OTHER INFORMATION: Synthetic Construct

<400> SEQUENCE: 712

|  |  |
|---|---|
| tttcgagttt gagt | 14 |

<210> SEQ ID NO 713
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 713
ttcgagtttg agtc                                                       14

<210> SEQ ID NO 714
<211> LENGTH: 14
<212> TYPE: DNA
<213> ORGANISM: Artificial Sequence
<220> FEATURE:
<223> OTHER INFORMATION: Synthetic Construct

<400> SEQUENCE: 714
tcgagtttga gtcg                                                       14

<210> SEQ ID NO 715
<211> LENGTH: 14
<212> TYPE: DNA
<213> ORGANISM: Artificial Sequence
<220> FEATURE:
<223> OTHER INFORMATION: Synthetic Construct

<400> SEQUENCE: 715
cgagtttgag tcgt                                                       14

<210> SEQ ID NO 716
<211> LENGTH: 14
<212> TYPE: DNA
<213> ORGANISM: Artificial Sequence
<220> FEATURE:
<223> OTHER INFORMATION: Synthetic Construct

<400> SEQUENCE: 716
gagtttgagt cgta                                                       14

<210> SEQ ID NO 717
<211> LENGTH: 14
<212> TYPE: DNA
<213> ORGANISM: Artificial Sequence
<220> FEATURE:
<223> OTHER INFORMATION: Synthetic Construct

<400> SEQUENCE: 717
agtttgagtc gtaa                                                       14

<210> SEQ ID NO 718
<211> LENGTH: 14
<212> TYPE: DNA
<213> ORGANISM: Artificial Sequence
<220> FEATURE:
<223> OTHER INFORMATION: Synthetic Construct

<400> SEQUENCE: 718
gtttgagtcg taat                                                       14

<210> SEQ ID NO 719
<211> LENGTH: 14
<212> TYPE: DNA
<213> ORGANISM: Artificial Sequence
<220> FEATURE:
<223> OTHER INFORMATION: Synthetic Construct

<400> SEQUENCE: 719
tttgagtcgt aatc                                                       14
```

<210> SEQ ID NO 720
<211> LENGTH: 14
<212> TYPE: DNA
<213> ORGANISM: Artificial Sequence
<220> FEATURE:
<223> OTHER INFORMATION: Synthetic Construct

<400> SEQUENCE: 720
ttgagtcgta atcg                                                             14

<210> SEQ ID NO 721
<211> LENGTH: 14
<212> TYPE: DNA
<213> ORGANISM: Artificial Sequence
<220> FEATURE:
<223> OTHER INFORMATION: Synthetic Construct

<400> SEQUENCE: 721
tgagtcgtaa tcgt                                                             14

<210> SEQ ID NO 722
<211> LENGTH: 14
<212> TYPE: DNA
<213> ORGANISM: Artificial Sequence
<220> FEATURE:
<223> OTHER INFORMATION: Synthetic Construct

<400> SEQUENCE: 722
gagtcgtaat cgtt                                                             14

<210> SEQ ID NO 723
<211> LENGTH: 14
<212> TYPE: DNA
<213> ORGANISM: Artificial Sequence
<220> FEATURE:
<223> OTHER INFORMATION: Synthetic Construct

<400> SEQUENCE: 723
agtcgtaatc gttg                                                             14

<210> SEQ ID NO 724
<211> LENGTH: 14
<212> TYPE: DNA
<213> ORGANISM: Artificial Sequence
<220> FEATURE:
<223> OTHER INFORMATION: Synthetic Construct

<400> SEQUENCE: 724
gtcgtaatcg ttgc                                                             14

<210> SEQ ID NO 725
<211> LENGTH: 14
<212> TYPE: DNA
<213> ORGANISM: Artificial Sequence
<220> FEATURE:
<223> OTHER INFORMATION: Synthetic Construct

<400> SEQUENCE: 725
tcgtaatcgt tgcg                                                             14

<210> SEQ ID NO 726
<211> LENGTH: 14
<212> TYPE: DNA
<213> ORGANISM: Artificial Sequence
<220> FEATURE:
<223> OTHER INFORMATION: Synthetic Construct

<400> SEQUENCE: 726
cgtaatcgtt gcgg                                                    14

<210> SEQ ID NO 727
<211> LENGTH: 14
<212> TYPE: DNA
<213> ORGANISM: Artificial Sequence
<220> FEATURE:
<223> OTHER INFORMATION: Synthetic Construct

<400> SEQUENCE: 727
gtaatcgttg cggt                                                    14

<210> SEQ ID NO 728
<211> LENGTH: 14
<212> TYPE: DNA
<213> ORGANISM: Artificial Sequence
<220> FEATURE:
<223> OTHER INFORMATION: Synthetic Construct

<400> SEQUENCE: 728
taatcgttgc ggta                                                    14

<210> SEQ ID NO 729
<211> LENGTH: 14
<212> TYPE: DNA
<213> ORGANISM: Artificial Sequence
<220> FEATURE:
<223> OTHER INFORMATION: Synthetic Construct

<400> SEQUENCE: 729
aatcgttgcg gtat                                                    14

<210> SEQ ID NO 730
<211> LENGTH: 14
<212> TYPE: DNA
<213> ORGANISM: Artificial Sequence
<220> FEATURE:
<223> OTHER INFORMATION: Synthetic Construct

<400> SEQUENCE: 730
atcgttgcgg tatt                                                    14

<210> SEQ ID NO 731
<211> LENGTH: 14
<212> TYPE: DNA
<213> ORGANISM: Artificial Sequence
<220> FEATURE:
<223> OTHER INFORMATION: Synthetic Construct

<400> SEQUENCE: 731
tcgttgcggt attt                                                    14

<210> SEQ ID NO 732
<211> LENGTH: 14
<212> TYPE: DNA
<213> ORGANISM: Artificial Sequence
<220> FEATURE:
<223> OTHER INFORMATION: Synthetic Construct

<400> SEQUENCE: 732
cgttgcggta tttt                                                    14

<210> SEQ ID NO 733

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 733
gttgcggtat tttg                                                         14

<210> SEQ ID NO 734
<211> LENGTH: 14
<212> TYPE: DNA
<213> ORGANISM: Artificial Sequence
<220> FEATURE:
<223> OTHER INFORMATION: Synthetic Construct

<400> SEQUENCE: 734
ttgcggtatt ttgt                                                         14

<210> SEQ ID NO 735
<211> LENGTH: 14
<212> TYPE: DNA
<213> ORGANISM: Artificial Sequence
<220> FEATURE:
<223> OTHER INFORMATION: Synthetic Construct

<400> SEQUENCE: 735
tgcggtattt tgtt                                                         14

<210> SEQ ID NO 736
<211> LENGTH: 14
<212> TYPE: DNA
<213> ORGANISM: Artificial Sequence
<220> FEATURE:
<223> OTHER INFORMATION: Synthetic Construct

<400> SEQUENCE: 736
gcggtatttt gttt                                                         14

<210> SEQ ID NO 737
<211> LENGTH: 14
<212> TYPE: DNA
<213> ORGANISM: Artificial Sequence
<220> FEATURE:
<223> OTHER INFORMATION: Synthetic Construct

<400> SEQUENCE: 737
cggtattttg tttc                                                         14

<210> SEQ ID NO 738
<211> LENGTH: 14
<212> TYPE: DNA
<213> ORGANISM: Artificial Sequence
<220> FEATURE:
<223> OTHER INFORMATION: Synthetic Construct

<400> SEQUENCE: 738
ggtattttgt ttcg                                                         14

<210> SEQ ID NO 739
<211> LENGTH: 14
<212> TYPE: DNA
<213> ORGANISM: Artificial Sequence
<220> FEATURE:
<223> OTHER INFORMATION: Synthetic Construct

<400> SEQUENCE: 739
``` gtatttttgtt tcgg                                                    14

<210> SEQ ID NO 740
<211> LENGTH: 14
<212> TYPE: DNA
<213> ORGANISM: Artificial Sequence
<220> FEATURE:
<223> OTHER INFORMATION: Synthetic Construct

<400> SEQUENCE: 740
tattttgttt cgga                                                     14

<210> SEQ ID NO 741
<211> LENGTH: 14
<212> TYPE: DNA
<213> ORGANISM: Artificial Sequence
<220> FEATURE:
<223> OTHER INFORMATION: Synthetic Construct

<400> SEQUENCE: 741
attttgtttc ggat                                                     14

<210> SEQ ID NO 742
<211> LENGTH: 14
<212> TYPE: DNA
<213> ORGANISM: Artificial Sequence
<220> FEATURE:
<223> OTHER INFORMATION: Synthetic Construct

<400> SEQUENCE: 742
ttttgtttcg gatt                                                     14

<210> SEQ ID NO 743
<211> LENGTH: 14
<212> TYPE: DNA
<213> ORGANISM: Artificial Sequence
<220> FEATURE:
<223> OTHER INFORMATION: Synthetic Construct

<400> SEQUENCE: 743
tttgtttcgg attc                                                     14

<210> SEQ ID NO 744
<211> LENGTH: 14
<212> TYPE: DNA
<213> ORGANISM: Artificial Sequence
<220> FEATURE:
<223> OTHER INFORMATION: Synthetic Construct

<400> SEQUENCE: 744
ttgtttcgga ttcg                                                     14

<210> SEQ ID NO 745
<211> LENGTH: 14
<212> TYPE: DNA
<213> ORGANISM: Artificial Sequence
<220> FEATURE:
<223> OTHER INFORMATION: Synthetic Construct

<400> SEQUENCE: 745
tgtttcggat tcgt                                                     14

<210> SEQ ID NO 746
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 746
gtttcggatt cgtg                                                     14

<210> SEQ ID NO 747
<211> LENGTH: 14
<212> TYPE: DNA
<213> ORGANISM: Artificial Sequence
<220> FEATURE:
<223> OTHER INFORMATION: Synthetic Construct

<400> SEQUENCE: 747
tttcggattc gtgt                                                     14

<210> SEQ ID NO 748
<211> LENGTH: 14
<212> TYPE: DNA
<213> ORGANISM: Artificial Sequence
<220> FEATURE:
<223> OTHER INFORMATION: Synthetic Construct

<400> SEQUENCE: 748
ttcggattcg tgtg                                                     14

<210> SEQ ID NO 749
<211> LENGTH: 14
<212> TYPE: DNA
<213> ORGANISM: Artificial Sequence
<220> FEATURE:
<223> OTHER INFORMATION: Synthetic Construct

<400> SEQUENCE: 749
tcggattcgt gtgc                                                     14

<210> SEQ ID NO 750
<211> LENGTH: 14
<212> TYPE: DNA
<213> ORGANISM: Artificial Sequence
<220> FEATURE:
<223> OTHER INFORMATION: Synthetic Construct

<400> SEQUENCE: 750
cggattcgtg tgcg                                                     14

<210> SEQ ID NO 751
<211> LENGTH: 14
<212> TYPE: DNA
<213> ORGANISM: Artificial Sequence
<220> FEATURE:
<223> OTHER INFORMATION: Synthetic Construct

<400> SEQUENCE: 751
ggattcgtgt gcgc                                                     14

<210> SEQ ID NO 752
<211> LENGTH: 14
<212> TYPE: DNA
<213> ORGANISM: Artificial Sequence
<220> FEATURE:
<223> OTHER INFORMATION: Synthetic Construct

<400> SEQUENCE: 752
gattcgtgtg cgcg                                                     14
```

<210> SEQ ID NO 753
<211> LENGTH: 14
<212> TYPE: DNA
<213> ORGANISM: Artificial Sequence
<220> FEATURE:
<223> OTHER INFORMATION: Synthetic Construct

<400> SEQUENCE: 753
attcgtgtgc gcgg                                              14

<210> SEQ ID NO 754
<211> LENGTH: 14
<212> TYPE: DNA
<213> ORGANISM: Artificial Sequence
<220> FEATURE:
<223> OTHER INFORMATION: Synthetic Construct

<400> SEQUENCE: 754
ttcgtgtgcg cggg                                              14

<210> SEQ ID NO 755
<211> LENGTH: 14
<212> TYPE: DNA
<213> ORGANISM: Artificial Sequence
<220> FEATURE:
<223> OTHER INFORMATION: Synthetic Construct

<400> SEQUENCE: 755
tcgtgtgcgc gggt                                              14

<210> SEQ ID NO 756
<211> LENGTH: 14
<212> TYPE: DNA
<213> ORGANISM: Artificial Sequence
<220> FEATURE:
<223> OTHER INFORMATION: Synthetic Construct

<400> SEQUENCE: 756
cgtgtgcgcg ggtt                                              14

<210> SEQ ID NO 757
<211> LENGTH: 14
<212> TYPE: DNA
<213> ORGANISM: Artificial Sequence
<220> FEATURE:
<223> OTHER INFORMATION: Synthetic Construct

<400> SEQUENCE: 757
gtgtgcgcgg gttg                                              14

<210> SEQ ID NO 758
<211> LENGTH: 14
<212> TYPE: DNA
<213> ORGANISM: Artificial Sequence
<220> FEATURE:
<223> OTHER INFORMATION: Synthetic Construct

<400> SEQUENCE: 758
tgtgcgcggg ttgc                                              14

<210> SEQ ID NO 759
<211> LENGTH: 14
<212> TYPE: DNA
<213> ORGANISM: Artificial Sequence
<220> FEATURE:

<223> OTHER INFORMATION: Synthetic Construct

<400> SEQUENCE: 759
gtgcgcgggt tgcg                                                              14

<210> SEQ ID NO 760
<211> LENGTH: 14
<212> TYPE: DNA
<213> ORGANISM: Artificial Sequence
<220> FEATURE:
<223> OTHER INFORMATION: Synthetic Construct

<400> SEQUENCE: 760
tgcgcgggtt gcgt                                                              14

<210> SEQ ID NO 761
<211> LENGTH: 14
<212> TYPE: DNA
<213> ORGANISM: Artificial Sequence
<220> FEATURE:
<223> OTHER INFORMATION: Synthetic Construct

<400> SEQUENCE: 761
gcgcgggttg cgtc                                                              14

<210> SEQ ID NO 762
<211> LENGTH: 14
<212> TYPE: DNA
<213> ORGANISM: Artificial Sequence
<220> FEATURE:
<223> OTHER INFORMATION: Synthetic Construct

<400> SEQUENCE: 762
cgcgggttgc gtcg                                                              14

<210> SEQ ID NO 763
<211> LENGTH: 14
<212> TYPE: DNA
<213> ORGANISM: Artificial Sequence
<220> FEATURE:
<223> OTHER INFORMATION: Synthetic Construct

<400> SEQUENCE: 763
ccgccgacac gcaa                                                              14

<210> SEQ ID NO 764
<211> LENGTH: 25
<212> TYPE: DNA
<213> ORGANISM: Artificial Sequence
<220> FEATURE:
<223> OTHER INFORMATION: Synthetic Construct

<400> SEQUENCE: 764
ttttgtttat tttgggtttg gtggt                                                  25

<210> SEQ ID NO 765
<211> LENGTH: 14
<212> TYPE: DNA
<213> ORGANISM: Artificial Sequence
<220> FEATURE:
<223> OTHER INFORMATION: Synthetic Construct

<400> SEQUENCE: 765
gcgggttgcg tcga                                                              14

```
<210> SEQ ID NO 766
<211> LENGTH: 14
<212> TYPE: DNA
<213> ORGANISM: Artificial Sequence
<220> FEATURE:
<223> OTHER INFORMATION: Synthetic Construct

<400> SEQUENCE: 766
cgggttgcgt cgag                                                        14

<210> SEQ ID NO 767
<211> LENGTH: 14
<212> TYPE: DNA
<213> ORGANISM: Artificial Sequence
<220> FEATURE:
<223> OTHER INFORMATION: Synthetic Construct

<400> SEQUENCE: 767
gggttgcgtc gagc                                                        14

<210> SEQ ID NO 768
<211> LENGTH: 14
<212> TYPE: DNA
<213> ORGANISM: Artificial Sequence
<220> FEATURE:
<223> OTHER INFORMATION: Synthetic Construct

<400> SEQUENCE: 768
ggttgcgtcg agcg                                                        14

<210> SEQ ID NO 769
<211> LENGTH: 14
<212> TYPE: DNA
<213> ORGANISM: Artificial Sequence
<220> FEATURE:
<223> OTHER INFORMATION: Synthetic Construct

<400> SEQUENCE: 769
gttgcgtcga gcgt                                                        14

<210> SEQ ID NO 770
<211> LENGTH: 14
<212> TYPE: DNA
<213> ORGANISM: Artificial Sequence
<220> FEATURE:
<223> OTHER INFORMATION: Synthetic Construct

<400> SEQUENCE: 770
ttgcgtcgag cgtt                                                        14

<210> SEQ ID NO 771
<211> LENGTH: 14
<212> TYPE: DNA
<213> ORGANISM: Artificial Sequence
<220> FEATURE:
<223> OTHER INFORMATION: Synthetic Construct

<400> SEQUENCE: 771
tgcgtcgagc gttg                                                        14

<210> SEQ ID NO 772
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 772
gcgtcgagcg ttgg                                                         14

<210> SEQ ID NO 773
<211> LENGTH: 14
<212> TYPE: DNA
<213> ORGANISM: Artificial Sequence
<220> FEATURE:
<223> OTHER INFORMATION: Synthetic Construct

<400> SEQUENCE: 773
cgtcgagcgt tggg                                                         14

<210> SEQ ID NO 774
<211> LENGTH: 14
<212> TYPE: DNA
<213> ORGANISM: Artificial Sequence
<220> FEATURE:
<223> OTHER INFORMATION: Synthetic Construct

<400> SEQUENCE: 774
gtcgagcgtt gggt                                                         14

<210> SEQ ID NO 775
<211> LENGTH: 14
<212> TYPE: DNA
<213> ORGANISM: Artificial Sequence
<220> FEATURE:
<223> OTHER INFORMATION: Synthetic Construct

<400> SEQUENCE: 775
tcgagcgttg ggta                                                         14

<210> SEQ ID NO 776
<211> LENGTH: 14
<212> TYPE: DNA
<213> ORGANISM: Artificial Sequence
<220> FEATURE:
<223> OTHER INFORMATION: Synthetic Construct

<400> SEQUENCE: 776
cgagcgttgg gtag                                                         14

<210> SEQ ID NO 777
<211> LENGTH: 14
<212> TYPE: DNA
<213> ORGANISM: Artificial Sequence
<220> FEATURE:
<223> OTHER INFORMATION: Synthetic Construct

<400> SEQUENCE: 777
gagcgttggg tagg                                                         14

<210> SEQ ID NO 778
<211> LENGTH: 14
<212> TYPE: DNA
<213> ORGANISM: Artificial Sequence
<220> FEATURE:
<223> OTHER INFORMATION: Synthetic Construct

<400> SEQUENCE: 778
agcgttgggt agga                                                         14

<210> SEQ ID NO 779
<211> LENGTH: 14

```
<212> TYPE: DNA
<213> ORGANISM: Artificial Sequence
<220> FEATURE:
<223> OTHER INFORMATION: Synthetic Construct

<400> SEQUENCE: 779
gcgttgggta ggag                                                      14

<210> SEQ ID NO 780
<211> LENGTH: 14
<212> TYPE: DNA
<213> ORGANISM: Artificial Sequence
<220> FEATURE:
<223> OTHER INFORMATION: Synthetic Construct

<400> SEQUENCE: 780
cgttgggtag gagg                                                      14

<210> SEQ ID NO 781
<211> LENGTH: 14
<212> TYPE: DNA
<213> ORGANISM: Artificial Sequence
<220> FEATURE:
<223> OTHER INFORMATION: Synthetic Construct

<400> SEQUENCE: 781
gttgggtagg aggt                                                      14

<210> SEQ ID NO 782
<211> LENGTH: 14
<212> TYPE: DNA
<213> ORGANISM: Artificial Sequence
<220> FEATURE:
<223> OTHER INFORMATION: Synthetic Construct

<400> SEQUENCE: 782
ttgggtagga ggtt                                                      14

<210> SEQ ID NO 783
<211> LENGTH: 14
<212> TYPE: DNA
<213> ORGANISM: Artificial Sequence
<220> FEATURE:
<223> OTHER INFORMATION: Synthetic Construct

<400> SEQUENCE: 783
tgggtaggag gttt                                                      14

<210> SEQ ID NO 784
<211> LENGTH: 14
<212> TYPE: DNA
<213> ORGANISM: Artificial Sequence
<220> FEATURE:
<223> OTHER INFORMATION: Synthetic Construct

<400> SEQUENCE: 784
gggtaggagg tttc                                                      14

<210> SEQ ID NO 785
<211> LENGTH: 14
<212> TYPE: DNA
<213> ORGANISM: Artificial Sequence
<220> FEATURE:
<223> OTHER INFORMATION: Synthetic Construct

<400> SEQUENCE: 785
```

```
ggtaggaggt ttcg                                                    14
```

<210> SEQ ID NO 786
<211> LENGTH: 14
<212> TYPE: DNA
<213> ORGANISM: Artificial Sequence
<220> FEATURE:
<223> OTHER INFORMATION: Synthetic Construct

<400> SEQUENCE: 786

```
gtaggaggtt tcgt                                                    14
```

<210> SEQ ID NO 787
<211> LENGTH: 14
<212> TYPE: DNA
<213> ORGANISM: Artificial Sequence
<220> FEATURE:
<223> OTHER INFORMATION: Synthetic Construct

<400> SEQUENCE: 787

```
taggaggttt cgtt                                                    14
```

<210> SEQ ID NO 788
<211> LENGTH: 14
<212> TYPE: DNA
<213> ORGANISM: Artificial Sequence
<220> FEATURE:
<223> OTHER INFORMATION: Synthetic Construct

<400> SEQUENCE: 788

```
aggaggtttc gttt                                                    14
```

<210> SEQ ID NO 789
<211> LENGTH: 14
<212> TYPE: DNA
<213> ORGANISM: Artificial Sequence
<220> FEATURE:
<223> OTHER INFORMATION: Synthetic Construct

<400> SEQUENCE: 789

```
ggaggtttcg tttt                                                    14
```

<210> SEQ ID NO 790
<211> LENGTH: 14
<212> TYPE: DNA
<213> ORGANISM: Artificial Sequence
<220> FEATURE:
<223> OTHER INFORMATION: Synthetic Construct

<400> SEQUENCE: 790

```
gaggtttcgt tttg                                                    14
```

<210> SEQ ID NO 791
<211> LENGTH: 14
<212> TYPE: DNA
<213> ORGANISM: Artificial Sequence
<220> FEATURE:
<223> OTHER INFORMATION: Synthetic Construct

<400> SEQUENCE: 791

```
aggtttcgtt ttgt                                                    14
```

<210> SEQ ID NO 792
<211> LENGTH: 14
<212> TYPE: DNA
<213> ORGANISM: Artificial Sequence
<220> FEATURE:
<223> OTHER INFORMATION: Synthetic Construct

<400> SEQUENCE: 792
ggtttcgttt tgtt                                                         14

<210> SEQ ID NO 793
<211> LENGTH: 14
<212> TYPE: DNA
<213> ORGANISM: Artificial Sequence
<220> FEATURE:
<223> OTHER INFORMATION: Synthetic Construct

<400> SEQUENCE: 793
gtttcgtttt gttt                                                         14

<210> SEQ ID NO 794
<211> LENGTH: 14
<212> TYPE: DNA
<213> ORGANISM: Artificial Sequence
<220> FEATURE:
<223> OTHER INFORMATION: Synthetic Construct

<400> SEQUENCE: 794
tttcgttttg tttt                                                         14

<210> SEQ ID NO 795
<211> LENGTH: 14
<212> TYPE: DNA
<213> ORGANISM: Artificial Sequence
<220> FEATURE:
<223> OTHER INFORMATION: Synthetic Construct

<400> SEQUENCE: 795
ttcgttttgt tttg                                                         14

<210> SEQ ID NO 796
<211> LENGTH: 14
<212> TYPE: DNA
<213> ORGANISM: Artificial Sequence
<220> FEATURE:
<223> OTHER INFORMATION: Synthetic Construct

<400> SEQUENCE: 796
tcgttttgtt ttgg                                                         14

<210> SEQ ID NO 797
<211> LENGTH: 14
<212> TYPE: DNA
<213> ORGANISM: Artificial Sequence
<220> FEATURE:
<223> OTHER INFORMATION: Synthetic Construct

<400> SEQUENCE: 797
cgttttgttt tggt                                                         14

<210> SEQ ID NO 798
<211> LENGTH: 14
<212> TYPE: DNA
<213> ORGANISM: Artificial Sequence
<220> FEATURE:
<223> OTHER INFORMATION: Synthetic Construct

<400> SEQUENCE: 798
gttttgtttt ggtt                                                         14

<210> SEQ ID NO 799
<211> LENGTH: 14
<212> TYPE: DNA
<213> ORGANISM: Artificial Sequence
<220> FEATURE:
<223> OTHER INFORMATION: Synthetic Construct

<400> SEQUENCE: 799
ttttgttttg gttg                                                        14

<210> SEQ ID NO 800
<211> LENGTH: 14
<212> TYPE: DNA
<213> ORGANISM: Artificial Sequence
<220> FEATURE:
<223> OTHER INFORMATION: Synthetic Construct

<400> SEQUENCE: 800
tttgttttgg ttgt                                                        14

<210> SEQ ID NO 801
<211> LENGTH: 14
<212> TYPE: DNA
<213> ORGANISM: Artificial Sequence
<220> FEATURE:
<223> OTHER INFORMATION: Synthetic Construct

<400> SEQUENCE: 801
ttgttttggt tgta                                                        14

<210> SEQ ID NO 802
<211> LENGTH: 14
<212> TYPE: DNA
<213> ORGANISM: Artificial Sequence
<220> FEATURE:
<223> OTHER INFORMATION: Synthetic Construct

<400> SEQUENCE: 802
tgttttggtt gtaa                                                        14

<210> SEQ ID NO 803
<211> LENGTH: 14
<212> TYPE: DNA
<213> ORGANISM: Artificial Sequence
<220> FEATURE:
<223> OTHER INFORMATION: Synthetic Construct

<400> SEQUENCE: 803
gttttggttg taag                                                        14

<210> SEQ ID NO 804
<211> LENGTH: 14
<212> TYPE: DNA
<213> ORGANISM: Artificial Sequence
<220> FEATURE:
<223> OTHER INFORMATION: Synthetic Construct

<400> SEQUENCE: 804
ttttggttgt aagt                                                        14

<210> SEQ ID NO 805
<211> LENGTH: 14
<212> TYPE: DNA
<213> ORGANISM: Artificial Sequence
<220> FEATURE:
<223> OTHER INFORMATION: Synthetic Construct

```
<400> SEQUENCE: 805
tttggttgta agta                                                    14

<210> SEQ ID NO 806
<211> LENGTH: 14
<212> TYPE: DNA
<213> ORGANISM: Artificial Sequence
<220> FEATURE:
<223> OTHER INFORMATION: Synthetic Construct

<400> SEQUENCE: 806
ttggttgtaa gtag                                                    14

<210> SEQ ID NO 807
<211> LENGTH: 14
<212> TYPE: DNA
<213> ORGANISM: Artificial Sequence
<220> FEATURE:
<223> OTHER INFORMATION: Synthetic Construct

<400> SEQUENCE: 807
tggttgtaag tagc                                                    14

<210> SEQ ID NO 808
<211> LENGTH: 14
<212> TYPE: DNA
<213> ORGANISM: Artificial Sequence
<220> FEATURE:
<223> OTHER INFORMATION: Synthetic Construct

<400> SEQUENCE: 808
ggttgtaagt agcg                                                    14

<210> SEQ ID NO 809
<211> LENGTH: 14
<212> TYPE: DNA
<213> ORGANISM: Artificial Sequence
<220> FEATURE:
<223> OTHER INFORMATION: Synthetic Construct

<400> SEQUENCE: 809
gttgtaagta gcgg                                                    14

<210> SEQ ID NO 810
<211> LENGTH: 14
<212> TYPE: DNA
<213> ORGANISM: Artificial Sequence
<220> FEATURE:
<223> OTHER INFORMATION: Synthetic Construct

<400> SEQUENCE: 810
ttgtaagtag cggt                                                    14

<210> SEQ ID NO 811
<211> LENGTH: 14
<212> TYPE: DNA
<213> ORGANISM: Artificial Sequence
<220> FEATURE:
<223> OTHER INFORMATION: Synthetic Construct

<400> SEQUENCE: 811
tgtaagtagc ggtt                                                    14

<210> SEQ ID NO 812
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 812
gtaagtagcg gttg                                                        14

<210> SEQ ID NO 813
<211> LENGTH: 14
<212> TYPE: DNA
<213> ORGANISM: Artificial Sequence
<220> FEATURE:
<223> OTHER INFORMATION: Synthetic Construct

<400> SEQUENCE: 813
taagtagcgg ttgg                                                        14

<210> SEQ ID NO 814
<211> LENGTH: 14
<212> TYPE: DNA
<213> ORGANISM: Artificial Sequence
<220> FEATURE:
<223> OTHER INFORMATION: Synthetic Construct

<400> SEQUENCE: 814
aagtagcggt tggg                                                        14

<210> SEQ ID NO 815
<211> LENGTH: 14
<212> TYPE: DNA
<213> ORGANISM: Artificial Sequence
<220> FEATURE:
<223> OTHER INFORMATION: Synthetic Construct

<400> SEQUENCE: 815
agtagcggtt ggga                                                        14

<210> SEQ ID NO 816
<211> LENGTH: 14
<212> TYPE: DNA
<213> ORGANISM: Artificial Sequence
<220> FEATURE:
<223> OTHER INFORMATION: Synthetic Construct

<400> SEQUENCE: 816
gtagcggttg ggag                                                        14

<210> SEQ ID NO 817
<211> LENGTH: 14
<212> TYPE: DNA
<213> ORGANISM: Artificial Sequence
<220> FEATURE:
<223> OTHER INFORMATION: Synthetic Construct

<400> SEQUENCE: 817
tagcggttgg gagt                                                        14

<210> SEQ ID NO 818
<211> LENGTH: 14
<212> TYPE: DNA
<213> ORGANISM: Artificial Sequence
<220> FEATURE:
<223> OTHER INFORMATION: Synthetic Construct

<400> SEQUENCE: 818
```
agcggttggg agta 14

<210> SEQ ID NO 819
<211> LENGTH: 14
<212> TYPE: DNA
<213> ORGANISM: Artificial Sequence
<220> FEATURE:
<223> OTHER INFORMATION: Synthetic Construct

<400> SEQUENCE: 819
gcggttggga gtag 14

<210> SEQ ID NO 820
<211> LENGTH: 14
<212> TYPE: DNA
<213> ORGANISM: Artificial Sequence
<220> FEATURE:
<223> OTHER INFORMATION: Synthetic Construct

<400> SEQUENCE: 820
cggttgggag tagt 14

<210> SEQ ID NO 821
<211> LENGTH: 14
<212> TYPE: DNA
<213> ORGANISM: Artificial Sequence
<220> FEATURE:
<223> OTHER INFORMATION: Synthetic Construct

<400> SEQUENCE: 821
ggttgggagt agtc 14

<210> SEQ ID NO 822
<211> LENGTH: 14
<212> TYPE: DNA
<213> ORGANISM: Artificial Sequence
<220> FEATURE:
<223> OTHER INFORMATION: Synthetic Construct

<400> SEQUENCE: 822
gttgggagta gtcg 14

<210> SEQ ID NO 823
<211> LENGTH: 14
<212> TYPE: DNA
<213> ORGANISM: Artificial Sequence
<220> FEATURE:
<223> OTHER INFORMATION: Synthetic Construct

<400> SEQUENCE: 823
ttgggagtag tcgg 14

<210> SEQ ID NO 824
<211> LENGTH: 14
<212> TYPE: DNA
<213> ORGANISM: Artificial Sequence
<220> FEATURE:
<223> OTHER INFORMATION: Synthetic Construct

<400> SEQUENCE: 824
tgggagtagt cggt 14

<210> SEQ ID NO 825
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 825
gggagtagtc ggtt                                                          14

<210> SEQ ID NO 826
<211> LENGTH: 14
<212> TYPE: DNA
<213> ORGANISM: Artificial Sequence
<220> FEATURE:
<223> OTHER INFORMATION: Synthetic Construct

<400> SEQUENCE: 826
tctcgtaact tcaa                                                          14

<210> SEQ ID NO 827
<211> LENGTH: 24
<212> TYPE: DNA
<213> ORGANISM: Artificial Sequence
<220> FEATURE:
<223> OTHER INFORMATION: Synthetic Construct

<400> SEQUENCE: 827
ggatgcgcgc gtcgtttagg gtgt                                               24

<210> SEQ ID NO 828
<211> LENGTH: 14
<212> TYPE: DNA
<213> ORGANISM: Artificial Sequence
<220> FEATURE:
<223> OTHER INFORMATION: Synthetic Construct

<400> SEQUENCE: 828
ggagtagtcg gttt                                                          14

<210> SEQ ID NO 829
<211> LENGTH: 14
<212> TYPE: DNA
<213> ORGANISM: Artificial Sequence
<220> FEATURE:
<223> OTHER INFORMATION: Synthetic Construct

<400> SEQUENCE: 829
gagtagtcgg tttt                                                          14

<210> SEQ ID NO 830
<211> LENGTH: 14
<212> TYPE: DNA
<213> ORGANISM: Artificial Sequence
<220> FEATURE:
<223> OTHER INFORMATION: Synthetic Construct

<400> SEQUENCE: 830
agtagtcggt tttt                                                          14

<210> SEQ ID NO 831
<211> LENGTH: 14
<212> TYPE: DNA
<213> ORGANISM: Artificial Sequence
<220> FEATURE:
<223> OTHER INFORMATION: Synthetic Construct

<400> SEQUENCE: 831
gtagtcggtt tttg                                                          14
```

<210> SEQ ID NO 832
<211> LENGTH: 14
<212> TYPE: DNA
<213> ORGANISM: Artificial Sequence
<220> FEATURE:
<223> OTHER INFORMATION: Synthetic Construct

<400> SEQUENCE: 832
tagtcggttt ttgg                                                     14

<210> SEQ ID NO 833
<211> LENGTH: 14
<212> TYPE: DNA
<213> ORGANISM: Artificial Sequence
<220> FEATURE:
<223> OTHER INFORMATION: Synthetic Construct

<400> SEQUENCE: 833
agtcggtttt tggg                                                     14

<210> SEQ ID NO 834
<211> LENGTH: 14
<212> TYPE: DNA
<213> ORGANISM: Artificial Sequence
<220> FEATURE:
<223> OTHER INFORMATION: Synthetic Construct

<400> SEQUENCE: 834
gtcggttttt gggg                                                     14

<210> SEQ ID NO 835
<211> LENGTH: 14
<212> TYPE: DNA
<213> ORGANISM: Artificial Sequence
<220> FEATURE:
<223> OTHER INFORMATION: Synthetic Construct

<400> SEQUENCE: 835
tcggtttttg ggga                                                     14

<210> SEQ ID NO 836
<211> LENGTH: 14
<212> TYPE: DNA
<213> ORGANISM: Artificial Sequence
<220> FEATURE:
<223> OTHER INFORMATION: Synthetic Construct

<400> SEQUENCE: 836
cggtttttgg ggaa                                                     14

<210> SEQ ID NO 837
<211> LENGTH: 14
<212> TYPE: DNA
<213> ORGANISM: Artificial Sequence
<220> FEATURE:
<223> OTHER INFORMATION: Synthetic Construct

<400> SEQUENCE: 837 ggttttggg gaat                                                      14

<210> SEQ ID NO 838
<211> LENGTH: 14
<212> TYPE: DNA
<213> ORGANISM: Artificial Sequence
<220> FEATURE:

<223> OTHER INFORMATION: Synthetic Construct

<400> SEQUENCE: 838
gtttttgggg aata                                                              14

<210> SEQ ID NO 839
<211> LENGTH: 14
<212> TYPE: DNA
<213> ORGANISM: Artificial Sequence
<220> FEATURE:
<223> OTHER INFORMATION: Synthetic Construct

<400> SEQUENCE: 839
tttttgggga atat                                                              14

<210> SEQ ID NO 840
<211> LENGTH: 24
<212> TYPE: DNA
<213> ORGANISM: Artificial Sequence
<220> FEATURE:
<223> OTHER INFORMATION: Synthetic Construct

<400> SEQUENCE: 840
gtagaaatta ataagtgaga gggc                                                   24

<210> SEQ ID NO 841
<211> LENGTH: 22
<212> TYPE: DNA
<213> ORGANISM: Artificial Sequence
<220> FEATURE:
<223> OTHER INFORMATION: Synthetic Construct

<400> SEQUENCE: 841
acgactcaaa ctcgaaaact cg                                                     22

<210> SEQ ID NO 842
<211> LENGTH: 22
<212> TYPE: DNA
<213> ORGANISM: Artificial Sequence
<220> FEATURE:
<223> OTHER INFORMATION: Synthetic Construct

<400> SEQUENCE: 842
ttcggggcgt agttgcgggc gg                                                     22

<210> SEQ ID NO 843
<211> LENGTH: 1120
<212> TYPE: DNA
<213> ORGANISM: Artificial Sequence
<220> FEATURE:
<223> OTHER INFORMATION: Intron of SDC2 gene

<400> SEQUENCE: 843
gagtgggcca ggcggaggat gcgcgcgccg tttagggtgt ttgaagctac gagaggagcc      60
cgcagggaat aggggagcgc cacctgggga accccagtc cccaagtata caccggagat      120
ccgctgggac aaatgcgctc gtccggtcac ccttccccc tcttcccttc ctcagaaaag      180
cgctgctcgc tggcgttacc ccgcggtccg cgggaatggg ggcaccgaga attgcggttt      240
ggtctagccg cagaggcccc tgaagtcact cccaacttct tcgccctcgg cgggtcttgc      300
tgcgtggtct gggaaggacg gaggggaaag ggtggcagga gggggagcc tgggtcgggc      360 cgcgaggga acgctccac tccgcgcgct cctcgagacc agggatgacc tggaaacttc      420
ggggtccctt cctccgcaca ccatccccc cgcgccagct ttcctgtttg actgcatgca      480

```
agttctgggg agatgggggc cagatttaag agacccgcga gtgtccagag agaaaagttt    540
gcaaaagttc ttttgtttga tgctccctgc ggctagggcg aggtaaccga cactacgtgg    600
aatcgcagta ggcgatccct caagggggata ctgggggagg cacggaacgc gtccgaaaat   660
gctgggacgc cggccactgg attcccagtc ctgcggcgac cccctcctcg ttgaggggtg    720
gaggttgcac cgcggggcgt cagggacggg aggacatttt cataggagtt acacgggagt    780
gccgcaagca gggcgaggcg gggtacgtgt gacacggcgc tcggcttcgg gtcgcctggc    840
cgctggggga cagaggcttc cctcccgcca cgctcgccct ctctggccct ggcggggcgc    900
ttctggggcc gggaggagtc tcgtctccgg cggagcgcct gccggcaccc agcttccctc    960
ccccgccctg gcggtgggaa cttgatttct ccttttggtc gcgcttcggg ggctggagct   1020
tgtttcccca cgtcgcccaa tgagcgccct ctaaagggaa ctgcctcctt ggcctcctct   1080
cgtccgcagc tgcctccacc tgggcgccag gagctctgtc                         1120
```

METHOD FOR DETECTING THE METHYLATION OF COLORECTAL-CANCER-SPECIFIC METHYLATION MARKER GENES FOR COLORECTAL CANCER DIAGNOSIS

CROSS-REFERENCE TO RELATED APPLICATIONS

This is a continuation-in-part application under 35 U.S.C. § 120 of U.S. patent application Ser. No. 13/508,534 filed May 7, 2012 and published as U.S. Patent Application Publication No. 2012/0264640, which in turn is a U.S. national phase under the provisions of 35 U.S.C. § 371 of International Patent Application No. PCT/KR2010/007030 filed Oct. 14, 2010, which in turn claims priority of Korean Patent Application No. 10-2009-0106445 filed Nov. 5, 2009. The disclosures of U.S. patent application Ser. No. 13/508, 534, International Patent Application No. PCT/KR2010/ 007030, and Korean Patent Application No. 10-2009-0106445 are hereby incorporated herein by reference in their respective entireties, for all purposes.

TECHNICAL FIELD

The present disclosure relates to a method for detecting CpG methylation of SDC2 (Syndecan 2) gene, a kit for detecting CpG methylation of SDC2 (Syndecan 2) gene, and a method for detecting CpG methylation of SDC2 (Syndecan 2) gene for a colorectal cancer diagnosis.

BACKGROUND ART

Even at the present time when medical science has advanced, the 5-year survival rate of cancer patients, particularly solid tumor patients (other than blood cancer patients) is less than 50%, and about ⅔ of all cancer patients are diagnosed at an advanced stage and almost all die within 2 years after cancer diagnosis. Such poor results in cancer therapy are not only the problem of therapeutic methods, but also due to the fact that it not easy to diagnose cancer at an early stage and to accurately diagnose advanced cancer and to carry out the follow-up of cancer patients after cancer therapy.

In current clinical practice, the diagnosis of cancer is confirmed by performing tissue biopsy after history taking, physical examination and clinical assessment, followed by radiographic testing and endoscopy if cancer is suspected. However, the diagnosis of cancer by the existing clinical practices is possible only when the number of cancer cells is more than a billion and the diameter of cancer is more than 1 cm. In this case, the cancer cells already have metastatic ability, and at least half thereof have already metastasized. Meanwhile, tumor markers for monitoring substances that are directly or indirectly produced from cancers are used in cancer screening, but they cause confusion due to limitations in accuracy, since up to about half thereof appear normal even in the presence of cancer, and they often appear positive even in the absence of cancer. Furthermore, the anticancer agents that are mainly used in cancer therapy have the problem that they show an effect only when the volume of cancer is small.

The reason why the diagnosis and treatment of cancer are difficult is that cancer cells are highly complex and variable. Cancer cells grow excessively and continuously, invading surrounding tissue and metastasize to distal organs leading to death. Despite the attack of an immune mechanism or anticancer therapy, cancer cells survive, continually develop, and cell groups that are most suitable for survival selectively propagate. Cancer cells are living bodies with a high degree of viability, which occur by the mutation of a large number of genes. In order that one cell is converted to a cancer cell and developed to a malignant cancer lump that is detectable in clinics, the mutation of a large number of genes must occur. Thus, in order to diagnose and treat cancer at the root, approaches at a gene level are necessary.

Recently, genetic analysis has been actively attempted to diagnose cancer. The simplest typical method is to detect the presence of ABL: BCR fusion genes (the genetic characteristic of leukemia) in blood by PCR. The method has an accuracy rate of more than 95%, and after the diagnosis and therapy of chronic myelocytic leukemia using this simple and easy genetic analysis, this method is being used for the assessment of the result and follow-up study. However, this method has the deficiency that it can be applied only to some blood cancers.

Furthermore, another method has been attempted, in which the presence of genes expressed by cancer cells is detected by RT-PCR and blotting, thereby diagnosing cancer cells present in blood cells. However, this method has shortcomings in that it can be applied only to some cancers, including prostate cancer and melanoma, has a high false positive rate. In addition, it is difficult to standardize detection and reading in this method, and its utility is also limited (Kopreski, M. S. et al., *Clin. Cancer Res.*, 5:1961, 1999; Miyashiro, I. et al., *Clin. Chem.*, 47:505, 2001).

Accordingly, methods of diagnosing cancer by measuring DNA methylation have recently been proposed. When the promoter CpG island of a certain gene is hyper-methylated, the expression of such a gene is silenced. This is interpreted to be a main mechanism by which the function of this gene is lost even when there is no mutation in the protein-coding sequence of the gene in a living body. In addition, this is analyzed as a factor by which the function of a number of tumor-suppressor genes in human cancer is lost. Thus, analysis of the methylation of the promoter CpG island of tumor-suppressor genes is very helpful in cancer research. An active attempt has been made to analyze the methylation of the promoter CpG island by methods such as methylation-specific PCR (hereinafter, referred to as "MSP") or automatic base sequencing and to use the analysis results for the diagnosis and screening of cancer.

A significant number of diseases are caused by genetic abnormalities, and the most frequent form of genetic abnormality is a change in the coding sequence of a gene. This genetic change is referred to as mutation. When any gene has a mutation, the structure and function of a protein encoded by the gene change, resulting in abnormalities and deletions, and this mutant protein causes disease. However, an abnormality in the expression of a specific gene can cause disease even in the absence of a mutation in the gene. A typical example thereof is methylation in which a methyl group is attached to the transcription regulatory region of a gene, that is, the cytosine base of the promoter CpG islands, and in this case, the expression of the gene is silenced. This is known as epigenetic change. This is transmitted to offspring and results in the loss of the expression of the relevant protein in the same manner as mutation. Most typically, the expression of tumor suppressor genes is silenced by the methylation of promoter CpG islands in cancer cells, resulting in carcinogenesis (Robertson, K. D. et al., *Carcinogensis*, 21:461, 2000).

For the accurate diagnosis of cancer, it is important to detect not only a mutated gene but also a mechanism by which the mutation of this gene occurs. In recent years, epigenetic changes were reported to be as important as these mutations, and a typical example of the epigenetic changes is the methylation of promoter CpG islands.

In the genomic DNA of mammal cells, there is the fifth base in addition to A, C, G and T, namely, 5-methylcytosine, in which a methyl group is attached to the fifth carbon of the cytosine ring (5-mC). 5-mC is always attached only to the C of a CG dinucleotide (5'-mCG-3'), which is frequently marked CpG. The C of CpG is mostly methylated by attachment with a methyl group. The methylation of this CpG inhibits a repetitive sequence in genomes, such as Alu or transposon, from being expressed. In addition, this CpG is a site where an epigenetic change in mammalian cells appears most often. The 5-mC of this CpG is naturally deaminated to T, and thus, the CpG in mammal genomes shows only 1% of frequency, which is much lower than a normal frequency ($1/4 \times 1/4 = 6.25\%$).

Regions in which CpG are exceptionally integrated are known as CpG islands. The CpG islands refer to sites which are 0.2-3 kb in length, and have a C+G content of more than 50% and a CpG ratio of more than 3.75%. There are about 45,000 CpG islands in the human genome, and they are mostly found in promoter regions regulating the expression of genes. Actually, the CpG islands occur in the promoters of housekeeping genes accounting for about 50% of human genes (Cross, S. et al., *Curr. Opin. Gene Develop.,* 5:309, 1995).

In the meantime, in the somatic cells of normal persons, the CpG islands of such housekeeping gene promoter sites are un-methylated, but imprinted genes and the genes on inactivated X chromosomes are methylated such that they are not expressed during development.

During a cancer-causing process, methylation is found in promoter CpG islands, and the restriction on the corresponding gene expression occurs. Particularly, if methylation occurs in the promoter CpG islands of tumor-suppressor genes that regulate cell cycle or apoptosis, restore DNA, are involved in the adhesion of cells and the interaction between cells, and/or suppress cell invasion and metastasis, such methylation blocks the expression and function of such genes in the same manner as the mutations of a coding sequence, thereby promoting the development and progression of cancer. In addition, partial methylation also occurs in the CpG islands according to aging.

An interesting fact is that, in the case of genes whose mutations are attributed to the development of cancer in congenital cancer but do not occur in acquired cancer, the methylation of promoter CpG islands occurs instead of mutation. Typical examples include the promoter methylation of genes, such as acquired renal cancer VHL (von Hippel Lindau), breast cancer BRCA1, colorectal cancer MLH1, and stomach cancer E-CAD. In addition, in about half of all cancers, the promoter methylation of p16 or the mutation of Rb occurs, and the remaining cancers show the mutation of p53 or the promoter methylation of p73, p 14 and the like.

An important fact is that an epigenetic change caused by promoter methylation causes a genetic change (i.e., the mutation of a coding sequence), and the development of cancer is progressed by the combination of such genetic and epigenetic changes. In a MLH1 gene as an example, there is the circumstance in which the function of one allele of the MLH1 gene in colorectal cancer cells is lost due to its mutation or deletion, and the remaining one allele does not function due to promoter methylation. In addition, if the function of MLH1, which is a DNA restoring gene, is lost due to promoter methylation, the occurrence of mutation in other important genes is facilitated to promote the development of cancer.

Most cancers show three common characteristics with respect to CpG, namely, hypermethylation of the promoter CpG islands of tumor-suppressor genes, hypomethylation of the remaining CpG base sites, and an increase in the activity of methylation enzyme, namely, DNA cytosine methyltransferase (DNMT) (Singal, R. & Ginder, G. D., *Blood,* 93:4059, 1999; Robertson, K. et al., *Carcinogensis,* 21:461, 2000; Malik, K. & Brown, K. W., *Brit. J. Cancer,* 83:1583, 2000).

When promoter CpG islands are methylated, the reason why the expression of the corresponding genes is blocked is not clearly established, but is presumed to be because a methyl CpG-binding protein (MECP) or a methyl CpG-binding domain protein (MBD), and histone deacetylase, bind to methylated cytosine, thereby causing a change in the chromatin structure of chromosomes and a change in histone protein.

It is unsettled whether the methylation of promoter CpG islands directly causes the development of cancer or is a secondary change after the development of cancer. However, it is clear that the promoter methylation of tumor-related genes is an important index to cancer, and thus can be used in many applications, including the diagnosis and early detection of cancer, the prediction of the risk of the development of cancer, the prognosis of cancer, follow-up examination after treatment, and the prediction of a response to anticancer therapy. Recently, an attempt to examine the promoter methylation of tumor-related genes in tissues, cells, blood, sputum, saliva, feces or urine and to use the examined results for the diagnosis and treatment of various cancers, has been actively conducted (Esteller, M. et al., *Cancer Res.,* 59:67, 1999; Sanchez-Cespedez, M. et al., *Cancer Res.,* 60:892, 2000; Ahlquist, D. A. et al., *Gastroenterol.,* 119:1219, 2000).

In order to maximize the accuracy of cancer diagnosis using promoter methylation, analyze the development of cancer according to each stage and discriminate a change according to cancer and aging, an examination that can accurately analyze the methylation of all the cytosine bases of promoter CpG islands is required. Currently, a standard method for this examination is a bisulfite genome-sequencing method, in which a sample DNA is treated with sodium bisulfite, and all regions of the CpG islands of a target gene to be examined is amplified by PCR, and then, the base sequence of the amplified regions is analyzed. However, this examination has the problem that there are limitations to the number of genes or samples that can be examined at a given time. Other problems are that automation is difficult, and much time and expense are required.

In the Johns Hopkins School of Medicine, the MD Anderson Cancer Center, Charité-Universitätsmedizin Berlin, etc., studies on promoter methylation of cancer-related genes have been actively conducted. The fundamental data thus obtained are interchanged through the DNA Methylation Society (DMS) and stored in MethDB (www.methdb.de). Meanwhile, EpiGenX Pharmaceuticals, Inc. is now developing therapeutic agents associated with the methylation of CpG islands, and Epigenomics, Inc. is now conducting studies to apply promoter methylation to cancer diagnosis by examining the promoter methylation using various techniques, such as DNA chips and MALDI-TOF.

Accordingly, the present inventors have made extensive efforts to develop an effective colorectal-cancer-specific methylation marker which makes it possible to diagnose cancer and the risk of carcinogenesis at an early stage and predict cancer prognosis. The present inventors have initially identified that SDC2 (NM_002998, Syndecan 2) gene, which is involved in cell migration, differentiation and proliferation, is methylated in colorectal cancer (Oh et al., J. Mol. Diag. 2013). The present inventors found candidate genes, which are hypermethylated in colorectal cancer tissues compared to normal tissues, by isolating methylated DNA from colon cancer tissues and normal tissues connected to colon cancer tissues from 12 colorectal cancer patients under stage I to stage IV and followed by DNA microarray analysis. After a series of verification processes, SDC2 was investigated as a promising methylation biomarker for early diagnosis of colorectal cancer. Through a clinical examination using tissues of 139 colorectal cancer patients, 97.8% of colon cancer tissues show hypermethylation, when comparing to methylation in normal tissues connected to colon cancer tissues, irrespective of stage. Sensitivity for the diagnosis of colorectal cancer was confirmed to 87% and specificity was confirmed to 95.2% in clinical examination using quantitative methylation-specific PCR for sera of 131 colon cancer patients under stage I to stage IV and 125 healthy subjects. Especially, the sensitivity for stage I was 92.3%, which means that the biomarker found by the inventors was useful in early diagnosis of colorectal cancer.

Under the current technical background, the inventors of the present application have completed the invention by confirming that the methylation of CpG island of SDC2 (Syndecan 2) gene could be detected with high sensitivity and specificity with primers comprising one or more CG, which are bound complementarily to the methylated SDC2 DNA.

As a result, the present inventors have found that SDC2 (NM_002998, Syndecan 2) is methylated specifically in colorectal cancer cells and that colorectal cancer can be diagnosed by measuring the degree of methylation using these genes as biomarkers, thereby completing the present disclosure.

DISCLOSURE OF INVENTION

To achieve the above objects, the present disclosure provides a method for detecting CpG methylation of SDC2 (Syndecan 2) gene, the method comprising the steps of: (a) isolating genomic DNA from a clinical sample; (b) treating the genomic DNA from step (a) with bisulfite; and (c) determining hypermethylation of the CpG of the SDC2 gene in the genomic DNA treated with bisulfite according the step (b) by using primer(s) to amplify a methylated CpG of the bisulfite-treated SDC2 gene.

The present disclosure also provides a kit for detecting CpG methylation of SDC2 (Syndecan 2) gene, comprising primer(s) to amplify a methylated CpG of the SDC2 gene.

The present disclosure also provides a method for detecting CpG methylation of SDC2 (Syndecan 2) gene for a colorectal cancer diagnosis, the method comprising the steps of: (a) isolating genomic DNA from a clinical sample; (b) treating the genomic DNA from step (a) with bisulfite; and (c) determining hypermethylation of the CpG of the SDC2 gene in the genomic DNA treated with bisulfite according the step (b) by using primer(s) to amplify a methylated CpG of the bisulfite-treated SDC2 gene, wherein a colorectal cancer is detected in the human subject based on increased CpG methylation of the SDC2 gene relative to that of a control.

Other features and embodiments of the present disclosure will be more apparent from the following detailed descriptions and the appended claims.

Effects of the Invention

According to the method for detecting CpG island methylation of SDC2 gene of the present disclosure, the CpG island methylation of SDC2 gene can be detected in a clinical sample at a high detection rate in an accurate, rapid and efficient manner.

BEST MODE FOR CARRYING OUT THE INVENTION

Figure 1:
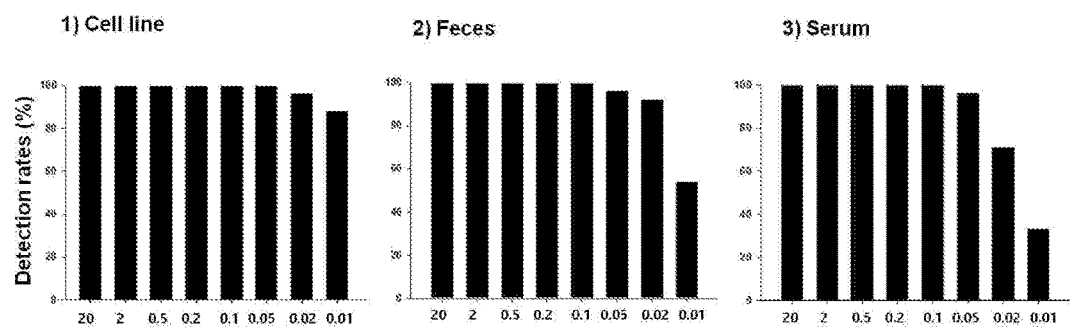
FIG. 1 is a graph diagram showing a detection rate at which SDC2 gene methylation is detected in various specimens using 808 sets of primers and probes used in the method according to the present disclosure.

Unless defined otherwise, all technical and scientific terms used herein have the same meaning as commonly understood by one of ordinary skill in the art to which the invention pertains. Generally, the nomenclatures used herein are well known and are commonly employed in the art.

The present disclosure is characterized in that the CpG islands of SDC2 (NM_002998, Syndecan 2) gene, which is methylated specifically in colorectal cancer cells, are used as a biomarker.

In one aspect, the present disclosure is directed to method for detecting CpG methylation of SDC2 (Syndecan 2) gene, the method comprising the steps of:

(a) isolating genomic DNA from a clinical sample;
(b) treating the genomic DNA from step (a) with bisulfite; and
(c) determining hypermethylation of the CpG of the SDC2 gene in the genomic DNA treated with bisulfite according the step (b) by using primer(s) to amplify a methylated CpG of the bisulfite-treated SDC2 gene.

As used herein, the term "sample", "clinical sample", or "specimen" is meant to include any biological body fluid, in its broadest sense, obtained from an individual, body fluid, a cell line, a tissue culture, depending on the type of assay that is to be performed. For example, the biological body fluid includes feces, blood, serum, plasma, and urine. It also includes cell, feces, urine, sputum, cell separated and flowed out from bronchoalveolar lavage fluid, paraffin tissue, and fine needle aspiration biopsy specimen. In other words, the clinical sample may be selected from the group consisting of, for example, tissue, biopsy, paraffin tissue, blood, serum, plasma, fine needle aspiration biopsy specimen, cell, feces, urine, sputum, cell separated and flowed out from bronchoalveolar lavage fluid, and combinations thereof, which are derived from a patient suspected of cancer or a subject to be diagnosed, but is not limited thereto. Methods for obtaining tissue biopsies and body fluids from mammals are well known in the art.

DNA is isolated from the clinical sample. DNA isolation may be performed using, for example, magnetic particles. Specifically, magnetic particles are allowed to bind to DNA in the clinical sample, and then an external magnetic field is applied to the sample to thereby isolate the DNA. The magnetic particles that are used in DNA isolation may have a particle size of about 50 to 2000 nm. The isolation of DNA from the clinical sample may be performed using any one of various DNA isolation kits or DNA isolation reagents similar thereto, which are commercialized and supplied.

For example, the isolated DNA may be treated with a reagent bisulfite, thereby modifying methylated DNA and unmethylated DNA differently. The genomic DNA nucleotide sequence of SDC2 gene CpG islands that can be methylated is represented by SEQ ID NO: 1. When the nucleotide sequence of SEQ ID NO: 1 is artificially modified by treatment with a reagent (e.g., bisulfite) that modifies methylated DNA and unmethylated DNA differently, cytosine bases methylated by the reagent may remain intact, and unmethylated cytosine bases may be converted to uracil or bases other than cytosine. Specifically, a nucleotide sequence corresponding to methylated SDC2 DNA is set forth in SEQ ID NO: 2.

In the present disclosure, the CpG islands may be located in the regulatory region including a promoter region, coding regions (e.g., exons), downstream of coding regions for example, enhancer region, and intron region of the genes.

Herein, the intron region of the SDC2 gene may be located between +681 and +1800 nucleotides (nt) from the transcription start site and may comprise a nucleotide sequence of SEQ ID NO: 843.

In the present disclosure, step (c) may be performed by a method selected from the group consisting of PCR, methylation-specific PCR, real-time methylation-specific PCR, PCR assay using a methylation DNA-specific binding protein, quantitative PCR, DNA chip-based assay, pyrosequencing, and bisulfite sequencing.

In the present disclosure, the method for detection of methylation is as follows:

(1) Methylation-specific PCR: When genomic DNA is treated with bisulfite, cytosine in the 5'-CpG'-3 region remains intact, if it was methylated, but the cytosine changes to uracil, if it was unmethylated. Accordingly, based on the base sequence converted after bisulfite treatment, PCR primer sets corresponding to a region having the 5'-CpG-3' base sequence are constructed. Herein, the constructed primer sets are two kinds of primer sets: a primer set corresponding to the methylated base sequence, and a primer set corresponding to the unmethylated base sequence. When genomic DNA is converted with bisulfite and then amplified by PCR using the above two kinds of primer sets, the PCR product is detected in the PCR mixture employing the primers corresponding to the methylated base sequence, if the genomic DNA was methylated, but the genomic DNA is detected in the PCR mixture employing the primers corresponding to the unmethylated, if the genomic DNA was unmethylated. This methylation can be quantitatively analyzed by agarose gel electrophoresis.

(2) Real-time methylation specific PCR: Real-time methylation-specific PCR is a real-time measurement method modified from the methylation-specific PCR method and comprises treating genomic DNA with bisulfite, designing PCR primers corresponding to the methylated base sequence, and performing real-time PCR using the primers. Methods of detecting the methylation of the genomic DNA include two methods: a method of detection using a TanMan probe complementary to the amplified base sequence; and a method of detection using Sybergreen. Thus, the real-time methylation-specific PCR allows selective quantitative analysis of methylated DNA. Herein, a standard curve is plotted using an in vitro methylated DNA sample, and a gene containing no 5'-CpG-3' sequence in the base sequence is also amplified as a negative control group for standardization to quantitatively analyze the degree of methylation.

(3) Pyrosequencing: The pyrosequencing method is a quantitative real-time sequencing method modified from the bisulfite sequencing method. Similarly to bisulfite sequencing, genomic DNA is converted by bisulfite treatment, and then, PCR primers corresponding to a region containing no 5'-CpG-3' base sequence are constructed. Specifically, the genomic DNA is treated with bisulfite, amplified using the PCR primers, and then subjected to real-time base sequence analysis using a sequencing primer. The degree of methylation is expressed as a methylation index by analyzing the amounts of cytosine and thymine in the 5'-CpG-3' region.

(4) PCR Using Methylated DNA-specific binding protein, quantitative PCR, and DNA Chip Assay: When a protein binding specifically only to methylated DNA is mixed with DNA, the protein binds specifically only to the methylated DNA. Thus, either PCR using a methylation-specific binding protein or a DNA chip assay allows selective isolation of only methylated DNA. Genomic DNA is mixed with a methylation-specific binding protein, and then only methylated DNA was selectively isolated. The isolated DNA is amplified using PCR primers corresponding to the promoter region, and then methylation of the DNA is measured by agarose gel electrophoresis.

In addition, methylation of DNA can also be measured by a quantitative PCR method, and methylated DNA isolated with a methylated DNA-specific binding protein can be labeled with a fluorescent probe and hybridized to a DNA chip containing complementary probes, thereby measuring methylation of the DNA. Herein, the methylated DNA-specific binding protein may be, but not limited to, McrBt.

(5) Detection of Differential Methylation—Methylation-Sensitive Restriction Endonuclease: Detection of differential methylation can be accomplished by bringing a nucleic acid sample into contact with a methylation-sensitive restriction endonuclease that cleaves only unmethylated CpG sites.

In a separate reaction, the sample is further brought into contact with an isoschizomer of the methylation-sensitive restriction enzyme that cleaves both methylated and unmethylated CpG-sites, thereby cleaving the methylated nucleic acid.

Specific primers are added to the nucleic acid sample, and the nucleic acid is amplified by any conventional method. The presence of an amplified product in the sample treated with the methylation-sensitive restriction enzyme but absence of an amplified product in the sample treated with the isoschizomer of the methylation-sensitive restriction enzyme indicates that methylation has occurred at the nucleic acid region assayed. However, the absence of an amplified product in the sample treated with the methylation-sensitive restriction enzyme together with the absence of an amplified product in the sample treated with the isoschizomer of the methylation-sensitive restriction enzyme indicates that no methylation has occurred at the nucleic acid region assayed.

As used herein, the term "methylation-sensitive restriction enzyme" refers to a restriction enzyme (e.g., SmaI) that includes CG as part of its recognition site and has activity when the C is methylated as compared to when the C is not methylated. Non-limiting examples of methylation-sensitive restriction enzymes include MspI, HpaII, BssHII, BstUI and NotI. Such enzymes can be used alone or in combination. Examples of other methylation-sensitive restriction enzymes include, but are not limited to SacII and EagI.

The isoschizomer of the methylation-sensitive restriction enzyme is a restriction enzyme that recognizes the same recognition site as the methylation-sensitive restriction enzyme but cleaves both methylated and unmethylated CGs. An example thereof includes MspI.

Primers of the present disclosure are designed to be "substantially" complementary to each strand of the locus to be amplified and include the appropriate G or C nucleotides as discussed above. This means that the primers must be sufficiently complementary to hybridize with their respective strands under polymerization reaction conditions. Primers of the present disclosure are used in the amplification process, which is an enzymatic chain reaction (e.g., PCR) in which that a target locus exponentially increases through a number of reaction steps. Typically, one primer is homologous with the negative (−) strand of the locus (antisense primer), and the other primer is homologous with the positive (+) strand (sense primer). After the primers have been annealed to denatured nucleic acid, the nucleic acid chain is extended by an enzyme such as DNA Polymerase I (Klenow), and reactants such as nucleotides, and, as a result, + and − strands containing the target locus sequence are newly synthesized. When the newly synthesized target locus is used as a template and subjected to repeated cycles of denaturing, primer annealing, and extension, exponential synthesis of the target locus sequence occurs. The resulting reaction product is a discrete nucleic acid duplex with termini corresponding to the ends of specific primers employed.

The amplification reaction is PCR which is commonly used in the art. However, alternative methods such as real-time PCR or linear amplification using isothermal enzyme may also be used. In addition, multiplex amplification reactions may also be used.

(6) Detection of Differential Methylation—Bisulfite Sequencing Method: Another method for detecting a methylated CpG-containing nucleic acid comprises the steps of: bringing a nucleic acid-containing sample into contact with an agent that modifies unmethylated cytosine; and amplifying the CpG-containing nucleic acid in the sample using CpG-specific oligonucleotide primers, wherein the oligonucleotide primers distinguish between modified methylated nucleic acid and non-methylated nucleic acid and detect the methylated nucleic acid. The amplification step is optional and desirable, but not essential. The method relies on the PCR reaction to distinguish between modified (e.g., chemically modified) methylated DNA and unmethylated DNA.

In the present disclosure, the primer(s) is, for example, 10-40 mer oligonucleotides that are complementary to methylated SDC2 DNA so as to be capable of amplifying the methylated SDC2 DNA. The primers may be designed to be "substantially" complementary to each strand of the locus to be amplified of a target DNA. This means that the primers must be sufficiently complementary to hybridize with their respective strands under polymerization reaction conditions.

The primers include forward and/or reverse primers, and the forward and/or reverse primers include one or more CGs or GCs.

Specifically, the forward primer may bind to a sequence complementary to the sequence of SEQ ID NO: 2 to specifically amplify the sequence complementary to the sequence of SEQ ID NO: 2, and may contain cytosine (C) at the 3' end. For example, the sequence of the methylated strand (sense strand) of SDC2 gene, converted by bisulfite, is set forth in SEQ ID NO: 2, and the forward primer can be designed to bind to a sequence complementary to the sequence of SEQ ID NO: 2 and to end with "C" of CG at the 3' end so as to more differentiate between methylated ("C") and unmethylated ("U", "T") SDC2 genes.

The reverse primer may bind to the nucleotide sequence of SEQ ID NO: 2 to amplify the nucleotide sequence of SEQ ID NO: 2, and may contain guanine G at the 3' end. For example, the reverse primer can be designed to bind complementarily to SEQ ID NO: 2 and contain guanine G at the 3' end so that the directionality thereof is opposite to that of the forward primer.

The reverse primer is primarily bind to the sequence of SEQ ID NO: 2 as a template to amplify the sequence of SEQ ID NO: 2, and the forward primer is secondarily bind to the amplified sequence so as to enable amplification of the sequence.

Specifically, the primer may comprise a primer pair including forward and reverse primers. For example, the primer may comprise a sequence having a homology of at least 80%, specifically at least 81%, 82%, 83%, 84%, 85%, 86%, 87%, 88%, 89%, 90%, 91%, 92%, 93%, 94%, 95%, 96%, 97%, 98% or 99%, to one or more sequences selected from the group consisting of SEQ ID NOs: 3, 4, 6-67, 69-100, 102-153, 155-216, 218-279, 281-342, 344-395, 397-448, 450-511, 513-574, 576-637, 639-700, 702-763, 765-826, and 828-841, but is not limited thereto. For example, the primer may comprise one or more sequences selected from the group consisting of SEQ ID NOs: 3, 4, 6-67, 69-100, 102-153, 155-216, 218-279, 281-342, 344-395, 397-448, 450-511, 513-574, 576-637, 639-700, 702-763, 765-826 and 828-841.

The forward primer may comprise a sequence having a homology of at least 80%, specifically at least 81%, 82%, 83%, 84%, 85%, 86%, 87%, 88%, 89%, 90%, 91%, 92%, 93%, 94%, 95%, 96%, 97%, 98% or 99%, to one or more sequences selected from the group consisting of SEQ ID NOs: 3, 6-65, 66, 69-98, 99, 102-151, 152, 155-214, 215, 218-277, 278, 281-340, 341, 344-393, 394, 397-446, 447, 450-509, 510, 513-572, 573, 576-635, 636, 639-698, 699, 702-761, 762, 765-824, 825, 828-840.

The reverse primer may comprise a sequence having a homology of at least 80%, specifically at least 81%, 82%, 83%, 84%, 85%, 86%, 87%, 88%, 89%, 90%, 91%, 92%, 93%, 94%, 95%, 96%, 97%, 98% or 99%, to one or more sequences selected from the group consisting of SEQ ID NOs: 4, 67, 100, 153, 216, 279, 342, 395, 448, 511, 574, 637, 700, 763, 826 and 841.

Specifically, the primer may comprise, for example, forward and reverse primers listed in Table 2 below.

The primer may comprise nucleotides subjected to either one modification or a combination of two or more modifications selected from among: modification in which an OH group at the 2' carbon position of a sugar structure in one or more nucleotides is substituted with —CH₃ (methyl), —OCH₃ (methoxy), —NH₂, —F (fluorine), —O-2-methoxyethyl-O-propyl, —O-2-methylthioethyl, —O-3-aminopropyl, —O-3-dimethylaminopropyl, —O—N-methylacetamido or —O-dimethylamidooxyethyl; modification in which oxygen in a sugar structure in nucleotides is substituted with sulfur; modification in which oxygen in a sugar structure in nucleotides is substituted with sulfur; and modification of a bond between nucleotides to a phosphorothioate, boranophosphate or methyl phosphonate bond, or subjected to modification to PNA (peptide nucleic acid), LNA (locked nucleic acid), UNA (unlocked nucleic acid), or inosine. Alternatively, the primer may comprise one or more nucleotides subjected to modification to 2'-5' phosphodiester linkage.

In some embodiments, the method may comprise a step of detecting methylation of target DNA by use of a self-reporting or energy transfer-labeled primer.

As used herein, the term "self-reporting" is also named "energy transfer labeled" and may be used interchangeably with "energy transfer labeled". As used herein, "self-reporting universal primer" may be used interchangeably with the term "energy transfer labeled primer".

"Self-reporting" or "energy transfer labeled" means that the primer is capable of self-quenching or self-probing such that when amplification does not occur, fluorescence is not emitted due to self-quenching, but when amplification occurs, quenching is released and fluorescence is emitted. Self-reporting or energy transfer-labeled substances include, but are not limited to, TaqMan probes, fluorophores and molecular beacons.

In some embodiments, the primer may further comprise a probe capable of hybridizing to the methylated SDC2 DNA to determine whether or not a product amplified with the primer would be produced.

A product amplified with the primer may be detected using any probe that can hybridize to, for example, target DNA to detect methylation. For example, the probe may contain one or more CpG dinucleotides. The probe may comprise a sequence having a homology of at least 80%, specifically at least 81%, 82%, 83%, 84%, 85%, 86%, 87%, 88%, 89%, 90%, 91%, 92%, 93%, 94%, 95%, 96%, 97%, 98% or 99%, to one or more sequences selected from the group consisting of SEQ ID NOs: 5, 68, 101, 154, 217, 280, 343, 396, 449, 512, 575, 638, 701, 764, 827 and 842, but is not limited thereto. The probe may comprise one or more sequences selected from the group consisting of SEQ ID NOs: 5, 68, 101, 154, 217, 280, 343, 396, 449, 512, 575, 638, 701, 764, 827 and 842. Specifically, the probe may comprise, for example, probes listed in Table 2 below.

The reverse primer is primarily bind to the sequence of SEQ ID NO: 2 as a template to amplify the sequence of SEQ ID NO: 2, and the forward primer and the probe is secondarily bind to the amplified sequence so that while amplification of the sequence proceeds, a signal by the probe or fluorescent dye can be emitted.

In nucleic acid hybridization reactions, the conditions used to achieve a particular level of stringency will vary depending on the nature of the nucleic acids being hybridized. For example, the length, degree of complementarity, nucleotide sequence composition (e.g., GC/AT content), and nucleic acid type (e.g., RNA/DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at room temperature (hybridization conditions); 0.2×SSC/0.1% SDS at room temperature (low stringency conditions); 0.2×SSC/0.1% SDS at 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary depending on the particular hybridization reaction involved, and can be determined empirically. In general, conditions of high stringency are used for the hybridization of the probe of interest.

In some embodiments, the probe may have a reporter or a quencher attached to both ends. The reporter may be one or more selected from the group consisting of FAM (6-carboxyfluorescein), Texas red, HEX (2', 4', 5', 7',-tetrachloro-6-carboxy-4,7-dichlorofluorescein), JOE, Cy3, and Cy5. The quencher may be one or more selected from the group consisting of TAMRA (6-carboxytetramethyl-rhodamine), BHQ1, BHQ2 and Dabcyl. The quencher may be one or more selected from the group consisting of TAMRA (6-carboxytetramethyl-rhodamine), BHQ1, BHQ2 and Dabcyl.

A method for screening methylation marker genes according to the present disclosure comprises the steps of: (a) isolating genomic DNAs from transformed cells and non-transformed cells; (b) reacting the isolated genomic DNAs with a methylated DNA-binding protein, thereby isolating methylated DNAs; and (c) amplifying the methylated DNAs, hybridizing the amplified DNAs to a CpG microarray, and then selecting genes showing the greatest difference in the degree of methylation between the normal cells and the cancer cells, thereby ensuring methylation marker genes.

The above method for screening biomarker genes can find genes which are differentially methylated in colorectal cancer as well as at various dysplasic stages of the tissue that progresses to colorectal cancer. The screened genes can be used for colorectal cancer screening, risk-assessment, prognosis, disease identification, the diagnosis of disease stages, and the selection of therapeutic targets.

The identification of genes that are methylated in colorectal cancer and abnormalities at various stages of colorectal cancer makes it possible to diagnose colorectal cancer at an early stage in an accurate and effective manner and allows methylation profiling of multiple genes and the identification of new targets for therapeutic intervention. Furthermore, the methylation data according to the present disclosure may be combined with other non-methylation related biomarker detection methods to obtain a more accurate system for colorectal cancer diagnosis.

According to the method of the present disclosure, the progression of colorectal cancer at various stages or phases can be diagnosed by determining the methylation stage of one or more nucleic acid biomarkers obtained from a sample. By comparing the methylation stage of a nucleic acid isolated from a sample at each stage of colorectal cancer with the methylation stage of one or more nucleic acids isolated from a sample in which there is no cell proliferative disorder of colorectal tissue, a specific stage of colorectal cancer in the sample can be detected. Herein, the methylation stage may be hypermethylation.

In one embodiment of the present disclosure, nucleic acid may be methylated in the regulatory region of a gene. In another embodiment, a gene which is involved in cell transformation can be diagnosed at an early stage by detecting methylation outside of the regulatory region of the gene, because methylation proceeds inwards from the outside of the gene.

In yet another embodiment of the present disclosure, cells that are likely to form colorectal cancer can be diagnosed at an early stage using the methylation marker genes. When genes confirmed to be methylated in cancer cells are methylated in cells that appear normal clinically or morphologically, this indicates that the normally appearing cells progress to cancer. Thus, colorectal cancer can be diagnosed at an early stage by detecting the methylation of colorectal cancer-specific genes in cells that appear normal.

The use of the methylation marker gene of the present disclosure allows for detection of a cellular proliferative disorder (dysplasia) of colorectal tissue in a sample. The detection method comprises bringing a sample comprising at least one nucleic acid isolated from a subject into contact with at least one agent capable of determining the methylation state of the nucleic acid. The method comprises detecting the methylation of at least one region in at least one nucleic acid, wherein the methylation of the nucleic acid differs from the methylation state of the same region of a nucleic acid present in a sample in which there is no abnormal growth (dysplastic progression) of colorectal cells.

In yet another embodiment of the present disclosure, the likelihood of progression of tissue to colorectal cancer can be evaluated by examining the methylation of a gene which is specifically methylated in colorectal cancer, and determining the methylation frequency of tissue that is likely to progress to colorectal cancer.

Thus, in another aspect, the present disclosure is directed to a method for detecting CpG methylation of SDC2 (Syndecan 2) gene for a colorectal cancer diagnosis, the method comprising the steps of:

(a) isolating genomic DNA from a clinical sample;
(b) treating the genomic DNA from step (a) with bisulfite; and
(c) determining hypermethylation of the CpG of the SDC2 gene in the genomic DNA treated with bisulfite according the step (b) by using primer(s) to amplify a methylated CpG of the bisulfite-treated SDC2 gene, wherein a colorectal cancer is detected in the human subject based on increased CpG methylation of the SDC2 gene relative to that of a control.

The method comprises determining the methylation status of SDC2 gene isolated from a sample, wherein the methylation status of the SDC2 gene is compared with the methylation stage of a SDC2 gene isolated from a sample in which there is no abnormal growth (dysplastic progression) of colorectal cells.

In another aspect, the present disclosure is directed to a kit for detecting CpG methylation of SDC2 (Syndecan 2) gene, comprising primer(s) to amplify a methylated CpG of the SDC2 gene.

The kit of the present disclosure makes it possible to determine the abnormal growth (dysplastic progression) of colorectal cells in a sample.

As used herein, the term "early detection" of cancer refers to discovering the likelihood of cancer prior to metastasis, and preferably before observation of a morphological change in a tissue or cell. Furthermore, the term "early detection" of cell transformation refers to the high probability of a cell to undergo transformation in its early stages before the cell is morphologically designated as being transformed.

As used herein, the term "hypermethylation" refers to the methylation of a CpG island. Hypermethylation as used herein refers to the presence of methylated alleles in one or more nucleic acids. Nucleic acids from a subject not having a cellular proliferative disorder of colorectal tissue contain no detectable methylated alleles when the same nucleic acids are examined.

In the present disclosure, "normal" cells refer to those that do not show any abnormal morphological or cytological changes. "Tumor" cells are cancer cells. "Non-tumor" cells are those cells that are part of the diseased tissue but are not considered to be the tumor portion.

As used herein, "predisposition" refers to the property of being susceptible to a cellular proliferative disorder. A subject having a predisposition to a cellular proliferative disorder has no cellular proliferative disorder, but is a subject having an increased likelihood of having a cellular proliferative disorder.

The term "nucleic acid" or "nucleic acid sequence" as used herein refers to an oligonucleotide, nucleotide or polynucleotide, or fragments thereof, or single-stranded or double-stranded DNA or RNA of genomic or synthetic origin, sense- or antisense-strand DNA or RNA of genomic or synthetic origin, peptide nucleic acid (PNA), or any DNA-like or RNA-like material of natural or synthetic origin. Typically, the CpG-containing nucleic acid is DNA. However, the inventive method may employ, for example, samples that contain DNA, or DNA and RNA containing mRNA, wherein DNA or RNA may be single-stranded or double-stranded, or a DNA-RNA hybrid may be included in the sample.

A mixture of nucleic acids in a single reactor (tube) may also be used. The specific nucleic acid sequence to be detected may be a fraction of a larger molecule or can be present initially as a discrete molecule, so that the specific sequence constitutes the entire nucleic acid. It is not necessary that the sequence to be studied be present initially in a pure form; the nucleic acid may be a minor fraction of a complex mixture, such as contained in whole human DNA.

Nucleic acids isolated from a subject are obtained in a biological sample from the subject. If it is desired to detect colorectal cancer or stages of colorectal cancer progression, the nucleic acid may be isolated from colorectal tissue by scraping or biopsy. Such samples may be obtained by various medical procedures known to those of skill in the art.

The present disclosure provides a kit useful for detecting CpG methylation of SDC2 (Syndecan 2) gene, comprising primer(s) to amplify a methylated CpG of the SDC2 gene.

Specifically, the primer may comprise a primer pair including forward and reverse primers. For example, the primer may comprise a sequence having a homology of at least 80%, specifically at least 81%, 82%, 83%, 84%, 85%, 86%, 87%, 88%, 89%, 90%, 91%, 92%, 93%, 94%, 95%, 96%, 97%, 98% or 99%, to one or more sequences selected from the group consisting of SEQ ID NOs: 3, 4, 6-67, 69-100, 102-153, 155-216, 218-279, 281-342, 344-395, 397-448, 450-511, 513-574, 576-637, 639-700, 702-763, 765-826, and 828-841, but is not limited thereto. For example, the primer may comprise one or more sequences selected from the group consisting of SEQ ID NOs: 3, 4, 6-67, 69-100, 102-153, 155-216, 218-279, 281-342, 344-395, 397-448, 450-511, 513-574, 576-637, 639-700, 702-763, 765-826 and 828-841.

The forward primer may comprise a sequence having a homology of at least 80%, specifically at least 81%, 82%, 83%, 84%, 85%, 86%, 87%, 88%, 89%, 90%, 91%, 92%, 93%, 94%, 95%, 96%, 97%, 98% or 99%, to one or more sequences selected from the group consisting of SEQ ID NOs: 3, 6-65, 66, 69-98, 99, 102-151, 152, 155-214, 215, 218-277, 278, 281-340, 341, 344-393, 394, 397-446, 447, 450-509, 510, 513-572, 573, 576-635, 636, 639-698, 699, 702-761, 762, 765-824, 825, 828-840.

The reverse primer may comprise a sequence having a homology of at least 80%, specifically at least 81%, 82%, 83%, 84%, 85%, 86%, 87%, 88%, 89%, 90%, 91%, 92%, 93%, 94%, 95%, 96%, 97%, 98% or 99%, to one or more sequences selected from the group consisting of SEQ ID NOs: 4, 67, 100, 153, 216, 279, 342, 395, 448, 511, 574, 637, 700, 763, 826 and 841.

In some embodiments, the primer may further comprise a probe capable of hybridizing to the methylated SDC2 DNA to determine whether or not a product amplified with the primer would be produced.

A product amplified with the primer may be detected using any probe that can hybridize to, for example, target DNA to detect methylation. For example, the probe may contain one or more CpG dinucleotides. The probe may comprise a sequence having a homology of at least 80%, specifically at least 81%, 82%, 83%, 84%, 85%, 86%, 87%, 88%, 89%, 90%, 91%, 92%, 93%, 94%, 95%, 96%, 97%, 98% or 99%, to one or more sequences selected from the group consisting of SEQ ID NOs: 5, 68, 101, 154, 217, 280, 343, 396, 449, 512, 575, 638, 701, 764, 827 and 842, but is not limited thereto. The probe may comprise one or more sequences selected from the group consisting of SEQ ID NOs: 5, 68, 101, 154, 217, 280, 343, 396, 449, 512, 575, 638, 701, 764, 827 and 842.

The kit of the present disclosure comprises a carrier means compartmentalized to receive a sample therein, one or more containers comprising a second container containing primers for amplification of a 5'-CpG-3' base sequence of methylated SDC 2 gene. Alternatively, a third container contains a probe for detecting an amplified product.

Carrier means are suited for containing one or more containers such as vials, tubes, and the like, each of the containers comprising one of the separate elements to be used in the method. In view of the description provided herein of the inventive method, those of skill in the art can readily determine the apportionment of the necessary reagents among the containers.

EXAMPLES

Hereinafter, the present disclosure will be described in further detail with reference to examples. It will be obvious to a person having ordinary skill in the art that these examples are illustrative purposes only and are not to be construed to limit the scope of the present disclosure.

Example 1: Detection of SDC2 Gene Methylation by Use of Methylated and Unmethylated Genomic DNAs For detection of SDC2 gene methylation, 808 sets of methylation-specific primers and probes (see Table 1) were designed, which are complementary to the sequence of SEQ ID NO: 2 corresponding to the SDC2 sequence after conversion by bisulfite. To test the abilities of these primers and probes to detect SDC2 gene methylation, the EpiTect PCR Control DNA set (Qiagen, Cat. No. 59695) was used. The EpiTect PCR Control DNA set is a DNA set obtained by converting methylated and unmethylated human genomic DNAs by bisulfite. Using these genomic DNAs, methylation-specific real-time PCR (qMSP) was performed using the 808 sets of methylation-specific primers and probes. The qMSP was performed using a Rotor-Gene Q PCR system (Qiagen). Specifically, a total of 20 μL of PCR reaction solution (containing 2 μl of template DNA; 4 μL of 5×AptaTaq DNA Master (Roche Diagnostics); 2 μL (2 pmole/μL) of PCR primer, 2 L (2 pmole/μL) of TaqMan probe; and 10 μL of D.W.) was prepared and subjected to PCR under the following conditions: treatment at 95° C. for 5 min, and then 40 cycles, each consisting of 15 sec at 95° C. and 1 min at suitable annealing temperature. Whether or not a PCR amplification product would be produced was determined by measuring the cycle threshold ($C_T$) value. The SDC2 gene methylation for each primer and probe set was measured by the $C_T$ value. It was determined that if the $C_T$ value was detected in methylated genomic DNA, methylation was normally detected, and if the $C_T$ value was not detected in unmethylated genomic DNA, the primer and probe set normally operated. It was shown that all the tested 808 sets of primers and probes normally detected SDC2 gene methylation (Table 2).

Table 1. Primer and probe sequences for detection of SDC2 gene methylation

TABLE 1

Primer and probe sequences for detection of SDC2 gene methylation

| Set | Primers | Sequences (5'-->3') | Size of amplified product (bp) | SEQ ID NO: |
|---|---|---|---|---|
| | F1 | GGAGAGAGGAAAAG | 140 | 3 |
| | R1 | CACGCCGATTAACA | | 4 |
| | P1 | AGTCGCGGCGTTTATTGGTTTTCGGAGT | | 5 |
| | F2 | GAGAGAGGAAAAGT | 139 | 6 |
| | R1 | CACGCCGATTAACA | | 4 |
| | P1 | AGTCGCGGCGTTTATTGGTTTTCGGAGT | | 5 |
| | F3 | AGAGAGGAAAAGTG | 138 | 7 |
| | R1 | CACGCCGATTAACA | | 4 |
| | P1 | AGTCGCGGCGTTTATTGGTTTTCGGAGT | | 5 |
| | F4 | GAGAGGAAAAGTGG | 137 | 8 |
| | R1 | CACGCCGATTAACA | | 4 |
| | P1 | AGTCGCGGCGTTTATTGGTTTTCGGAGT | | 5 |
| | F5 | AGAGGAAAAGTGGG | 136 | 9 |
| | R1 | CACGCCGATTAACA | | 4 |
| | P1 | AGTCGCGGCGTTTATTGGTTTTCGGAGT | | 5 |
| | F6 | GAGGAAAAGTGGGG | 135 | 10 |
| | R1 | CACGCCGATTAACA | | 4 |
| | P1 | AGTCGCGGCGTTTATTGGTTTTCGGAGT | | 5 |

TABLE 1-continued

Primer and probe sequences for detection of SDC2 gene methylation

| Set | Primers | Sequences (5'-->3') | Size of amplified product (bp) | SEQ ID NO: |
|---|---|---|---|---|
| | F7 | AGGAAAAGTGGGGA | 134 | 11 |
| | R1 | CACGCCGATTAACA | | 4 |
| | P1 | AGTCGCGGCGTTTATTGGTTTTCGGAGT | | 5 |
| | F8 | GGAAAAGTGGGGAG | 133 | 12 |
| | R1 | CACGCCGATTAACA | | 4 |
| | P1 | AGTCGCGGCGTTTATTGGTTTTCGGAGT | | 5 |
| | F9 | GAAAAGTGGGGAGA | 132 | 13 |
| | R1 | CACGCCGATTAACA | | 4 |
| | P1 | AGTCGCGGCGTTTATTGGTTTTCGGAGT | | 5 |
| 0 | F10 | AAAAGTGGGGAGAG | 131 | 14 |
| | R1 | CACGCCGATTAACA | | 4 |
| | P1 | AGTCGCGGCGTTTATTGGTTTTCGGAGT | | 5 |
| 1 | F11 | AAAGTGGGGAGAGA | 130 | 15 |
| | R1 | CACGCCGATTAACA | | 4 |
| | P1 | AGTCGCGGCGTTTATTGGTTTTCGGAGT | | 5 |
| 2 | F12 | AAGTGGGGAGAGAA | 129 | 16 |
| | R1 | CACGCCGATTAACA | | 4 |
| | P1 | AGTCGCGGCGTTTATTGGTTTTCGGAGT | | 5 |
| 3 | F13 | AGTGGGGAGAGAAA | 128 | 17 |
| | R1 | CACGCCGATTAACA | | 4 |
| | P1 | AGTCGCGGCGTTTATTGGTTTTCGGAGT | | 5 |
| 4 | F14 | GTGGGGAGAGAAAG | 127 | 18 |
| | R1 | CACGCCGATTAACA | | 4 |
| | P1 | AGTCGCGGCGTTTATTGGTTTTCGGAGT | | 5 |
| 5 | F15 | TGGGGAGAGAAAGG | 126 | 19 |
| | R1 | CACGCCGATTAACA | | 4 |
| | P1 | AGTCGCGGCGTTTATTGGTTTTCGGAGT | | 5 |
| 6 | F16 | GGGGAGAGAAAGGA | 125 | 20 |
| | R1 | CACGCCGATTAACA | | 4 |
| | P1 | AGTCGCGGCGTTTATTGGTTTTCGGAGT | | 5 |
| 7 | F17 | GGGAGAGAAAGGAA | 124 | 21 |
| | R1 | CACGCCGATTAACA | | 4 |
| | P1 | AGTCGCGGCGTTTATTGGTTTTCGGAGT | | 5 |
| 8 | F18 | GGAGAGAAAGGAAG | 123 | 22 |
| | R1 | CACGCCGATTAACA | | 4 |
| | P1 | AGTCGCGGCGTTTATTGGTTTTCGGAGT | | 5 |
| 9 | F19 | GAGAGAAAGGAAGA | 122 | 23 |
| | R1 | CACGCCGATTAACA | | 4 |
| | P1 | AGTCGCGGCGTTTATTGGTTTTCGGAGT | | 5 |
| 0 | F20 | AGAGAAAGGAAGAA | 121 | 24 |
| | R1 | CACGCCGATTAACA | | 4 |
| | P1 | AGTCGCGGCGTTTATTGGTTTTCGGAGT | | 5 |
| 1 | F21 | GAGAAAGGAAGAAA | 120 | 25 |
| | R1 | CACGCCGATTAACA | | 4 |
| | P1 | AGTCGCGGCGTTTATTGGTTTTCGGAGT | | 5 |
| 2 | F22 | AGAAAGGAAGAAAA | 119 | 26 |
| | R1 | CACGCCGATTAACA | | 4 |
| | P1 | AGTCGCGGCGTTTATTGGTTTTCGGAGT | | 5 |
| 3 | F23 | GAAAGGAAGAAAAG | 118 | 27 |
| | R1 | CACGCCGATTAACA | | 4 |
| | P1 | AGTCGCGGCGTTTATTGGTTTTCGGAGT | | 5 |
| 4 | F24 | AAAGGAAGAAAAGG | 117 | 28 |
| | R1 | CACGCCGATTAACA | | 4 |
| | P1 | AGTCGCGGCGTTTATTGGTTTTCGGAGT | | 5 |

TABLE 1-continued

Primer and probe sequences for detection of SDC2 gene methylation

| Set | Primers | Sequences (5'-->3') | Size of amplified product (bp) | SEQ ID NO: |
|---|---|---|---|---|
| 5 | F25 | AAGGAAGAAAAGGA | 116 | 29 |
|  | R1 | CACGCCGATTAACA |  | 4 |
|  | P1 | AGTCGCGGCGTTTATTGGTTTTCGGAGT |  | 5 |
| 6 | F26 | AGGAAGAAAAGGAT | 115 | 30 |
|  | R1 | CACGCCGATTAACA |  | 4 |
|  | P1 | AGTCGCGGCGTTTATTGGTTTTCGGAGT |  | 5 |
| 7 | F27 | GGAAGAAAAGGATT | 114 | 31 |
|  | R1 | CACGCCGATTAACA |  | 4 |
|  | P1 | AGTCGCGGCGTTTATTGGTTTTCGGAGT |  | 5 |
| 8 | F28 | GAAGAAAAGGATTG | 113 | 32 |
|  | R1 | CACGCCGATTAACA |  | 4 |
|  | P1 | AGTCGCGGCGTTTATTGGTTTTCGGAGT |  | 5 |
| 9 | F29 | AAGAAAAGGATTGA | 112 | 33 |
|  | R1 | CACGCCGATTAACA |  | 4 |
|  | P1 | AGTCGCGGCGTTTATTGGTTTTCGGAGT |  | 5 |
| 0 | F30 | AGAAAAGGATTGAG | 111 | 34 |
|  | R1 | CACGCCGATTAACA |  | 4 |
|  | P1 | AGTCGCGGCGTTTATTGGTTTTCGGAGT |  | 5 |
| 1 | F31 | GAAAAGGATTGAGA | 110 | 35 |
|  | R1 | CACGCCGATTAACA |  | 4 |
|  | P1 | AGTCGCGGCGTTTATTGGTTTTCGGAGT |  | 5 |
| 2 | F32 | AAAAGGATTGAGAA | 109 | 36 |
|  | R1 | CACGCCGATTAACA |  | 4 |
|  | P1 | AGTCGCGGCGTTTATTGGTTTTCGGAGT |  | 5 |
| 3 | F33 | AAAGGATTGAGAAA | 108 | 37 |
|  | R1 | CACGCCGATTAACA |  | 4 |
|  | P1 | AGTCGCGGCGTTTATTGGTTTTCGGAGT |  | 5 |
| 4 | F34 | AAGGATTGAGAAAA | 107 | 38 |
|  | R1 | CACGCCGATTAACA |  | 4 |
|  | P1 | AGTCGCGGCGTTTATTGGTTTTCGGAGT |  | 5 |
| 5 | F35 | AGGATTGAGAAAAC | 106 | 39 |
|  | R1 | CACGCCGATTAACA |  | 4 |
|  | P1 | AGTCGCGGCGTTTATTGGTTTTCGGAGT |  | 5 |
| 6 | F36 | GGATTGAGAAAACG | 105 | 40 |
|  | R1 | CACGCCGATTAACA |  | 4 |
|  | P1 | AGTCGCGGCGTTTATTGGTTTTCGGAGT |  | 5 |
| 7 | F37 | GATTGAGAAAACGT | 104 | 41 |
|  | R1 | CACGCCGATTAACA |  | 4 |
|  | P1 | AGTCGCGGCGTTTATTGGTTTTCGGAGT |  | 5 |
| 8 | F38 | ATTGAGAAAACGTA | 103 | 42 |
|  | R1 | CACGCCGATTAACA |  | 4 |
|  | P1 | AGTCGCGGCGTTTATTGGTTTTCGGAGT |  | 5 |
| 9 | F39 | TTGAGAAAACGTAG | 102 | 43 |
|  | R1 | CACGCCGATTAACA |  | 4 |
|  | P1 | AGTCGCGGCGTTTATTGGTTTTCGGAGT |  | 5 |
| 0 | F40 | TGAGAAAACGTAGG | 101 | 44 |
|  | R1 | CACGCCGATTAACA |  | 4 |
|  | P1 | AGTCGCGGCGTTTATTGGTTTTCGGAGT |  | 5 |
| 1 | F41 | GAGAAAACGTAGGA | 100 | 45 |
|  | R1 | CACGCCGATTAACA |  | 4 |
|  | P1 | AGTCGCGGCGTTTATTGGTTTTCGGAGT |  | 5 |
| 2 | F42 | AGAAAACGTAGGAG | 99 | 46 |
|  | R1 | CACGCCGATTAACA |  | 4 |
|  | P1 | AGTCGCGGCGTTTATTGGTTTTCGGAGT |  | 5 |

TABLE 1 -continued

Primer and probe sequences for detection of SDC2 gene methylation

| Set | Primers | Sequences (5'-->3') | Size of amplified product (bp) | SEQ ID NO: |
|---|---|---|---|---|
| 3 | F43 | GAAAACGTAGGAGT | 98 | 47 |
|   | R1  | CACGCCGATTAACA |    | 4  |
|   | P1  | AGTCGCGGCGTTTATTGGTTTTCGGAGT | | 5 |
| 4 | F44 | AAAACGTAGGAGTT | 97 | 48 |
|   | R1  | CACGCCGATTAACA |    | 4  |
|   | P1  | AGTCGCGGCGTTTATTGGTTTTCGGAGT | | 5 |
| 5 | F45 | AAACGTAGGAGTTT | 96 | 49 |
|   | R1  | CACGCCGATTAACA |    | 4  |
|   | P1  | AGTCGCGGCGTTTATTGGTTTTCGGAGT | | 5 |
| 6 | F46 | AACGTAGGAGTTTT | 95 | 50 |
|   | R1  | CACGCCGATTAACA |    | 4  |
|   | P1  | AGTCGCGGCGTTTATTGGTTTTCGGAGT | | 5 |
| 7 | F47 | ACGTAGGAGTTTTG | 94 | 51 |
|   | R1  | CACGCCGATTAACA |    | 4  |
|   | P1  | AGTCGCGGCGTTTATTGGTTTTCGGAGT | | 5 |
| 8 | F48 | CGTAGGAGTTTTGG | 93 | 52 |
|   | R1  | CACGCCGATTAACA |    | 4  |
|   | P1  | AGTCGCGGCGTTTATTGGTTTTCGGAGT | | 5 |
| 9 | F49 | GTAGGAGTTTTGGT | 92 | 53 |
|   | R1  | CACGCCGATTAACA |    | 4  |
|   | P1  | AGTCGCGGCGTTTATTGGTTTTCGGAGT | | 5 |
| 0 | F50 | TAGGAGTTTTGGTT | 91 | 54 |
|   | R1  | CACGCCGATTAACA |    | 4  |
|   | P1  | AGTCGCGGCGTTTATTGGTTTTCGGAGT | | 5 |
| 1 | F51 | AGGAGTTTTGGTTT | 90 | 55 |
|   | R1  | CACGCCGATTAACA |    | 4  |
|   | P1  | AGTCGCGGCGTTTATTGGTTTTCGGAGT | | 5 |
| 2 | F52 | GGAGTTTTGGTTTG | 89 | 56 |
|   | R1  | CACGCCGATTAACA |    | 4  |
|   | P1  | AGTCGCGGCGTTTATTGGTTTTCGGAGT | | 5 |
| 3 | F53 | GAGTTTTGGTTTGT | 88 | 57 |
|   | R1  | CACGCCGATTAACA |    | 4  |
|   | P1  | AGTCGCGGCGTTTATTGGTTTTCGGAGT | | 5 |
| 4 | F54 | AGTTTTGGTTTGTC | 87 | 58 |
|   | R1  | CACGCCGATTAACA |    | 4  |
|   | P1  | AGTCGCGGCGTTTATTGGTTTTCGGAGT | | 5 |
| 5 | F55 | GTTTTGGTTTGTCG | 86 | 59 |
|   | R1  | CACGCCGATTAACA |    | 4  |
|   | P1  | AGTCGCGGCGTTTATTGGTTTTCGGAGT | | 5 |
| 6 | F56 | TTTTGGTTTGTCGG | 85 | 60 |
|   | R1  | CACGCCGATTAACA |    | 4  |
|   | P1  | AGTCGCGGCGTTTATTGGTTTTCGGAGT | | 5 |
| 7 | F57 | TTTGGTTTGTCGGT | 84 | 61 |
|   | R1  | CACGCCGATTAACA |    | 4  |
|   | P1  | AGTCGCGGCGTTTATTGGTTTTCGGAGT | | 5 |
| 8 | F58 | TTGGTTTGTCGGTG | 83 | 62 |
|   | R1  | CACGCCGATTAACA |    | 4  |
|   | P1  | AGTCGCGGCGTTTATTGGTTTTCGGAGT | | 5 |
| 9 | F59 | TGGTTTGTCGGTGA | 82 | 63 |
|   | R1  | CACGCCGATTAACA |    | 4  |
|   | P1  | AGTCGCGGCGTTTATTGGTTTTCGGAGT | | 5 |
| 0 | F60 | GGTTTGTCGGTGAG | 81 | 64 |
|   | R1  | CACGCCGATTAACA |    | 4  |
|   | P1  | AGTCGCGGCGTTTATTGGTTTTCGGAGT | | 5 |

TABLE 1-continued

Primer and probe sequences for detection of SDC2 gene methylation

| Set | Primers | Sequences (5'-->3') | Size of amplified product (bp) | SEQ ID NO: |
|---|---|---|---|---|
| 1 | F61 | GTTTGTCGGTGAGT | 80 | 65 |
|   | R1  | CACGCCGATTAACA |    | 4 |
|   | P1  | AGTCGCGGCGTTTATTGGTTTTCGGAGT | | 5 |
| 2 | F62 | TTTGTCGGTGAGTA | 110 | 66 |
|   | R2  | AATAAACCCGAAAA |    | 67 |
|   | P2  | CGGCGTGTAATTTTGTAGGAATTT |  | 68 |
| 3 | F63 | TTGTCGGTGAGTAG | 109 | 69 |
|   | R2  | AATAAACCCGAAAA |    | 67 |
|   | P2  | CGGCGTGTAATTTTGTAGGAATTT |  | 68 |
| 4 | F64 | TGTCGGTGAGTAGA | 108 | 70 |
|   | R2  | AATAAACCCGAAAA |    | 67 |
|   | P2  | CGGCGTGTAATTTTGTAGGAATTT |  | 68 |
| 5 | F65 | GTCGGTGAGTAGAG | 107 | 71 |
|   | R2  | AATAAACCCGAAAA |    | 67 |
|   | P2  | CGGCGTGTAATTTTGTAGGAATTT |  | 68 |
| 6 | F66 | TCGGTGAGTAGAGT | 106 | 72 |
|   | R2  | AATAAACCCGAAAA |    | 67 |
|   | P2  | CGGCGTGTAATTTTGTAGGAATTT |  | 68 |
| 7 | F67 | CGGTGAGTAGAGTC | 105 | 73 |
|   | R2  | AATAAACCCGAAAA |    | 67 |
|   | P2  | CGGCGTGTAATTTTGTAGGAATTT |  | 68 |
| 8 | F68 | GGTGAGTAGAGTCG | 104 | 74 |
|   | R2  | AATAAACCCGAAAA |    | 67 |
|   | P2  | CGGCGTGTAATTTTGTAGGAATTT |  | 68 |
| 9 | F69 | GTGAGTAGAGTCGG | 103 | 75 |
|   | R2  | AATAAACCCGAAAA |    | 67 |
|   | P2  | CGGCGTGTAATTTTGTAGGAATTT |  | 68 |
| 0 | F70 | TGAGTAGAGTCGGC | 102 | 76 |
|   | R2  | AATAAACCCGAAAA |    | 67 |
|   | P2  | CGGCGTGTAATTTTGTAGGAATTT |  | 68 |
| 1 | F71 | GAGTAGAGTCGGCG | 101 | 77 |
|   | R2  | AATAAACCCGAAAA |    | 67 |
|   | P2  | CGGCGTGTAATTTTGTAGGAATTT |  | 68 |
| 2 | F72 | AGTAGAGTCGGCGT | 100 | 78 |
|   | R2  | AATAAACCCGAAAA |    | 67 |
|   | P2  | CGGCGTGTAATTTTGTAGGAATTT |  | 68 |
| 3 | F73 | GTAGAGTCGGCGTA | 99 | 79 |
|   | R2  | AATAAACCCGAAAA |    | 67 |
|   | P2  | CGGCGTGTAATTTTGTAGGAATTT |  | 68 |
| 4 | F74 | TAGAGTCGGCGTAG | 98 | 80 |
|   | R2  | AATAAACCCGAAAA |    | 67 |
|   | P2  | CGGCGTGTAATTTTGTAGGAATTT |  | 68 |
| 5 | F75 | AGAGTCGGCGTAGT | 97 | 81 |
|   | R2  | AATAAACCCGAAAA |    | 67 |
|   | P2  | CGGCGTGTAATTTTGTAGGAATTT |  | 68 |
| 6 | F76 | GAGTCGGCGTAGTT | 96 | 82 |
|   | R2  | AATAAACCCGAAAA |    | 67 |
|   | P2  | CGGCGTGTAATTTTGTAGGAATTT |  | 68 |
| 7 | F77 | AGTCGGCGTAGTTA | 95 | 83 |
|   | R2  | AATAAACCCGAAAA |    | 67 |
|   | P2  | CGGCGTGTAATTTTGTAGGAATTT |  | 68 |
| 8 | F78 | GTCGGCGTAGTTAT | 94 | 84 |
|   | R2  | AATAAACCCGAAAA |    | 67 |
|   | P2  | CGGCGTGTAATTTTGTAGGAATTT |  | 68 |

TABLE 1-continued

Primer and probe sequences for detection of SDC2 gene methylation

| Set | Primers | Sequences (5'-->3') | Size of amplified product (bp) | SEQ ID NO: |
|---|---|---|---|---|
| 9 | F79 | TCGGCGTAGTTATA | 93 | 85 |
|   | R2 | AATAAACCCGAAAA |  | 67 |
|   | P2 | CGGCGTGTAATTTTGTAGGAATTT |  | 68 |
| 0 | F80 | CGGCGTAGTTATAG | 92 | 86 |
|   | R2 | AATAAACCCGAAAA |  | 67 |
|   | P2 | CGGCGTGTAATTTTGTAGGAATTT |  | 68 |
| 1 | F81 | GGCGTAGTTATAGC | 91 | 87 |
|   | R2 | AATAAACCCGAAAA |  | 67 |
|   | P2 | CGGCGTGTAATTTTGTAGGAATTT |  | 68 |
| 2 | F82 | GCGTAGTTATAGCG | 90 | 88 |
|   | R2 | AATAAACCCGAAAA |  | 67 |
|   | P2 | CGGCGTGTAATTTTGTAGGAATTT |  | 68 |
| 3 | F83 | CGTAGTTATAGCGC | 89 | 89 |
|   | R2 | AATAAACCCGAAAA |  | 67 |
|   | P2 | CGGCGTGTAATTTTGTAGGAATTT |  | 68 |
| 4 | F84 | GTAGTTATAGCGCG | 88 | 90 |
|   | R2 | AATAAACCCGAAAA |  | 67 |
|   | P2 | CGGCGTGTAATTTTGTAGGAATTT |  | 68 |
| 5 | F85 | TAGTTATAGCGCGG | 87 | 91 |
|   | R2 | AATAAACCCGAAAA |  | 67 |
|   | P2 | CGGCGTGTAATTTTGTAGGAATTT |  | 68 |
| 6 | F86 | AGTTATAGCGCGGA | 86 | 92 |
|   | R2 | AATAAACCCGAAAA |  | 67 |
|   | P2 | CGGCGTGTAATTTTGTAGGAATTT |  | 68 |
| 7 | F87 | GTTATAGCGCGGAG | 85 | 93 |
|   | R2 | AATAAACCCGAAAA |  | 67 |
|   | P2 | CGGCGTGTAATTTTGTAGGAATTT |  | 68 |
| 8 | F88 | TTATAGCGCGGAGT | 84 | 94 |
|   | R2 | AATAAACCCGAAAA |  | 67 |
|   | P2 | CGGCGTGTAATTTTGTAGGAATTT |  | 68 |
| 9 | F89 | TATAGCGCGGAGTC | 83 | 95 |
|   | R2 | AATAAACCCGAAAA |  | 67 |
|   | P2 | CGGCGTGTAATTTTGTAGGAATTT |  | 68 |
| 0 | F90 | ATAGCGCGGAGTCG | 82 | 96 |
|   | R2 | AATAAACCCGAAAA |  | 67 |
|   | P2 | CGGCGTGTAATTTTGTAGGAATTT |  | 68 |
| 1 | F91 | TAGCGCGGAGTCGC | 81 | 97 |
|   | R2 | AATAAACCCGAAAA |  | 67 |
|   | P2 | CGGCGTGTAATTTTGTAGGAATTT |  | 68 |
| 2 | F92 | AGCGCGGAGTCGCG | 80 | 98 |
|   | R2 | AATAAACCCGAAAA |  | 67 |
|   | P2 | CGGCGTGTAATTTTGTAGGAATTT |  | 68 |
| 3 | F93 | GCGCGGAGTCGCGG | 130 | 99 |
|   | R3 | CTCCGAACTCCCCT |  | 100 |
|   | P3 | CGTTTTTTTTTTTAGTCGTTT |  | 101 |
| 4 | F94 | CGCGGAGTCGCGGC | 129 | 102 |
|   | R3 | CTCCGAACTCCCCT |  | 100 |
|   | P3 | CGTTTTTTTTTTTAGTCGTTT |  | 101 |
| 5 | F95 | GCGGAGTCGCGGCG | 128 | 103 |
|   | R3 | CTCCGAACTCCCCT |  | 100 |
|   | P3 | CGTTTTTTTTTTTAGTCGTTT |  | 101 |
| 6 | F96 | CGGAGTCGCGGCGT | 127 | 104 |
|   | R3 | CTCCGAACTCCCCT |  | 100 |
|   | P3 | CGTTTTTTTTTTTAGTCGTTT |  | 101 |

TABLE 1-continued

Primer and probe sequences for detection of SDC2 gene methylation

| Set | Primers | Sequences (5'-->3') | Size of amplified product (bp) | SEQ ID NO: |
|---|---|---|---|---|
| 7 | F97 | GGAGTCGCGGCGTT | 126 | 105 |
|  | R3 | CTCCGAACTCCCCT |  | 100 |
|  | P3 | CGTTTTTTTTTTTAGTCGTTT |  | 101 |
| 8 | F98 | GAGTCGCGGCGTTT | 125 | 106 |
|  | R3 | CTCCGAACTCCCCT |  | 100 |
|  | P3 | CGTTTTTTTTTTTAGTCGTTT |  | 101 |
| 9 | F99 | AGTCGCGGCGTTTA | 124 | 107 |
|  | R3 | CTCCGAACTCCCCT |  | 100 |
|  | P3 | CGTTTTTTTTTTTAGTCGTTT |  | 101 |
| 00 | F100 | GTCGCGGCGTTTAT | 123 | 108 |
|  | R3 | CTCCGAACTCCCCT |  | 100 |
|  | P3 | CGTTTTTTTTTTTAGTCGTTT |  | 101 |
| 01 | F101 | TCGCGGCGTTTATT | 122 | 109 |
|  | R3 | CTCCGAACTCCCCT |  | 100 |
|  | P3 | CGTTTTTTTTTTTAGTCGTTT |  | 101 |
| 02 | F102 | CGCGGCGTTTATTG | 121 | 110 |
|  | R3 | CTCCGAACTCCCCT |  | 100 |
|  | P3 | CGTTTTTTTTTTTAGTCGTTT |  | 101 |
| 03 | F103 | GCGGCGTTTATTGG | 120 | 111 |
|  | R3 | CTCCGAACTCCCCT |  | 100 |
|  | P3 | CGTTTTTTTTTTTAGTCGTTT |  | 101 |
| 04 | F104 | CGGCGTTTATTGGT | 119 | 112 |
|  | R3 | CTCCGAACTCCCCT |  | 100 |
|  | P3 | CGTTTTTTTTTTTAGTCGTTT |  | 101 |
| 05 | F105 | GGCGTTTATTGGTT | 118 | 113 |
|  | R3 | CTCCGAACTCCCCT |  | 100 |
|  | P3 | CGTTTTTTTTTTTAGTCGTTT |  | 101 |
| 06 | F106 | GCGTTTATTGGTTT | 117 | 114 |
|  | R3 | CTCCGAACTCCCCT |  | 100 |
|  | P3 | CGTTTTTTTTTTTAGTCGTTT |  | 101 |
| 07 | F107 | CGTTTATTGGTTTT | 116 | 115 |
|  | R3 | CTCCGAACTCCCCT |  | 100 |
|  | P3 | CGTTTTTTTTTTTAGTCGTTT |  | 101 |
| 08 | F108 | GTTTATTGGTTTTC | 115 | 116 |
|  | R3 | CTCCGAACTCCCCT |  | 100 |
|  | P3 | CGTTTTTTTTTTTAGTCGTTT |  | 101 |
| 09 | F109 | TTTATTGGTTTTCG | 114 | 117 |
|  | R3 | CTCCGAACTCCCCT |  | 100 |
|  | P3 | CGTTTTTTTTTTTAGTCGTTT |  | 101 |
| 10 | F110 | TTATTGGTTTTCGG | 113 | 118 |
|  | R3 | CTCCGAACTCCCCT |  | 100 |
|  | P3 | CGTTTTTTTTTTTAGTCGTTT |  | 101 |
| 11 | F111 | TATTGGTTTTCGGA | 112 | 119 |
|  | R3 | CTCCGAACTCCCCT |  | 100 |
|  | P3 | CGTTTTTTTTTTTAGTCGTTT |  | 101 |
| 12 | F112 | ATTGGTTTTCGGAG | 111 | 120 |
|  | R3 | CTCCGAACTCCCCT |  | 100 |
|  | P3 | CGTTTTTTTTTTTAGTCGTTT |  | 101 |
| 13 | F113 | TTGGTTTTCGGAGT | 110 | 121 |
|  | R3 | CTCCGAACTCCCCT |  | 100 |
|  | P3 | CGTTTTTTTTTTTAGTCGTTT |  | 101 |
| 14 | F114 | TGGTTTTCGGAGTT | 109 | 122 |
|  | R3 | CTCCGAACTCCCCT |  | 100 |
|  | P3 | CGTTTTTTTTTTTAGTCGTTT |  | 101 |

TABLE 1-continued

Primer and probe sequences for detection of SDC2 gene methylation

| Set | Primers | Sequences (5'-->3') | Size of amplified product (bp) | SEQ ID NO: |
|---|---|---|---|---|
| 15 | F115 | GGTTTTCGGAGTTG | 108 | 123 |
|  | R3 | CTCCGAACTCCCCT |  | 100 |
|  | P3 | CGTTTTTTTTTTTAGTCGTTT |  | 101 |
| 16 | F116 | GTTTTCGGAGTTGT | 107 | 124 |
|  | R3 | CTCCGAACTCCCCT |  | 100 |
|  | P3 | CGTTTTTTTTTTTAGTCGTTT |  | 101 |
| 17 | F117 | TTTTCGGAGTTGTT | 106 | 125 |
|  | R3 | CTCCGAACTCCCCT |  | 100 |
|  | P3 | CGTTTTTTTTTTTAGTCGTTT |  | 101 |
| 18 | F118 | TTTCGGAGTTGTTA | 105 | 126 |
|  | R3 | CTCCGAACTCCCCT |  | 100 |
|  | P3 | CGTTTTTTTTTTTAGTCGTTT |  | 101 |
| 19 | F119 | TTCGGAGTTGTTAA | 104 | 127 |
|  | R3 | CTCCGAACTCCCCT |  | 100 |
|  | P3 | CGTTTTTTTTTTTAGTCGTTT |  | 101 |
| 20 | F120 | TCGGAGTTGTTAAT | 103 | 128 |
|  | R3 | CTCCGAACTCCCCT |  | 100 |
|  | P3 | CGTTTTTTTTTTTAGTCGTTT |  | 101 |
| 21 | F121 | CGGAGTTGTTAATC | 102 | 129 |
|  | R3 | CTCCGAACTCCCCT |  | 100 |
|  | P3 | CGTTTTTTTTTTTAGTCGTTT |  | 101 |
| 22 | F122 | GGAGTTGTTAATCG | 101 | 130 |
|  | R3 | CTCCGAACTCCCCT |  | 100 |
|  | P3 | CGTTTTTTTTTTTAGTCGTTT |  | 101 |
| 23 | F123 | GAGTTGTTAATCGG | 100 | 131 |
|  | R3 | CTCCGAACTCCCCT |  | 100 |
|  | P3 | CGTTTTTTTTTTTAGTCGTTT |  | 101 |
| 24 | F124 | AGTTGTTAATCGGC | 99 | 132 |
|  | R3 | CTCCGAACTCCCCT |  | 100 |
|  | P3 | CGTTTTTTTTTTTAGTCGTTT |  | 101 |
| 25 | F125 | GTTGTTAATCGGCG | 98 | 133 |
|  | R3 | CTCCGAACTCCCCT |  | 100 |
|  | P3 | CGTTTTTTTTTTTAGTCGTTT |  | 101 |
| 26 | F126 | TTGTTAATCGGCGT | 97 | 134 |
|  | R3 | CTCCGAACTCCCCT |  | 100 |
|  | P3 | CGTTTTTTTTTTTAGTCGTTT |  | 101 |
| 27 | F127 | TGTTAATCGGCGTG | 96 |  |
|  | R3 | CTCCGAACTCCCCT |  | 100 |
|  | P3 | CGTTTTTTTTTTTAGTCGTTT |  | 101 |
| 28 | F128 | GTTAATCGGCGTGT | 95 | 136 |
|  | R3 | CTCCGAACTCCCCT |  | 100 |
|  | P3 | CGTTTTTTTTTTTAGTCGTTT |  | 101 |
| 29 | F129 | TTAATCGGCGTGTA | 94 | 137 |
|  | R3 | CTCCGAACTCCCCT |  | 100 |
|  | P3 | CGTTTTTTTTTTTAGTCGTTT |  | 101 |
| 30 | F130 | TAATCGGCGTGTAA | 93 | 138 |
|  | R3 | CTCCGAACTCCCCT |  | 100 |
|  | P3 | CGTTTTTTTTTTTAGTCGTTT |  | 101 |
| 31 | F131 | AATCGGCGTGTAAT | 92 | 139 |
|  | R3 | CTCCGAACTCCCCT |  | 100 |
|  | P3 | CGTTTTTTTTTTTAGTCGTTT |  | 101 |
| 32 | F132 | ATCGGCGTGTAATT | 91 | 140 |
|  | R3 | CTCCGAACTCCCCT |  | 100 |
|  | P3 | CGTTTTTTTTTTTAGTCGTTT |  | 101 |

TABLE 1-continued

Primer and probe sequences for detection of SDC2 gene methylation

| Set | Primers | Sequences (5'-->3') | Size of amplified product (bp) | SEQ ID NO: |
|---|---|---|---|---|
| 33 | F133 | TCGGCGTGTAATTT | 90 | 141 |
|  | R3 | CTCCGAACTCCCCT |  | 100 |
|  | P3 | CGTTTTTTTTTTTAGTCGTTT |  | 101 |
| 34 | F134 | CGGCGTGTAATTTT | 89 | 142 |
|  | R3 | CTCCGAACTCCCCT |  | 100 |
|  | P3 | CGTTTTTTTTTTTAGTCGTTT |  | 101 |
| 35 | F135 | GGCGTGTAATTTTG | 88 | 143 |
|  | R3 | CTCCGAACTCCCCT |  | 100 |
|  | P3 | CGTTTTTTTTTTTAGTCGTTT |  | 101 |
| 36 | F136 | GCGTGTAATTTTGT | 87 | 144 |
|  | R3 | CTCCGAACTCCCCT |  | 100 |
|  | P3 | CGTTTTTTTTTTTAGTCGTTT |  | 101 |
| 37 | F137 | CGTGTAATTTTGTA | 86 | 145 |
|  | R3 | CTCCGAACTCCCCT |  | 100 |
|  | P3 | CGTTTTTTTTTTTAGTCGTTT |  | 101 |
| 38 | F138 | GTGTAATTTTGTAG | 85 | 146 |
|  | R3 | CTCCGAACTCCCCT |  | 100 |
|  | P3 | CGTTTTTTTTTTTAGTCGTTT |  | 101 |
| 39 | F139 | TGTAATTTTGTAGG | 84 | 147 |
|  | R3 | CTCCGAACTCCCCT |  | 100 |
|  | P3 | CGTTTTTTTTTTTAGTCGTTT |  | 101 |
| 40 | F140 | GTAATTTTGTAGGA | 83 | 148 |
|  | R3 | CTCCGAACTCCCCT |  | 100 |
|  | P3 | CGTTTTTTTTTTTAGTCGTTT |  | 101 |
| 41 | F141 | TAATTTTGTAGGAA | 82 | 149 |
|  | R3 | CTCCGAACTCCCCT |  | 100 |
|  | P3 | CGTTTTTTTTTTTAGTCGTTT |  | 101 |
| 42 | F142 | AATTTTGTAGGAAT | 81 | 150 |
|  | R3 | CTCCGAACTCCCCT |  | 100 |
|  | P3 | CGTTTTTTTTTTTAGTCGTTT |  | 101 |
| 43 | F143 | ATTTTGTAGGAATT | 80 | 151 |
|  | R3 | CTCCGAACTCCCCT |  | 100 |
|  | P3 | CGTTTTTTTTTTTAGTCGTTT |  | 101 |
| 44 | F144 | TTTTGTAGGAATTT | 140 | 152 |
|  | R4 | CGAATCCTCCTCCT |  | 153 |
|  | P4 | TTAGAGGAAAAGAAGAGGAGGAGA |  | 154 |
| 45 | F145 | TTTGTAGGAATTTT | 139 | 155 |
|  | R4 | CGAATCCTCCTCCT |  | 153 |
|  | P4 | TTAGAGGAAAAGAAGAGGAGGAGA |  | 154 |
| 46 | F146 | TTGTAGGAATTTTT | 138 | 156 |
|  | R4 | CGAATCCTCCTCCT |  | 153 |
|  | P4 | TTAGAGGAAAAGAAGAGGAGGAGA |  | 154 |
| 47 | F147 | TGTAGGAATTTTTT | 137 | 157 |
|  | R4 | CGAATCCTCCTCCT |  | 153 |
|  | P4 | TTAGAGGAAAAGAAGAGGAGGAGA |  | 154 |
| 48 | F148 | GTAGGAATTTTTTT | 136 | 158 |
|  | R4 | CGAATCCTCCTCCT |  | 153 |
|  | P4 | TTAGAGGAAAAGAAGAGGAGGAGA |  | 154 |
| 49 | F149 | TAGGAATTTTTTTC | 135 | 159 |
|  | R4 | CGAATCCTCCTCCT |  | 153 |
|  | P4 | TTAGAGGAAAAGAAGAGGAGGAGA |  | 154 |
| 50 | F150 | AGGAATTTTTTTCG | 134 | 160 |
|  | R4 | CGAATCCTCCTCCT |  | 153 |
|  | P4 | TTAGAGGAAAAGAAGAGGAGGAGA |  | 154 |

TABLE 1-continued

Primer and probe sequences for detection of SDC2 gene methylation

| Set | Primers | Sequences (5'-->3') | Size of amplified product (bp) | SEQ ID NO: |
|---|---|---|---|---|
| 51 | F151 | GGAATTTTTTCGG | 133 | 161 |
|  | R4 | CGAATCCTCCTCCT |  | 153 |
|  | P4 | TTAGAGGAAAAGAAGAGGAGGAGA |  | 154 |
| 52 | F152 | GAATTTTTTCGGG | 132 | 162 |
|  | R4 | CGAATCCTCCTCCT |  | 153 |
|  | P4 | TTAGAGGAAAAGAAGAGGAGGAGA |  | 154 |
| 53 | F153 | AATTTTTTTCGGGT | 131 | 163 |
|  | R4 | CGAATCCTCCTCCT |  | 153 |
|  | P4 | TTAGAGGAAAAGAAGAGGAGGAGA |  | 154 |
| 54 | F154 | ATTTTTTTCGGGTT | 130 | 164 |
|  | R4 | CGAATCCTCCTCCT |  | 153 |
|  | P4 | TTAGAGGAAAAGAAGAGGAGGAGA |  | 154 |
| 55 | F155 | TTTTTTTCGGGTTT | 129 | 165 |
|  | R4 | CGAATCCTCCTCCT |  | 153 |
|  | P4 | TTAGAGGAAAAGAAGAGGAGGAGA |  | 154 |
| 56 | F156 | TTTTTTCGGGTTTA | 128 | 166 |
|  | R4 | CGAATCCTCCTCCT |  | 153 |
|  | P4 | TTAGAGGAAAAGAAGAGGAGGAGA |  | 154 |
| 57 | F157 | TTTTTCGGGTTTAT | 127 | 167 |
|  | R4 | CGAATCCTCCTCCT |  | 153 |
|  | P4 | TTAGAGGAAAAGAAGAGGAGGAGA |  | 154 |
| 58 | F158 | TTTTCGGGTTTATT | 126 | 168 |
|  | R4 | CGAATCCTCCTCCT |  | 153 |
|  | P4 | TTAGAGGAAAAGAAGAGGAGGAGA |  | 154 |
| 59 | F159 | TTTCGGGTTTATTT | 125 | 169 |
|  | R4 | CGAATCCTCCTCCT |  | 153 |
|  | P4 | TTAGAGGAAAAGAAGAGGAGGAGA |  | 154 |
| 60 | F160 | TTCGGGTTTATTTG | 124 | 170 |
|  | R4 | CGAATCCTCCTCCT |  | 153 |
|  | P4 | TTAGAGGAAAAGAAGAGGAGGAGA |  | 154 |
| 61 | F161 | TCGGGTTTATTTGG | 123 | 171 |
|  | R4 | CGAATCCTCCTCCT |  | 153 |
|  | P4 | TTAGAGGAAAAGAAGAGGAGGAGA |  | 154 |
| 62 | F162 | CGGGTTTATTTGGG | 122 | 172 |
|  | R4 | CGAATCCTCCTCCT |  | 153 |
|  | P4 | TTAGAGGAAAAGAAGAGGAGGAGA |  | 154 |
| 63 | F163 | GGGTTTATTTGGGA | 121 | 173 |
|  | R4 | CGAATCCTCCTCCT |  | 153 |
|  | P4 | TTAGAGGAAAAGAAGAGGAGGAGA |  | 154 |
| 64 | F164 | GGTTTATTTGGGAG | 120 | 174 |
|  | R4 | CGAATCCTCCTCCT |  | 153 |
|  | P4 | TTAGAGGAAAAGAAGAGGAGGAGA |  | 154 |
| 65 | F165 | GTTTATTTGGGAGT | 119 | 175 |
|  | R4 | CGAATCCTCCTCCT |  | 153 |
|  | P4 | TTAGAGGAAAAGAAGAGGAGGAGA |  | 154 |
| 66 | F166 | TTTATTTGGGAGTT | 118 | 176 |
|  | R4 | CGAATCCTCCTCCT |  | 153 |
|  | P4 | TTAGAGGAAAAGAAGAGGAGGAGA |  | 154 |
| 67 | F167 | TTATTTGGGAGTTA | 117 | 177 |
|  | R4 | CGAATCCTCCTCCT |  | 153 |
|  | P4 | TTAGAGGAAAAGAAGAGGAGGAGA |  | 154 |
| 68 | F168 | TATTTGGGAGTTAT | 116 | 178 |
|  | R4 | CGAATCCTCCTCCT |  | 153 |
|  | P4 | TTAGAGGAAAAGAAGAGGAGGAGA |  | 154 |

TABLE 1 -continued

Primer and probe sequences for detection of SDC2 gene methylation

| Set | Primers | Sequences (5'-->3') | Size of amplified product (bp) | SEQ ID NO: |
|---|---|---|---|---|
| 69 | F169 | ATTTGGGAGTTATA | 115 | 179 |
| | R4 | CGAATCCTCCTCCT | | 153 |
| | P4 | TTAGAGGAAAAGAAGAGGAGGAGA | | 154 |
| 70 | F170 | TTTGGGAGTTATAT | 114 | 180 |
| | R4 | CGAATCCTCCTCCT | | 153 |
| | P4 | TTAGAGGAAAAGAAGAGGAGGAGA | | 154 |
| 71 | F171 | TTGGGAGTTATATT | 113 | 181 |
| | R4 | CGAATCCTCCTCCT | | 153 |
| | P4 | TTAGAGGAAAAGAAGAGGAGGAGA | | 154 |
| 72 | F172 | TGGGAGTTATATTG | 112 | 182 |
| | R4 | CGAATCCTCCTCCT | | 153 |
| | P4 | TTAGAGGAAAAGAAGAGGAGGAGA | | 154 |
| 73 | F173 | GGGAGTTATATTGT | 111 | 183 |
| | R4 | CGAATCCTCCTCCT | | 153 |
| | P4 | TTAGAGGAAAAGAAGAGGAGGAGA | | 154 |
| 74 | F174 | GGAGTTATATTGTC | 110 | 184 |
| | R4 | CGAATCCTCCTCCT | | 153 |
| | P4 | TTAGAGGAAAAGAAGAGGAGGAGA | | 154 |
| 75 | F175 | GAGTTATATTGTCG | 109 | 185 |
| | R4 | CGAATCCTCCTCCT | | 153 |
| | P4 | TTAGAGGAAAAGAAGAGGAGGAGA | | 154 |
| 76 | F176 | AGTTATATTGTCGT | 108 | 186 |
| | R4 | CGAATCCTCCTCCT | | 153 |
| | P4 | TTAGAGGAAAAGAAGAGGAGGAGA | | 154 |
| 77 | F177 | GTTATATTGTCGTT | 107 | 187 |
| | R4 | CGAATCCTCCTCCT | | 153 |
| | P4 | TTAGAGGAAAAGAAGAGGAGGAGA | | 154 |
| 78 | F178 | TTATATTGTCGTTT | 106 | 188 |
| | R4 | CGAATCCTCCTCCT | | 153 |
| | P4 | TTAGAGGAAAAGAAGAGGAGGAGA | | 154 |
| 79 | F179 | TATATTGTCGTTTT | 105 | 189 |
| | R4 | CGAATCCTCCTCCT | | 153 |
| | P4 | TTAGAGGAAAAGAAGAGGAGGAGA | | 154 |
| 80 | F180 | ATATTGTCGTTTTT | 104 | 190 |
| | R4 | CGAATCCTCCTCCT | | 153 |
| | P4 | TTAGAGGAAAAGAAGAGGAGGAGA | | 154 |
| 81 | F181 | TATTGTCGTTTTTT | 103 | 191 |
| | R4 | CGAATCCTCCTCCT | | 153 |
| | P4 | TTAGAGGAAAAGAAGAGGAGGAGA | | 154 |
| 82 | F182 | ATTGTCGTTTTTTT | 102 | 192 |
| | R4 | CGAATCCTCCTCCT | | 153 |
| | P4 | TTAGAGGAAAAGAAGAGGAGGAGA | | 154 |
| 83 | F183 | TTGTCGTTTTTTTT | 101 | 193 |
| | R4 | CGAATCCTCCTCCT | | 153 |
| | P4 | TTAGAGGAAAAGAAGAGGAGGAGA | | 154 |
| 84 | F184 | TGTCGTTTTTTTTT | 100 | 194 |
| | R4 | CGAATCCTCCTCCT | | 153 |
| | P4 | TTAGAGGAAAAGAAGAGGAGGAGA | | 154 |
| 85 | F185 | GTCGTTTTTTTTT | 99 | 195 |
| | R4 | CGAATCCTCCTCCT | | 153 |
| | P4 | TTAGAGGAAAAGAAGAGGAGGAGA | | 154 |
| 86 | F186 | TCGTTTTTTTTTT | 98 | 196 |
| | R4 | CGAATCCTCCTCCT | | 153 |
| | P4 | TTAGAGGAAAAGAAGAGGAGGAGA | | 154 |

TABLE 1-continued

Primer and probe sequences for detection of SDC2 gene methylation

| Set | Primers | Sequences (5'-->3') | Size of amplified product (bp) | SEQ ID NO: |
|---|---|---|---|---|
| 87 | F187 | CGTTTTTTTTTTT | 97 | 197 |
|  | R4 | CGAATCCTCCTCCT |  | 153 |
|  | P4 | TTAGAGGAAAAGAAGAGGAGGAGA |  | 154 |
| 88 | F188 | GTTTTTTTTTTTA | 96 | 198 |
|  | R4 | CGAATCCTCCTCCT |  | 153 |
|  | P4 | TTAGAGGAAAAGAAGAGGAGGAGA |  | 154 |
| 89 | F189 | TTTTTTTTTTTAG | 95 | 199 |
|  | R4 | CGAATCCTCCTCCT |  | 153 |
|  | P4 | TTAGAGGAAAAGAAGAGGAGGAGA |  | 154 |
| 90 | F190 | TTTTTTTTTTAGT | 94 | 200 |
|  | R4 | CGAATCCTCCTCCT |  | 153 |
|  | P4 | TTAGAGGAAAAGAAGAGGAGGAGA |  | 154 |
| 91 | F191 | TTTTTTTTTAGTC | 93 | 201 |
|  | R4 | CGAATCCTCCTCCT |  | 153 |
|  | P4 | TTAGAGGAAAAGAAGAGGAGGAGA |  | 154 |
| 92 | F192 | TTTTTTTTAGTCG | 92 | 202 |
|  | R4 | CGAATCCTCCTCCT |  | 153 |
|  | P4 | TTAGAGGAAAAGAAGAGGAGGAGA |  | 154 |
| 93 | F193 | TTTTTTTAGTCGT | 91 | 203 |
|  | R4 | CGAATCCTCCTCCT |  | 153 |
|  | P4 | TTAGAGGAAAAGAAGAGGAGGAGA |  | 154 |
| 94 | F194 | TTTTTTAGTCGTT | 90 | 204 |
|  | R4 | CGAATCCTCCTCCT |  | 153 |
|  | P4 | TTAGAGGAAAAGAAGAGGAGGAGA |  | 154 |
| 95 | F195 | TTTTTAGTCGTTT | 89 | 205 |
|  | R4 | CGAATCCTCCTCCT |  | 153 |
|  | P4 | TTAGAGGAAAAGAAGAGGAGGAGA |  | 154 |
| 96 | F196 | TTTTAGTCGTTTA | 88 | 206 |
|  | R4 | CGAATCCTCCTCCT |  | 153 |
|  | P4 | TTAGAGGAAAAGAAGAGGAGGAGA |  | 154 |
| 97 | F197 | TTTAGTCGTTTAG | 87 | 207 |
|  | R4 | CGAATCCTCCTCCT |  | 153 |
|  | P4 | TTAGAGGAAAAGAAGAGGAGGAGA |  | 154 |
| 98 | F198 | TTAGTCGTTTAGG | 86 | 208 |
|  | R4 | CGAATCCTCCTCCT |  | 153 |
|  | P4 | TTAGAGGAAAAGAAGAGGAGGAGA |  | 154 |
| 99 | F199 | TAGTCGTTTAGGG | 85 | 209 |
|  | R4 | CGAATCCTCCTCCT |  | 153 |
|  | P4 | TTAGAGGAAAAGAAGAGGAGGAGA |  | 154 |
| 00 | F200 | TAGTCGTTTAGGGG | 84 | 210 |
|  | R4 | CGAATCCTCCTCCT |  | 153 |
|  | P4 | TTAGAGGAAAAGAAGAGGAGGAGA |  | 154 |
| 01 | F201 | AGTCGTTTAGGGGA | 83 | 211 |
|  | R4 | CGAATCCTCCTCCT |  | 153 |
|  | P4 | TTAGAGGAAAAGAAGAGGAGGAGA |  | 154 |
| 02 | F202 | GTCGTTTAGGGGAG | 82 | 212 |
|  | R4 | CGAATCCTCCTCCT |  | 153 |
|  | P4 | TTAGAGGAAAAGAAGAGGAGGAGA |  | 154 |
| 03 | F203 | TCGTTTAGGGGAGT | 81 | 213 |
|  | R4 | CGAATCCTCCTCCT |  | 153 |
|  | P4 | TTAGAGGAAAAGAAGAGGAGGAGA |  | 154 |
| 04 | F204 | CGTTTAGGGGAGTT | 80 | 214 |
|  | R4 | CGAATCCTCCTCCT |  | 153 |
|  | P4 | TTAGAGGAAAAGAAGAGGAGGAGA |  | 154 |

TABLE 1 -continued

Primer and probe sequences for detection of SDC2 gene methylation

| Set | Primers | Sequences (5'-->3') | Size of amplified product (bp) | SEQ ID NO: |
|---|---|---|---|---|
| 05 | F205 | GTTTAGGGGAGTTC | 140 | 215 |
|  | R5 | CAAACGAAACCACT |  | 216 |
|  | P5 | AGGGGCGTAGTCGCGGAGTT |  | 217 |
| 06 | F206 | TTTAGGGGAGTTCG | 139 | 218 |
|  | R5 | CAAACGAAACCACT |  | 216 |
|  | P5 | AGGGGCGTAGTCGCGGAGTT |  | 217 |
| 07 | F207 | TTAGGGGAGTTCGG | 138 | 219 |
|  | R5 | CAAACGAAACCACT |  | 216 |
|  | P5 | AGGGGCGTAGTCGCGGAGTT |  | 217 |
| 08 | F208 | TAGGGGAGTTCGGA | 137 | 220 |
|  | R5 | CAAACGAAACCACT |  | 216 |
|  | P5 | AGGGGCGTAGTCGCGGAGTT |  | 217 |
| 09 | F209 | AGGGGAGTTCGGAG | 136 | 221 |
|  | R5 | CAAACGAAACCACT |  | 216 |
|  | P5 | AGGGGCGTAGTCGCGGAGTT |  | 217 |
| 10 | F210 | GGGGAGTTCGGAGA | 135 | 222 |
|  | R5 | CAAACGAAACCACT |  | 216 |
|  | P5 | AGGGGCGTAGTCGCGGAGTT |  | 217 |
| 11 | F211 | GGGAGTTCGGAGAA | 134 | 223 |
|  | R5 | CAAACGAAACCACT |  | 216 |
|  | P5 | AGGGGCGTAGTCGCGGAGTT |  | 217 |
| 12 | F212 | GGAGTTCGGAGAAG | 133 | 224 |
|  | R5 | CAAACGAAACCACT |  | 216 |
|  | P5 | AGGGGCGTAGTCGCGGAGTT |  | 217 |
| 13 | F213 | GAGTTCGGAGAAGT | 132 | 225 |
|  | R5 | CAAACGAAACCACT |  | 216 |
|  | P5 | AGGGGCGTAGTCGCGGAGTT |  | 217 |
| 14 | F214 | AGTTCGGAGAAGTA | 131 | 226 |
|  | R5 | CAAACGAAACCACT |  | 216 |
|  | P5 | AGGGGCGTAGTCGCGGAGTT |  | 217 |
| 15 | F215 | GTTCGGAGAAGTAG | 130 | 227 |
|  | R5 | CAAACGAAACCACT |  | 216 |
|  | P5 | AGGGGCGTAGTCGCGGAGTT |  | 217 |
| 16 | F216 | TTCGGAGAAGTAGG | 129 | 228 |
|  | R5 | CAAACGAAACCACT |  | 216 |
|  | P5 | AGGGGCGTAGTCGCGGAGTT |  | 217 |
| 17 | F217 | TCGGAGAAGTAGGT | 128 | 229 |
|  | R5 | CAAACGAAACCACT |  | 216 |
|  | P5 | AGGGGCGTAGTCGCGGAGTT |  | 217 |
| 18 | F218 | CGGAGAAGTAGGTT | 127 | 230 |
|  | R5 | CAAACGAAACCACT |  | 216 |
|  | P5 | AGGGGCGTAGTCGCGGAGTT |  | 217 |
| 19 | F219 | GGAGAAGTAGGTTT | 126 | 231 |
|  | R5 | CAAACGAAACCACT |  | 216 |
|  | P5 | AGGGGCGTAGTCGCGGAGTT |  | 217 |
| 20 | F220 | GAGAAGTAGGTTTA | 125 | 232 |
|  | R5 | CAAACGAAACCACT |  | 216 |
|  | P5 | AGGGGCGTAGTCGCGGAGTT |  | 217 |
| 21 | F221 | AGAAGTAGGTTTAG | 124 | 233 |
|  | R5 | CAAACGAAACCACT |  | 216 |
|  | P5 | AGGGGCGTAGTCGCGGAGTT |  | 217 |
| 22 | F222 | GAAGTAGGTTTAGG | 123 | 234 |
|  | R5 | CAAACGAAACCACT |  | 216 |
|  | P5 | AGGGGCGTAGTCGCGGAGTT |  | 217 |

TABLE 1 -continued

Primer and probe sequences for detection of SDC2 gene methylation

| Set | Primers | Sequences (5'-->3') | Size of amplified product (bp) | SEQ ID NO: |
|---|---|---|---|---|
| 23 | F223 | AAGTAGGTTTAGGA | 122 | 235 |
|  | R5 | CAAACGAAACCACT |  | 216 |
|  | P5 | AGGGGCGTAGTCGCGGAGTT |  | 217 |
| 24 | F224 | AGTAGGTTTAGGAG | 121 | 236 |
|  | R5 | CAAACGAAACCACT |  | 216 |
|  | P5 | AGGGGCGTAGTCGCGGAGTT |  | 217 |
| 25 | F225 | GTAGGTTTAGGAGG | 120 | 237 |
|  | R5 | CAAACGAAACCACT |  | 216 |
|  | P5 | AGGGGCGTAGTCGCGGAGTT |  | 217 |
| 26 | F226 | TAGGTTTAGGAGGG | 119 | 238 |
|  | R5 | CAAACGAAACCACT |  | 216 |
|  | P5 | AGGGGCGTAGTCGCGGAGTT |  | 217 |
| 27 | F227 | AGGTTTAGGAGGGA | 118 | 239 |
|  | R5 | CAAACGAAACCACT |  | 216 |
|  | P5 | AGGGGCGTAGTCGCGGAGTT |  | 217 |
| 28 | F228 | GGTTTAGGAGGGAG | 117 | 240 |
|  | R5 | CAAACGAAACCACT |  | 216 |
|  | P5 | AGGGGCGTAGTCGCGGAGTT |  | 217 |
| 29 | F229 | GTTTAGGAGGGAGG | 116 | 241 |
|  | R5 | CAAACGAAACCACT |  | 216 |
|  | P5 | AGGGGCGTAGTCGCGGAGTT |  | 217 |
| 30 | F230 | TTTAGGAGGGAGGG | 115 | 242 |
|  | R5 | CAAACGAAACCACT |  | 216 |
|  | P5 | AGGGGCGTAGTCGCGGAGTT |  | 217 |
| 31 | F231 | TTAGGAGGGAGGGA | 114 | 243 |
|  | R5 | CAAACGAAACCACT |  | 216 |
|  | P5 | AGGGGCGTAGTCGCGGAGTT |  | 217 |
| 32 | F232 | TAGGAGGGAGGGAG | 113 | 244 |
|  | R5 | CAAACGAAACCACT |  | 216 |
|  | P5 | AGGGGCGTAGTCGCGGAGTT |  | 217 |
| 33 | F233 | AGGAGGGAGGGAGT | 112 | 245 |
|  | R5 | CAAACGAAACCACT |  | 216 |
|  | P5 | AGGGGCGTAGTCGCGGAGTT |  | 217 |
| 34 | F234 | GGAGGGAGGGAGTT | 111 | 246 |
|  | R5 | CAAACGAAACCACT |  | 216 |
|  | P5 | AGGGGCGTAGTCGCGGAGTT |  | 217 |
| 35 | F235 | GAGGGAGGGAGTTA | 110 | 247 |
|  | R5 | CAAACGAAACCACT |  | 216 |
|  | P5 | AGGGGCGTAGTCGCGGAGTT |  | 217 |
| 36 | F236 | AGGGAGGGAGTTAG | 109 | 248 |
|  | R5 | CAAACGAAACCACT |  | 216 |
|  | P5 | AGGGGCGTAGTCGCGGAGTT |  | 217 |
| 37 | F237 | GGGAGGGAGTTAGA | 108 | 249 |
|  | R5 | CAAACGAAACCACT |  | 216 |
|  | P5 | AGGGGCGTAGTCGCGGAGTT |  | 217 |
| 38 | F238 | GGAGGGAGTTAGAG | 107 | 250 |
|  | R5 | CAAACGAAACCACT |  | 216 |
|  | P5 | AGGGGCGTAGTCGCGGAGTT |  | 217 |
| 39 | F239 | GAGGGAGTTAGAGG | 106 | 251 |
|  | R5 | CAAACGAAACCACT |  | 216 |
|  | P5 | AGGGGCGTAGTCGCGGAGTT |  | 217 |
| 40 | F240 | AGGGAGTTAGAGGA | 105 | 252 |
|  | R5 | CAAACGAAACCACT |  | 216 |
|  | P5 | AGGGGCGTAGTCGCGGAGTT |  | 217 |

TABLE 1 -continued

Primer and probe sequences for detection of SDC2 gene methylation

| Set | Primers | Sequences (5'-->3') | Size of amplified product (bp) | SEQ ID NO: |
|---|---|---|---|---|
| 41 | F241 | GGGAGTTAGAGGAA | 104 | 253 |
|  | R5 | CAAACGAAACCACT |  | 216 |
|  | P5 | AGGGGCGTAGTCGCGGAGTT |  | 217 |
| 42 | F242 | GGAGTTAGAGGAAA | 103 | 254 |
|  | R5 | CAAACGAAACCACT |  | 216 |
|  | P5 | AGGGGCGTAGTCGCGGAGTT |  | 217 |
| 43 | F243 | GAGTTAGAGGAAAA | 102 | 255 |
|  | R5 | CAAACGAAACCACT |  | 216 |
|  | P5 | AGGGGCGTAGTCGCGGAGTT |  | 217 |
| 44 | F244 | AGTTAGAGGAAAAG | 101 | 256 |
|  | R5 | CAAACGAAACCACT |  | 216 |
|  | P5 | AGGGGCGTAGTCGCGGAGTT |  | 217 |
| 45 | F245 | GTTAGAGGAAAAGA | 100 | 257 |
|  | R5 | CAAACGAAACCACT |  | 216 |
|  | P5 | AGGGGCGTAGTCGCGGAGTT |  | 217 |
| 46 | F246 | TTAGAGGAAAAGAA | 99 | 258 |
|  | R5 | CAAACGAAACCACT |  | 216 |
|  | P5 | AGGGGCGTAGTCGCGGAGTT |  | 217 |
| 47 | F247 | TAGAGGAAAAGAAG | 98 | 259 |
|  | R5 | CAAACGAAACCACT |  | 216 |
|  | P5 | AGGGGCGTAGTCGCGGAGTT |  | 217 |
| 48 | F248 | AGAGGAAAAGAAGA | 97 | 260 |
|  | R5 | CAAACGAAACCACT |  | 216 |
|  | P5 | AGGGGCGTAGTCGCGGAGTT |  | 217 |
| 49 | F249 | GAGGAAAAGAAGAG | 96 | 261 |
|  | R5 | CAAACGAAACCACT |  | 216 |
|  | P5 | AGGGGCGTAGTCGCGGAGTT |  | 217 |
| 50 | F250 | AGGAAAAGAAGAGG | 95 | 262 |
|  | R5 | CAAACGAAACCACT |  | 216 |
|  | P5 | AGGGGCGTAGTCGCGGAGTT |  | 217 |
| 51 | F251 | GGAAAAGAAGAGGA | 94 | 263 |
|  | R5 | CAAACGAAACCACT |  | 216 |
|  | P5 | AGGGGCGTAGTCGCGGAGTT |  | 217 |
| 52 | F252 | GAAAAGAAGAGGAG | 93 | 264 |
|  | R5 | CAAACGAAACCACT |  | 216 |
|  | P5 | AGGGGCGTAGTCGCGGAGTT |  | 217 |
| 53 | F253 | AAAAGAAGAGGAGG | 92 | 265 |
|  | R5 | CAAACGAAACCACT |  | 216 |
|  | P5 | AGGGGCGTAGTCGCGGAGTT |  | 217 |
| 54 | F254 | AAAGAAGAGGAGGA | 91 | 266 |
|  | R5 | CAAACGAAACCACT |  | 216 |
|  | P5 | AGGGGCGTAGTCGCGGAGTT |  | 217 |
| 55 | F255 | AAGAAGAGGAGGAG | 90 | 267 |
|  | R5 | CAAACGAAACCACT |  | 216 |
|  | P5 | AGGGGCGTAGTCGCGGAGTT |  | 217 |
| 56 | F256 | AGAAGAGGAGGAGA | 89 | 268 |
|  | R5 | CAAACGAAACCACT |  | 216 |
|  | P5 | AGGGGCGTAGTCGCGGAGTT |  | 217 |
| 57 | F257 | GAAGAGGAGGAGAA | 88 | 269 |
|  | R5 | CAAACGAAACCACT |  | 216 |
|  | P5 | AGGGGCGTAGTCGCGGAGTT |  | 217 |
| 58 | F258 | AAGAGGAGGAGAAG | 87 | 270 |
|  | R5 | CAAACGAAACCACT |  | 216 |
|  | P5 | AGGGGCGTAGTCGCGGAGTT |  | 217 |

TABLE 1-continued

Primer and probe sequences for detection of SDC2 gene methylation

| Set | Primers | Sequences (5'-->3') | Size of amplified product (bp) | SEQ ID NO: |
|---|---|---|---|---|
| 59 | F259 | AGAGGAGGAGAAGG | 86 | 271 |
|  | R5 | CAAACGAAACCACT |  | 216 |
|  | P5 | AGGGGCGTAGTCGCGGAGTT |  | 217 |
| 60 | F260 | GAGGAGGAGAAGGA | 85 | 272 |
|  | R5 | CAAACGAAACCACT |  | 216 |
|  | P5 | AGGGGCGTAGTCGCGGAGTT |  | 217 |
| 61 | F261 | AGGAGGAGAAGGAG | 84 | 273 |
|  | R5 | CAAACGAAACCACT |  | 216 |
|  | P5 | AGGGGCGTAGTCGCGGAGTT |  | 217 |
| 62 | F262 | GGAGGAGAAGGAGG | 83 | 274 |
|  | R5 | CAAACGAAACCACT |  | 216 |
|  | P5 | AGGGGCGTAGTCGCGGAGTT |  | 217 |
| 63 | F263 | GAGGAGAAGGAGGA | 82 | 275 |
|  | R5 | CAAACGAAACCACT |  | 216 |
|  | P5 | AGGGGCGTAGTCGCGGAGTT |  | 217 |
| 64 | F264 | AGGAGAAGGAGGAG | 81 | 276 |
|  | R5 | CAAACGAAACCACT |  | 216 |
|  | P5 | AGGGGCGTAGTCGCGGAGTT |  | 217 |
| 65 | F265 | GGAGAAGGAGGAGG | 80 | 277 |
|  | R5 | CAAACGAAACCACT |  | 216 |
|  | P5 | AGGGGCGTAGTCGCGGAGTT |  | 217 |
| 66 | F266 | GAGAAGGAGGAGGA | 140 | 278 |
|  | R6 | ACGACGAAAACGCG |  | 279 |
|  | P6 | CGGAGTTTTAGTCGCGCGGATCG |  | 280 |
| 67 | F267 | AGAAGGAGGAGGAT | 139 | 281 |
|  | R6 | ACGACGAAAACGCG |  | 279 |
|  | P6 | CGGAGTTTTAGTCGCGCGGATCG |  | 280 |
| 68 | F268 | GAAGGAGGAGGATT | 138 | 282 |
|  | R6 | ACGACGAAAACGCG |  | 279 |
|  | P6 | CGGAGTTTTAGTCGCGCGGATCG |  | 280 |
| 69 | F269 | AAGGAGGAGGATTC | 137 | 283 |
|  | R6 | ACGACGAAAACGCG |  | 279 |
|  | P6 | CGGAGTTTTAGTCGCGCGGATCG |  | 280 |
| 70 | F270 | AGGAGGAGGATTCG | 136 | 284 |
|  | R6 | ACGACGAAAACGCG |  | 279 |
|  | P6 | CGGAGTTTTAGTCGCGCGGATCG |  | 280 |
| 71 | F271 | GGAGGAGGATTCGG | 135 | 285 |
|  | R6 | ACGACGAAAACGCG |  | 279 |
|  | P6 | CGGAGTTTTAGTCGCGCGGATCG |  | 280 |
| 72 | F272 | GAGGAGGATTCGGG | 134 | 286 |
|  | R6 | ACGACGAAAACGCG |  | 279 |
|  | P6 | CGGAGTTTTAGTCGCGCGGATCG |  | 280 |
| 73 | F273 | AGGAGGATTCGGGG | 133 | 287 |
|  | R6 | ACGACGAAAACGCG |  | 279 |
|  | P6 | CGGAGTTTTAGTCGCGCGGATCG |  | 280 |
| 74 | F274 | GGAGGATTCGGGGA | 132 | 288 |
|  | R6 | ACGACGAAAACGCG |  | 279 |
|  | P6 | CGGAGTTTTAGTCGCGCGGATCG |  | 280 |
| 75 | F275 | GAGGATTCGGGGAG | 131 | 289 |
|  | R6 | ACGACGAAAACGCG |  | 279 |
|  | P6 | CGGAGTTTTAGTCGCGCGGATCG |  | 280 |
| 76 | F276 | AGGATTCGGGGAGG | 130 | 290 |
|  | R6 | ACGACGAAAACGCG |  | 279 |
|  | P6 | CGGAGTTTTAGTCGCGCGGATCG |  | 280 |

TABLE 1-continued

Primer and probe sequences for detection of SDC2 gene methylation

| Set | Primers | Sequences (5'-->3') | Size of amplified product (bp) | SEQ ID NO: |
|---|---|---|---|---|
| 77 | F277 | GGATTCGGGGAGGG | 129 | 291 |
|  | R6 | ACGACGAAAACGCG |  | 279 |
|  | P6 | CGGAGTTTTAGTCGCGCGGATCG |  | 280 |
| 78 | F278 | GATTCGGGGAGGGA | 128 | 292 |
|  | R6 | ACGACGAAAACGCG |  | 279 |
|  | P6 | CGGAGTTTTAGTCGCGCGGATCG |  | 280 |
| 79 | F279 | ATTCGGGGAGGGAG | 127 | 293 |
|  | R6 | ACGACGAAAACGCG |  | 279 |
|  | P6 | CGGAGTTTTAGTCGCGCGGATCG |  | 280 |
| 80 | F280 | TTCGGGGAGGGAGG | 126 | 294 |
|  | R6 | ACGACGAAAACGCG |  | 279 |
|  | P6 | CGGAGTTTTAGTCGCGCGGATCG |  | 280 |
| 81 | F281 | TCGGGGAGGGAGGC | 125 | 295 |
|  | R6 | ACGACGAAAACGCG |  | 279 |
|  | P6 | CGGAGTTTTAGTCGCGCGGATCG |  | 280 |
| 82 | F282 | CGGGGAGGGAGGCG | 124 | 296 |
|  | R6 | ACGACGAAAACGCG |  | 279 |
|  | P6 | CGGAGTTTTAGTCGCGCGGATCG |  | 280 |
| 83 | F283 | GGGGAGGGAGGCGC | 123 | 297 |
|  | R6 | ACGACGAAAACGCG |  | 279 |
|  | P6 | CGGAGTTTTAGTCGCGCGGATCG |  | 280 |
| 84 | F284 | GGGAGGGAGGCGCG | 122 | 298 |
|  | R6 | ACGACGAAAACGCG |  | 279 |
|  | P6 | CGGAGTTTTAGTCGCGCGGATCG |  | 280 |
| 85 | F285 | GGAGGGAGGCGCGG | 121 | 299 |
|  | R6 | ACGACGAAAACGCG |  | 279 |
|  | P6 | CGGAGTTTTAGTCGCGCGGATCG |  | 280 |
| 86 | F286 | GAGGGAGGCGCGGC | 120 | 300 |
|  | R6 | ACGACGAAAACGCG |  | 279 |
|  | P6 | CGGAGTTTTAGTCGCGCGGATCG |  | 280 |
| 87 | F287 | AGGGAGGCGCGGCG | 119 | 301 |
|  | R6 | ACGACGAAAACGCG |  | 279 |
|  | P6 | CGGAGTTTTAGTCGCGCGGATCG |  | 280 |
| 88 | F288 | GGGAGGCGCGGCGC | 118 | 302 |
|  | R6 | ACGACGAAAACGCG |  | 279 |
|  | P6 | CGGAGTTTTAGTCGCGCGGATCG |  | 280 |
| 89 | F289 | GGAGGCGCGGCGCG | 117 | 303 |
|  | R6 | ACGACGAAAACGCG |  | 279 |
|  | P6 | CGGAGTTTTAGTCGCGCGGATCG |  | 280 |
| 90 | F290 | GAGGCGCGGCGCGG | 116 | 304 |
|  | R6 | ACGACGAAAACGCG |  | 279 |
|  | P6 | CGGAGTTTTAGTCGCGCGGATCG |  | 280 |
| 91 | F291 | AGGCGCGGCGCGGG | 115 | 305 |
|  | R6 | ACGACGAAAACGCG |  | 279 |
|  | P6 | CGGAGTTTTAGTCGCGCGGATCG |  | 280 |
| 92 | F292 | GGCGCGGCGCGGGA | 114 | 306 |
|  | R6 | ACGACGAAAACGCG |  | 279 |
|  | P6 | CGGAGTTTTAGTCGCGCGGATCG |  | 280 |
| 93 | F293 | GCGCGGCGCGGGAG | 113 | 279 |
|  | R6 | ACGACGAAAACGCG |  | 307 |
|  | P6 | CGGAGTTTTAGTCGCGCGGATCG |  | 280 |
| 94 | F294 | CGCGGCGCGGGAGG | 112 | 308 |
|  | R6 | ACGACGAAAACGCG |  | 279 |
|  | P6 | CGGAGTTTTAGTCGCGCGGATCG |  | 280 |

TABLE 1-continued

Primer and probe sequences for detection of SDC2 gene methylation

| Set | Primers | Sequences (5'-->3') | Size of amplified product (bp) | SEQ ID NO: |
|---|---|---|---|---|
| 95 | F295 | GCGGCGCGGGAGGA | 111 | 309 |
|  | R6 | ACGACGAAAACGCG |  | 279 |
|  | P6 | CGGAGTTTTAGTCGCGCGGATCG |  | 280 |
| 96 | F296 | CGGCGCGGGAGGAG | 110 | 310 |
|  | R6 | ACGACGAAAACGCG |  | 279 |
|  | P6 | CGGAGTTTTAGTCGCGCGGATCG |  | 280 |
| 97 | F297 | GGCGCGGGAGGAGG | 109 | 311 |
|  | R6 | ACGACGAAAACGCG |  | 279 |
|  | P6 | CGGAGTTTTAGTCGCGCGGATCG |  | 280 |
| 98 | F298 | GCGCGGGAGGAGGA | 108 | 312 |
|  | R6 | ACGACGAAAACGCG |  | 279 |
|  | P6 | CGGAGTTTTAGTCGCGCGGATCG |  | 280 |
| 99 | F299 | CGCGGGAGGAGGAG | 107 | 313 |
|  | R6 | ACGACGAAAACGCG |  | 279 |
|  | P6 | CGGAGTTTTAGTCGCGCGGATCG |  | 280 |
| 00 | F300 | GCGGGAGGAGGAGG | 106 | 314 |
|  | R6 | ACGACGAAAACGCG |  | 279 |
|  | P6 | CGGAGTTTTAGTCGCGCGGATCG |  | 280 |
| 01 | F301 | CGGGAGGAGGAGGG | 105 | 315 |
|  | R6 | ACGACGAAAACGCG |  | 279 |
|  | P6 | CGGAGTTTTAGTCGCGCGGATCG |  | 280 |
| 02 | F302 | GGGAGGAGGAGGGG | 104 | 316 |
|  | R6 | ACGACGAAAACGCG |  | 279 |
|  | P6 | CGGAGTTTTAGTCGCGCGGATCG |  | 280 |
| 03 | F303 | GGAGGAGGAGGGGC | 103 | 317 |
|  | R6 | ACGACGAAAACGCG |  | 279 |
|  | P6 | CGGAGTTTTAGTCGCGCGGATCG |  | 280 |
| 04 | F304 | GAGGAGGAGGGGCG | 102 | 318 |
|  | R6 | ACGACGAAAACGCG |  | 279 |
|  | P6 | CGGAGTTTTAGTCGCGCGGATCG |  | 280 |
| 05 | F305 | AGGAGGAGGGGCGT | 101 | 319 |
|  | R6 | ACGACGAAAACGCG |  | 279 |
|  | P6 | CGGAGTTTTAGTCGCGCGGATCG |  | 280 |
| 06 | F306 | GGAGGAGGGGCGTA | 100 | 320 |
|  | R6 | ACGACGAAAACGCG |  | 279 |
|  | P6 | CGGAGTTTTAGTCGCGCGGATCG |  | 280 |
| 07 | F307 | GAGGAGGGGCGTAG | 99 | 321 |
|  | R6 | ACGACGAAAACGCG |  | 279 |
|  | P6 | CGGAGTTTTAGTCGCGCGGATCG |  | 280 |
| 08 | F308 | AGGAGGGGCGTAGT | 98 | 322 |
|  | R6 | ACGACGAAAACGCG |  | 279 |
|  | P6 | CGGAGTTTTAGTCGCGCGGATCG |  | 280 |
| 09 | F309 | GGAGGGGCGTAGTC | 97 | 323 |
|  | R6 | ACGACGAAAACGCG |  | 279 |
|  | P6 | CGGAGTTTTAGTCGCGCGGATCG |  | 280 |
| 10 | F310 | GAGGGGCGTAGTCG | 96 | 324 |
|  | R6 | ACGACGAAAACGCG |  | 279 |
|  | P6 | CGGAGTTTTAGTCGCGCGGATCG |  | 280 |
| 11 | F311 | AGGGGCGTAGTCGC | 95 | 325 |
|  | R6 | ACGACGAAAACGCG |  | 279 |
|  | P6 | CGGAGTTTTAGTCGCGCGGATCG |  | 280 |
| 12 | F312 | GGGGCGTAGTCGCG | 94 | 326 |
|  | R6 | ACGACGAAAACGCG |  | 279 |
|  | P6 | CGGAGTTTTAGTCGCGCGGATCG |  | 280 |

TABLE 1 -continued

Primer and probe sequences for detection of SDC2 gene methylation

| Set | Primers | Sequences (5'-->3') | Size of amplified product (bp) | SEQ ID NO: |
|---|---|---|---|---|
| 13 | F313 | GGGCGTAGTCGCGG | 93 | 327 |
|  | R6 | ACGACGAAAACGCG |  | 279 |
|  | P6 | CGGAGTTTTAGTCGCGCGGATCG |  | 280 |
| 14 | F314 | GGCGTAGTCGCGGA | 92 | 328 |
|  | R6 | ACGACGAAAACGCG |  | 279 |
|  | P6 | CGGAGTTTTAGTCGCGCGGATCG |  | 280 |
| 15 | F315 | GCGTAGTCGCGGAG | 91 | 329 |
|  | R6 | ACGACGAAAACGCG |  | 279 |
|  | P6 | CGGAGTTTTAGTCGCGCGGATCG |  | 280 |
| 16 | F316 | CGTAGTCGCGGAGT | 90 | 330 |
|  | R6 | ACGACGAAAACGCG |  | 279 |
|  | P6 | CGGAGTTTTAGTCGCGCGGATCG |  | 280 |
| 17 | F317 | GTAGTCGCGGAGTT | 89 | 331 |
|  | R6 | ACGACGAAAACGCG |  | 279 |
|  | P6 | CGGAGTTTTAGTCGCGCGGATCG |  | 280 |
| 18 | F318 | TAGTCGCGGAGTTA | 88 | 332 |
|  | R6 | ACGACGAAAACGCG |  | 279 |
|  | P6 | CGGAGTTTTAGTCGCGCGGATCG |  | 280 |
| 19 | F319 | AGTCGCGGAGTTAG | 87 | 333 |
|  | R6 | ACGACGAAAACGCG |  | 279 |
|  | P6 | CGGAGTTTTAGTCGCGCGGATCG |  | 280 |
| 20 | F320 | GTCGCGGAGTTAGT | 86 | 334 |
|  | R6 | ACGACGAAAACGCG |  | 279 |
|  | P6 | CGGAGTTTTAGTCGCGCGGATCG |  | 280 |
| 21 | F321 | TCGCGGAGTTAGTG | 85 | 335 |
|  | R6 | ACGACGAAAACGCG |  | 279 |
|  | P6 | CGGAGTTTTAGTCGCGCGGATCG |  | 280 |
| 22 | F322 | CGCGGAGTTAGTGG | 84 | 336 |
|  | R6 | ACGACGAAAACGCG |  | 279 |
|  | P6 | CGGAGTTTTAGTCGCGCGGATCG |  | 280 |
| 23 | F323 | GCGGAGTTAGTGGT | 83 | 337 |
|  | R6 | ACGACGAAAACGCG |  | 279 |
|  | P6 | CGGAGTTTTAGTCGCGCGGATCG |  | 280 |
| 24 | F324 | CGGAGTTAGTGGTT | 82 | 338 |
|  | R6 | ACGACGAAAACGCG |  | 279 |
|  | P6 | CGGAGTTTTAGTCGCGCGGATCG |  | 280 |
| 25 | F325 | GGAGTTAGTGGTTT | 81 | 339 |
|  | R6 | ACGACGAAAACGCG |  | 279 |
|  | P6 | CGGAGTTTTAGTCGCGCGGATCG |  | 280 |
| 26 | F326 | GAGTTAGTGGTTTC | 80 | 340 |
|  | R6 | ACGACGAAAACGCG |  | 279 |
|  | P6 | CGGAGTTTTAGTCGCGCGGATCG |  | 280 |
| 27 | F327 | AGTTAGTGGTTTCG | 130 | 341 |
|  | R7 | AAATAAATTCGCTA |  | 342 |
|  | P7 | TTTGTCGTAGTTTTTTTTAAGT |  | 343 |
| 28 | F328 | GTTAGTGGTTTCGT | 129 | 344 |
|  | R7 | AAATAAATTCGCTA |  | 342 |
|  | P7 | TTTGTCGTAGTTTTTTTTAAGT |  | 343 |
| 29 | F329 | TTAGTGGTTTCGTT | 128 | 345 |
|  | R7 | AAATAAATTCGCTA |  | 342 |
|  | P7 | TTTGTCGTAGTTTTTTTTAAGT |  | 343 |
| 30 | F330 | TAGTGGTTTCGTTT | 127 | 346 |
|  | R7 | AAATAAATTCGCTA |  | 342 |
|  | P7 | TTTGTCGTAGTTTTTTTTAAGT |  | 343 |

TABLE 1-continued

Primer and probe sequences for detection of SDC2 gene methylation

| Set | Primers | Sequences (5'-->3') | Size of amplified product (bp) | SEQ ID NO: |
|---|---|---|---|---|
| 31 | F331 | AGTGGTTTCGTTTG | 126 | 347 |
|  | R7 | AAATAAATTCGCTA |  | 342 |
|  | P7 | TTTGTCGTAGTTTTTTTTTAAGT |  | 343 |
| 32 | F332 | GTGGTTTCGTTTGG | 125 | 348 |
|  | R7 | AAATAAATTCGCTA |  | 342 |
|  | P7 | TTTGTCGTAGTTTTTTTTTAAGT |  | 343 |
| 33 | F333 | TGGTTTCGTTTGGA | 124 | 349 |
|  | R7 | AAATAAATTCGCTA |  | 342 |
|  | P7 | TTTGTCGTAGTTTTTTTTTAAGT |  | 343 |
| 34 | F334 | GGTTTCGTTTGGAC | 123 | 350 |
|  | R7 | AAATAAATTCGCTA |  | 342 |
|  | P7 | TTTGTCGTAGTTTTTTTTTAAGT |  | 343 |
| 35 | F335 | GTTTCGTTTGGACG | 122 | 351 |
|  | R7 | AAATAAATTCGCTA |  | 342 |
|  | P7 | TTTGTCGTAGTTTTTTTTTAAGT |  | 343 |
| 36 | F336 | TTTCGTTTGGACGC | 121 | 352 |
|  | R7 | AAATAAATTCGCTA |  | 342 |
|  | P7 | TTTGTCGTAGTTTTTTTTTAAGT |  | 343 |
| 37 | F337 | TTCGTTTGGACGCG | 120 | 353 |
|  | R7 | AAATAAATTCGCTA |  | 342 |
|  | P7 | TTTGTCGTAGTTTTTTTTTAAGT |  | 343 |
| 38 | F338 | TCGTTTGGACGCGT | 119 | 354 |
|  | R7 | AAATAAATTCGCTA |  | 342 |
|  | P7 | TTTGTCGTAGTTTTTTTTTAAGT |  | 343 |
| 39 | F339 | CGTTTGGACGCGTT | 118 | 355 |
|  | R7 | AAATAAATTCGCTA |  | 342 |
|  | P7 | TTTGTCGTAGTTTTTTTTTAAGT |  | 343 |
| 40 | F340 | GTTTGGACGCGTTG | 117 | 356 |
|  | R7 | AAATAAATTCGCTA |  | 342 |
|  | P7 | TTTGTCGTAGTTTTTTTTTAAGT |  | 343 |
| 41 | F341 | TTTGGACGCGTTGT | 116 | 357 |
|  | R7 | AAATAAATTCGCTA |  | 342 |
|  | P7 | TTTGTCGTAGTTTTTTTTTAAGT |  | 343 |
| 42 | F342 | TTGGACGCGTTGTT | 115 | 358 |
|  | R7 | AAATAAATTCGCTA |  | 342 |
|  | P7 | TTTGTCGTAGTTTTTTTTTAAGT |  | 343 |
| 43 | F343 | TGGACGCGTTGTTT | 114 | 359 |
|  | R7 | AAATAAATTCGCTA |  | 342 |
|  | P7 | TTTGTCGTAGTTTTTTTTTAAGT |  | 343 |
| 44 | F344 | GGACGCGTTGTTTT | 113 | 360 |
|  | R7 | AAATAAATTCGCTA |  | 342 |
|  | P7 | TTTGTCGTAGTTTTTTTTTAAGT |  | 343 |
| 45 | F345 | GACGCGTTGTTTTT | 112 | 361 |
|  | R7 | AAATAAATTCGCTA |  | 342 |
|  | P7 | TTTGTCGTAGTTTTTTTTTAAGT |  | 343 |
| 46 | F346 | ACGCGTTGTTTTTT | 111 | 362 |
|  | R7 | AAATAAATTCGCTA |  | 342 |
|  | P7 | TTTGTCGTAGTTTTTTTTTAAGT |  | 343 |
| 47 | F347 | CGCGTTGTTTTTTA | 110 | 363 |
|  | R7 | AAATAAATTCGCTA |  | 342 |
|  | P7 | TTTGTCGTAGTTTTTTTTTAAGT |  | 343 |
| 48 | F348 | GCGTTGTTTTTTAG | 109 | 364 |
|  | R7 | AAATAAATTCGCTA |  | 342 |
|  | P7 | TTTGTCGTAGTTTTTTTTTAAGT |  | 343 |

TABLE 1-continued

Primer and probe sequences for detection of SDC2 gene methylation

| Set | Primers | Sequences (5'-->3') | Size of amplified product (bp) | SEQ ID NO: |
|---|---|---|---|---|
| 49 | F349 | CGTTGTTTTTTAGA | 108 | 365 |
|  | R7 | AAATAAATTCGCTA |  | 342 |
|  | P7 | TTTGTCGTAGTTTTTTTTTAAGT |  | 343 |
| 50 | F350 | GTTGTTTTTAGAT | 107 | 366 |
|  | R7 | AAATAAATTCGCTA |  | 342 |
|  | P7 | TTTGTCGTAGTTTTTTTTTAAGT |  | 343 |
| 51 | F351 | TTGTTTTTAGATA | 106 | 367 |
|  | R7 | AAATAAATTCGCTA |  | 342 |
|  | P7 | TTTGTCGTAGTTTTTTTTTAAGT |  | 343 |
| 52 | F352 | TGTTTTTAGATAT | 105 | 368 |
|  | R7 | AAATAAATTCGCTA |  | 342 |
|  | P7 | TTTGTCGTAGTTTTTTTTTAAGT |  | 343 |
| 53 | F353 | GTTTTTAGATATT | 104 | 369 |
|  | R7 | AAATAAATTCGCTA |  | 342 |
|  | P7 | TTTGTCGTAGTTTTTTTTTAAGT |  | 343 |
| 54 | F354 | TTTTTAGATATTT | 103 | 370 |
|  | R7 | AAATAAATTCGCTA |  | 342 |
|  | P7 | TTTGTCGTAGTTTTTTTTTAAGT |  | 343 |
| 55 | F355 | TTTTAGATATTTT | 102 | 371 |
|  | R7 | AAATAAATTCGCTA |  | 342 |
|  | P7 | TTTGTCGTAGTTTTTTTTTAAGT |  | 343 |
| 56 | F356 | TTTTAGATATTTTC | 101 | 372 |
|  | R7 | AAATAAATTCGCTA |  | 342 |
|  | P7 | TTTGTCGTAGTTTTTTTTTAAGT |  | 343 |
| 57 | F357 | TTTAGATATTTTCG | 100 | 373 |
|  | R7 | AAATAAATTCGCTA |  | 342 |
|  | P7 | TTTGTCGTAGTTTTTTTTTAAGT |  | 343 |
| 58 | F358 | TTAGATATTTTCGG | 99 | 374 |
|  | R7 | AAATAAATTCGCTA |  | 342 |
|  | P7 | TTTGTCGTAGTTTTTTTTTAAGT |  | 343 |
| 59 | F359 | TAGATATTTTCGGA | 98 | 375 |
|  | R7 | AAATAAATTCGCTA |  | 342 |
|  | P7 | TTTGTCGTAGTTTTTTTTTAAGT |  | 343 |
| 60 | F360 | AGATATTTTCGGAG | 97 | 376 |
|  | R7 | AAATAAATTCGCTA |  | 342 |
|  | P7 | TTTGTCGTAGTTTTTTTTTAAGT |  | 343 |
| 61 | F361 | GATATTTTCGGAGT | 96 | 377 |
|  | R7 | AAATAAATTCGCTA |  | 342 |
|  | P7 | TTTGTCGTAGTTTTTTTTTAAGT |  | 343 |
| 62 | F362 | ATATTTTCGGAGTT | 95 | 378 |
|  | R7 | AAATAAATTCGCTA |  | 342 |
|  | P7 | TTTGTCGTAGTTTTTTTTTAAGT |  | 343 |
| 63 | F363 | TATTTTCGGAGTTT | 94 | 379 |
|  | R7 | AAATAAATTCGCTA |  | 342 |
|  | P7 | TTTGTCGTAGTTTTTTTTTAAGT |  | 343 |
| 64 | F364 | ATTTTCGGAGTTTT | 93 | 380 |
|  | R7 | AAATAAATTCGCTA |  | 342 |
|  | P7 | TTTGTCGTAGTTTTTTTTTAAGT |  | 343 |
| 65 | F365 | TTTTCGGAGTTTTA | 92 | 381 |
|  | R7 | AAATAAATTCGCTA |  | 342 |
|  | P7 | TTTGTCGTAGTTTTTTTTTAAGT |  | 343 |
| 66 | F366 | TTTCGGAGTTTTAG | 91 | 382 |
|  | R7 | AAATAAATTCGCTA |  | 342 |
|  | P7 | TTTGTCGTAGTTTTTTTTTAAGT |  | 343 |

TABLE 1-continued

Primer and probe sequences for detection of SDC2 gene methylation

| Set | Primers | Sequences (5'-->3') | Size of amplified product (bp) | SEQ ID NO: |
|---|---|---|---|---|
| 67 | F367 | TTCGGAGTTTTAGT | 90 | 383 |
|  | R7 | AAATAAATTCGCTA |  | 342 |
|  | P7 | TTTGTCGTAGTTTTTTTTTAAGT |  | 343 |
| 68 | F368 | TCGGAGTTTTAGTC | 89 | 384 |
|  | R7 | AAATAAATTCGCTA |  | 342 |
|  | P7 | TTTGTCGTAGTTTTTTTTTAAGT |  | 343 |
| 69 | F369 | CGGAGTTTTAGTCG | 88 | 385 |
|  | R7 | AAATAAATTCGCTA |  | 342 |
|  | P7 | TTTGTCGTAGTTTTTTTTTAAGT |  | 343 |
| 70 | F370 | GGAGTTTTAGTCGC | 87 | 386 |
|  | R7 | AAATAAATTCGCTA |  | 342 |
|  | P7 | TTTGTCGTAGTTTTTTTTTAAGT |  | 343 |
| 71 | F371 | GAGTTTTAGTCGCG | 86 | 387 |
|  | R7 | AAATAAATTCGCTA |  | 342 |
|  | P7 | TTTGTCGTAGTTTTTTTTTAAGT |  | 343 |
| 72 | F372 | AGTTTTAGTCGCGC | 85 | 388 |
|  | R7 | AAATAAATTCGCTA |  | 342 |
|  | P7 | TTTGTCGTAGTTTTTTTTTAAGT |  | 343 |
| 73 | F373 | GTTTTAGTCGCGCG | 84 | 389 |
|  | R7 | AAATAAATTCGCTA |  | 342 |
|  | P7 | TTTGTCGTAGTTTTTTTTTAAGT |  | 343 |
| 74 | F374 | TTTTAGTCGCGCGG | 83 | 390 |
|  | R7 | AAATAAATTCGCTA |  | 342 |
|  | P7 | TTTGTCGTAGTTTTTTTTTAAGT |  | 343 |
| 75 | F375 | TTTAGTCGCGCGGA | 82 | 391 |
|  | R7 | AAATAAATTCGCTA |  | 342 |
|  | P7 | TTTGTCGTAGTTTTTTTTTAAGT |  | 343 |
| 76 | F376 | TTAGTCGCGCGGAT | 81 | 392 |
|  | R7 | AAATAAATTCGCTA |  | 342 |
|  | P7 | TTTGTCGTAGTTTTTTTTTAAGT |  | 343 |
| 77 | F377 | TAGTCGCGCGGATC | 80 | 393 |
|  | R7 | AAATAAATTCGCTA |  | 342 |
|  | P7 | TTTGTCGTAGTTTTTTTTTAAGT |  | 343 |
| 78 | F378 | AGTCGCGCGGATCG | 130 | 394 |
|  | R8 | ACTCCTCCGCGAAC |  | 395 |
|  | P8 | AATTGAATTTCGGTACGGGAAGGA |  | 396 |
| 79 | F379 | GTCGCGCGGATCGC | 129 | 397 |
|  | R8 | ACTCCTCCGCGAAC |  | 395 |
|  | P8 | AATTGAATTTCGGTACGGGAAGGA |  | 396 |
| 80 | F380 | TCGCGCGGATCGCG | 128 | 398 |
|  | R8 | ACTCCTCCGCGAAC |  | 395 |
|  | P8 | AATTGAATTTCGGTACGGGAAGGA |  | 396 |
| 81 | F381 | CGCGCGGATCGCGC | 127 | 399 |
|  | R8 | ACTCCTCCGCGAAC |  | 395 |
|  | P8 | AATTGAATTTCGGTACGGGAAGGA |  | 396 |
| 82 | F382 | GCGCGGATCGCGCG | 126 | 400 |
|  | R8 | ACTCCTCCGCGAAC |  | 395 |
|  | P8 | AATTGAATTTCGGTACGGGAAGGA |  | 396 |
| 83 | F383 | CGCGGATCGCGCGT | 125 | 401 |
|  | R8 | ACTCCTCCGCGAAC |  | 395 |
|  | P8 | AATTGAATTTCGGTACGGGAAGGA |  | 396 |
| 84 | F384 | GCGGATCGCGCGTT | 124 | 402 |
|  | R8 | ACTCCTCCGCGAAC |  | 395 |
|  | P8 | AATTGAATTTCGGTACGGGAAGGA |  | 396 |

TABLE 1-continued

Primer and probe sequences for detection of SDC2 gene methylation

| Set | Primers | Sequences (5'-->3') | Size of amplified product (bp) | SEQ ID NO: |
|---|---|---|---|---|
| 85 | F385 | CGGATCGCGCGTTT | 123 | 403 |
|  | R8 | ACTCCTCCGCGAAC |  | 395 |
|  | P8 | AATTGAATTTCGGTACGGGAAAGGA |  | 396 |
| 86 | F386 | GGATCGCGCGTTTT | 122 | 404 |
|  | R8 | ACTCCTCCGCGAAC |  | 395 |
|  | P8 | AATTGAATTTCGGTACGGGAAAGGA |  | 396 |
| 87 | F387 | GATCGCGCGTTTTC | 121 | 405 |
|  | R8 | ACTCCTCCGCGAAC |  | 395 |
|  | P8 | AATTGAATTTCGGTACGGGAAAGGA |  | 396 |
| 88 | F388 | ATCGCGCGTTTTCG | 120 | 406 |
|  | R8 | ACTCCTCCGCGAAC |  | 395 |
|  | P8 | AATTGAATTTCGGTACGGGAAAGGA |  | 396 |
| 89 | F389 | TCGCGCGTTTTCGT | 119 | 407 |
|  | R8 | ACTCCTCCGCGAAC |  | 395 |
|  | P8 | AATTGAATTTCGGTACGGGAAAGGA |  | 396 |
| 90 | F390 | CGCGCGTTTTCGTC | 118 | 408 |
|  | R8 | ACTCCTCCGCGAAC |  | 395 |
|  | P8 | AATTGAATTTCGGTACGGGAAAGGA |  | 396 |
| 91 | F391 | GCGCGTTTTCGTCG | 117 | 409 |
|  | R8 | ACTCCTCCGCGAAC |  | 395 |
|  | P8 | AATTGAATTTCGGTACGGGAAAGGA |  | 396 |
| 92 | F392 | CGCGTTTTCGTCGT | 116 | 410 |
|  | R8 | ACTCCTCCGCGAAC |  | 395 |
|  | P8 | AATTGAATTTCGGTACGGGAAAGGA |  | 396 |
| 93 | F393 | GCGTTTTCGTCGTT | 115 | 411 |
|  | R8 | ACTCCTCCGCGAAC |  | 395 |
|  | P8 | AATTGAATTTCGGTACGGGAAAGGA |  | 396 |
| 94 | F394 | CGTTTTCGTCGTTT | 114 | 412 |
|  | R8 | ACTCCTCCGCGAAC |  | 395 |
|  | P8 | AATTGAATTTCGGTACGGGAAAGGA |  | 396 |
| 95 | F395 | GTTTTCGTCGTTTT | 113 | 413 |
|  | R8 | ACTCCTCCGCGAAC |  | 395 |
|  | P8 | AATTGAATTTCGGTACGGGAAAGGA |  | 396 |
| 96 | F396 | TTTTCGTCGTTTTG | 112 | 414 |
|  | R8 | ACTCCTCCGCGAAC |  | 395 |
|  | P8 | AATTGAATTTCGGTACGGGAAAGGA |  | 396 |
| 97 | F397 | TTTCGTCGTTTTGT | 111 | 415 |
|  | R8 | ACTCCTCCGCGAAC |  | 395 |
|  | P8 | AATTGAATTTCGGTACGGGAAAGGA |  | 396 |
| 98 | F398 | TTCGTCGTTTTGTT | 110 | 416 |
|  | R8 | ACTCCTCCGCGAAC |  | 395 |
|  | P8 | AATTGAATTTCGGTACGGGAAAGGA |  | 396 |
| 99 | F399 | TCGTCGTTTTGTTT | 109 | 417 |
|  | R8 | ACTCCTCCGCGAAC |  | 395 |
|  | P8 | AATTGAATTTCGGTACGGGAAAGGA |  | 396 |
| 00 | F400 | CGTCGTTTTGTTTT | 108 | 418 |
|  | R8 | ACTCCTCCGCGAAC |  | 395 |
|  | P8 | AATTGAATTTCGGTACGGGAAAGGA |  | 396 |
| 01 | F401 | GTCGTTTTGTTTTT | 107 | 419 |
|  | R8 | ACTCCTCCGCGAAC |  | 395 |
|  | P8 | AATTGAATTTCGGTACGGGAAAGGA |  | 396 |
| 02 | F402 | TCGTTTTGTTTTTA | 106 | 420 |
|  | R8 | ACTCCTCCGCGAAC |  | 395 |
|  | P8 | AATTGAATTTCGGTACGGGAAAGGA |  | 396 |

TABLE 1 -continued

Primer and probe sequences for detection of SDC2 gene methylation

| Set | Primers | Sequences (5'-->3') | Size of amplified product (bp) | SEQ ID NO: |
|---|---|---|---|---|
| 03 | F403 | CGTTTTGTTTTTAA | 105 | 421 |
|  | R8 | ACTCCTCCGCGAAC |  | 395 |
|  | P8 | AATTGAATTTCGGTACGGGAAGGA |  | 396 |
| 04 | F404 | GTTTTGTTTTTAAA | 104 | 422 |
|  | R8 | ACTCCTCCGCGAAC |  | 395 |
|  | P8 | AATTGAATTTCGGTACGGGAAGGA |  | 396 |
| 05 | F405 | TTTTGTTTTTAAAT | 103 | 423 |
|  | R8 | ACTCCTCCGCGAAC |  | 395 |
|  | P8 | AATTGAATTTCGGTACGGGAAGGA |  | 396 |
| 06 | F406 | TTTGTTTTTAAATT | 102 | 424 |
|  | R8 | ACTCCTCCGCGAAC |  | 395 |
|  | P8 | AATTGAATTTCGGTACGGGAAGGA |  | 396 |
| 07 | F407 | TTGTTTTTAAATTT | 101 | 425 |
|  | R8 | ACTCCTCCGCGAAC |  | 395 |
|  | P8 | AATTGAATTTCGGTACGGGAAGGA |  | 396 |
| 08 | F408 | TGTTTTTAAATTTT | 100 | 426 |
|  | R8 | ACTCCTCCGCGAAC |  | 395 |
|  | P8 | AATTGAATTTCGGTACGGGAAGGA |  | 396 |
| 09 | F409 | GTTTTTAAATTTTT | 99 | 427 |
|  | R8 | ACTCCTCCGCGAAC |  | 395 |
|  | P8 | AATTGAATTTCGGTACGGGAAGGA |  | 396 |
| 10 | F410 | TTTTTAAATTTTTG | 98 | 428 |
|  | R8 | ACTCCTCCGCGAAC |  | 395 |
|  | P8 | AATTGAATTTCGGTACGGGAAGGA |  | 396 |
| 11 | F411 | TTTTAAATTTTTGT | 97 | 429 |
|  | R8 | ACTCCTCCGCGAAC |  | 395 |
|  | P8 | AATTGAATTTCGGTACGGGAAGGA |  | 396 |
| 12 | F412 | TTTAAATTTTTGTC | 96 | 430 |
|  | R8 | ACTCCTCCGCGAAC |  | 395 |
|  | P8 | AATTGAATTTCGGTACGGGAAGGA |  | 396 |
| 13 | F413 | TTAAATTTTTGTCG | 95 | 431 |
|  | R8 | ACTCCTCCGCGAAC |  | 395 |
|  | P8 | AATTGAATTTCGGTACGGGAAGGA |  | 396 |
| 14 | F414 | TAAATTTTTGTCGT | 94 | 432 |
|  | R8 | ACTCCTCCGCGAAC |  | 395 |
|  | P8 | AATTGAATTTCGGTACGGGAAGGA |  | 396 |
| 15 | F415 | AAATTTTTGTCGTA | 93 | 433 |
|  | R8 | ACTCCTCCGCGAAC |  | 395 |
|  | P8 | AATTGAATTTCGGTACGGGAAGGA |  | 396 |
| 16 | F416 | AATTTTTGTCGTAG | 92 | 434 |
|  | R8 | ACTCCTCCGCGAAC |  | 395 |
|  | P8 | AATTGAATTTCGGTACGGGAAGGA |  | 396 |
| 17 | F417 | ATTTTTGTCGTAGT | 91 | 435 |
|  | R8 | ACTCCTCCGCGAAC |  | 395 |
|  | P8 | AATTGAATTTCGGTACGGGAAGGA |  | 396 |
| 18 | F418 | TTTTTGTCGTAGTT | 90 | 436 |
|  | R8 | ACTCCTCCGCGAAC |  | 395 |
|  | P8 | AATTGAATTTCGGTACGGGAAGGA |  | 396 |
| 19 | F419 | TTTTGTCGTAGTTT | 89 | 437 |
|  | R8 | ACTCCTCCGCGAAC |  | 395 |
|  | P8 | AATTGAATTTCGGTACGGGAAGGA |  | 396 |
| 20 | F420 | TTTGTCGTAGTTTT | 88 | 438 |
|  | R8 | ACTCCTCCGCGAAC |  | 395 |
|  | P8 | AATTGAATTTCGGTACGGGAAGGA |  | 396 |

TABLE 1 -continued

Primer and probe sequences for detection of SDC2 gene methylation

| Set | Primers | Sequences (5'-->3') | Size of amplified product (bp) | SEQ ID NO: |
|---|---|---|---|---|
| 21 | F421 | TTGTCGTAGTTTTTT | 87 | 439 |
|  | R8 | ACTCCTCCGCGAAC |  | 395 |
|  | P8 | AATTGAATTTCGGTACGGGAAAGGA |  | 396 |
| 22 | F422 | TGTCGTAGTTTTTTT | 86 | 440 |
|  | R8 | ACTCCTCCGCGAAC |  | 395 |
|  | P8 | AATTGAATTTCGGTACGGGAAAGGA |  | 396 |
| 23 | F423 | GTCGTAGTTTTTTTT | 85 | 441 |
|  | R8 | ACTCCTCCGCGAAC |  | 395 |
|  | P8 | AATTGAATTTCGGTACGGGAAAGGA |  | 396 |
| 24 | F424 | TCGTAGTTTTTTTTT | 84 | 442 |
|  | R8 | ACTCCTCCGCGAAC |  | 395 |
|  | P8 | AATTGAATTTCGGTACGGGAAAGGA |  | 396 |
| 25 | F425 | CGTAGTTTTTTTTTT | 83 | 443 |
|  | R8 | ACTCCTCCGCGAAC |  | 395 |
|  | P8 | AATTGAATTTCGGTACGGGAAAGGA |  | 396 |
| 26 | F426 | GTAGTTTTTTTTTA | 82 | 444 |
|  | R8 | ACTCCTCCGCGAAC |  | 395 |
|  | P8 | AATTGAATTTCGGTACGGGAAAGGA |  | 396 |
| 27 | F427 | TAGTTTTTTTTAA | 81 | 445 |
|  | R8 | ACTCCTCCGCGAAC |  | 395 |
|  | P8 | AATTGAATTTCGGTACGGGAAAGGA |  | 396 |
| 28 | F428 | AGTTTTTTTTAAG | 80 | 446 |
|  | R8 | ACTCCTCCGCGAAC |  | 395 |
|  | P8 | AATTGAATTTCGGTACGGGAAAGGA |  | 396 |
| 29 | F429 | GTTTTTTTTAAGT | 140 | 447 |
|  | R9 | CACGAAATTAATAC |  | 448 |
|  | P9 | GTTTTAGAGAGTAGTTTTTTCGGA |  | 449 |
| 30 | F430 | TTTTTTTTAAGTT | 139 | 450 |
|  | R9 | CACGAAATTAATAC |  | 448 |
|  | P9 | GTTTTAGAGAGTAGTTTTTTCGGA |  | 449 |
| 31 | F431 | TTTTTTTAAGTTA | 138 | 451 |
|  | R9 | CACGAAATTAATAC |  | 448 |
|  | P9 | GTTTTAGAGAGTAGTTTTTTCGGA |  | 449 |
| 32 | F432 | TTTTTTAAGTTAG | 137 | 452 |
|  | R9 | CACGAAATTAATAC |  | 448 |
|  | P9 | GTTTTAGAGAGTAGTTTTTTCGGA |  | 449 |
| 33 | F433 | TTTTTAAGTTAGC | 136 | 453 |
|  | R9 | CACGAAATTAATAC |  | 448 |
|  | P9 | GTTTTAGAGAGTAGTTTTTTCGGA |  | 449 |
| 34 | F434 | TTTTAAGTTAGCG | 135 | 454 |
|  | R9 | CACGAAATTAATAC |  | 448 |
|  | P9 | GTTTTAGAGAGTAGTTTTTTCGGA |  | 449 |
| 35 | F435 | TTTAAGTTAGCGA | 134 | 455 |
|  | R9 | CACGAAATTAATAC |  | 448 |
|  | P9 | GTTTTAGAGAGTAGTTTTTTCGGA |  | 449 |
| 36 | F436 | TTAAGTTAGCGAA | 133 | 456 |
|  | R9 | CACGAAATTAATAC |  | 448 |
|  | P9 | GTTTTAGAGAGTAGTTTTTTCGGA |  | 449 |
| 37 | F437 | TAAGTTAGCGAAT | 132 | 457 |
|  | R9 | CACGAAATTAATAC |  | 448 |
|  | P9 | GTTTTAGAGAGTAGTTTTTTCGGA |  | 449 |
| 38 | F438 | TAAGTTAGCGAATT | 131 | 458 |
|  | R9 | CACGAAATTAATAC |  | 448 |
|  | P9 | GTTTTAGAGAGTAGTTTTTTCGGA |  | 449 |

TABLE 1-continued

Primer and probe sequences for detection of SDC2 gene methylation

| Set | Primers | Sequences (5'-->3') | Size of amplified product (bp) | SEQ ID NO: |
|---|---|---|---|---|
| 39 | F439 | AAGTTAGCGAATTT | 130 | 459 |
|  | R9 | CACGAAATTAATAC |  | 448 |
|  | P9 | GTTTTAGAGAGTAGTTTTTTCGGA |  | 449 |
| 40 | F440 | AGTTAGCGAATTTA | 129 | 460 |
|  | R9 | CACGAAATTAATAC |  | 448 |
|  | P9 | GTTTTAGAGAGTAGTTTTTTCGGA |  | 449 |
| 41 | F441 | GTTAGCGAATTTAT | 128 | 461 |
|  | R9 | CACGAAATTAATAC |  | 448 |
|  | P9 | GTTTTAGAGAGTAGTTTTTTCGGA |  | 449 |
| 42 | F442 | TTAGCGAATTTATT | 127 | 462 |
|  | R9 | CACGAAATTAATAC |  | 448 |
|  | P9 | GTTTTAGAGAGTAGTTTTTTCGGA |  | 449 |
| 43 | F443 | TAGCGAATTTATTT | 126 | 463 |
|  | R9 | CACGAAATTAATAC |  | 448 |
|  | P9 | GTTTTAGAGAGTAGTTTTTTCGGA |  | 449 |
| 44 | F444 | AGCGAATTTATTTT | 125 | 464 |
|  | R9 | CACGAAATTAATAC |  | 448 |
|  | P9 | GTTTTAGAGAGTAGTTTTTTCGGA |  | 449 |
| 45 | F445 | GCGAATTTATTTTT | 124 | 465 |
|  | R9 | CACGAAATTAATAC |  | 448 |
|  | P9 | GTTTTAGAGAGTAGTTTTTTCGGA |  | 449 |
| 46 | F446 | CGAATTTATTTTTT | 123 | 466 |
|  | R9 | CACGAAATTAATAC |  | 448 |
|  | P9 | GTTTTAGAGAGTAGTTTTTTCGGA |  | 449 |
| 47 | F447 | GAATTTATTTTTTA | 122 | 467 |
|  | R9 | CACGAAATTAATAC |  | 448 |
|  | P9 | GTTTTAGAGAGTAGTTTTTTCGGA |  | 449 |
| 48 | F448 | AATTTATTTTTTAA | 121 | 468 |
|  | R9 | CACGAAATTAATAC |  | 448 |
|  | P9 | GTTTTAGAGAGTAGTTTTTTCGGA |  | 449 |
| 49 | F449 | ATTTATTTTTTAAA | 120 | 469 |
|  | R9 | CACGAAATTAATAC |  | 448 |
|  | P9 | GTTTTAGAGAGTAGTTTTTTCGGA |  | 449 |
| 50 | F450 | TTTATTTTTTAAAA | 119 | 470 |
|  | R9 | CACGAAATTAATAC |  | 448 |
|  | P9 | GTTTTAGAGAGTAGTTTTTTCGGA |  | 449 |
| 51 | F451 | TTATTTTTTAAAAT | 118 | 471 |
|  | R9 | CACGAAATTAATAC |  | 448 |
|  | P9 | GTTTTAGAGAGTAGTTTTTTCGGA |  | 449 |
| 52 | F452 | TATTTTTTAAAATT | 117 | 472 |
|  | R9 | CACGAAATTAATAC |  | 448 |
|  | P9 | GTTTTAGAGAGTAGTTTTTTCGGA |  | 449 |
| 53 | F453 | ATTTTTTAAAATTA | 116 | 473 |
|  | R9 | CACGAAATTAATAC |  | 448 |
|  | P9 | GTTTTAGAGAGTAGTTTTTTCGGA |  | 449 |
| 54 | F454 | TTTTTTAAAATTAG | 115 | 474 |
|  | R9 | CACGAAATTAATAC |  | 448 |
|  | P9 | GTTTTAGAGAGTAGTTTTTTCGGA |  | 449 |
| 55 | F455 | TTTTTAAAATTAGA | 114 | 475 |
|  | R9 | CACGAAATTAATAC |  | 448 |
|  | P9 | GTTTTAGAGAGTAGTTTTTTCGGA |  | 449 |
| 56 | F456 | TTTTAAAATTAGAA | 113 | 476 |
|  | R9 | CACGAAATTAATAC |  | 448 |
|  | P9 | GTTTTAGAGAGTAGTTTTTTCGGA |  | 449 |

TABLE 1 -continued

Primer and probe sequences for detection of SDC2 gene methylation

| Set | Primers | Sequences (5'-->3') | Size of amplified product (bp) | SEQ ID NO: |
|---|---|---|---|---|
| 57 | F457 | TTTAAAATTAGAAA | 112 | 477 |
|  | R9 | CACGAAATTAATAC |  | 448 |
|  | P9 | GTTTTAGAGAGTAGTTTTTTCGGA |  | 449 |
| 58 | F458 | TTAAAATTAGAAAT | 111 | 478 |
|  | R9 | CACGAAATTAATAC |  | 448 |
|  | P9 | GTTTTAGAGAGTAGTTTTTTCGGA |  | 449 |
| 59 | F459 | TAAAATTAGAAATT | 110 | 479 |
|  | R9 | CACGAAATTAATAC |  | 448 |
|  | P9 | GTTTTAGAGAGTAGTTTTTTCGGA |  | 449 |
| 60 | F460 | AAAATTAGAAATTG | 109 | 480 |
|  | R9 | CACGAAATTAATAC |  | 448 |
|  | P9 | GTTTTAGAGAGTAGTTTTTTCGGA |  | 449 |
| 61 | F461 | AAATTAGAAATTGA | 108 | 481 |
|  | R9 | CACGAAATTAATAC |  | 448 |
|  | P9 | GTTTTAGAGAGTAGTTTTTTCGGA |  | 449 |
| 62 | F462 | AATTAGAAATTGAA | 107 | 482 |
|  | R9 | CACGAAATTAATAC |  | 448 |
|  | P9 | GTTTTAGAGAGTAGTTTTTTCGGA |  | 449 |
| 63 | F463 | ATTAGAAATTGAAT | 106 | 483 |
|  | R9 | CACGAAATTAATAC |  | 448 |
|  | P9 | GTTTTAGAGAGTAGTTTTTTCGGA |  | 449 |
| 64 | F464 | TTAGAAATTGAATT | 105 | 484 |
|  | R9 | CACGAAATTAATAC |  | 448 |
|  | P9 | GTTTTAGAGAGTAGTTTTTTCGGA |  | 449 |
| 65 | F465 | TAGAAATTGAATTT | 104 | 485 |
|  | R9 | CACGAAATTAATAC |  | 448 |
|  | P9 | GTTTTAGAGAGTAGTTTTTTCGGA |  | 449 |
| 66 | F466 | AGAAATTGAATTTC | 103 | 486 |
|  | R9 | CACGAAATTAATAC |  | 448 |
|  | P9 | GTTTTAGAGAGTAGTTTTTTCGGA |  | 449 |
| 67 | F467 | GAAATTGAATTTCG | 102 | 487 |
|  | R9 | CACGAAATTAATAC |  | 448 |
|  | P9 | GTTTTAGAGAGTAGTTTTTTCGGA |  | 449 |
| 68 | F468 | AAATTGAATTTCGG | 101 | 488 |
|  | R9 | CACGAAATTAATAC |  | 448 |
|  | P9 | GTTTTAGAGAGTAGTTTTTTCGGA |  | 449 |
| 69 | F469 | AATTGAATTTCGGT | 100 | 489 |
|  | R9 | CACGAAATTAATAC |  | 448 |
|  | P9 | GTTTTAGAGAGTAGTTTTTTCGGA |  | 449 |
| 70 | F470 | ATTGAATTTCGGTA | 99 | 490 |
|  | R9 | CACGAAATTAATAC |  | 448 |
|  | P9 | GTTTTAGAGAGTAGTTTTTTCGGA |  | 449 |
| 71 | F471 | TTGAATTTCGGTAC | 98 | 491 |
|  | R9 | CACGAAATTAATAC |  | 448 |
|  | P9 | GTTTTAGAGAGTAGTTTTTTCGGA |  | 449 |
| 72 | F472 | TGAATTTCGGTACG | 97 | 492 |
|  | R9 | CACGAAATTAATAC |  | 448 |
|  | P9 | GTTTTAGAGAGTAGTTTTTTCGGA |  | 449 |
| 73 | F473 | GAATTTCGGTACGG | 96 | 493 |
|  | R9 | CACGAAATTAATAC |  | 448 |
|  | P9 | GTTTTAGAGAGTAGTTTTTTCGGA |  | 449 |
| 74 | F474 | AATTTCGGTACGGG | 95 | 494 |
|  | R9 | CACGAAATTAATAC |  | 448 |
|  | P9 | GTTTTAGAGAGTAGTTTTTTCGGA |  | 449 |

TABLE 1 -continued

Primer and probe sequences for detection of SDC2 gene methylation

| Set | Primers | Sequences (5'-->3') | Size of amplified product (bp) | SEQ ID NO: |
|---|---|---|---|---|
| 75 | F475 | ATTTCGGTACGGGA | 94 | 495 |
|  | R9 | CACGAAATTAATAC |  | 448 |
|  | P9 | GTTTTAGAGAGTAGTTTTTTCGGA |  | 449 |
| 76 | F476 | TTTCGGTACGGGAA | 93 | 496 |
|  | R9 | CACGAAATTAATAC |  | 448 |
|  | P9 | GTTTTAGAGAGTAGTTTTTTCGGA |  | 449 |
| 77 | F477 | TTCGGTACGGGAAA | 92 | 497 |
|  | R9 | CACGAAATTAATAC |  | 448 |
|  | P9 | GTTTTAGAGAGTAGTTTTTTCGGA |  | 449 |
| 78 | F478 | TCGGTACGGGAAAG | 91 | 498 |
|  | R9 | CACGAAATTAATAC |  | 448 |
|  | P9 | GTTTTAGAGAGTAGTTTTTTCGGA |  | 449 |
| 79 | F479 | CGGTACGGGAAAGG | 90 | 499 |
|  | R9 | CACGAAATTAATAC |  | 448 |
|  | P9 | GTTTTAGAGAGTAGTTTTTTCGGA |  | 449 |
| 80 | F480 | GGTACGGGAAAGGA | 89 | 500 |
|  | R9 | CACGAAATTAATAC |  | 448 |
|  | P9 | GTTTTAGAGAGTAGTTTTTTCGGA |  | 449 |
| 81 | F481 | GTACGGGAAAGGAG | 88 | 501 |
|  | R9 | CACGAAATTAATAC |  | 448 |
|  | P9 | GTTTTAGAGAGTAGTTTTTTCGGA |  | 449 |
| 82 | F482 | TACGGGAAAGGAGT | 87 | 502 |
|  | R9 | CACGAAATTAATAC |  | 448 |
|  | P9 | GTTTTAGAGAGTAGTTTTTTCGGA |  | 449 |
| 83 | F483 | ACGGGAAAGGAGTT | 86 | 503 |
|  | R9 | CACGAAATTAATAC |  | 448 |
|  | P9 | GTTTTAGAGAGTAGTTTTTTCGGA |  | 449 |
| 84 | F484 | CGGGAAAGGAGTTC | 85 | 504 |
|  | R9 | CACGAAATTAATAC |  | 448 |
|  | P9 | GTTTTAGAGAGTAGTTTTTTCGGA |  | 449 |
| 85 | F485 | GGGAAAGGAGTTCG | 84 | 505 |
|  | R9 | CACGAAATTAATAC |  | 448 |
|  | P9 | GTTTTAGAGAGTAGTTTTTTCGGA |  | 449 |
| 86 | F486 | GGAAAGGAGTTCGC | 83 | 506 |
|  | R9 | CACGAAATTAATAC |  | 448 |
|  | P9 | GTTTTAGAGAGTAGTTTTTTCGGA |  | 449 |
| 87 | F487 | GAAAGGAGTTCGCG | 82 | 507 |
|  | R9 | CACGAAATTAATAC |  | 448 |
|  | P9 | GTTTTAGAGAGTAGTTTTTTCGGA |  | 449 |
| 88 | F488 | AAAGGAGTTCGCGG | 81 | 508 |
|  | R9 | CACGAAATTAATAC |  | 448 |
|  | P9 | GTTTTAGAGAGTAGTTTTTTCGGA |  | 449 |
| 89 | F489 | AAGGAGTTCGCGGA | 80 | 509 |
|  | R9 | CACGAAATTAATAC |  | 448 |
|  | P9 | GTTTTAGAGAGTAGTTTTTTCGGA |  | 449 |
| 90 | F490 | AGGAGTTCGCGGAG | 140 | 510 |
|  | R10 | CGCCCGCAACTACG |  | 511 |
|  | P10 | GTGAGAGGGCGTCGCGTTTTCGGGG |  | 512 |
| 91 | F491 | GGAGTTCGCGGAGG | 139 | 513 |
|  | R10 | CGCCCGCAACTACG |  | 511 |
|  | P10 | GTGAGAGGGCGTCGCGTTTTCGGGG |  | 512 |
| 92 | F492 | GAGTTCGCGGAGGA | 138 | 514 |
|  | R10 | CGCCCGCAACTACG |  | 511 |
|  | P10 | GTGAGAGGGCGTCGCGTTTTCGGGG |  | 512 |

TABLE 1-continued

Primer and probe sequences for detection of SDC2 gene methylation

| Set | Primers | Sequences (5'-->3') | Size of amplified product (bp) | SEQ ID NO: |
|---|---|---|---|---|
| 93 | F493 | AGTTCGCGGAGGAG | 137 | 515 |
|  | R10 | CGCCCGCAACTACG |  | 511 |
|  | P10 | GTGAGAGGGCGTCGCGTTTTCGGGG |  | 512 |
| 94 | F494 | GTTCGCGGAGGAGT | 136 | 516 |
|  | R10 | CGCCCGCAACTACG |  | 511 |
|  | P10 | GTGAGAGGGCGTCGCGTTTTCGGGG |  | 512 |
| 95 | F495 | TTCGCGGAGGAGTA | 135 | 517 |
|  | R10 | CGCCCGCAACTACG |  | 511 |
|  | P10 | GTGAGAGGGCGTCGCGTTTTCGGGG |  | 512 |
| 96 | F496 | TCGCGGAGGAGTAA | 134 | 518 |
|  | R10 | CGCCCGCAACTACG |  | 511 |
|  | P10 | GTGAGAGGGCGTCGCGTTTTCGGGG |  | 512 |
| 97 | F497 | CGCGGAGGAGTAAA | 133 | 519 |
|  | R10 | CGCCCGCAACTACG |  | 511 |
|  | P10 | GTGAGAGGGCGTCGCGTTTTCGGGG |  | 512 |
| 98 | F498 | GCGGAGGAGTAAAA | 132 | 520 |
|  | R10 | CGCCCGCAACTACG |  | 511 |
|  | P10 | GTGAGAGGGCGTCGCGTTTTCGGGG |  | 512 |
| 99 | F499 | CGGAGGAGTAAAAT | 131 | 521 |
|  | R10 | CGCCCGCAACTACG |  | 511 |
|  | P10 | GTGAGAGGGCGTCGCGTTTTCGGGG |  | 512 |
| 00 | F500 | GGAGGAGTAAAATT | 130 | 522 |
|  | R10 | CGCCCGCAACTACG |  | 511 |
|  | P10 | GTGAGAGGGCGTCGCGTTTTCGGGG |  | 512 |
| 01 | F501 | GAGGAGTAAAATTA | 129 | 523 |
|  | R10 | CGCCCGCAACTACG |  | 511 |
|  | P10 | GTGAGAGGGCGTCGCGTTTTCGGGG |  | 512 |
| 02 | F502 | AGGAGTAAAATTAT | 128 | 524 |
|  | R10 | CGCCCGCAACTACG |  | 511 |
|  | P10 | GTGAGAGGGCGTCGCGTTTTCGGGG |  | 512 |
| 03 | F503 | GGAGTAAAATTATA | 127 | 525 |
|  | R10 | CGCCCGCAACTACG |  | 511 |
|  | P10 | GTGAGAGGGCGTCGCGTTTTCGGGG |  | 512 |
| 04 | F504 | GAGTAAAATTATAG | 126 | 526 |
|  | R10 | CGCCCGCAACTACG |  | 511 |
|  | P10 | GTGAGAGGGCGTCGCGTTTTCGGGG |  | 512 |
| 05 | F505 | AGTAAAATTATAGT | 125 | 527 |
|  | R10 | CGCCCGCAACTACG |  | 511 |
|  | P10 | GTGAGAGGGCGTCGCGTTTTCGGGG |  | 512 |
| 06 | F506 | GTAAAATTATAGTA | 124 | 528 |
|  | R10 | CGCCCGCAACTACG |  | 511 |
|  | P10 | GTGAGAGGGCGTCGCGTTTTCGGGG |  | 512 |
| 07 | F507 | TAAAATTATAGTAG | 123 | 529 |
|  | R10 | CGCCCGCAACTACG |  | 511 |
|  | P10 | GTGAGAGGGCGTCGCGTTTTCGGGG |  | 512 |
| 08 | F508 | AAAATTATAGTAGA | 122 | 530 |
|  | R10 | CGCCCGCAACTACG |  | 511 |
|  | P10 | GTGAGAGGGCGTCGCGTTTTCGGGG |  | 512 |
| 09 | F509 | AAATTATAGTAGAG | 121 | 531 |
|  | R10 | CGCCCGCAACTACG |  | 511 |
|  | P10 | GTGAGAGGGCGTCGCGTTTTCGGGG |  | 512 |
| 10 | F510 | AATTATAGTAGAGT | 120 | 532 |
|  | R10 | CGCCCGCAACTACG |  | 511 |
|  | P10 | GTGAGAGGGCGTCGCGTTTTCGGGG |  | 512 |

TABLE 1-continued

Primer and probe sequences for detection of SDC2 gene methylation

| Set | Primers | Sequences (5'-->3') | Size of amplified product (bp) | SEQ ID NO: |
|---|---|---|---|---|
| 11 | F511 | ATTATAGTAGAGTA | 119 | 533 |
|  | R10 | CGCCCGCAACTACG |  | 511 |
|  | P10 | GTGAGAGGGCGTCGCGTTTTCGGGG |  | 512 |
| 12 | F512 | TTATAGTAGAGTAA | 118 | 534 |
|  | R10 | CGCCCGCAACTACG |  | 511 |
|  | P10 | GTGAGAGGGCGTCGCGTTTTCGGGG |  | 512 |
| 13 | F513 | TATAGTAGAGTAAG | 117 | 535 |
|  | R10 | CGCCCGCAACTACG |  | 511 |
|  | P10 | GTGAGAGGGCGTCGCGTTTTCGGGG |  | 512 |
| 14 | F514 | ATAGTAGAGTAAGA | 116 | 536 |
|  | R10 | CGCCCGCAACTACG |  | 511 |
|  | P10 | GTGAGAGGGCGTCGCGTTTTCGGGG |  | 512 |
| 15 | F515 | TAGTAGAGTAAGAA | 115 | 537 |
|  | R10 | CGCCCGCAACTACG |  | 511 |
|  | P10 | GTGAGAGGGCGTCGCGTTTTCGGGG |  | 512 |
| 16 | F516 | AGTAGAGTAAGAAG | 114 | 538 |
|  | R10 | CGCCCGCAACTACG |  | 511 |
|  | P10 | GTGAGAGGGCGTCGCGTTTTCGGGG |  | 512 |
| 17 | F517 | GTAGAGTAAGAAGA | 113 | 539 |
|  | R10 | CGCCCGCAACTACG |  | 511 |
|  | P10 | GTGAGAGGGCGTCGCGTTTTCGGGG |  | 512 |
| 18 | F518 | TAGAGTAAGAAGAG | 112 | 540 |
|  | R10 | CGCCCGCAACTACG |  | 511 |
|  | P10 | GTGAGAGGGCGTCGCGTTTTCGGGG |  | 512 |
| 19 | F519 | AGAGTAAGAAGAGT | 111 | 541 |
|  | R10 | CGCCCGCAACTACG |  | 511 |
|  | P10 | GTGAGAGGGCGTCGCGTTTTCGGGG |  | 512 |
| 20 | F520 | GAGTAAGAAGAGTT | 110 | 542 |
|  | R10 | CGCCCGCAACTACG |  | 511 |
|  | P10 | GTGAGAGGGCGTCGCGTTTTCGGGG |  | 512 |
| 21 | F521 | AGTAAGAAGAGTTT | 109 | 543 |
|  | R10 | CGCCCGCAACTACG |  | 511 |
|  | P10 | GTGAGAGGGCGTCGCGTTTTCGGGG |  | 512 |
| 22 | F522 | GTAAGAAGAGTTTT | 108 | 544 |
|  | R10 | CGCCCGCAACTACG |  | 511 |
|  | P10 | GTGAGAGGGCGTCGCGTTTTCGGGG |  | 512 |
| 23 | F523 | TAAGAAGAGTTTTA | 107 | 545 |
|  | R10 | CGCCCGCAACTACG |  | 511 |
|  | P10 | GTGAGAGGGCGTCGCGTTTTCGGGG |  | 512 |
| 24 | F524 | AAGAAGAGTTTTAG | 106 | 546 |
|  | R10 | CGCCCGCAACTACG |  | 511 |
|  | P10 | GTGAGAGGGCGTCGCGTTTTCGGGG |  | 512 |
| 25 | F525 | AGAAGAGTTTTAGA | 105 | 547 |
|  | R10 | CGCCCGCAACTACG |  | 511 |
|  | P10 | GTGAGAGGGCGTCGCGTTTTCGGGG |  | 512 |
| 26 | F526 | GAAGAGTTTTAGAG | 104 | 548 |
|  | R10 | CGCCCGCAACTACG |  | 511 |
|  | P10 | GTGAGAGGGCGTCGCGTTTTCGGGG |  | 512 |
| 27 | F527 | AAGAGTTTTAGAGA | 103 | 549 |
|  | R10 | CGCCCGCAACTACG |  | 511 |
|  | P10 | GTGAGAGGGCGTCGCGTTTTCGGGG |  | 512 |
| 28 | F528 | AGAGTTTTAGAGAG | 102 | 550 |
|  | R10 | CGCCCGCAACTACG |  | 511 |
|  | P10 | GTGAGAGGGCGTCGCGTTTTCGGGG |  | 512 |

TABLE 1-continued

Primer and probe sequences for detection of SDC2 gene methylation

| Set | Primers | Sequences (5'-->3') | Size of amplified product (bp) | SEQ ID NO: |
|---|---|---|---|---|
| 29 | F529 | GAGTTTTAGAGAGT | 101 | 551 |
|    | R10  | CGCCCGCAACTACG |     | 511 |
|    | P10  | GTGAGAGGGCGTCGCGTTTTCGGGG |  | 512 |
| 30 | F530 | AGTTTTAGAGAGTA | 100 | 552 |
|    | R10  | CGCCCGCAACTACG |     | 511 |
|    | P10  | GTGAGAGGGCGTCGCGTTTTCGGGG |  | 512 |
| 31 | F531 | GTTTTAGAGAGTAG | 99 | 553 |
|    | R10  | CGCCCGCAACTACG |    | 511 |
|    | P10  | GTGAGAGGGCGTCGCGTTTTCGGGG | | 512 |
| 32 | F532 | TTTTAGAGAGTAGT | 98 | 554 |
|    | R10  | CGCCCGCAACTACG |    | 511 |
|    | P10  | GTGAGAGGGCGTCGCGTTTTCGGGG | | 512 |
| 33 | F533 | TTTAGAGAGTAGTT | 97 | 555 |
|    | R10  | CGCCCGCAACTACG |    | 511 |
|    | P10  | GTGAGAGGGCGTCGCGTTTTCGGGG | | 512 |
| 34 | F534 | TTAGAGAGTAGTTT | 96 | 556 |
|    | R10  | CGCCCGCAACTACG |    | 511 |
|    | P10  | GTGAGAGGGCGTCGCGTTTTCGGGG | | 512 |
| 35 | F535 | TAGAGAGTAGTTTT | 95 | 557 |
|    | R10  | CGCCCGCAACTACG |    | 511 |
|    | P10  | GTGAGAGGGCGTCGCGTTTTCGGGG | | 512 |
| 36 | F536 | AGAGAGTAGTTTTT | 94 | 558 |
|    | R10  | CGCCCGCAACTACG |    | 511 |
|    | P10  | GTGAGAGGGCGTCGCGTTTTCGGGG | | 512 |
| 37 | F537 | GAGAGTAGTTTTTT | 93 | 559 |
|    | R10  | CGCCCGCAACTACG |    | 511 |
|    | P10  | GTGAGAGGGCGTCGCGTTTTCGGGG | | 512 |
| 38 | F538 | AGAGTAGTTTTTTC | 92 | 560 |
|    | R10  | CGCCCGCAACTACG |    | 511 |
|    | P10  | GTGAGAGGGCGTCGCGTTTTCGGGG | | 512 |
| 39 | F539 | GAGTAGTTTTTTCG | 91 | 561 |
|    | R10  | CGCCCGCAACTACG |    | 511 |
|    | P10  | GTGAGAGGGCGTCGCGTTTTCGGGG | | 512 |
| 40 | F540 | AGTAGTTTTTTCGG | 90 | 562 |
|    | R10  | CGCCCGCAACTACG |    | 511 |
|    | P10  | GTGAGAGGGCGTCGCGTTTTCGGGG | | 512 |
| 41 | F541 | GTAGTTTTTTCGGA | 89 | 563 |
|    | R10  | CGCCCGCAACTACG |    | 511 |
|    | P10  | GTGAGAGGGCGTCGCGTTTTCGGGG | | 512 |
| 42 | F542 | TAGTTTTTTCGGAG | 88 | 564 |
|    | R10  | CGCCCGCAACTACG |    | 511 |
|    | P10  | GTGAGAGGGCGTCGCGTTTTCGGGG | | 512 |
| 43 | F543 | AGTTTTTTCGGAGT | 87 | 565 |
|    | R10  | CGCCCGCAACTACG |    | 511 |
|    | P10  | GTGAGAGGGCGTCGCGTTTTCGGGG | | 512 |
| 44 | F544 | GTTTTTTCGGAGTA | 86 | 566 |
|    | R10  | CGCCCGCAACTACG |    | 511 |
|    | P10  | GTGAGAGGGCGTCGCGTTTTCGGGG | | 512 |
| 45 | F545 | TTTTTTCGGAGTAT | 85 | 567 |
|    | R10  | CGCCCGCAACTACG |    | 511 |
|    | P10  | GTGAGAGGGCGTCGCGTTTTCGGGG | | 512 |
| 46 | F546 | TTTTTCGGAGTATT | 84 | 568 |
|    | R10  | CGCCCGCAACTACG |    | 511 |
|    | P10  | GTGAGAGGGCGTCGCGTTTTCGGGG | | 512 |

TABLE 1-continued

Primer and probe sequences for detection of SDC2 gene methylation

| Set | Primers | Sequences (5'-->3') | Size of amplified product (bp) | SEQ ID NO: |
|---|---|---|---|---|
| 47 | F547 | TTTTCGGAGTATTA | 83 | 569 |
|  | R10 | CGCCCGCAACTACG |  | 511 |
|  | P10 | GTGAGAGGGCGTCGCGTTTTCGGGG |  | 512 |
| 48 | F548 | TTTCGGAGTATTAA | 82 | 570 |
|  | R10 | CGCCCGCAACTACG |  | 511 |
|  | P10 | GTGAGAGGGCGTCGCGTTTTCGGGG |  | 512 |
| 49 | F549 | TTCGGAGTATTAAT | 81 | 571 |
|  | R10 | CGCCCGCAACTACG |  | 511 |
|  | P10 | GTGAGAGGGCGTCGCGTTTTCGGGG |  | 512 |
| 50 | F550 | TCGGAGTATTAATT | 80 | 572 |
|  | R10 | CGCCCGCAACTACG |  | 511 |
|  | P10 | GTGAGAGGGCGTCGCGTTTTCGGGG |  | 512 |
| 51 | F551 | CGGAGTATTAATTT | 140 | 573 |
|  | R11 | CTCGAAAACTCGAA |  | 574 |
|  | P11 | AAGCGAGCGTTTTCGAGTTTCGAG |  | 575 |
| 52 | F552 | GGAGTATTAATTTC | 139 | 576 |
|  | R11 | CTCGAAAACTCGAA |  | 574 |
|  | P11 | AAGCGAGCGTTTTCGAGTTTCGAG |  | 575 |
| 53 | F553 | GAGTATTAATTTCG | 138 | 577 |
|  | R11 | CTCGAAAACTCGAA |  | 574 |
|  | P11 | AAGCGAGCGTTTTCGAGTTTCGAG |  | 575 |
| 54 | F554 | AGTATTAATTTCGT | 137 | 578 |
|  | R11 | CTCGAAAACTCGAA |  | 574 |
|  | P11 | AAGCGAGCGTTTTCGAGTTTCGAG |  | 575 |
| 55 | F555 | GTATTAATTTCGTG | 136 | 579 |
|  | R11 | CTCGAAAACTCGAA |  | 574 |
|  | P11 | AAGCGAGCGTTTTCGAGTTTCGAG |  | 575 |
| 56 | F556 | TATTAATTTCGTGT | 135 | 580 |
|  | R11 | CTCGAAAACTCGAA |  | 574 |
|  | P11 | AAGCGAGCGTTTTCGAGTTTCGAG |  | 575 |
| 57 | F557 | ATTAATTTCGTGTC | 134 | 581 |
|  | R11 | CTCGAAAACTCGAA |  | 574 |
|  | P11 | AAGCGAGCGTTTTCGAGTTTCGAG |  | 575 |
| 58 | F558 | TTAATTTCGTGTCG | 133 | 582 |
|  | R11 | CTCGAAAACTCGAA |  | 574 |
|  | P11 | AAGCGAGCGTTTTCGAGTTTCGAG |  | 575 |
| 59 | F559 | TAATTTCGTGTCGG | 132 | 583 |
|  | R11 | CTCGAAAACTCGAA |  | 574 |
|  | P11 | AAGCGAGCGTTTTCGAGTTTCGAG |  | 575 |
| 60 | F560 | AATTTCGTGTCGGG | 131 | 584 |
|  | R11 | CTCGAAAACTCGAA |  | 574 |
|  | P11 | AAGCGAGCGTTTTCGAGTTTCGAG |  | 575 |
| 61 | F561 | ATTTCGTGTCGGGA | 130 | 585 |
|  | R11 | CTCGAAAACTCGAA |  | 574 |
|  | P11 | AAGCGAGCGTTTTCGAGTTTCGAG |  | 575 |
| 62 | F562 | TTTCGTGTCGGGAG | 129 | 586 |
|  | R11 | CTCGAAAACTCGAA |  | 574 |
|  | P11 | AAGCGAGCGTTTTCGAGTTTCGAG |  | 575 |
| 63 | F563 | TTCGTGTCGGGAGT | 128 | 587 |
|  | R11 | CTCGAAAACTCGAA |  | 574 |
|  | P11 | AAGCGAGCGTTTTCGAGTTTCGAG |  | 575 |
| 64 | F564 | TCGTGTCGGGAGTG | 127 | 588 |
|  | R11 | CTCGAAAACTCGAA |  | 574 |
|  | P11 | AAGCGAGCGTTTTCGAGTTTCGAG |  | 575 |

TABLE 1 -continued

Primer and probe sequences for detection of SDC2 gene methylation

| Set | Primers | Sequences (5'-->3') | Size of amplified product (bp) | SEQ ID NO: |
|---|---|---|---|---|
| 65 | F565 | CGTGTCGGGAGTGT | 126 | 589 |
|  | R11 | CTCGAAAACTCGAA |  | 574 |
|  | P11 | AAGCGAGCGTTTTCGAGTTTCGAG |  | 575 |
| 66 | F566 | GTGTCGGGAGTGTA | 125 | 590 |
|  | R11 | CTCGAAAACTCGAA |  | 574 |
|  | P11 | AAGCGAGCGTTTTCGAGTTTCGAG |  | 575 |
| 67 | F567 | TGTCGGGAGTGTAG | 124 | 591 |
|  | R11 | CTCGAAAACTCGAA |  | 574 |
|  | P11 | AAGCGAGCGTTTTCGAGTTTCGAG |  | 575 |
| 68 | F568 | GTCGGGAGTGTAGA | 123 | 592 |
|  | R11 | CTCGAAAACTCGAA |  | 574 |
|  | P11 | AAGCGAGCGTTTTCGAGTTTCGAG |  | 575 |
| 69 | F569 | TCGGGAGTGTAGAA | 122 | 593 |
|  | R11 | CTCGAAAACTCGAA |  | 574 |
|  | P11 | AAGCGAGCGTTTTCGAGTTTCGAG |  | 575 |
| 70 | F570 | CGGGAGTGTAGAAA | 121 | 594 |
|  | R11 | CTCGAAAACTCGAA |  | 574 |
|  | P11 | AAGCGAGCGTTTTCGAGTTTCGAG |  | 575 |
| 71 | F571 | GGGAGTGTAGAAAT | 120 | 595 |
|  | R11 | CTCGAAAACTCGAA |  | 574 |
|  | P11 | AAGCGAGCGTTTTCGAGTTTCGAG |  | 575 |
| 72 | F572 | GGAGTGTAGAAATT | 119 | 596 |
|  | R11 | CTCGAAAACTCGAA |  | 574 |
|  | P11 | AAGCGAGCGTTTTCGAGTTTCGAG |  | 575 |
| 73 | F573 | GAGTGTAGAAATTA | 118 | 597 |
|  | R11 | CTCGAAAACTCGAA |  | 574 |
|  | P11 | AAGCGAGCGTTTTCGAGTTTCGAG |  | 575 |
| 74 | F574 | AGTGTAGAAATTAA | 117 | 598 |
|  | R11 | CTCGAAAACTCGAA |  | 574 |
|  | P11 | AAGCGAGCGTTTTCGAGTTTCGAG |  | 575 |
| 75 | F575 | GTGTAGAAATTAAT | 116 | 599 |
|  | R11 | CTCGAAAACTCGAA |  | 574 |
|  | P11 | AAGCGAGCGTTTTCGAGTTTCGAG |  | 575 |
| 76 | F576 | TGTAGAAATTAATA | 115 | 600 |
|  | R11 | CTCGAAAACTCGAA |  | 574 |
|  | P11 | AAGCGAGCGTTTTCGAGTTTCGAG |  | 575 |
| 77 | F577 | GTAGAAATTAATAA | 114 | 601 |
|  | R11 | CTCGAAAACTCGAA |  | 574 |
|  | P11 | AAGCGAGCGTTTTCGAGTTTCGAG |  | 575 |
| 78 | F578 | TAGAAATTAATAAG | 113 | 602 |
|  | R11 | CTCGAAAACTCGAA |  | 574 |
|  | P11 | AAGCGAGCGTTTTCGAGTTTCGAG |  | 575 |
| 79 | F579 | AGAAATTAATAAGT | 112 | 603 |
|  | R11 | CTCGAAAACTCGAA |  | 574 |
|  | P11 | AAGCGAGCGTTTTCGAGTTTCGAG |  | 575 |
| 80 | F580 | GAAATTAATAAGTG | 111 | 604 |
|  | R11 | CTCGAAAACTCGAA |  | 574 |
|  | P11 | AAGCGAGCGTTTTCGAGTTTCGAG |  | 575 |
| 81 | F581 | AAATTAATAAGTGA | 110 | 605 |
|  | R11 | CTCGAAAACTCGAA |  | 574 |
|  | P11 | AAGCGAGCGTTTTCGAGTTTCGAG |  | 575 |
| 82 | F582 | AATTAATAAGTGAG | 109 | 606 |
|  | R11 | CTCGAAAACTCGAA |  | 574 |
|  | P11 | AAGCGAGCGTTTTCGAGTTTCGAG |  | 575 |

TABLE 1 -continued

Primer and probe sequences for detection of SDC2 gene methylation

| Set | Primers | Sequences (5'-->3') | Size of amplified product (bp) | SEQ ID NO: |
|---|---|---|---|---|
| 83 | F583 | ATTAATAAGTGAGA | 108 | 607 |
|  | R11 | CTCGAAAACTCGAA |  | 574 |
|  | P11 | AAGCGAGCGTTTTCGAGTTTCGAG |  | 575 |
| 84 | F584 | TTAATAAGTGAGAG | 107 | 608 |
|  | R11 | CTCGAAAACTCGAA |  | 574 |
|  | P11 | AAGCGAGCGTTTTCGAGTTTCGAG |  | 575 |
| 85 | F585 | TAATAAGTGAGAGG | 106 | 609 |
|  | R11 | CTCGAAAACTCGAA |  | 574 |
|  | P11 | AAGCGAGCGTTTTCGAGTTTCGAG |  | 575 |
| 86 | F586 | AATAAGTGAGAGGG | 105 | 610 |
|  | R11 | CTCGAAAACTCGAA |  | 574 |
|  | P11 | AAGCGAGCGTTTTCGAGTTTCGAG |  | 575 |
| 87 | F587 | ATAAGTGAGAGGGC | 104 | 611 |
|  | R11 | CTCGAAAACTCGAA |  | 574 |
|  | P11 | AAGCGAGCGTTTTCGAGTTTCGAG |  | 575 |
| 88 | F588 | TAAGTGAGAGGGCG | 103 | 612 |
|  | R11 | CTCGAAAACTCGAA |  | 574 |
|  | P11 | AAGCGAGCGTTTTCGAGTTTCGAG |  | 575 |
| 89 | F589 | AAGTGAGAGGGCGT | 102 | 613 |
|  | R11 | CTCGAAAACTCGAA |  | 574 |
|  | P11 | AAGCGAGCGTTTTCGAGTTTCGAG |  | 575 |
| 90 | F590 | AGTGAGAGGGCGTC | 101 | 614 |
|  | R11 | CTCGAAAACTCGAA |  | 574 |
|  | P11 | AAGCGAGCGTTTTCGAGTTTCGAG |  | 575 |
| 91 | F591 | GTGAGAGGGCGTCG | 100 | 615 |
|  | R11 | CTCGAAAACTCGAA |  | 574 |
|  | P11 | AAGCGAGCGTTTTCGAGTTTCGAG |  | 575 |
| 92 | F592 | TGAGAGGGCGTCGC | 99 | 616 |
|  | R11 | CTCGAAAACTCGAA |  | 574 |
|  | P11 | AAGCGAGCGTTTTCGAGTTTCGAG |  | 575 |
| 93 | F593 | GAGAGGGCGTCGCG | 98 | 617 |
|  | R11 | CTCGAAAACTCGAA |  | 574 |
|  | P11 | AAGCGAGCGTTTTCGAGTTTCGAG |  | 575 |
| 94 | F594 | AGAGGGCGTCGCGT | 79 | 618 |
|  | R11 | CTCGAAAACTCGAA |  | 574 |
|  | P11 | AAGCGAGCGTTTTCGAGTTTCGAG |  | 575 |
| 95 | F595 | GAGGGCGTCGCGTT | 96 | 619 |
|  | R11 | CTCGAAAACTCGAA |  | 574 |
|  | P11 | AAGCGAGCGTTTTCGAGTTTCGAG |  | 575 |
| 96 | F596 | AGGGCGTCGCGTTT | 95 | 620 |
|  | R11 | CTCGAAAACTCGAA |  | 574 |
|  | P11 | AAGCGAGCGTTTTCGAGTTTCGAG |  | 575 |
| 97 | F597 | GGGCGTCGCGTTTT | 94 | 621 |
|  | R11 | CTCGAAAACTCGAA |  | 574 |
|  | P11 | AAGCGAGCGTTTTCGAGTTTCGAG |  | 575 |
| 98 | F598 | GGCGTCGCGTTTTC | 93 | 622 |
|  | R11 | CTCGAAAACTCGAA |  | 574 |
|  | P11 | AAGCGAGCGTTTTCGAGTTTCGAG |  | 575 |
| 99 | F599 | GCGTCGCGTTTTCG | 92 | 623 |
|  | R11 | CTCGAAAACTCGAA |  | 574 |
|  | P11 | AAGCGAGCGTTTTCGAGTTTCGAG |  | 575 |
| 00 | F600 | CGTCGCGTTTTCGG | 91 | 624 |
|  | R11 | CTCGAAAACTCGAA |  | 574 |
|  | P11 | AAGCGAGCGTTTTCGAGTTTCGAG |  | 575 |

TABLE 1-continued

Primer and probe sequences for detection of SDC2 gene methylation

| Set | Primers | Sequences (5'-->3') | Size of amplified product (bp) | SEQ ID NO: |
|---|---|---|---|---|
| 01 | F601 | GTCGCGTTTTCGGG | 90 | 625 |
| | R11 | CTCGAAAACTCGAA | | 574 |
| | P11 | AAGCGAGCGTTTTCGAGTTTCGAG | | 575 |
| 02 | F602 | TCGCGTTTTCGGGG | 89 | 626 |
| | R11 | CTCGAAAACTCGAA | | 574 |
| | P11 | AAGCGAGCGTTTTCGAGTTTCGAG | | 575 |
| 03 | F603 | CGCGTTTTCGGGGC | 88 | 627 |
| | R11 | CTCGAAAACTCGAA | | 574 |
| | P11 | AAGCGAGCGTTTTCGAGTTTCGAG | | 575 |
| 04 | F604 | GCGTTTTCGGGGCG | 87 | 628 |
| | R11 | CTCGAAAACTCGAA | | 574 |
| | P11 | AAGCGAGCGTTTTCGAGTTTCGAG | | 575 |
| 05 | F605 | CGTTTTCGGGGCGT | 86 | 629 |
| | R11 | CTCGAAAACTCGAA | | 574 |
| | P11 | AAGCGAGCGTTTTCGAGTTTCGAG | | 575 |
| 06 | F606 | GTTTTCGGGGCGTA | 85 | 630 |
| | R11 | CTCGAAAACTCGAA | | 574 |
| | P11 | AAGCGAGCGTTTTCGAGTTTCGAG | | 575 |
| 07 | F607 | TTTTCGGGGCGTAG | 84 | 631 |
| | R11 | CTCGAAAACTCGAA | | 574 |
| | P11 | AAGCGAGCGTTTTCGAGTTTCGAG | | 575 |
| 08 | F608 | TTTCGGGGCGTAGT | 83 | 632 |
| | R11 | CTCGAAAACTCGAA | | 574 |
| | P11 | AAGCGAGCGTTTTCGAGTTTCGAG | | 575 |
| 09 | F609 | TTCGGGGCGTAGTT | 82 | 633 |
| | R11 | CTCGAAAACTCGAA | | 574 |
| | P11 | AAGCGAGCGTTTTCGAGTTTCGAG | | 575 |
| 10 | F610 | TCGGGGCGTAGTTG | 81 | 634 |
| | R11 | CTCGAAAACTCGAA | | 574 |
| | P11 | AAGCGAGCGTTTTCGAGTTTCGAG | | 575 |
| 11 | F611 | CGGGGCGTAGTTGC | 80 | 635 |
| | R11 | CTCGAAAACTCGAA | | 574 |
| | P11 | AAGCGAGCGTTTTCGAGTTTCGAG | | 575 |
| 12 | F612 | GGGGCGTAGTTGCG | 140 | 636 |
| | R12 | CGCTCGACGCAACC | | 637 |
| | P12 | TATTTTGTTTCGGATTCGTGTGCGCG | | 638 |
| 13 | F613 | GGGCGTAGTTGCGG | 139 | 639 |
| | R12 | CGCTCGACGCAACC | | 637 |
| | P12 | TATTTTGTTTCGGATTCGTGTGCGCG | | 638 |
| 14 | F614 | GGCGTAGTTGCGGG | 138 | 640 |
| | R12 | CGCTCGACGCAACC | | 637 |
| | P12 | TATTTTGTTTCGGATTCGTGTGCGCG | | 638 |
| 15 | F615 | GCGTAGTTGCGGGC | 137 | 641 |
| | R12 | CGCTCGACGCAACC | | 637 |
| | P12 | TATTTTGTTTCGGATTCGTGTGCGCG | | 638 |
| 16 | F616 | CGTAGTTGCGGGCG | 136 | 642 |
| | R12 | CGCTCGACGCAACC | | 637 |
| | P12 | TATTTTGTTTCGGATTCGTGTGCGCG | | 638 |
| 17 | F617 | GTAGTTGCGGGCGG | 135 | 643 |
| | R12 | CGCTCGACGCAACC | | 637 |
| | P12 | TATTTTGTTTCGGATTCGTGTGCGCG | | 638 |
| 18 | F618 | TAGTTGCGGGCGGC | 134 | 644 |
| | R12 | CGCTCGACGCAACC | | 637 |
| | P12 | TATTTTGTTTCGGATTCGTGTGCGCG | | 638 |

TABLE 1 -continued

Primer and probe sequences for detection of SDC2 gene methylation

| Set | Primers | Sequences (5'-->3') | Size of amplified product (bp) | SEQ ID NO: |
|---|---|---|---|---|
| 19 | F619 | AGTTGCGGGCGGCG | 133 | 645 |
|  | R12 | CGCTCGACGCAACC |  | 637 |
|  | P12 | TATTTTGTTTCGGATTCGTGTGCGCG |  | 638 |
| 20 | F620 | GTTGCGGGCGGCGG | 132 | 646 |
|  | R12 | CGCTCGACGCAACC |  | 637 |
|  | P12 | TATTTTGTTTCGGATTCGTGTGCGCG |  | 638 |
| 21 | F621 | TTGCGGGCGGCGGG | 131 | 647 |
|  | R12 | CGCTCGACGCAACC |  | 637 |
|  | P12 | TATTTTGTTTCGGATTCGTGTGCGCG |  | 638 |
| 22 | F622 | TGCGGGCGGCGGGA | 130 | 648 |
|  | R12 | CGCTCGACGCAACC |  | 637 |
|  | P12 | TATTTTGTTTCGGATTCGTGTGCGCG |  | 638 |
| 23 | F623 | GCGGGCGGCGGGAG | 129 | 649 |
|  | R12 | CGCTCGACGCAACC |  | 637 |
|  | P12 | TATTTTGTTTCGGATTCGTGTGCGCG |  | 638 |
| 24 | F624 | CGGGCGGCGGGAGT | 128 | 650 |
|  | R12 | CGCTCGACGCAACC |  | 637 |
|  | P12 | TATTTTGTTTCGGATTCGTGTGCGCG |  | 638 |
| 25 | F625 | GGGCGGCGGGAGTA | 127 | 651 |
|  | R12 | CGCTCGACGCAACC |  | 637 |
|  | P12 | TATTTTGTTTCGGATTCGTGTGCGCG |  | 638 |
| 26 | F626 | GGCGGCGGGAGTAG | 126 | 652 |
|  | R12 | CGCTCGACGCAACC |  | 637 |
|  | P12 | TATTTTGTTTCGGATTCGTGTGCGCG |  | 638 |
| 27 | F627 | GCGGCGGGAGTAGG | 125 | 653 |
|  | R12 | CGCTCGACGCAACC |  | 637 |
|  | P12 | TATTTTGTTTCGGATTCGTGTGCGCG |  | 638 |
| 28 | F628 | CGGCGGGAGTAGGC | 124 | 654 |
|  | R12 | CGCTCGACGCAACC |  | 637 |
|  | P12 | TATTTTGTTTCGGATTCGTGTGCGCG |  | 638 |
| 29 | F629 | GGCGGGAGTAGGCG | 123 | 655 |
|  | R12 | CGCTCGACGCAACC |  | 637 |
|  | P12 | TATTTTGTTTCGGATTCGTGTGCGCG |  | 638 |
| 30 | F630 | GCGGGAGTAGGCGT | 122 | 656 |
|  | R12 | CGCTCGACGCAACC |  | 637 |
|  | P12 | TATTTTGTTTCGGATTCGTGTGCGCG |  | 638 |
| 31 | F631 | CGGGAGTAGGCGTA | 121 | 657 |
|  | R12 | CGCTCGACGCAACC |  | 637 |
|  | P12 | TATTTTGTTTCGGATTCGTGTGCGCG |  | 638 |
| 32 | F632 | GGGAGTAGGCGTAG | 120 | 658 |
|  | R12 | CGCTCGACGCAACC |  | 637 |
|  | P12 | TATTTTGTTTCGGATTCGTGTGCGCG |  | 638 |
| 33 | F633 | GGAGTAGGCGTAGG | 119 | 659 |
|  | R12 | CGCTCGACGCAACC |  | 637 |
|  | P12 | TATTTTGTTTCGGATTCGTGTGCGCG |  | 638 |
| 34 | F634 | GAGTAGGCGTAGGA | 118 | 660 |
|  | R12 | CGCTCGACGCAACC |  | 637 |
|  | P12 | TATTTTGTTTCGGATTCGTGTGCGCG |  | 638 |
| 35 | F635 | AGTAGGCGTAGGAG | 117 | 661 |
|  | R12 | CGCTCGACGCAACC |  | 637 |
|  | P12 | TATTTTGTTTCGGATTCGTGTGCGCG |  | 638 |
| 36 | F636 | GTAGGCGTAGGAGG | 116 | 662 |
|  | R12 | CGCTCGACGCAACC |  | 637 |
|  | P12 | TATTTTGTTTCGGATTCGTGTGCGCG |  | 638 |

TABLE 1 -continued

Primer and probe sequences for detection of SDC2 gene methylation

| Set | Primers | Sequences (5'-->3') | Size of amplified product (bp) | SEQ ID NO: |
|---|---|---|---|---|
| 37 | F637 | TAGGCGTAGGAGGA | 115 | 663 |
|  | R12 | CGCTCGACGCAACC |  | 637 |
|  | P12 | TATTTTGTTTCGGATTCGTGTGCGCG |  | 638 |
| 38 | F638 | AGGCGTAGGAGGAG | 114 | 664 |
|  | R12 | CGCTCGACGCAACC |  | 637 |
|  | P12 | TATTTTGTTTCGGATTCGTGTGCGCG |  | 638 |
| 39 | F639 | GGCGTAGGAGGAGG | 113 | 665 |
|  | R12 | CGCTCGACGCAACC |  | 637 |
|  | P12 | TATTTTGTTTCGGATTCGTGTGCGCG |  | 638 |
| 40 | F640 | GCGTAGGAGGAGGA | 112 | 666 |
|  | R12 | CGCTCGACGCAACC |  | 637 |
|  | P12 | TATTTTGTTTCGGATTCGTGTGCGCG |  | 638 |
| 41 | F641 | CGTAGGAGGAGGAA | 111 | 667 |
|  | R12 | CGCTCGACGCAACC |  | 637 |
|  | P12 | TATTTTGTTTCGGATTCGTGTGCGCG |  | 638 |
| 42 | F642 | GTAGGAGGAGGAAG | 110 | 668 |
|  | R12 | CGCTCGACGCAACC |  | 637 |
|  | P12 | TATTTTGTTTCGGATTCGTGTGCGCG |  | 638 |
| 43 | F643 | TAGGAGGAGGAAGC | 109 | 669 |
|  | R12 | CGCTCGACGCAACC |  | 637 |
|  | P12 | TATTTTGTTTCGGATTCGTGTGCGCG |  | 638 |
| 44 | F644 | AGGAGGAGGAAGCG | 108 | 670 |
|  | R12 | CGCTCGACGCAACC |  | 637 |
|  | P12 | TATTTTGTTTCGGATTCGTGTGCGCG |  | 638 |
| 45 | F645 | GGAGGAGGAAGCGA | 107 | 671 |
|  | R12 | CGCTCGACGCAACC |  | 637 |
|  | P12 | TATTTTGTTTCGGATTCGTGTGCGCG |  | 638 |
| 46 | F646 | GAGGAGGAAGCGAG | 106 | 672 |
|  | R12 | CGCTCGACGCAACC |  | 637 |
|  | P12 | TATTTTGTTTCGGATTCGTGTGCGCG |  | 638 |
| 47 | F647 | AGGAGGAAGCGAGC | 105 | 673 |
|  | R12 | CGCTCGACGCAACC |  | 637 |
|  | P12 | TATTTTGTTTCGGATTCGTGTGCGCG |  | 638 |
| 48 | F648 | GGAGGAAGCGAGCG | 104 | 674 |
|  | R12 | CGCTCGACGCAACC |  | 637 |
|  | P12 | TATTTTGTTTCGGATTCGTGTGCGCG |  | 638 |
| 49 | F649 | GAGGAAGCGAGCGT | 103 | 675 |
|  | R12 | CGCTCGACGCAACC |  | 637 |
|  | P12 | TATTTTGTTTCGGATTCGTGTGCGCG |  | 638 |
| 50 | F650 | AGGAAGCGAGCGTT | 102 | 676 |
|  | R12 | CGCTCGACGCAACC |  | 637 |
|  | P12 | TATTTTGTTTCGGATTCGTGTGCGCG |  | 638 |
| 51 | F651 | GGAAGCGAGCGTTT | 101 | 677 |
|  | R12 | CGCTCGACGCAACC |  | 637 |
|  | P12 | TATTTTGTTTCGGATTCGTGTGCGCG |  | 638 |
| 52 | F652 | GAAGCGAGCGTTTT | 100 | 678 |
|  | R12 | CGCTCGACGCAACC |  | 637 |
|  | P12 | TATTTTGTTTCGGATTCGTGTGCGCG |  | 638 |
| 53 | F653 | AAGCGAGCGTTTTC | 99 | 679 |
|  | R12 | CGCTCGACGCAACC |  | 637 |
|  | P12 | TATTTTGTTTCGGATTCGTGTGCGCG |  | 638 |
| 54 | F654 | AGCGAGCGTTTTCG | 98 | 680 |
|  | R12 | CGCTCGACGCAACC |  | 637 |
|  | P12 | TATTTTGTTTCGGATTCGTGTGCGCG |  | 638 |

TABLE 1-continued

Primer and probe sequences for detection of SDC2 gene methylation

| Set | Primers | Sequences (5'-->3') | Size of amplified product (bp) | SEQ ID NO: |
|---|---|---|---|---|
| 55 | F655 | GCGAGCGTTTTCGA | 97 | 681 |
|  | R12 | CGCTCGACGCAACC |  | 637 |
|  | P12 | TATTTTGTTTCGGATTCGTGTGCGCG |  | 638 |
| 56 | F656 | CGAGCGTTTTCGAG | 96 | 682 |
|  | R12 | CGCTCGACGCAACC |  | 637 |
|  | P12 | TATTTTGTTTCGGATTCGTGTGCGCG |  | 638 |
| 57 | F657 | GAGCGTTTTCGAGT | 95 | 683 |
|  | R12 | CGCTCGACGCAACC |  | 637 |
|  | P12 | TATTTTGTTTCGGATTCGTGTGCGCG |  | 638 |
| 58 | F658 | AGCGTTTTCGAGTT | 94 | 684 |
|  | R12 | CGCTCGACGCAACC |  | 637 |
|  | P12 | TATTTTGTTTCGGATTCGTGTGCGCG |  | 638 |
| 59 | F659 | GCGTTTTCGAGTTT | 93 | 685 |
|  | R12 | CGCTCGACGCAACC |  | 637 |
|  | P12 | TATTTTGTTTCGGATTCGTGTGCGCG |  | 638 |
| 60 | F660 | CGTTTTCGAGTTTC | 92 | 686 |
|  | R12 | CGCTCGACGCAACC |  | 637 |
|  | P12 | TATTTTGTTTCGGATTCGTGTGCGCG |  | 638 |
| 61 | F661 | GTTTTCGAGTTTCG | 91 | 687 |
|  | R12 | CGCTCGACGCAACC |  | 637 |
|  | P12 | TATTTTGTTTCGGATTCGTGTGCGCG |  | 638 |
| 62 | F662 | TTTTCGAGTTTCGA | 90 | 688 |
|  | R12 | CGCTCGACGCAACC |  | 637 |
|  | P12 | TATTTTGTTTCGGATTCGTGTGCGCG |  | 638 |
| 63 | F663 | TTTCGAGTTTCGAG | 89 | 689 |
|  | R12 | CGCTCGACGCAACC |  | 637 |
|  | P12 | TATTTTGTTTCGGATTCGTGTGCGCG |  | 638 |
| 64 | F664 | TTCGAGTTTCGAGT | 88 | 690 |
|  | R12 | CGCTCGACGCAACC |  | 637 |
|  | P12 | TATTTTGTTTCGGATTCGTGTGCGCG |  | 638 |
| 65 | F665 | TCGAGTTTCGAGTT | 87 | 691 |
|  | R12 | CGCTCGACGCAACC |  | 637 |
|  | P12 | TATTTTGTTTCGGATTCGTGTGCGCG |  | 638 |
| 66 | F666 | CGAGTTTCGAGTTC | 86 | 692 |
|  | R12 | CGCTCGACGCAACC |  | 637 |
|  | P12 | TATTTTGTTTCGGATTCGTGTGCGCG |  | 638 |
| 67 | F667 | GAGTTTCGAGTTCG | 85 | 693 |
|  | R12 | CGCTCGACGCAACC |  | 637 |
|  | P12 | TATTTTGTTTCGGATTCGTGTGCGCG |  | 638 |
| 68 | F668 | AGTTTCGAGTTCGA | 84 | 694 |
|  | R12 | CGCTCGACGCAACC |  | 637 |
|  | P12 | TATTTTGTTTCGGATTCGTGTGCGCG |  | 638 |
| 69 | F669 | GTTTCGAGTTCGAG | 83 | 695 |
|  | R12 | CGCTCGACGCAACC |  | 637 |
|  | P12 | TATTTTGTTTCGGATTCGTGTGCGCG |  | 638 |
| 70 | F670 | TTTCGAGTTCGAGT | 82 | 696 |
|  | R12 | CGCTCGACGCAACC |  | 637 |
|  | P12 | TATTTTGTTTCGGATTCGTGTGCGCG |  | 638 |
| 71 | F671 | TTCGAGTTCGAGTT | 81 | 697 |
|  | R12 | CGCTCGACGCAACC |  | 637 |
|  | P12 | TATTTTGTTTCGGATTCGTGTGCGCG |  | 638 |
| 72 | F672 | TCGAGTTCGAGTTT | 80 | 698 |
|  | R12 | CGCTCGACGCAACC |  | 637 |
|  | P12 | TATTTTGTTTCGGATTCGTGTGCGCG |  | 638 |

TABLE 1-continued

Primer and probe sequences for detection of SDC2 gene methylation

| Set | Primers | Sequences (5'-->3') | Size of amplified product (bp) | SEQ ID NO: |
|---|---|---|---|---|
| 73 | F673 | CGAGTTCGAGTTTT | 140 | 699 |
|  | R13 | CAAAAACCGACTAC |  | 700 |
|  | P13 | TTTGGTTGTAAGTAGCGGTTGGGA |  | 701 |
| 74 | F674 | GAGTTCGAGTTTTC | 139 | 702 |
|  | R13 | CAAAAACCGACTAC |  | 700 |
|  | P13 | TTTGGTTGTAAGTAGCGGTTGGGA |  | 701 |
| 75 | F675 | AGTTCGAGTTTTCG | 138 | 703 |
|  | R13 | CAAAAACCGACTAC |  | 700 |
|  | P13 | TTTGGTTGTAAGTAGCGGTTGGGA |  | 701 |
| 76 | F676 | GTTCGAGTTTTCGA | 137 | 704 |
|  | R13 | CAAAAACCGACTAC |  | 700 |
|  | P13 | TTTGGTTGTAAGTAGCGGTTGGGA |  | 701 |
| 77 | F677 | TTCGAGTTTTCGAG | 136 | 705 |
|  | R13 | CAAAAACCGACTAC |  | 700 |
|  | P13 | TTTGGTTGTAAGTAGCGGTTGGGA |  | 701 |
| 78 | F678 | TCGAGTTTTCGAGT | 135 | 706 |
|  | R13 | CAAAAACCGACTAC |  | 700 |
|  | P13 | TTTGGTTGTAAGTAGCGGTTGGGA |  | 701 |
| 79 | F679 | CGAGTTTTCGAGTT | 134 | 707 |
|  | R13 | CAAAAACCGACTAC |  | 700 |
|  | P13 | TTTGGTTGTAAGTAGCGGTTGGGA |  | 701 |
| 80 | F680 | GAGTTTTCGAGTTT | 133 | 708 |
|  | R13 | CAAAAACCGACTAC |  | 700 |
|  | P13 | TTTGGTTGTAAGTAGCGGTTGGGA |  | 701 |
| 81 | F681 | AGTTTTCGAGTTTG | 132 | 709 |
|  | R13 | CAAAAACCGACTAC |  | 700 |
|  | P13 | TTTGGTTGTAAGTAGCGGTTGGGA |  | 701 |
| 82 | F682 | GTTTTCGAGTTTGA | 131 | 710 |
|  | R13 | CAAAAACCGACTAC |  | 700 |
|  | P13 | TTTGGTTGTAAGTAGCGGTTGGGA |  | 701 |
| 83 | F683 | TTTTCGAGTTTGAG | 130 | 711 |
|  | R13 | CAAAAACCGACTAC |  | 700 |
|  | P13 | TTTGGTTGTAAGTAGCGGTTGGGA |  | 701 |
| 84 | F684 | TTTCGAGTTTGAGT | 129 | 712 |
|  | R13 | CAAAAACCGACTAC |  | 700 |
|  | P13 | TTTGGTTGTAAGTAGCGGTTGGGA |  | 701 |
| 85 | F685 | TTCGAGTTTGAGTC | 128 | 713 |
|  | R13 | CAAAAACCGACTAC |  | 700 |
|  | P13 | TTTGGTTGTAAGTAGCGGTTGGGA |  | 701 |
| 86 | F686 | TCGAGTTTGAGTCG | 127 | 714 |
|  | R13 | CAAAAACCGACTAC |  | 700 |
|  | P13 | TTTGGTTGTAAGTAGCGGTTGGGA |  | 701 |
| 87 | F687 | CGAGTTTGAGTCGT | 126 | 715 |
|  | R13 | CAAAAACCGACTAC |  | 700 |
|  | P13 | TTTGGTTGTAAGTAGCGGTTGGGA |  | 701 |
| 88 | F688 | GAGTTTGAGTCGTA | 125 | 716 |
|  | R13 | CAAAAACCGACTAC |  | 700 |
|  | P13 | TTTGGTTGTAAGTAGCGGTTGGGA |  | 701 |
| 89 | F689 | AGTTTGAGTCGTAA | 124 | 717 |
|  | R13 | CAAAAACCGACTAC |  | 700 |
|  | P13 | TTTGGTTGTAAGTAGCGGTTGGGA |  | 701 |
| 90 | F690 | GTTTGAGTCGTAAT | 123 | 718 |
|  | R13 | CAAAAACCGACTAC |  | 700 |
|  | P13 | TTTGGTTGTAAGTAGCGGTTGGGA |  | 701 |

TABLE 1-continued

Primer and probe sequences for detection of SDC2 gene methylation

| Set | Primers | Sequences (5'-->3') | Size of amplified product (bp) | SEQ ID NO: |
|---|---|---|---|---|
| 91 | F691 | TTTGAGTCGTAATC | 122 | 719 |
|  | R13 | CAAAAACCGACTAC |  | 700 |
|  | P13 | TTTGGTTGTAAGTAGCGGTTGGGA |  | 701 |
| 92 | F692 | TTGAGTCGTAATCG | 121 | 720 |
|  | R13 | CAAAAACCGACTAC |  | 700 |
|  | P13 | TTTGGTTGTAAGTAGCGGTTGGGA |  | 701 |
| 93 | F693 | TGAGTCGTAATCGT | 120 | 721 |
|  | R13 | CAAAAACCGACTAC |  | 700 |
|  | P13 | TTTGGTTGTAAGTAGCGGTTGGGA |  | 701 |
| 94 | F694 | GAGTCGTAATCGTT | 119 | 722 |
|  | R13 | CAAAAACCGACTAC |  | 700 |
|  | P13 | TTTGGTTGTAAGTAGCGGTTGGGA |  | 701 |
| 95 | F695 | AGTCGTAATCGTTG | 118 | 723 |
|  | R13 | CAAAAACCGACTAC |  | 700 |
|  | P13 | TTTGGTTGTAAGTAGCGGTTGGGA |  | 701 |
| 96 | F696 | GTCGTAATCGTTGC | 117 | 724 |
|  | R13 | CAAAAACCGACTAC |  | 700 |
|  | P13 | TTTGGTTGTAAGTAGCGGTTGGGA |  | 701 |
| 97 | F697 | TCGTAATCGTTGCG | 116 | 725 |
|  | R13 | CAAAAACCGACTAC |  | 700 |
|  | P13 | TTTGGTTGTAAGTAGCGGTTGGGA |  | 701 |
| 98 | F698 | CGTAATCGTTGCGG | 115 | 726 |
|  | R13 | CAAAAACCGACTAC |  | 700 |
|  | P13 | TTTGGTTGTAAGTAGCGGTTGGGA |  | 701 |
| 99 | F699 | GTAATCGTTGCGGT | 114 | 727 |
|  | R13 | CAAAAACCGACTAC |  | 700 |
|  | P13 | TTTGGTTGTAAGTAGCGGTTGGGA |  | 701 |
| 00 | F700 | TAATCGTTGCGGTA | 113 | 728 |
|  | R13 | CAAAAACCGACTAC |  | 700 |
|  | P13 | TTTGGTTGTAAGTAGCGGTTGGGA |  | 701 |
| 01 | F701 | AATCGTTGCGGTAT | 112 | 729 |
|  | R13 | CAAAAACCGACTAC |  | 700 |
|  | P13 | TTTGGTTGTAAGTAGCGGTTGGGA |  | 701 |
| 02 | F702 | ATCGTTGCGGTATT | 111 | 730 |
|  | R13 | CAAAAACCGACTAC |  | 700 |
|  | P13 | TTTGGTTGTAAGTAGCGGTTGGGA |  | 701 |
| 03 | F703 | TCGTTGCGGTATTT | 110 | 731 |
|  | R13 | CAAAAACCGACTAC |  | 700 |
|  | P13 | TTTGGTTGTAAGTAGCGGTTGGGA |  | 701 |
| 04 | F704 | CGTTGCGGTATTTT | 109 | 732 |
|  | R13 | CAAAAACCGACTAC |  | 700 |
|  | P13 | TTTGGTTGTAAGTAGCGGTTGGGA |  | 701 |
| 05 | F705 | GTTGCGGTATTTTG | 108 | 733 |
|  | R13 | CAAAAACCGACTAC |  | 700 |
|  | P13 | TTTGGTTGTAAGTAGCGGTTGGGA |  | 701 |
| 06 | F706 | TTGCGGTATTTTGT | 107 | 734 |
|  | R13 | CAAAAACCGACTAC |  | 700 |
|  | P13 | TTTGGTTGTAAGTAGCGGTTGGGA |  | 701 |
| 07 | F707 | TGCGGTATTTTGTT | 106 | 735 |
|  | R13 | CAAAAACCGACTAC |  | 700 |
|  | P13 | TTTGGTTGTAAGTAGCGGTTGGGA |  | 701 |
| 08 | F708 | GCGGTATTTTGTTT | 105 | 736 |
|  | R13 | CAAAAACCGACTAC |  | 700 |
|  | P13 | TTTGGTTGTAAGTAGCGGTTGGGA |  | 701 |

TABLE 1-continued

Primer and probe sequences for detection of SDC2 gene methylation

| Set | Primers | Sequences (5'-->3') | Size of amplified product (bp) | SEQ ID NO: |
|---|---|---|---|---|
| 09 | F709 | CGGTATTTTGTTTC | 104 | 737 |
|  | R13 | CAAAAACCGACTAC |  | 700 |
|  | P13 | TTTGGTTGTAAGTAGCGGTTGGGA |  | 701 |
| 10 | F710 | GGTATTTTGTTTCG | 103 | 738 |
|  | R13 | CAAAAACCGACTAC |  | 700 |
|  | P13 | TTTGGTTGTAAGTAGCGGTTGGGA |  | 701 |
| 11 | F711 | GTATTTTGTTTCGG | 102 | 739 |
|  | R13 | CAAAAACCGACTAC |  | 700 |
|  | P13 | TTTGGTTGTAAGTAGCGGTTGGGA |  | 701 |
| 12 | F712 | TATTTTGTTTCGGA | 101 | 740 |
|  | R13 | CAAAAACCGACTAC |  | 700 |
|  | P13 | TTTGGTTGTAAGTAGCGGTTGGGA |  | 701 |
| 13 | F713 | ATTTTGTTTCGGAT | 100 | 741 |
|  | R13 | CAAAAACCGACTAC |  | 700 |
|  | P13 | TTTGGTTGTAAGTAGCGGTTGGGA |  | 701 |
| 14 | F714 | TTTTGTTTCGGATT | 99 | 742 |
|  | R13 | CAAAAACCGACTAC |  | 700 |
|  | P13 | TTTGGTTGTAAGTAGCGGTTGGGA |  | 701 |
| 15 | F715 | TTTGTTTCGGATTC | 98 | 743 |
|  | R13 | CAAAAACCGACTAC |  | 700 |
|  | P13 | TTTGGTTGTAAGTAGCGGTTGGGA |  | 701 |
| 16 | F716 | TTGTTTCGGATTCG | 97 | 744 |
|  | R13 | CAAAAACCGACTAC |  | 700 |
|  | P13 | TTTGGTTGTAAGTAGCGGTTGGGA |  | 701 |
| 17 | F717 | TGTTTCGGATTCGT | 96 | 745 |
|  | R13 | CAAAAACCGACTAC |  | 700 |
|  | P13 | TTTGGTTGTAAGTAGCGGTTGGGA |  | 701 |
| 18 | F718 | GTTTCGGATTCGTG | 95 | 746 |
|  | R13 | CAAAAACCGACTAC |  | 700 |
|  | P13 | TTTGGTTGTAAGTAGCGGTTGGGA |  | 701 |
| 19 | F719 | TTTCGGATTCGTGT | 94 | 747 |
|  | R13 | CAAAAACCGACTAC |  | 700 |
|  | P13 | TTTGGTTGTAAGTAGCGGTTGGGA |  | 701 |
| 20 | F720 | TTCGGATTCGTGTG | 93 | 748 |
|  | R13 | CAAAAACCGACTAC |  | 700 |
|  | P13 | TTTGGTTGTAAGTAGCGGTTGGGA |  | 701 |
| 21 | F721 | TCGGATTCGTGTGC | 92 | 749 |
|  | R13 | CAAAAACCGACTAC |  | 700 |
|  | P13 | TTTGGTTGTAAGTAGCGGTTGGGA |  | 701 |
| 22 | F722 | CGGATTCGTGTGCG | 91 | 750 |
|  | R13 | CAAAAACCGACTAC |  | 700 |
|  | P13 | TTTGGTTGTAAGTAGCGGTTGGGA |  | 701 |
| 23 | F723 | GGATTCGTGTGCGC | 90 | 751 |
|  | R13 | CAAAAACCGACTAC |  | 700 |
|  | P13 | TTTGGTTGTAAGTAGCGGTTGGGA |  | 701 |
| 24 | F724 | GATTCGTGTGCGCG | 89 | 752 |
|  | R13 | CAAAAACCGACTAC |  | 700 |
|  | P13 | TTTGGTTGTAAGTAGCGGTTGGGA |  | 701 |
| 25 | F725 | ATTCGTGTGCGCGG | 88 | 753 |
|  | R13 | CAAAAACCGACTAC |  | 700 |
|  | P13 | TTTGGTTGTAAGTAGCGGTTGGGA |  | 701 |
| 26 | F726 | TTCGTGTGCGCGGG | 87 | 754 |
|  | R13 | CAAAAACCGACTAC |  | 700 |
|  | P13 | TTTGGTTGTAAGTAGCGGTTGGGA |  | 701 |

TABLE 1-continued

Primer and probe sequences for detection of SDC2 gene methylation

| Set | Primers | Sequences (5'-->3') | Size of amplified product (bp) | SEQ ID NO: |
|---|---|---|---|---|
| 27 | F727 | TCGTGTGCGCGGGT | 86 | 755 |
|  | R13 | CAAAAACCGACTAC |  | 700 |
|  | P13 | TTTGGTTGTAAGTAGCGGTTGGGA |  | 701 |
| 28 | F728 | CGTGTGCGCGGGTT | 85 | 756 |
|  | R13 | CAAAAACCGACTAC |  | 700 |
|  | P13 | TTTGGTTGTAAGTAGCGGTTGGGA |  | 701 |
| 29 | F729 | GTGTGCGCGGGTTG | 84 | 757 |
|  | R13 | CAAAAACCGACTAC |  | 700 |
|  | P13 | TTTGGTTGTAAGTAGCGGTTGGGA |  | 701 |
| 30 | F730 | TGTGCGCGGGTTGC | 83 | 758 |
|  | R13 | CAAAAACCGACTAC |  | 700 |
|  | P13 | TTTGGTTGTAAGTAGCGGTTGGGA |  | 701 |
| 31 | F731 | GTGCGCGGGTTGCG | 82 | 759 |
|  | R13 | CAAAAACCGACTAC |  | 700 |
|  | P13 | TTTGGTTGTAAGTAGCGGTTGGGA |  | 701 |
| 32 | F732 | TGCGCGGGTTGCGT | 81 | 760 |
|  | R13 | CAAAAACCGACTAC |  | 700 |
|  | P13 | TTTGGTTGTAAGTAGCGGTTGGGA |  | 701 |
| 33 | F733 | GCGCGGGTTGCGTC | 80 | 761 |
|  | R13 | CAAAAACCGACTAC |  | 700 |
|  | P13 | TTTGGTTGTAAGTAGCGGTTGGGA |  | 701 |
| 34 | F734 | CGCGGGTTGCGTCG | 140 | 762 |
|  | R14 | CCGCCGACACGCAA |  | 763 |
|  | P14 | TTTTGTTTATTTTGGGTTTGGTGGT |  | 764 |
| 35 | F735 | GCGGGTTGCGTCGA | 139 | 765 |
|  | R14 | CCGCCGACACGCAA |  | 763 |
|  | P14 | TTTTGTTTATTTTGGGTTTGGTGGT |  | 764 |
| 36 | F736 | CGGGTTGCGTCGAG | 138 | 766 |
|  | R14 | CCGCCGACACGCAA |  | 763 |
|  | P14 | TTTTGTTTATTTTGGGTTTGGTGGT |  | 764 |
| 37 | F737 | GGGTTGCGTCGAGC | 137 | 767 |
|  | R14 | CCGCCGACACGCAA |  | 763 |
|  | P14 | TTTTGTTTATTTTGGGTTTGGTGGT |  | 764 |
| 38 | F738 | GGTTGCGTCGAGCG | 136 | 768 |
|  | R14 | CCGCCGACACGCAA |  | 763 |
|  | P14 | TTTTGTTTATTTTGGGTTTGGTGGT |  | 764 |
| 39 | F739 | GTTGCGTCGAGCGT | 135 | 769 |
|  | R14 | CCGCCGACACGCAA |  | 763 |
|  | P14 | TTTTGTTTATTTTGGGTTTGGTGGT |  | 764 |
| 40 | F740 | TTGCGTCGAGCGTT | 134 | 770 |
|  | R14 | CCGCCGACACGCAA |  | 763 |
|  | P14 | TTTTGTTTATTTTGGGTTTGGTGGT |  | 764 |
| 41 | F741 | TGCGTCGAGCGTTG | 133 | 771 |
|  | R14 | CCGCCGACACGCAA |  | 763 |
|  | P14 | TTTTGTTTATTTTGGGTTTGGTGGT |  | 764 |
| 42 | F742 | GCGTCGAGCGTTGG | 132 | 772 |
|  | R14 | CCGCCGACACGCAA |  | 763 |
|  | P14 | TTTTGTTTATTTTGGGTTTGGTGGT |  | 764 |
| 43 | F743 | CGTCGAGCGTTGGG | 131 | 773 |
|  | R14 | CCGCCGACACGCAA |  | 763 |
|  | P14 | TTTTGTTTATTTTGGGTTTGGTGGT |  | 764 |
| 44 | F744 | GTCGAGCGTTGGGT | 130 | 774 |
|  | R14 | CCGCCGACACGCAA |  | 763 |
|  | P14 | TTTTGTTTATTTTGGGTTTGGTGGT |  | 764 |

TABLE 1 -continued

Primer and probe sequences for detection of SDC2 gene methylation

| Set | Primers | Sequences (5'-->3') | Size of amplified product (bp) | SEQ ID NO: |
|---|---|---|---|---|
| 45 | F745 | TCGAGCGTTGGGTA | 129 | 775 |
| | R14 | CCGCCGACACGCAA | | 763 |
| | P14 | TTTTGTTTATTTTGGGTTTGGTGGT | | 764 |
| 46 | F746 | CGAGCGTTGGGTAG | 128 | 776 |
| | R14 | CCGCCGACACGCAA | | 763 |
| | P14 | TTTTGTTTATTTTGGGTTTGGTGGT | | 764 |
| 47 | F747 | GAGCGTTGGGTAGG | 127 | 777 |
| | R14 | CCGCCGACACGCAA | | 763 |
| | P14 | TTTTGTTTATTTTGGGTTTGGTGGT | | 764 |
| 48 | F748 | AGCGTTGGGTAGGA | 126 | 778 |
| | R14 | CCGCCGACACGCAA | | 763 |
| | P14 | TTTTGTTTATTTTGGGTTTGGTGGT | | 764 |
| 49 | F749 | GCGTTGGGTAGGAG | 125 | 779 |
| | R14 | CCGCCGACACGCAA | | 763 |
| | P14 | TTTTGTTTATTTTGGGTTTGGTGGT | | 764 |
| 50 | F750 | CGTTGGGTAGGAGG | 124 | 780 |
| | R14 | CCGCCGACACGCAA | | 763 |
| | P14 | TTTTGTTTATTTTGGGTTTGGTGGT | | 764 |
| 51 | F751 | GTTGGGTAGGAGGT | 123 | 781 |
| | R14 | CCGCCGACACGCAA | | 763 |
| | P14 | TTTTGTTTATTTTGGGTTTGGTGGT | | 764 |
| 52 | F752 | TTGGGTAGGAGGTT | 122 | 782 |
| | R14 | CCGCCGACACGCAA | | 763 |
| | P14 | TTTTGTTTATTTTGGGTTTGGTGGT | | 764 |
| 53 | F753 | TGGGTAGGAGGTTT | 121 | 783 |
| | R14 | CCGCCGACACGCAA | | 763 |
| | P14 | TTTTGTTTATTTTGGGTTTGGTGGT | | 764 |
| 54 | F754 | GGGTAGGAGGTTTC | 120 | 784 |
| | R14 | CCGCCGACACGCAA | | 763 |
| | P14 | TTTTGTTTATTTTGGGTTTGGTGGT | | 764 |
| 55 | F755 | GGTAGGAGGTTTCG | 119 | 785 |
| | R14 | CCGCCGACACGCAA | | 763 |
| | P14 | TTTTGTTTATTTTGGGTTTGGTGGT | | 764 |
| 56 | F756 | GTAGGAGGTTTCGT | 118 | 786 |
| | R14 | CCGCCGACACGCAA | | 763 |
| | P14 | TTTTGTTTATTTTGGGTTTGGTGGT | | 764 |
| 57 | F757 | TAGGAGGTTTCGTT | 117 | 787 |
| | R14 | CCGCCGACACGCAA | | 763 |
| | P14 | TTTTGTTTATTTTGGGTTTGGTGGT | | 764 |
| 58 | F758 | AGGAGGTTTCGTTT | 116 | 788 |
| | R14 | CCGCCGACACGCAA | | 763 |
| | P14 | TTTTGTTTATTTTGGGTTTGGTGGT | | 764 |
| 59 | F759 | GGAGGTTTCGTTTT | 115 | 789 |
| | R14 | CCGCCGACACGCAA | | 763 |
| | P14 | TTTTGTTTATTTTGGGTTTGGTGGT | | 764 |
| 60 | F760 | GAGGTTTCGTTTTG | 114 | 790 |
| | R14 | CCGCCGACACGCAA | | 763 |
| | P14 | TTTTGTTTATTTTGGGTTTGGTGGT | | 764 |
| 61 | F761 | AGGTTTCGTTTTGT | 113 | 791 |
| | R14 | CCGCCGACACGCAA | | 763 |
| | P14 | TTTTGTTTATTTTGGGTTTGGTGGT | | 764 |
| 62 | F762 | GGTTTCGTTTTGTT | 112 | 792 |
| | R14 | CCGCCGACACGCAA | | 763 |
| | P14 | TTTTGTTTATTTTGGGTTTGGTGGT | | 764 |

TABLE 1 -continued

Primer and probe sequences for detection of SDC2 gene methylation

| Set | Primers | Sequences (5'-->3') | Size of amplified product (bp) | SEQ ID NO: |
|---|---|---|---|---|
| 63 | F763 | GTTTCGTTTTGTTT | 111 | 793 |
|  | R14 | CCGCCGACACGCAA |  | 763 |
|  | P14 | TTTTGTTTATTTTGGGTTTGGTGGT |  | 764 |
| 64 | F764 | TTTCGTTTTGTTTT | 110 | 794 |
|  | R14 | CCGCCGACACGCAA |  | 763 |
|  | P14 | TTTTGTTTATTTTGGGTTTGGTGGT |  | 764 |
| 65 | F765 | TTCGTTTTGTTTTG | 109 | 795 |
|  | R14 | CCGCCGACACGCAA |  | 763 |
|  | P14 | TTTTGTTTATTTTGGGTTTGGTGGT |  | 764 |
| 66 | F766 | TCGTTTTGTTTTGG | 108 | 796 |
|  | R14 | CCGCCGACACGCAA |  | 763 |
|  | P14 | TTTTGTTTATTTTGGGTTTGGTGGT |  | 764 |
| 67 | F767 | CGTTTTGTTTTGGT | 107 | 797 |
|  | R14 | CCGCCGACACGCAA |  | 763 |
|  | P14 | TTTTGTTTATTTTGGGTTTGGTGGT |  | 764 |
| 68 | F768 | GTTTTGTTTTGGTT | 106 | 798 |
|  | R14 | CCGCCGACACGCAA |  | 763 |
|  | P14 | TTTTGTTTATTTTGGGTTTGGTGGT |  | 764 |
| 69 | F769 | TTTTGTTTTGGTTG | 105 | 799 |
|  | R14 | CCGCCGACACGCAA |  | 763 |
|  | P14 | TTTTGTTTATTTTGGGTTTGGTGGT |  | 764 |
| 70 | F770 | TTTGTTTTGGTTGT | 104 | 800 |
|  | R14 | CCGCCGACACGCAA |  | 763 |
|  | P14 | TTTTGTTTATTTTGGGTTTGGTGGT |  | 764 |
| 71 | F771 | TTGTTTTGGTTGTA | 103 | 801 |
|  | R14 | CCGCCGACACGCAA |  | 763 |
|  | P14 | TTTTGTTTATTTTGGGTTTGGTGGT |  | 764 |
| 72 | F772 | TGTTTTGGTTGTAA | 102 | 802 |
|  | R14 | CCGCCGACACGCAA |  | 763 |
|  | P14 | TTTTGTTTATTTTGGGTTTGGTGGT |  | 764 |
| 73 | F773 | GTTTTGGTTGTAAG | 101 | 803 |
|  | R14 | CCGCCGACACGCAA |  | 763 |
|  | P14 | TTTTGTTTATTTTGGGTTTGGTGGT |  | 764 |
| 74 | F774 | TTTTGGTTGTAAGT | 100 | 804 |
|  | R14 | CCGCCGACACGCAA |  | 763 |
|  | P14 | TTTTGTTTATTTTGGGTTTGGTGGT |  | 764 |
| 75 | F775 | TTTGGTTGTAAGTA | 99 | 805 |
|  | R14 | CCGCCGACACGCAA |  | 763 |
|  | P14 | TTTTGTTTATTTTGGGTTTGGTGGT |  | 764 |
| 76 | F776 | TTGGTTGTAAGTAG | 98 | 806 |
|  | R14 | CCGCCGACACGCAA |  | 763 |
|  | P14 | TTTTGTTTATTTTGGGTTTGGTGGT |  | 764 |
| 77 | F777 | TGGTTGTAAGTAGC | 97 | 807 |
|  | R14 | CCGCCGACACGCAA |  | 763 |
|  | P14 | TTTTGTTTATTTTGGGTTTGGTGGT |  | 764 |
| 78 | F778 | GGTTGTAAGTAGCG | 96 | 808 |
|  | R14 | CCGCCGACACGCAA |  | 763 |
|  | P14 | TTTTGTTTATTTTGGGTTTGGTGGT |  | 764 |
| 79 | F779 | GTTGTAAGTAGCGG | 95 | 809 |
|  | R14 | CCGCCGACACGCAA |  | 763 |
|  | P14 | TTTTGTTTATTTTGGGTTTGGTGGT |  | 764 |
| 80 | F780 | TTGTAAGTAGCGGT | 94 | 810 |
|  | R14 | CCGCCGACACGCAA |  | 763 |
|  | P14 | TTTTGTTTATTTTGGGTTTGGTGGT |  | 764 |

TABLE 1-continued

Primer and probe sequences for detection of SDC2 gene methylation

| Set | Primers | Sequences (5'-->3') | Size of amplified product (bp) | SEQ ID NO: |
|---|---|---|---|---|
| 81 | F781 | TGTAAGTAGCGGTT | 93 | 811 |
| | R14 | CCGCCGACACGCAA | | 763 |
| | P14 | TTTTGTTTATTTTGGGTTTGGTGGT | | 764 |
| 82 | F782 | GTAAGTAGCGGTTG | 92 | 812 |
| | R14 | CCGCCGACACGCAA | | 763 |
| | P14 | TTTTGTTTATTTTGGGTTTGGTGGT | | 764 |
| 83 | F783 | TAAGTAGCGGTTGG | 91 | 813 |
| | R14 | CCGCCGACACGCAA | | 763 |
| | P14 | TTTTGTTTATTTTGGGTTTGGTGGT | | 764 |
| 84 | F784 | AAGTAGCGGTTGGG | 90 | 814 |
| | R14 | CCGCCGACACGCAA | | 763 |
| | P14 | TTTTGTTTATTTTGGGTTTGGTGGT | | 764 |
| 85 | F785 | AGTAGCGGTTGGGA | 89 | 815 |
| | R14 | CCGCCGACACGCAA | | 763 |
| | P14 | TTTTGTTTATTTTGGGTTTGGTGGT | | 764 |
| 86 | F786 | GTAGCGGTTGGGAG | 88 | 816 |
| | R14 | CCGCCGACACGCAA | | 763 |
| | P14 | TTTTGTTTATTTTGGGTTTGGTGGT | | 764 |
| 87 | F787 | TAGCGGTTGGGAGT | 87 | 817 |
| | R14 | CCGCCGACACGCAA | | 763 |
| | P14 | TTTTGTTTATTTTGGGTTTGGTGGT | | 764 |
| 88 | F788 | AGCGGTTGGGAGTA | 86 | 818 |
| | R14 | CCGCCGACACGCAA | | 763 |
| | P14 | TTTTGTTTATTTTGGGTTTGGTGGT | | 764 |
| 89 | F789 | GCGGTTGGGAGTAG | 85 | 819 |
| | R14 | CCGCCGACACGCAA | | 763 |
| | P14 | TTTTGTTTATTTTGGGTTTGGTGGT | | 764 |
| 90 | F790 | CGGTTGGGAGTAGT | 84 | 820 |
| | R14 | CCGCCGACACGCAA | | 763 |
| | P14 | TTTTGTTTATTTTGGGTTTGGTGGT | | 764 |
| 91 | F791 | GGTTGGGAGTAGTC | 83 | 821 |
| | R14 | CCGCCGACACGCAA | | 763 |
| | P14 | TTTTGTTTATTTTGGGTTTGGTGGT | | 764 |
| 92 | F792 | GTTGGGAGTAGTCG | 82 | 822 |
| | R14 | CCGCCGACACGCAA | | 763 |
| | P14 | TTTTGTTTATTTTGGGTTTGGTGGT | | 764 |
| 93 | F793 | TTGGGAGTAGTCGG | 81 | 823 |
| | R14 | CCGCCGACACGCAA | | 763 |
| | P14 | TTTTGTTTATTTTGGGTTTGGTGGT | | 764 |
| 94 | F794 | TGGGAGTAGTCGGT | 80 | 824 |
| | R14 | CCGCCGACACGCAA | | 763 |
| | P14 | TTTTGTTTATTTTGGGTTTGGTGGT | | 764 |
| 95 | F795 | GGGAGTAGTCGGTT | 140 | 825 |
| | R15 | TCTCGTAACTTCAA | | 826 |
| | P15 | GGATGCGCGCGTCGTTTAGGGTGT | | 827 |
| 96 | F796 | GGAGTAGTCGGTTT | 139 | 828 |
| | R15 | TCTCGTAACTTCAA | | 826 |
| | P15 | GGATGCGCGCGTCGTTTAGGGTGT | | 827 |
| 97 | F797 | GAGTAGTCGGTTTT | 138 | 829 |
| | R15 | TCTCGTAACTTCAA | | 826 |
| | P15 | GGATGCGCGCGTCGTTTAGGGTGT | | 827 |
| 98 | F798 | AGTAGTCGGTTTTT | 137 | 830 |
| | R15 | TCTCGTAACTTCAA | | 826 |
| | P15 | GGATGCGCGCGTCGTTTAGGGTGT | | 827 |

TABLE 1 -continued

Primer and probe sequences for detection of SDC2 gene methylation

| Set | Primers | Sequences (5'-->3') | Size of amplified product (bp) | SEQ ID NO: |
|---|---|---|---|---|
| 99 | F799 | GTAGTCGGTTTTTG | 136 | 831 |
|  | R15 | TCTCGTAACTTCAA |  | 826 |
|  | P15 | GGATGCGCGCGTCGTTTAGGGTGT |  | 827 |
| 00 | F800 | TAGTCGGTTTTTGG | 135 | 832 |
|  | R15 | TCTCGTAACTTCAA |  | 826 |
|  | P15 | GGATGCGCGCGTCGTTTAGGGTGT |  | 827 |
| 01 | F801 | AGTCGGTTTTTGGG | 134 | 833 |
|  | R15 | TCTCGTAACTTCAA |  | 826 |
|  | P15 | GGATGCGCGCGTCGTTTAGGGTGT |  | 827 |
| 02 | F802 | GTCGGTTTTTGGGG | 133 | 834 |
|  | R15 | TCTCGTAACTTCAA |  | 826 |
|  | P15 | GGATGCGCGCGTCGTTTAGGGTGT |  | 827 |
| 03 | F803 | TCGGTTTTTGGGGA | 132 | 835 |
|  | R15 | TCTCGTAACTTCAA |  | 826 |
|  | P15 | GGATGCGCGCGTCGTTTAGGGTGT |  | 827 |
| 04 | F804 | CGGTTTTTGGGGAA | 131 | 836 |
|  | R15 | TCTCGTAACTTCAA |  | 826 |
|  | P15 | GGATGCGCGCGTCGTTTAGGGTGT |  | 827 |
| 05 | F805 | GGTTTTTGGGGAAT | 130 | 837 |
|  | R15 | TCTCGTAACTTCAA |  | 826 |
|  | P15 | GGATGCGCGCGTCGTTTAGGGTGT |  | 827 |
| 06 | F806 | GTTTTTGGGGAATA | 129 | 838 |
|  | R15 | TCTCGTAACTTCAA |  | 826 |
|  | P15 | GGATGCGCGCGTCGTTTAGGGTGT |  | 827 |
| 07 | F807 | TTTTTGGGGAATAT | 128 | 839 |
|  | R15 | TCTCGTAACTTCAA |  | 826 |
|  | P15 | GGATGCGCGCGTCGTTTAGGGTGT |  | 827 |
| 08 | F808 | GTAGAAATTAATAAGTGAGAGGGC | 124 | 840 |
|  | R16 | ACGACTCAAACTCGAAAACTCG |  | 841 |
|  | P16 | TTCGGGGCGTAGTTGCGGCGG |  | 842 |

FIG. 1 shows a graph diagram showing a detection rate at which SDC2 gene methylation is detected in various specimens using 12 sets among 808 sets of primers and probes as an example used in the method according to the present disclosure. There occurs an amplification curve in the methylated DNA, there does not occur an amplification curve in a group using the non-methylated DNA and distilled water (D.W) as a template.

TABLE 2

Primer and probe sequences for detection of SDC2 gene methylation

| Set of primer and probe | qMSP CT value | |
|---|---|---|
|  | Methylated DNA | Non-methylated DNA |
| 1 | 24.6 | N.D |
| 2 | 24.4 | N.D |
| 3 | 24.2 | N.D |
| 4 | 25.1 | N.D |
| 5 | 24.9 | N.D |
| 6 | 25.9 | N.D |
| 7 | 27.6 | N.D |
| 8 | 24.3 | N.D |
| 9 | 24.3 | N.D |
| 10 | 23.9 | N.D |
| 11 | 25.3 | N.D |
| 12 | 26.4 | N.D |
| 13 | 27.4 | N.D |
| 14 | 26.3 | N.D |
| 15 | 25.2 | N.D |
| 16 | 24.3 | N.D |
| 17 | 24.3 | N.D |
| 18 | 28.3 | N.D |
| 19 | 25.3 | N.D |
| 20 | 26.4 | N.D |
| 21 | 27.4 | N.D |
| 22 | 26.3 | N.D |
| 23 | 25.2 | N.D |
| 24 | 25.7 | N.D |
| 25 | 27.6 | N.D |
| 26 | 27.8 | N.D |
| 27 | 29.3 | N.D |
| 28 | 25.4 | N.D |
| 29 | 25.7 | N.D |
| 30 | 27.4 | N.D |
| 31 | 24.3 | N.D |
| 32 | 28.3 | N.D |
| 33 | 25.3 | N.D |
| 34 | 26.4 | N.D |

TABLE 2-continued

Primer and probe sequences for detection of SDC2 gene methylation

| Set of primer and probe | qMSP CT value | |
|---|---|---|
| | Methylated DNA | Non-methylated DNA |
| 35 | 27.4 | N.D |
| 36 | 26.3 | N.D |
| 37 | 25.2 | N.D |
| 38 | 25.7 | N.D |
| 39 | 27.6 | N.D |
| 40 | 27.8 | N.D |
| 41 | 29.3 | N.D |
| 42 | 25.4 | N.D |
| 43 | 25.7 | N.D |
| 44 | 27.4 | N.D |
| 45 | 28.2 | N.D |
| 46 | 27.2 | N.D |
| 47 | 24.2 | N.D |
| 48 | 27.9 | N.D |
| 49 | 28.6 | N.D |
| 50 | 28.4 | N.D |
| 51 | 24.4 | N.D |
| 52 | 24.2 | N.D |
| 53 | 25.1 | N.D |
| 54 | 24.9 | N.D |
| 55 | 25.9 | N.D |
| 56 | 27.6 | N.D |
| 57 | 24.3 | N.D |
| 58 | 24.3 | N.D |
| 59 | 25.7 | N.D |
| 60 | 27.4 | N.D |
| 61 | 28.2 | N.D |
| 62 | 27.2 | N.D |
| 63 | 24.2 | N.D |
| 64 | 27.9 | N.D |
| 65 | 28.6 | N.D |
| 66 | 28.4 | N.D |
| 67 | 24.4 | N.D |
| 68 | 24.2 | N.D |
| 69 | 25.1 | N.D |
| 70 | 24.9 | N.D |
| 71 | 25.9 | N.D |
| 72 | 27.6 | N.D |
| 73 | 24.3 | N.D |
| 74 | 24.3 | N.D |
| 75 | 28.3 | N.D |
| 76 | 25.3 | N.D |
| 77 | 26.4 | N.D |
| 78 | 27.4 | N.D |
| 79 | 26.3 | N.D |
| 80 | 25.2 | N.D |
| 81 | 25.7 | N.D |
| 82 | 28.2 | N.D |
| 83 | 27.2 | N.D |
| 84 | 24.2 | N.D |
| 85 | 27.9 | N.D |
| 86 | 28.6 | N.D |
| 87 | 28.4 | N.D |
| 88 | 24.4 | N.D |
| 89 | 24.2 | N.D |
| 90 | 25.1 | N.D |
| 91 | 24.9 | N.D |
| 92 | 25.9 | N.D |
| 93 | 27.6 | N.D |
| 94 | 24.3 | N.D |
| 95 | 24.2 | N.D |
| 96 | 25.2 | N.D |
| 97 | 25.7 | N.D |
| 98 | 27.6 | N.D |
| 99 | 27.8 | N.D |
| 100 | 29.1 | N.D |
| 101 | 25.4 | N.D |
| 102 | 25.7 | N.D |
| 103 | 27.4 | N.D |
| 104 | 28.2 | N.D |
| 105 | 27.2 | N.D |
| 106 | 24.2 | N.D |
| 107 | 27.9 | N.D |
| 108 | 28.6 | N.D |
| 109 | 28.4 | N.D |
| 110 | 24.4 | N.D |
| 111 | 24.2 | N.D |
| 112 | 25.1 | N.D |
| 113 | 24.9 | N.D |
| 114 | 25.9 | N.D |
| 115 | 27.6 | N.D |
| 116 | 24.3 | N.D |
| 117 | 24.3 | N.D |
| 118 | 28.3 | N.D |
| 119 | 25.3 | N.D |
| 120 | 26.4 | N.D |
| 121 | 27.8 | N.D |
| 122 | 29.3 | N.D |
| 123 | 25.4 | N.D |
| 124 | 25.7 | N.D |
| 125 | 27.4 | N.D |
| 126 | 28.2 | N.D |
| 127 | 27.2 | N.D |
| 128 | 24.2 | N.D |
| 129 | 27.9 | N.D |
| 130 | 28.6 | N.D |
| 131 | 28.4 | N.D |
| 132 | 24.4 | N.D |
| 133 | 24.2 | N.D |
| 134 | 25.1 | N.D |
| 135 | 24.9 | N.D |
| 136 | 28.4 | N.D |
| 137 | 24.4 | N.D |
| 138 | 24.2 | N.D |
| 139 | 25.1 | N.D |
| 140 | 24.9 | N.D |
| 141 | 25.9 | N.D |
| 142 | 27.6 | N.D |
| 143 | 24.3 | N.D |
| 144 | 24.3 | N.D |
| 145 | 28.3 | N.D |
| 146 | 25.3 | N.D |
| 147 | 26.4 | N.D |
| 148 | 27.4 | N.D |
| 149 | 26.3 | N.D |
| 150 | 25.2 | N.D |
| 151 | 25.7 | N.D |
| 152 | 27.6 | N.D |
| 153 | 27.8 | N.D |
| 154 | 29.3 | N.D |
| 155 | 25.4 | N.D |
| 156 | 27.4 | N.D |
| 157 | 26.3 | N.D |
| 158 | 25.2 | N.D |
| 159 | 25.7 | N.D |
| 160 | 27.6 | N.D |
| 161 | 27.8 | N.D |
| 162 | 29.3 | N.D |
| 163 | 25.4 | N.D |
| 164 | 25.7 | N.D |
| 165 | 27.4 | N.D |
| 166 | 28.2 | N.D |
| 167 | 27.2 | N.D |
| 168 | 24.2 | N.D |
| 169 | 27.9 | N.D |
| 170 | 28.6 | N.D |
| 171 | 28.4 | N.D |
| 172 | 24.4 | N.D |
| 173 | 24.2 | N.D |
| 174 | 25.1 | N.D |
| 175 | 24.9 | N.D |
| 176 | 25.9 | N.D |
| 177 | 27.6 | N.D |
| 178 | 24.3 | N.D |
| 179 | 24.2 | N.D |
| 180 | 27.6 | N.D |
| 181 | 27.8 | N.D |
| 182 | 29.3 | N.D |

TABLE 2-continued

Primer and probe sequences for detection of SDC2 gene methylation

| Set of primer and probe | qMSP CT value Methylated DNA | qMSP CT value Non-methylated DNA |
|---|---|---|
| 183 | 25.4 | N.D |
| 184 | 25.7 | N.D |
| 185 | 27.4 | N.D |
| 186 | 28.2 | N.D |
| 187 | 27.2 | N.D |
| 188 | 24.2 | N.D |
| 189 | 27.9 | N.D |
| 190 | 28.6 | N.D |
| 191 | 28.4 | N.D |
| 192 | 24.4 | N.D |
| 193 | 24.2 | N.D |
| 194 | 25.1 | N.D |
| 195 | 24.9 | N.D |
| 196 | 25.9 | N.D |
| 197 | 27.6 | N.D |
| 198 | 24.3 | N.D |
| 199 | 24.3 | N.D |
| 200 | 28.4 | N.D |
| 201 | 28.2 | N.D |
| 202 | 27.2 | N.D |
| 203 | 24.2 | N.D |
| 204 | 27.9 | N.D |
| 205 | 28.6 | N.D |
| 206 | 28.4 | N.D |
| 207 | 24.4 | N.D |
| 208 | 24.2 | N.D |
| 209 | 25.1 | N.D |
| 210 | 24.9 | N.D |
| 211 | 25.9 | N.D |
| 212 | 27.6 | N.D |
| 213 | 24.3 | N.D |
| 214 | 24.3 | N.D |
| 215 | 28.3 | N.D |
| 216 | 25.3 | N.D |
| 217 | 26.4 | N.D |
| 218 | 27.4 | N.D |
| 219 | 26.3 | N.D |
| 220 | 25.2 | N.D |
| 221 | 25.7 | N.D |
| 222 | 27.6 | N.D |
| 223 | 27.8 | N.D |
| 224 | 29.3 | N.D |
| 225 | 24.4 | N.D |
| 226 | 24.2 | N.D |
| 227 | 25.1 | N.D |
| 228 | 24.9 | N.D |
| 229 | 25.9 | N.D |
| 230 | 27.6 | N.D |
| 231 | 24.3 | N.D |
| 232 | 24.3 | N.D |
| 233 | 28.3 | N.D |
| 234 | 25.3 | N.D |
| 235 | 26.4 | N.D |
| 236 | 27.4 | N.D |
| 237 | 26.3 | N.D |
| 238 | 25.2 | N.D |
| 239 | 25.7 | N.D |
| 240 | 27.6 | N.D |
| 241 | 27.8 | N.D |
| 242 | 29.3 | N.D |
| 243 | 25.4 | N.D |
| 244 | 25.7 | N.D |
| 245 | 27.4 | N.D |
| 246 | 28.2 | N.D |
| 247 | 27.2 | N.D |
| 248 | 24.2 | N.D |
| 249 | 25.3 | N.D |
| 250 | 26.3 | N.D |
| 251 | 25.9 | N.D |
| 252 | 26.4 | N.D |
| 253 | 27.4 | N.D |
| 254 | 26.3 | N.D |
| 255 | 25.2 | N.D |
| 256 | 25.7 | N.D |
| 257 | 27.6 | N.D |
| 258 | 27.8 | N.D |
| 259 | 29.3 | N.D |
| 260 | 25.4 | N.D |
| 261 | 25.7 | N.D |
| 262 | 27.4 | N.D |
| 263 | 27.4 | N.D |
| 264 | 26.3 | N.D |
| 265 | 25.2 | N.D |
| 266 | 25.7 | N.D |
| 267 | 27.6 | N.D |
| 268 | 27.8 | N.D |
| 269 | 29.3 | N.D |
| 270 | 25.4 | N.D |
| 271 | 25.7 | N.D |
| 272 | 27.4 | N.D |
| 273 | 26.3 | N.D |
| 274 | 25.2 | N.D |
| 275 | 25.7 | N.D |
| 276 | 27.6 | N.D |
| 277 | 27.8 | N.D |
| 278 | 29.3 | N.D |
| 279 | 25.4 | N.D |
| 280 | 25.7 | N.D |
| 281 | 27.4 | N.D |
| 282 | 28.2 | N.D |
| 283 | 27.2 | N.D |
| 284 | 27.4 | N.D |
| 285 | 26.3 | N.D |
| 286 | 25.2 | N.D |
| 287 | 25.7 | N.D |
| 288 | 27.6 | N.D |
| 289 | 27.8 | N.D |
| 290 | 29.3 | N.D |
| 291 | 27.3 | N.D |
| 292 | 25.2 | N.D |
| 293 | 26.2 | N.D |
| 294 | 27.4 | N.D |
| 295 | 26.3 | N.D |
| 296 | 25.2 | N.D |
| 297 | 25.7 | N.D |
| 298 | 27.6 | N.D |
| 299 | 27.8 | N.D |
| 300 | 24.0 | N.D |
| 301 | 26.3 | N.D |
| 302 | 25.2 | N.D |
| 303 | 25.7 | N.D |
| 304 | 27.6 | N.D |
| 305 | 27.8 | N.D |
| 306 | 29.3 | N.D |
| 307 | 25.4 | N.D |
| 308 | 25.7 | N.D |
| 309 | 27.4 | N.D |
| 310 | 24.2 | N.D |
| 311 | 27.9 | N.D |
| 312 | 28.6 | N.D |
| 313 | 28.4 | N.D |
| 314 | 24.4 | N.D |
| 315 | 24.2 | N.D |
| 316 | 25.1 | N.D |
| 317 | 24.9 | N.D |
| 318 | 25.9 | N.D |
| 319 | 27.6 | N.D |
| 320 | 24.3 | N.D |
| 321 | 24.3 | N.D |
| 322 | 28.3 | N.D |
| 323 | 25.3 | N.D |
| 324 | 26.4 | N.D |
| 325 | 27.4 | N.D |
| 326 | 26.3 | N.D |
| 327 | 25.2 | N.D |
| 328 | 27.6 | N.D |
| 329 | 27.8 | N.D |
| 330 | 29.3 | N.D |

TABLE 2-continued

Primer and probe sequences for detection of SDC2 gene methylation

| Set of primer and probe | qMSP CT value | |
|---|---|---|
| | Methylated DNA | Non-methylated DNA |
| 331 | 25.4 | N.D |
| 332 | 27.4 | N.D |
| 333 | 26.3 | N.D |
| 334 | 25.2 | N.D |
| 335 | 25.7 | N.D |
| 336 | 27.6 | N.D |
| 337 | 27.8 | N.D |
| 338 | 29.3 | N.D |
| 339 | 24.3 | N.D |
| 340 | 25.2 | N.D |
| 341 | 26.8 | N.D |
| 342 | 27.4 | N.D |
| 343 | 28.2 | N.D |
| 344 | 27.2 | N.D |
| 345 | 24.2 | N.D |
| 346 | 27.9 | N.D |
| 347 | 28.6 | N.D |
| 348 | 28.4 | N.D |
| 349 | 24.4 | N.D |
| 350 | 24.2 | N.D |
| 351 | 25.1 | N.D |
| 352 | 27.4 | N.D |
| 353 | 26.3 | N.D |
| 354 | 25.2 | N.D |
| 355 | 25.7 | N.D |
| 356 | 27.6 | N.D |
| 357 | 27.9 | N.D |
| 358 | 28.6 | N.D |
| 359 | 28.4 | N.D |
| 360 | 24.4 | N.D |
| 361 | 24.2 | N.D |
| 362 | 25.1 | N.D |
| 363 | 24.9 | N.D |
| 364 | 25.9 | N.D |
| 365 | 27.6 | N.D |
| 366 | 24.3 | N.D |
| 367 | 25.8 | N.D |
| 368 | 26.1 | N.D |
| 369 | 27.7 | N.D |
| 370 | 25.3 | N.D |
| 371 | 27.9 | N.D |
| 372 | 28.6 | N.D |
| 373 | 28.4 | N.D |
| 374 | 24.4 | N.D |
| 375 | 24.2 | N.D |
| 376 | 25.1 | N.D |
| 377 | 24.9 | N.D |
| 378 | 25.9 | N.D |
| 379 | 27.6 | N.D |
| 380 | 24.3 | N.D |
| 381 | 27.4 | N.D |
| 382 | 26.3 | N.D |
| 383 | 25.2 | N.D |
| 384 | 25.7 | N.D |
| 385 | 27.6 | N.D |
| 386 | 27.8 | N.D |
| 387 | 29.3 | N.D |
| 388 | 25.1 | N.D |
| 389 | 26.4 | N.D |
| 390 | 27.4 | N.D |
| 391 | 26.3 | N.D |
| 392 | 25.2 | N.D |
| 393 | 25.7 | N.D |
| 394 | 27.6 | N.D |
| 395 | 27.8 | N.D |
| 396 | 29.3 | N.D |
| 397 | 25.4 | N.D |
| 398 | 25.7 | N.D |
| 399 | 27.4 | N.D |
| 400 | 24.4 | N.D |
| 401 | 27.2 | N.D |
| 402 | 24.2 | N.D |
| 403 | 27.9 | N.D |
| 404 | 27.6 | N.D |
| 405 | 24.2 | N.D |
| 406 | 27.9 | N.D |
| 407 | 28.6 | N.D |
| 408 | 28.4 | N.D |
| 409 | 24.4 | N.D |
| 410 | 24.2 | N.D |
| 411 | 25.1 | N.D |
| 412 | 24.9 | N.D |
| 413 | 25.9 | N.D |
| 414 | 27.6 | N.D |
| 415 | 24.3 | N.D |
| 416 | 24.3 | N.D |
| 417 | 28.3 | N.D |
| 418 | 25.3 | N.D |
| 419 | 27.4 | N.D |
| 420 | 26.3 | N.D |
| 421 | 25.2 | N.D |
| 422 | 25.7 | N.D |
| 423 | 27.6 | N.D |
| 424 | 27.8 | N.D |
| 425 | 29.3 | N.D |
| 426 | 27.9 | N.D |
| 427 | 28.6 | N.D |
| 428 | 28.4 | N.D |
| 429 | 24.4 | N.D |
| 430 | 24.2 | N.D |
| 431 | 25.1 | N.D |
| 432 | 24.9 | N.D |
| 433 | 25.9 | N.D |
| 434 | 27.6 | N.D |
| 435 | 24.3 | N.D |
| 436 | 27.4 | N.D |
| 437 | 26.3 | N.D |
| 438 | 25.2 | N.D |
| 439 | 25.7 | N.D |
| 440 | 27.6 | N.D |
| 441 | 27.8 | N.D |
| 442 | 29.3 | N.D |
| 443 | 25.4 | N.D |
| 444 | 27.4 | N.D |
| 445 | 26.3 | N.D |
| 446 | 25.2 | N.D |
| 447 | 25.7 | N.D |
| 448 | 27.6 | N.D |
| 449 | 27.8 | N.D |
| 450 | 29.3 | N.D |
| 451 | 28.2 | N.D |
| 452 | 27.2 | N.D |
| 453 | 24.2 | N.D |
| 454 | 27.9 | N.D |
| 455 | 28.6 | N.D |
| 456 | 28.4 | N.D |
| 457 | 24.4 | N.D |
| 458 | 24.2 | N.D |
| 459 | 25.1 | N.D |
| 460 | 24.9 | N.D |
| 461 | 24.2 | N.D |
| 462 | 27.9 | N.D |
| 463 | 28.6 | N.D |
| 464 | 28.4 | N.D |
| 465 | 24.4 | N.D |
| 466 | 24.2 | N.D |
| 467 | 25.1 | N.D |
| 468 | 24.9 | N.D |
| 469 | 25.9 | N.D |
| 470 | 27.6 | N.D |
| 471 | 24.3 | N.D |
| 472 | 24.3 | N.D |
| 473 | 28.3 | N.D |
| 474 | 25.3 | N.D |
| 475 | 26.4 | N.D |
| 476 | 27.4 | N.D |
| 477 | 26.3 | N.D |
| 478 | 25.2 | N.D |

TABLE 2-continued

Primer and probe sequences for detection of SDC2 gene methylation

| Set of primer and probe | qMSP CT value Methylated DNA | Non-methylated DNA |
|---|---|---|
| 479 | 27.8 | N.D |
| 480 | 29.3 | N.D |
| 481 | 25.4 | N.D |
| 482 | 25.7 | N.D |
| 483 | 27.4 | N.D |
| 484 | 28.2 | N.D |
| 485 | 27.4 | N.D |
| 486 | 26.3 | N.D |
| 487 | 25.2 | N.D |
| 488 | 25.7 | N.D |
| 489 | 27.6 | N.D |
| 490 | 27.8 | N.D |
| 491 | 29.3 | N.D |
| 492 | 25.4 | N.D |
| 493 | 27.4 | N.D |
| 494 | 26.3 | N.D |
| 495 | 25.2 | N.D |
| 496 | 25.7 | N.D |
| 497 | 27.6 | N.D |
| 498 | 27.8 | N.D |
| 499 | 29.3 | N.D |
| 500 | 25.4 | N.D |
| 501 | 27.9 | N.D |
| 502 | 28.6 | N.D |
| 503 | 28.4 | N.D |
| 504 | 24.4 | N.D |
| 505 | 24.2 | N.D |
| 506 | 25.1 | N.D |
| 507 | 24.9 | N.D |
| 508 | 25.9 | N.D |
| 509 | 27.6 | N.D |
| 510 | 24.3 | N.D |
| 511 | 25.5 | N.D |
| 512 | 27.8 | N.D |
| 513 | 28.2 | N.D |
| 514 | 26.1 | N.D |
| 515 | 27.4 | N.D |
| 516 | 26.3 | N.D |
| 517 | 25.2 | N.D |
| 518 | 25.7 | N.D |
| 519 | 27.6 | N.D |
| 520 | 27.8 | N.D |
| 521 | 29.3 | N.D |
| 522 | 26.2 | N.D |
| 523 | 25.3 | N.D |
| 524 | 28.2 | N.D |
| 525 | 27.4 | N.D |
| 526 | 28.2 | N.D |
| 527 | 27.2 | N.D |
| 528 | 24.2 | N.D |
| 529 | 27.9 | N.D |
| 530 | 28.6 | N.D |
| 531 | 28.4 | N.D |
| 532 | 24.4 | N.D |
| 533 | 24.2 | N.D |
| 534 | 25.1 | N.D |
| 535 | 24.9 | N.D |
| 536 | 25.9 | N.D |
| 537 | 27.6 | N.D |
| 538 | 25.2 | N.D |
| 539 | 25.7 | N.D |
| 540 | 27.6 | N.D |
| 541 | 27.4 | N.D |
| 542 | 26.3 | N.D |
| 543 | 25.2 | N.D |
| 544 | 25.7 | N.D |
| 545 | 27.6 | N.D |
| 546 | 27.8 | N.D |
| 547 | 29.3 | N.D |
| 548 | 25.4 | N.D |
| 549 | 25.7 | N.D |
| 550 | 27.4 | N.D |
| 551 | 28.2 | N.D |
| 552 | 27.2 | N.D |
| 553 | 24.2 | N.D |
| 554 | 27.4 | N.D |
| 555 | 26.3 | N.D |
| 556 | 25.2 | N.D |
| 557 | 25.7 | N.D |
| 558 | 27.6 | N.D |
| 559 | 27.8 | N.D |
| 560 | 29.3 | N.D |
| 561 | 28.4 | N.D |
| 562 | 24.4 | N.D |
| 563 | 24.2 | N.D |
| 564 | 25.1 | N.D |
| 565 | 24.9 | N.D |
| 566 | 25.9 | N.D |
| 567 | 27.6 | N.D |
| 568 | 24.3 | N.D |
| 569 | 24.3 | N.D |
| 570 | 28.3 | N.D |
| 571 | 25.3 | N.D |
| 572 | 26.4 | N.D |
| 573 | 27.4 | N.D |
| 574 | 26.3 | N.D |
| 575 | 25.2 | N.D |
| 576 | 25.7 | N.D |
| 577 | 27.6 | N.D |
| 578 | 27.8 | N.D |
| 579 | 29.3 | N.D |
| 580 | 25.4 | N.D |
| 581 | 25.7 | N.D |
| 582 | 27.4 | N.D |
| 583 | 28.2 | N.D |
| 584 | 27.2 | N.D |
| 585 | 24.2 | N.D |
| 586 | 24.2 | N.D |
| 587 | 26.3 | N.D |
| 588 | 25.2 | N.D |
| 589 | 25.7 | N.D |
| 590 | 27.6 | N.D |
| 591 | 27.8 | N.D |
| 592 | 29.3 | N.D |
| 593 | 27.4 | N.D |
| 594 | 28.2 | N.D |
| 595 | 27.2 | N.D |
| 596 | 24.2 | N.D |
| 597 | 27.9 | N.D |
| 598 | 28.6 | N.D |
| 599 | 28.4 | N.D |
| 600 | 27.0 | N.D |
| 601 | 24.2 | N.D |
| 602 | 25.1 | N.D |
| 603 | 24.9 | N.D |
| 604 | 25.9 | N.D |
| 605 | 24.2 | N.D |
| 606 | 27.9 | N.D |
| 607 | 28.6 | N.D |
| 608 | 28.4 | N.D |
| 609 | 24.4 | N.D |
| 610 | 24.2 | N.D |
| 611 | 25.1 | N.D |
| 612 | 24.9 | N.D |
| 613 | 25.9 | N.D |
| 614 | 27.6 | N.D |
| 615 | 24.3 | N.D |
| 616 | 24.3 | N.D |
| 617 | 28.3 | N.D |
| 618 | 25.3 | N.D |
| 619 | 26.4 | N.D |
| 620 | 27.4 | N.D |
| 621 | 26.3 | N.D |
| 622 | 25.2 | N.D |
| 623 | 26.3 | N.D |
| 624 | 25.2 | N.D |
| 625 | 25.7 | N.D |
| 626 | 27.6 | N.D |

TABLE 2-continued

Primer and probe sequences for detection of SDC2 gene methylation

| Set of primer and probe | qMSP CT value | |
|---|---|---|
| | Methylated DNA | Non-methylated DNA |
| 627 | 27.8 | N.D |
| 628 | 29.3 | N.D |
| 629 | 25.4 | N.D |
| 630 | 25.7 | N.D |
| 631 | 27.4 | N.D |
| 632 | 28.2 | N.D |
| 633 | 27.2 | N.D |
| 634 | 24.2 | N.D |
| 635 | 27.4 | N.D |
| 636 | 26.3 | N.D |
| 637 | 25.2 | N.D |
| 638 | 25.7 | N.D |
| 639 | 27.6 | N.D |
| 640 | 27.8 | N.D |
| 641 | 29.3 | N.D |
| 642 | 24.2 | N.D |
| 643 | 27.9 | N.D |
| 644 | 28.6 | N.D |
| 645 | 28.4 | N.D |
| 646 | 24.4 | N.D |
| 647 | 24.2 | N.D |
| 648 | 25.1 | N.D |
| 649 | 24.9 | N.D |
| 650 | 25.9 | N.D |
| 651 | 27.6 | N.D |
| 652 | 26.1 | N.D |
| 653 | 24.8 | N.D |
| 654 | 25.5 | N.D |
| 655 | 25.7 | N.D |
| 656 | 24.9 | N.D |
| 657 | 24.2 | N.D |
| 658 | 25.5 | N.D |
| 659 | 25.4 | N.D |
| 660 | 26.8 | N.D |
| 661 | 26.9 | N.D |
| 662 | 24.7 | N.D |
| 663 | 25.5 | N.D |
| 664 | 27.4 | N.D |
| 665 | 26.3 | N.D |
| 666 | 25.2 | N.D |
| 667 | 25.7 | N.D |
| 668 | 27.6 | N.D |
| 669 | 27.8 | N.D |
| 670 | 27.9 | N.D |
| 671 | 28.6 | N.D |
| 672 | 28.4 | N.D |
| 673 | 24.4 | N.D |
| 674 | 24.2 | N.D |
| 675 | 25.1 | N.D |
| 676 | 24.9 | N.D |
| 677 | 25.9 | N.D |
| 678 | 27.6 | N.D |
| 679 | 24.3 | N.D |
| 680 | 27.4 | N.D |
| 681 | 26.3 | N.D |
| 682 | 25.2 | N.D |
| 683 | 25.7 | N.D |
| 684 | 27.6 | N.D |
| 685 | 27.8 | N.D |
| 686 | 29.3 | N.D |
| 687 | 25.4 | N.D |
| 688 | 25.7 | N.D |
| 689 | 24.2 | N.D |
| 690 | 25.7 | N.D |
| 691 | 25.6 | N.D |
| 692 | 24.7 | N.D |
| 693 | 27.4 | N.D |
| 694 | 26.3 | N.D |
| 695 | 25.2 | N.D |
| 696 | 25.7 | N.D |
| 697 | 27.6 | N.D |
| 698 | 27.9 | N.D |
| 699 | 28.6 | N.D |
| 700 | 28.4 | N.D |
| 701 | 24.4 | N.D |
| 702 | 24.2 | N.D |
| 703 | 25.1 | N.D |
| 704 | 24.9 | N.D |
| 705 | 25.9 | N.D |
| 706 | 27.6 | N.D |
| 707 | 24.3 | N.D |
| 708 | 29.3 | N.D |
| 709 | 25.4 | N.D |
| 710 | 25.7 | N.D |
| 711 | 27.4 | N.D |
| 712 | 28.2 | N.D |
| 713 | 27.2 | N.D |
| 714 | 24.2 | N.D |
| 715 | 27.9 | N.D |
| 716 | 28.6 | N.D |
| 717 | 28.4 | N.D |
| 718 | 24.4 | N.D |
| 719 | 24.2 | N.D |
| 720 | 25.1 | N.D |
| 721 | 24.9 | N.D |
| 722 | 25.9 | N.D |
| 723 | 27.6 | N.D |
| 724 | 24.3 | N.D |
| 725 | 24.3 | N.D |
| 726 | 28.3 | N.D |
| 727 | 25.3 | N.D |
| 728 | 26.4 | N.D |
| 729 | 27.4 | N.D |
| 730 | 26.3 | N.D |
| 731 | 25.2 | N.D |
| 732 | 27.9 | N.D |
| 733 | 28.6 | N.D |
| 734 | 28.4 | N.D |
| 735 | 24.4 | N.D |
| 736 | 29.5 | N.D |
| 737 | 25.1 | N.D |
| 738 | 24.9 | N.D |
| 739 | 25.9 | N.D |
| 740 | 27.6 | N.D |
| 741 | 25.4 | N.D |
| 742 | 26.3 | N.D |
| 743 | 27.8 | N.D |
| 744 | 25.8 | N.D |
| 745 | 24.1 | N.D |
| 746 | 24.2 | N.D |
| 747 | 27.9 | N.D |
| 748 | 27.9 | N.D |
| 749 | 28.6 | N.D |
| 750 | 28.4 | N.D |
| 751 | 24.4 | N.D |
| 752 | 24.2 | N.D |
| 753 | 25.1 | N.D |
| 754 | 24.9 | N.D |
| 755 | 25.9 | N.D |
| 756 | 27.6 | N.D |
| 757 | 24.3 | N.D |
| 758 | 28.3 | N.D |
| 759 | 25.3 | N.D |
| 760 | 24.5 | N.D |
| 761 | 27.4 | N.D |
| 762 | 26.3 | N.D |
| 763 | 25.2 | N.D |
| 764 | 27.6 | N.D |
| 765 | 27.8 | N.D |
| 766 | 29.3 | N.D |
| 767 | 25.4 | N.D |
| 768 | 27.4 | N.D |
| 769 | 26.3 | N.D |
| 770 | 25.2 | N.D |
| 771 | 25.7 | N.D |
| 772 | 27.6 | N.D |
| 773 | 27.9 | N.D |
| 774 | 28.6 | N.D |

TABLE 2-continued

Primer and probe sequences for detection of SDC2 gene methylation

| Set of primer and probe | qMSP CT value | |
|---|---|---|
| | Methylated DNA | Non-methylated DNA |
| 775 | 28.4 | N.D |
| 776 | 24.4 | N.D |
| 777 | 24.2 | N.D |
| 778 | 25.1 | N.D |
| 779 | 24.9 | N.D |
| 780 | 25.9 | N.D |
| 781 | 27.6 | N.D |
| 782 | 24.3 | N.D |
| 783 | 25.2 | N.D |
| 784 | 27.9 | N.D |
| 785 | 28.6 | N.D |
| 786 | 28.4 | N.D |
| 787 | 24.4 | N.D |
| 788 | 24.2 | N.D |
| 789 | 25.1 | N.D |
| 790 | 24.9 | N.D |
| 791 | 25.9 | N.D |
| 792 | 27.6 | N.D |
| 793 | 24.3 | N.D |
| 794 | 24.2 | N.D |
| 795 | 27.9 | N.D |
| 796 | 28.6 | N.D |
| 797 | 28.4 | N.D |
| 798 | 24.4 | N.D |
| 799 | 24.2 | N.D |
| 800 | 24.2 | N.D |
| 801 | 24.9 | N.D |
| 802 | 25.9 | N.D |
| 803 | 27.6 | N.D |
| 804 | 25.4 | N.D |
| 805 | 25.3 | N.D |
| 806 | 26.2 | N.D |
| 807 | 27.1 | N.D |
| 808 | 23.7 | N.D |

N.D: Not Detected

Figure 2:
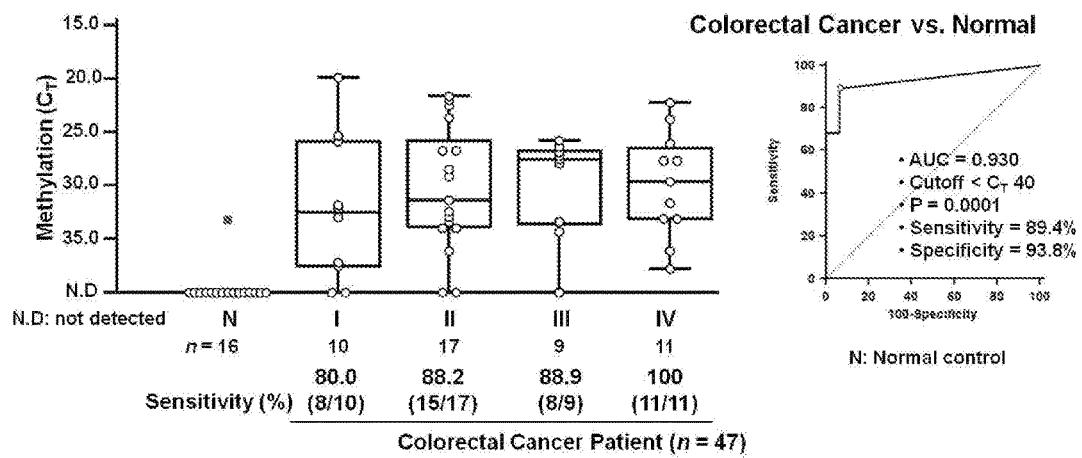
FIG. 2 is a graph diagram showing a degree of methylation of the SDC2 gene in fecal samples of normal persons and colorectal patients using 808 sets of primers and probes used in the method according to the present disclosure.
Figure 3:
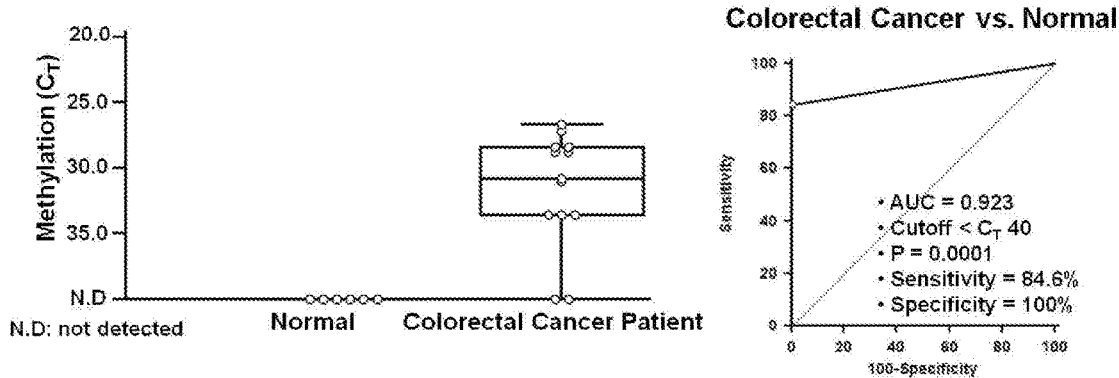
FIG. 3 is a graph diagram showing a degree of methylation of the SDC2 gene in serum samples of normal persons and colorectal patients using 808 sets of primers and probes used in the method according to the present disclosure.

Example 2: Detection of SDC2 Gene Methylation in DNA of Cell Line, Feces and Serum Specimens The abilities of the above-described primers and probes to detect SDC2 gene methylation in various specimens were examined. To this end, set No. 808 that showed the lowest $C_T$ value of 23.7 in methylated DNA in the methylation measurement experiments performed using methylated and unmethylated DNAs was selected by way of example. In order to examine whether or not SDC2 gene methylation would be detected in various specimens, varying amounts (from 20 ng to 0.01 ng) of the genomic DNA of SDC2-methylated colorectal cancer cell line HCT116 (ATCC, CCL247) were spiked to 20 ng of the genomic DNA of SDC2 gene-unmethylated cell line MRC-5 (Korean Cell Line Bank, KCLB No. 10171), DNA isolated from 1.0 mL of SDC2 gene-unmethylated human serum, and 2.0 µg of SDC2 gene-unmethylated human feces DNA, and then qMSP was performed repeatedly 24 times in the same manner as described in Example 1, thereby determining the detection rate of SDC2 gene methylation (FIG. 2). FIG. 3 shows the detection rate of SDC2 gene methylation in each of the specimens. The cell line DNA showed a detection rate of 100% in a genomic DNA amount ranging from 20 ng to 0.05 ng, and showed detection rates of 96% and 88% at 0.02 g and 0.01 ng, respectively. The feces DNA showed a detection rate of 100% in a genomic DNA amount ranging from 20 ng to 0.1 ng, and showed detection rates of 96%, 92% and 54% at 0.05 ng, 0.02 ng and 0.01 ng, respectively. The serum DNA showed a detection rate of 100% in a genomic DNA amount ranging from 20 ng to 0.1 ng, and showed detection rates of 96%, 71% and 33% at 0.05 ng, 0.02 ng and 0.01 ng, respectively. In conclusion, it was shown that SDC2 gene methylation could be detected in various specimens, including cell lines, feces and serum.

TABLE 3

Detection rates of SDC2 gene methylation in various specimens

| HCT116 genomic DNA (ng) | Detection rates (%) | | |
|---|---|---|---|
| | Cell line | Feces | Serum |
| 100 | 100 | 100 | 100 |
| 2 | 100 | 100 | 100 |
| 0.5 | 100 | 100 | 100 |
| 0.2 | 100 | 100 | 100 |
| 0.1 | 100 | 100 | 100 |
| 0.05 | 100 | 96 | 96 |
| 0.02 | 96 | 92 | 71 |
| 0.01 | 88 | 54 | 33 |
| 0 | 0 | 0 | 0 |

Example 3: Detection of SDC2 Gene Methylation in DNA of Clinical Feces and Serum Samples The abilities of the primers and probes to detect SDC2 gene methylation in various specimens were examined again. To this end, set No. 808 that showed the lowest $C_T$ value of 23.7 in methylated DNA in the methylation measurement experiments performed using methylated and unmethylated DNAs was selected by way of example. In order to examine whether or not SDC2 gene methylation would be detected in clinical feces samples, genomic DNA was isolated from each of 47 colorectal cancer patients and 16 normal persons. 2.0 µg of the isolated genomic DNA was converted with bisulfite by use of the EZ DNA Methylation Gold kit (Zymo Research) according to the manufacturer's instructions, and eluted with 10 µL of distilled water. Using these genomic DNAs, methylation-specific real-time PCR (qMSP) was performed using the 808 sets of methylation-specific primers and probes. The qMSP was performed using a Rotor-Gene Q PCR system (Qiagen). Specifically, a total of 20 µL of PCR reaction solution (containing 2 µl of template DNA; 4 µL of 5× AptaTaq DNA Master (Roche Diagnostics); 2 µL (2 pmole/µL) of PCR primer, 2 µL (2 pmole/µL) of TaqMan probe; and 10 µL of D.W.) was prepared and subjected to PCR under the following conditions: treatment at 95° C. for 5 min, and then 40 cycles, each consisting of 15 sec at 95° C. and 1 min at an annealing temperature of 60° C. Whether or not a PCR amplification product would be produced was determined by measuring the cycle threshold ($C_T$) value.

Using the $C_T$ value, sensitivity and specificity for diagnosis of colorectal cancer were evaluated by ROC analysis (MedCalc program, Belgium). As a result, it was shown that sensitivity for diagnosis of colorectal cancer was 89.4% (42/47), and specificity for diagnosis of colorectal cancer was 93.8% (1/16), indicating that sensitivity and specificity for diagnosis of colorectal cancer were excellent (FIG. 2).

In addition, In order to examine whether or not SDC2 gene methylation would be detected in clinical serum samples from colorectal cancer patients, genomic DNA was isolated from each of 13 colorectal cancer patients and 6 normal persons. The isolated genomic DNA was converted with bisulfite by use of the EZ DNA Methylation Gold kit (Zymo Research) according to the manufacturer's instructions, and eluted with 10 μL of distilled water. Using these genomic DNAs, methylation of SDC2 gene was measured in the same manner as in the above Example using the 808 sets of methylation-specific primers and probes. Using the $C_T$ value, sensitivity and specificity for diagnosis of colorectal cancer were evaluated by ROC analysis (MedCalc program, Belgium). As a result, it was shown that sensitivity for diagnosis of colorectal cancer was 84.6% (11/13), and specificity for diagnosis of colorectal cancer was 100% (0/6), indicating that sensitivity and specificity for diagnosis of colorectal cancer were excellent (FIG. 3).

What is claimed is:

1. A method for detecting CpG methylation of SDC2 (Syndecan 2) gene, the method comprising the steps of:
   (a) isolating genomic DNA from a clinical sample;
   (b) treating the genomic DNA from step (a) with bisulfite; and
   (c) measuring methylation of a CpG of the SDC2 gene in the genomic DNA treated with bisulfite according the step (b) by using a primer pair comprising
   a primer comprising the sequence of SEQ ID NO: 574; and
   a primer comprising the sequence of any one of SEQ ID NOs: 573, 577 to 594, and 612 to 635,
to amplify a methylated CpG of the bisulfite-treated SDC2 gene.

2. The method according to claim 1, wherein step (c) is performed by a method selected from the group consisting of PCR, methylation specific PCR, real-time methylation specific PCR, PCR using a methylated DNA-specific binding protein, quantitative PCR, pyrosequencing, and bisulfite sequencing.

3. The method according to claim 1, wherein step (c) comprises measuring a CpG methylation of a regulatory region or intron region of SDC2 gene in the clinical sample.

4. The method of claim 1, wherein the primer(s) of step (c) comprises at least one or more CpG dinucleotide in a region which hybridizes to the methylated CpG of SDC2.

5. The method according to claim 1, further comprising confirming whether an amplified product of methylated CpG of SDC2 gene is produced by using probe(s) capable of hybridizing with a methylated CpG of SDC2 comprising at least one or more CpG dinucleotide in a region which hybridizes to the methylated CpG of SDC2.

6. The method according to claim 5, wherein the probe(s) comprises sequence(s) of SEQ ID NO: 575.

7. A method for detecting CpG methylation of SDC2 (Syndecan 2) gene for a colorectal cancer diagnosis, the method comprising the steps of:
   (a) isolating genomic DNA from a clinical sample;
   (b) treating the genomic DNA from step (a) with bisulfite; and
   (c) measuring methylation of a CpG of the SDC2 gene in the genomic DNA treated with bisulfite according the step (b) by using a primer pair comprising
   a primer comprising the sequence of SEQ ID NO: 574; and
   a primer comprising the sequence of any one of SEQ ID NOs: 573, 577 to 594, and 612 to 635,
to amplify a methylated CpG of the bisulfite-treated SDC2 gene, wherein a colorectal cancer is detected in a human subject based on increased CpG methylation of the SDC2 gene relative to that of a control.

8. The method according to claim 7, wherein step (c) is performed by a method selected from the group consisting of PCR, methylation specific PCR, real-time methylation specific PCR, PCR using a methylated DNA-specific binding protein, quantitative PCR, pyrosequencing, and bisulfite sequencing.

9. The method according to claim 7, wherein step (c) comprises measuring a CpG methylation of a regulatory region or intron region of SDC2 gene in the clinical sample.

10. The method of claim 7, wherein the primer(s) of step (c) comprises at least one or more CpG dinucleotide in a region which hybridizes to the methylated CpG of SDC2.

11. The method according to claim 7, further comprising confirming whether an amplified product of methylated CpG of SDC2 gene is produced by using probe(s) capable of hybridizing with a methylated CpG of SDC2 comprising at least one or more CpG dinucleotide in a region which hybridizes to the methylated CpG of SDC2.

12. The method according to claim 11, wherein the probe(s) comprises sequence(s) of SEQ ID NO: 575.

* * * * *